United States Patent
Ren et al.

(10) Patent No.: US 9,345,706 B2
(45) Date of Patent: *May 24, 2016

(54) BENZOXAZOLE KINASE INHIBITORS AND METHODS OF USE

(71) Applicant: Intellikine LLC, La Jolla, CA (US)

(72) Inventors: Pingda Ren, San Diego, CA (US); Yi Liu, San Diego, CA (US); Troy Edward Wilson, San Marino, CA (US); Liansheng Li, San Diego, CA (US); Katrina Chan, San Diego, CA (US)

(73) Assignee: Intellikine, LLC, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/727,336

(22) Filed: Jun. 1, 2015

(65) Prior Publication Data

US 2015/0306105 A1    Oct. 29, 2015

Related U.S. Application Data

(60) Continuation of application No. 13/893,187, filed on May 13, 2013, which is a division of application No. 12/586,309, filed on Sep. 17, 2009, now Pat. No. 8,476,282.

(60) Provisional application No. 61/230,655, filed on Jul. 31, 2009, provisional application No. 61/214,261, filed on Apr. 20, 2009, provisional application No. 61/201,923, filed on Dec. 16, 2008, provisional application No. 61/198,200, filed on Nov. 3, 2008.

(51) Int. Cl.

| | |
|---|---|
| *A61K 31/519* | (2006.01) |
| *C07D 487/04* | (2006.01) |
| *C07D 413/04* | (2006.01) |
| *C07D 413/14* | (2006.01) |
| *A61K 31/275* | (2006.01) |
| *A61K 45/06* | (2006.01) |
| *C07F 5/02* | (2006.01) |
| *A61K 31/337* | (2006.01) |
| *A61K 31/455* | (2006.01) |
| *A61K 31/5377* | (2006.01) |
| *A61K 31/7068* | (2006.01) |
| *A61K 39/395* | (2006.01) |

(52) U.S. Cl.
CPC .......... *A61K 31/519* (2013.01); *A61K 31/275* (2013.01); *A61K 31/337* (2013.01); *A61K 31/455* (2013.01); *A61K 31/5377* (2013.01); *A61K 31/7068* (2013.01); *A61K 39/3955* (2013.01); *A61K 45/06* (2013.01); *C07D 413/04* (2013.01); *C07D 413/14* (2013.01); *C07D 487/04* (2013.01); *C07F 5/025* (2013.01)

(58) Field of Classification Search
CPC .................. C07D 487/04; A61K 31/519
See application file for complete search history.

(56) References Cited

U.S. PATENT DOCUMENTS

| | | | |
|---|---|---|---|
| 5,593,997 A | 1/1997 | Dow et al. | |
| 6,390,821 B1 | 5/2002 | Shokat | |
| 6,521,417 B1 | 2/2003 | Shokat | |
| 6,552,192 B1 | 4/2003 | Hanus et al. | |
| 6,624,119 B1 | 9/2003 | Reinhard et al. | |
| 6,800,633 B2 | 10/2004 | Castelhano et al. | |
| 7,026,461 B1 | 4/2006 | Shokat | |
| 7,049,116 B2 | 5/2006 | Shokat | |
| 7,148,228 B2 | 12/2006 | Kasibhatla et al. | |
| 7,271,262 B2 | 9/2007 | LaGreca et al. | |
| 2001/0024833 A1 | 9/2001 | Laborde et al. | |
| 2002/0016976 A1 | 2/2002 | Shokat | |
| 2002/0156081 A1 | 10/2002 | Hirst et al. | |
| 2003/0180924 A1 | 9/2003 | DeSimone | |
| 2003/0187001 A1 | 10/2003 | Calderwood et al. | |
| 2005/0085472 A1 | 4/2005 | Tanaka et al. | |
| 2005/0197340 A1 | 9/2005 | Arora et al. | |
| 2006/0235031 A1 | 10/2006 | Arnold et al. | |
| 2006/0246551 A1 | 11/2006 | Stack et al. | |
| 2007/0054915 A1 | 3/2007 | Arora et al. | |
| 2007/0072897 A1 | 3/2007 | Mahaney et al. | |
| 2007/0099871 A1 | 5/2007 | Davis et al. | |
| 2007/0112005 A1 | 5/2007 | Chen et al. | |
| 2007/0149521 A1 | 6/2007 | Crew et al. | |
| 2007/0203143 A1 | 8/2007 | Sheppard et al. | |
| 2007/0213355 A1 | 9/2007 | Capraro et al. | |
| 2007/0224672 A1 | 9/2007 | Leban et al. | |
| 2007/0249598 A1 | 10/2007 | Wang et al. | |
| 2007/0254883 A1 | 11/2007 | Crew et al. | |
| 2007/0293516 A1 | 12/2007 | Knight et al. | |
| 2008/0032960 A1 | 2/2008 | Knight et al. | |
| 2010/0004235 A1 | 1/2010 | Schirok et al. | |

FOREIGN PATENT DOCUMENTS

| | | |
|---|---|---|
| EP | 0773023 A1 | 5/1997 |
| JP | 61109797 | 5/1986 |

(Continued)

OTHER PUBLICATIONS

"Nexavar (sorafenib) dosing, indications, interactions, adverse effects, and more", Medscape Reference, WebMD, retrieved Sep. 7, 2015, pp. 1-4.*
Cancer Therapy Advisor, Feb. 1, 2012, < http://www.cancertherapyadvisor.com/general-oncology/targeted-therapy-with-pi3-kinase-inhibitors/article/225657/> downloaded Sep. 7, 2015.*
Abdel-Mohsen. Synthesis, Reactions and Antimicrobial Activity of 2-AmiN-4-(8quiNliN1-5-ye-1-(p-tolyl)-pyrrole-3-carbonitrile. Bull. Korean Chem. Soc. 2005;26(5):719-728.

(Continued)

*Primary Examiner* — Susanna Moore
(74) *Attorney, Agent, or Firm* — Honigman Miller Schwartz and Cohn LLP; Lucy X. Yang; Jonathan P. O'Brien

(57) ABSTRACT

The present invention provides chemical entities or compounds and pharmaceutical compositions thereof that are capable of modulating certain protein kinases such as mTor, tyrosine kinases, and/or lipid kinases such as PI3 kinase. Also provided in the present invention are methods of using these compositions to modulate activities of one or more of these kinases, especially for therapeutic applications.

1 Claim, 20 Drawing Sheets

(56) References Cited

FOREIGN PATENT DOCUMENTS

| | | |
|---|---|---|
| WO | WO9417803 | 8/1994 |
| WO | WO9631510 | 10/1996 |
| WO | WO9640706 | 12/1996 |
| WO | WO9715658 | 5/1997 |
| WO | WO9814450 | 4/1998 |
| WO | WO0042042 | 7/2000 |
| WO | WO0119829 | 3/2001 |
| WO | WO02076986 | 10/2002 |
| WO | WO03000187 | 1/2003 |
| WO | WO2005044181 | 5/2005 |
| WO | WO2005047289 | 5/2005 |
| WO | WO2005074603 | 8/2005 |
| WO | WO2005085248 | 9/2005 |
| WO | WO2005097800 | 10/2005 |
| WO | WO2005113556 | 12/2005 |
| WO | WO2006050946 | 5/2006 |
| WO | WO2006068760 | 6/2006 |
| WO | WO2007023115 | 3/2007 |
| WO | WO2007075554 | 7/2007 |
| WO | WO2007103308 | 9/2007 |
| WO | WO2007106503 | 9/2007 |
| WO | WO2007112005 | 10/2007 |
| WO | WO2007114926 | 10/2007 |
| WO | WO2007126841 | 11/2007 |
| WO | WO2007134828 | 11/2007 |
| WO | WO2008031594 | 3/2008 |
| WO | WO2008083070 | 7/2008 |
| WO | WO2008127226 | 10/2008 |
| WO | WO2009021990 | 2/2009 |
| WO | WO2009064802 | 5/2009 |
| WO | WO2009088986 | 7/2009 |
| WO | WO2009088990 | 7/2009 |
| WO | WO2009114870 | 9/2009 |
| WO | WO2009114874 | 9/2009 |
| WO | WO2010006072 | 1/2010 |
| WO | WO2010006086 | 1/2010 |
| WO | WO2010036380 | 4/2010 |
| WO | WO2010129816 | 11/2010 |

OTHER PUBLICATIONS

Apsel, et al. Targeted polypharmacology: discovery of dual inhibitors of tyrosine and phosphoiNsitide kinases. Nat Chem Biol. 2008 Nv;4(11):691-9.

Bhat, et al. Pyrazolopyrimidine nucleosides. 12. Synthesis and biological activity of certain pyrazolo[3,4-d]pyrimidine nucleosides related to adeNsine. J Med Chem. Oct. 1981;24(10):1165-72.

Bishop, A.C. et al. "Generation of moNspecific naNmolar tyrosine kinase inhibitors via a chemical genetic approach", Journal of the American Chemical Society, American Chemical Society, Washington, DC, US, vol. 121, N. 4, 1999, pp. 629-631.

Ding, S., et al. "A Combinatorial Scaffold Approach Toward Kinase-Directed Heterocycle Libraries", J. Am. Chem. Soc. (2002) 124(8):1594-1596.

Farag, et al. Synthesis and reactivity of 2-(benzothiazol-2-yl)-1-bromo-1,2-ethanedione-1-arylhydrazones. Heteroatom Chemistry. 1997; 8(1):45-50.

Feldman, et al. Active-site inhibitors of mTOR target rapamycin-resistant outputs of mTORC1 and mTORC2. PLoS Biol. Feb. 10, 2009;7(2):371-383.

Kraybill, B.C. et al. "Inhibitor scaffolds as new allele specific kinase substrates", Journal of the American Chemical Society, American Chemical Society, Washington, DC, US, vol. 124, N. 41, Oct. 16, 2002, pp. 12118-12128.

Kreutzberger, et al. 5-Substituierte 4-AmiNpyrimidine durch AmiNmethinylierung von Acetonitrilen. Liebigs Ann. Chem. 1977:537-544.

Lee, et al. All roads lead to mTOR: integrating inflammation and tumor angiogenesis . . . Cell Cycle. 2007;6(24):3011-3014.

Majumder, et al. mTOR inhibition reverses Akt-dependent prostate intraepithelial neoplasia through regulation of apoptotic and HIF-1-dependent pathways. Nature Medicine. 2004;10:594-601.

McMahon, et al. VEGF receptor signaling in tumor angiogenesis. The Oncologist. (2000); 5(suppl 1): 3-10.

Niswender, C.M., et al. "Protein Engineering of Protein Kinase A Catalytic Subunits Results in the Acquisition of Nvel Inhibitor Sensitivity", The Journal of Biological Chemistry (2002) 277(32):28916-28922.

Petrie, et al. A Nvel biotinylated adenylate analogue derived from pyrazolo[3,4-d]pyrimidine for labeling DNA probes. Bioconjug Chem. Nov.-Dec. 1991;2(6):441-6.

Sam, et al. Benzoxazoles: Potent Skeletal Muscle Relaxants. J Pharm Sci. May 1964; 53:538-44.

Tanaka, M., et al. "An Unbiased Cell Morphology-Based Screen for New, Biologically Active Small Molecules", PLoS Biology (2005) 3(5):0764-0776.

Walker et al., Molecular Cell, 2000, 6(4) 909-919.

Wilder, L., et al. "7-Alkyl- and 7-Cycloalkyl-5-aryl-pyrrolo[2,3-d]pyrimidines-Potent Inhibitors of the Tyrosine Kinase c-Src," Bioorganic & Medicinal Chemistry Letters (2001) 11(6):849-852.

Wu et al. Organic Letters (2003), 5(20), 3587-3590.

Wymann et al., Molecular & Cellu.ar Biology, 1996 16 1722-1734.

Yaguchi et al., Proc. Amer. Assoc. Cancer Res. 46 2005, Abstract 1961.

\* cited by examiner

Figure 1A

| Human cancer | Cell lines | Positive drugs | IC$_{50}$ ($\mu$ M) | |
|---|---|---|---|---|
| | | | Positive drug | Subject Compound |
| Fibrosarcoma | HT-1080 | Doxorubicin | +++ | +++ |
| Pancreatic Cancer | MIAPACA-2 | 5-FU | + | ++ |
| | Bx-PC-3 | | ++ | +++++ |
| | PANC-1 | Cisplatin | + | 1 |
| Kindney Cancer | 786-O | 5-FU | +++ | +++ |
| Live Cancer | Hep3B | Cisplatin | ++ | ++ |
| | HepG2 | 5-FU | ++ | ++ |
| Osteosarcoma | SK-HEP-1 | Doxorubicin | +++ | +++ |
| | 143b | | ++ | +++ |
| Melanoma | A375 | | ++ | +++ |
| | SK-MEL-5 | | ++ | ++ |
| Nasopharyngeal | CNE2 | Cisplatin | ++ | +++ |
| Gastric Cancer | MCG803 | | ++ | ++ |
| | BGC823 | | ++ | +++ |
| Ovarian Cancer | SKOV3 | | + | ++ |
| | OVCAR3 | | + | +++ |
| CML | K562 | | + | +++ |
| Oral Cancer | KB | | + | +++ |
| Orthotopic Multiple Myeloma | RPIM-8226 | | + | +++++ |

Figure 1B

| Human cancer | Cell lines | Positive drugs | IC$_{50}$ (μM) | |
|---|---|---|---|---|
| | | | Positive drug | Subject Compound |
| Breast Cancer | BT474 | Doxorubicin | ++ | +++ |
| | MCF-7 | Cisplatin | + | ++++ |
| | MCF-7-218 | Doxorubicin | +++ | +++ |
| | MCF-7-FL | Doxorubicin | +++ | ++++ |
| | MDA-MB231 | | + | ++++ |
| | SKBR3 | Cisplatin | ++ | +++ |
| Prostate Cancer | DU-145 | | ++ | ++ |
| | LNCaP | Paclitaxel | + | ++ |
| | PC-3 | Irinotecom | + | ++++ |
| Colorectal Cancer | Colo205 | Cisplatin | ++ | +++ |
| | DLD-1 | | +++ | ++++ |
| | HCT-116 | 5-FU | +++ | ++ |
| | HT-29 | | + | ++ |
| | LoVo | | ++ | +++ |
| | SW620 | | + | ++++ |
| Lung Cancer | A549 | Cisplatin | ++ | +++ |
| | Calu-6 | | ++ | ++++ |
| | NCI-H226 | | ++ | +++ |
| | NCI-H460 | | ++ | ++++ |
| | SK-MES-1 | | + | + |
| Glioblastoma | U87MG | | ++ | +++ |

Lipid kinase selectivity

| | PI3K Class I* | | | | PI3-Kinases Class II** | | PI3K Class III** | PI4K** | |
|---|---|---|---|---|---|---|---|---|---|
| | mTOR | PI3Kα | PI3Kβ | PI3Kγ | PI3Kδ | PI3KC2α | PI3KC2β | VPS34 | PI4Kα | PI4Kβ | PIKK** |
| | | | | | | | | | | | DNA-PK |
| IC$_{50}$ (nM) | ~1.0 | >200 | >5000 | >200 | >150 | >100 | >1000 | >1000 | >1000 | >1000 | 10 |

Protein kinase selectivity

| % Inhibition @ 1 µM | number of kinases (Invitrogen ~220 protein kinases) | number of kinases (Ambit ~350 protein kinases)*** |
|---|---|---|
| > 90% | 0 | 8 |
| 65% ~ 90% | 8 | 15 |

Figure 6

| Cellular Data | |
|---|---|
| PC3 Cell Proliferation (IC$_{50}$) * | 3 nM |
| PC3 Cellular pAKT (IC$_{50}$) * | < 10nM |
| 30 primary derived patient cell lines proliferation inhibition (average IC$_{50}$) ** | 18nM |
| Human Whole Blood pAKT IC$_{50}$ shift * | < 2X |

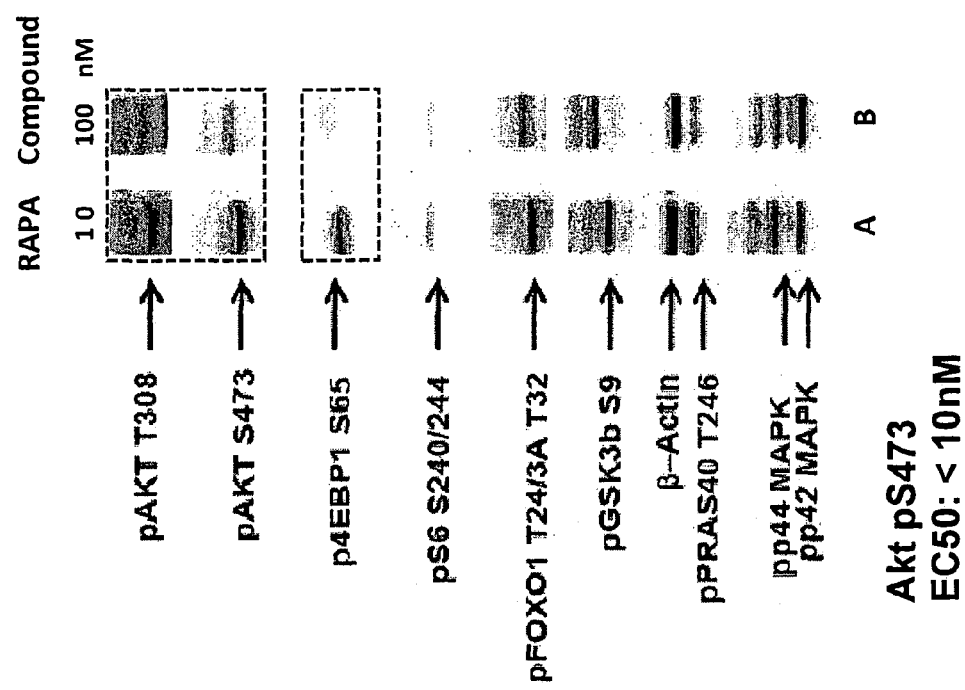
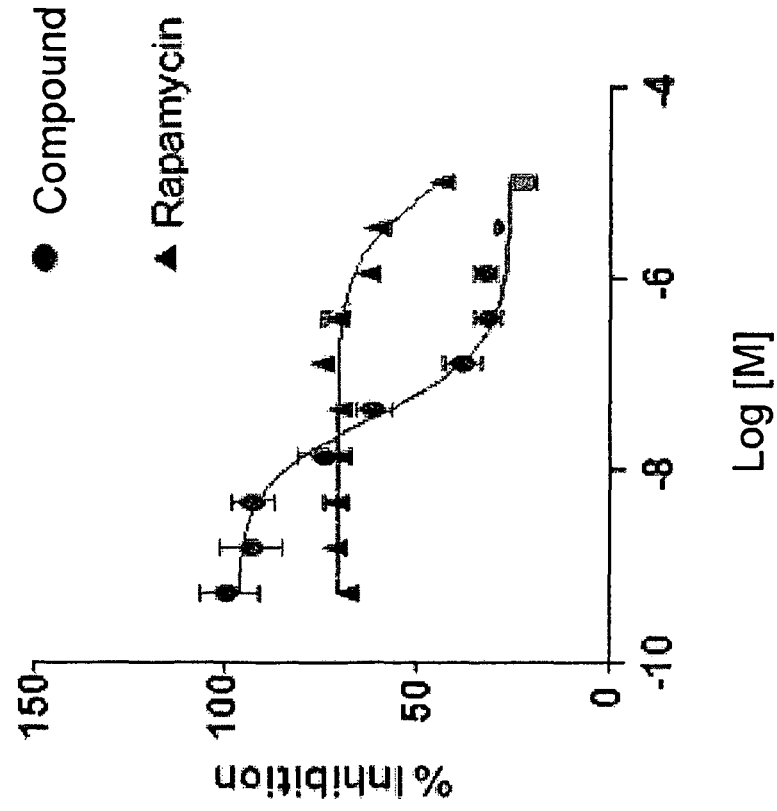
Figure 7
Figure 7A Cell proliferation
Figure 7B

Figure 8A

| Tissue Type | Cell lines | Compound IC$_{50}$ (nM) | Mutations |
|---|---|---|---|
| Colon | SW620 | 1 | KRAS G12V |
| | DLD-1 | 1 | PI3KCA E545K, KRAS G13D |
| | LoVo | 35 | KRAS G13D |
| | Colo205 | 19 | BRAF V600E |
| | HCT-116 | 11 | PI3KCA H1047R, KRAS G13D |
| | HT-29 | 905 | PI3KCA P449T, BRAF V600E |
| Lung | NCI-H226 | 5 | |
| | SK-MES-1 | 42 | |
| | A549 | 8 | KRAS G12S |
| | Calu-6 | 41 | KRAS Q61K |
| | NCI-H460 | 310 | PI3KCA E545K, KRAS Q61H |

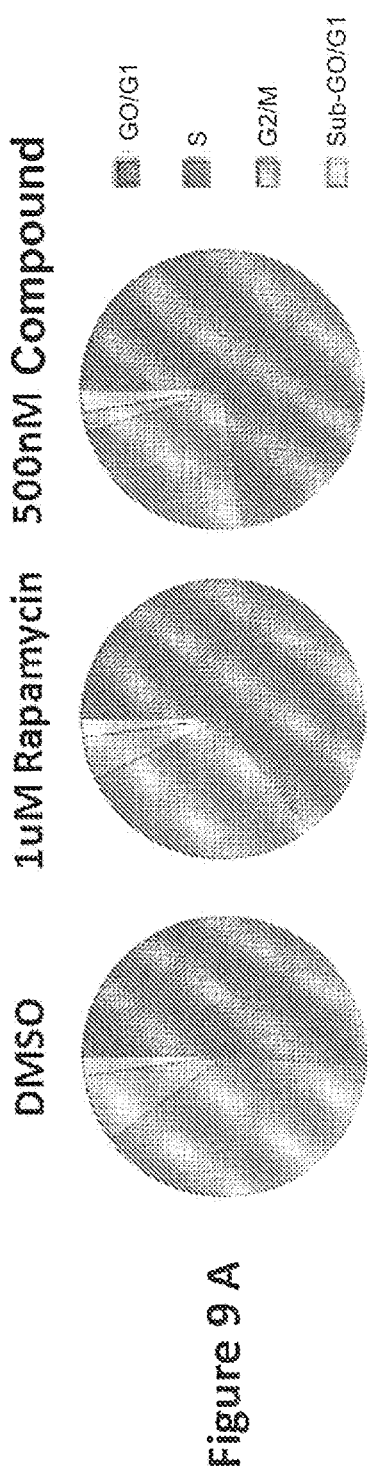
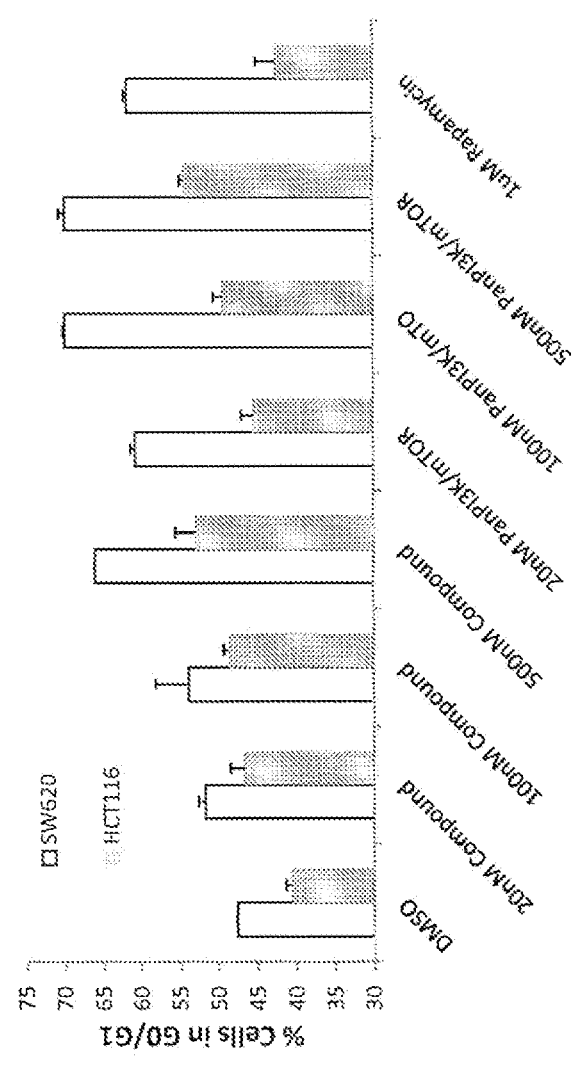
Figure 9 A
Figure 9 B

BENZOXAZOLE KINASE INHIBITORS AND METHODS OF USE

PRIORITY CLAIM

This application is a continuation of U.S. patent application Ser. No. 13/893,187 filed May 13, 2013, which is a divisional of U.S. patent application Ser. No. 12/586,309 filed Sep. 17, 2009, issued as U.S. Pat. No. 8,476,282 on Jul. 2, 2013, which claims priority under 35 U.S.C. §119(e) to U.S. Provisional Patent Application No. 61/230,655, filed Jul. 31, 2009, U.S. Provisional Patent Application No. 61/214,261, filed Apr. 20, 2009, U.S. Provisional Patent Application No. 61/201,923, filed Dec. 16, 2008, and U.S. Provisional Patent Application No. 61/198,200, filed Nov. 3, 2008. The entire contents of the aforementioned applications are herein incorporated by reference.

BACKGROUND OF THE INVENTION

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules, play a role in many different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (such as PI3-kinases, PI4-Kinases), diacylglycerol kinases, and sphingosine kinases.

The phosphoinositide 3-kinases (PI3Ks) signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation (Katso et al., 2001). The class I PI3Ks (p110α, p110β, p110δ, and p110γ) are typically activated by tyrosine kinases or G-protein coupled receptors to generate phosphatidylinositol-3,4,5-trisphosphate ($PIP_3$), which engages downstream effectors such as those in the Akt/PDK1 pathway, mTOR, the Tec family kinases, and the Rho family GTPases. The class II and III PI3-Ks play a key role in intracellular trafficking through the synthesis of PI(3)P and PI(3,4)P2. The PIKKs are protein kinases that control cell growth (mTORC1) or monitor genomic integrity (ATM, ATR, DNA-PK, and hSmg-1).

The production of $PIP_3$ initiates potent growth and survival signals. In some epithelial cancers the PI3K pathway is activated by direct genetic mutation. As PI3K signaling pathway plays a pivotal role in cell proliferation and differentiation, inhibition of this pathway is believed to be beneficial in hyperproliferative diseases.

Downstream mediators of the PI3K signal transduction pathway include Akt and mammalian target of rapamycin (mTOR). Akt possesses a plckstrin homology (PH) domain that bind PIP3, leading to Akt kinase activation. Akt phosphorylates many substrates and is a central downstream effector of PI3K for diverse cellular responses. Full activation of Akt typically requires phosphorylation of T308 in the activation loop and S473 in a hydrophobic motif. One important function of Akt is to augment the activity of mTOR, through phosphorylation of TSC2 and other mechanisms.

mTOR is a serine-threonine kinase related to the lipid kinases of the PI3K family. mTOR has been implicated in a wide range of biological processes including cell growth, cell proliferation, cell motility and survival. Disregulation of the mTOR pathway has been reported in various types of cancer. mTOR is a multifunctional kinase that integrates growth factor and nutrient signals to regulate protein translation, nutrient uptake, autophagy, and mitochondrial function.

mTOR exists in two complexes, mTORC1 and mTORC2. mTORC1 contains the raptor subunit and mTORC2 contains rictor. These complexes are differentially regulated, and have distinct substrate specificities and rapamycin sensitivity. For example, mTORC1 phosphorylates S6 kinase (S6K) and 4EBP1, promoting increased translation and ribosome biogenesis to facilitate cell growth and cell cycle progression. S6K also acts in a feedback pathway to attenuate PI3K/Akt activation. mTORC2 is generally insensitive to rapamycin. mTORC2 is though to modulate growth factor signaling by phosphorylating the C-terminal hydrophobic motif of some AGC kinases such as Akt. In many cellular contexts, mTORC2 is required for phosphorylation of the S473 site of Akt.

Over the past decade, mTOR has drawn considerable attention due to its role in cell growth control and its involvement in human diseases. mTor has been implicated in a wide range of disorders including but not limited to cancer, diabetes, obesity, cardiovascular diseases and neurological disorders. It has been shown that mTOR modulates many fundamental biological processes including transcription, translation, autophagy, actin organization and ribosome biogenesis by integrating intracellular and extracellular signals, such as signals mediated by growth factors, nutrients, energy levels and cellular stress.

As such, kinases particularly protein kinases such as mTor and Akt, as well as lipid kinases such as PI3Ks are prime targets for drug development. The present invention addresses this need in the art by providing a new class of kinase inhibitors.

SUMMARY OF THE INVENTION

In one aspect of the invention, compounds are provided of the Formula I'-A':

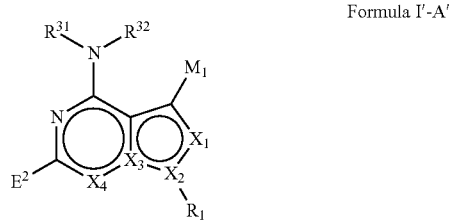

Formula I'-A' or a pharmaceutically acceptable salt thereof, wherein:

$X_1$ is N or C-$E^1$, $X_2$ is N, $X_3$ is C, and $X_4$ is C—$R^9$ or N; or $X_1$ is N or C-$E^1$, $X_2$ is C, $X_3$ is N, and $X_4$ is C—$R^9$ or N; and wherein no more than two nitrogen ring atoms are adjacent;

$R_1$ is H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —C(=O)—, —C(=O)O—, —C(=O)N($R^{31}$)—, —S—, —S(O)—, —S(O)$_2$—, —S(O)$_2$N($R^{31}$)—, or —N($R^{31}$)—;

$M_1$ is benzoxazolyl substituted with —(W$^2$)$_k$—$R^2$;

k is 0 or 1;

$E^1$ and $E^2$ are independently —(W$^1$)$_j$—$R^4$;

j in $E^1$ or j in $E^2$, is independently 0 or 1;

$W^1$ is —O—, —N$R^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$W^2$ is —O—, —N$R^7$—, —S(O)$_{0-2}$—, —C(O)—, —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R^3$ and $R^4$ are independently hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, —SC(=O)N$R^{31}R^{32}$, aryl, hetaryl, $C_{1-4}$alkyl, $C_{1-10}$alkyl, $C_{3-8}$cycloalkyl, $C_{1-10}$alkyl-$C_{3-8}$cycloalkyl, —$C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl $C_{2-10}$alkenyl, aryl $C_{2-10}$alkynyl, aryl-heterocyclyl, hetaryl-$C_{1-10}$alkyl, hetaryl-$C_{2-10}$alkenyl, hetaryl $C_{2-10}$alkynyl, hetaryl $C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, or —SC(=O)N$R^{31}R^{32}$, and wherein each of said alkyl, cycloalkyl, heterocyclyl, or heteroalkyl moiety is unsubstituted or is substituted with one or more halo, —OH, —$R^{31}$, —CF$_3$, —OCF$_3$, —O$R^{31}$, —O-aryl, —N$R^{31}R^{32}$, —N$R^{34}R^{35}$, —C(O)$R^{31}$, —CO$_2R^{31}$, —C(=O)N$R^{34}R^{35}$, or —C(=O)N$R^{31}R^{32}$;

$R^5$ is hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, or —SC(=O)N$R^{31}R^{32}$;

$R^2$ is hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, —SC(=O)N$R^{31}R^{32}$, aryl (e.g. bicyclic aryl, unsubstituted aryl, or substituted monocyclic aryl), hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenyl-hetaryl, $C_{2-10}$alkenylheteroalkyl, $C_{2-10}$alkenylheterocyclyl, $C_{2-10}$alkenyl-$C_{3-8}$cycloalkyl, $C_{2-10}$alkynylaryl, $C_{2-10}$alkynyl-hetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)$ $NR^{32}R^{33}$, —$NR^{31}S(O)_{0-2}R^{32}$, —$C(=S)OR^{31}$, —$C(=O)$ $SR^{31}$, —$NR^{31}C(=NR^{32})NR^{33}R^{32}$, —$NR^{31}C(=NR^{32})$ $OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)$ $OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

each of $R^{31}$, $R^{32}$, and $R^{33}$ is independently H or $C_{1-10}$alkyl, wherein the $C_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl$)(C_{1-10}$alkyl$)$, —NH $(C_{1-10}$alkyl$)$, —NH(aryl), —$NR^{34}R^{35}$, —$C(O)(C_{1-10}$alkyl$)$, —$C(O)(C_{1-10}$alkyl-aryl$)$, —$C(O)$(aryl), —$CO_2$—$C_{1-10}$alkyl, —$CO_2$—$C_{1-10}$alkylaryl, —$CO_2$-aryl, —$C(=O)$ $N(C_{1-10}$alkyl$)(C_{1-10}$alkyl$)$, —$C(=O)NH(C_{1-10}$alkyl$)$, —$C(=O)NR^{34}R^{35}$, —$C(=O)NH_2$, —$OCF_3$, —O($C_{1-10}$alkyl), —O-aryl, —N(aryl)($C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$ aryl, —$SO_2N$(aryl), —$SO_2N$ $(C_{1-10}$alkyl$)(C_{1-10}$alkyl$)$, —$SO_2NH(C_{1-10}$alkyl$)$ or —$SO_2$ $NR^{34}R^{35}$;

$R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom;

each of $R^7$ and $R^8$ is independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, —$C(=O)NR^{34}R^{35}$, —$NO_2$, —CN, —$S(O)_{0-2}C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, —$C(=O)NR^{31}R^{32}$, —$C(=O)$ $NR^{34}R^{35}$, —$SO_2NR^{34}R^{35}$, —$SO_2NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, —$C(=O)NR^{34}R^{35}$, —$NO_2$, —CN, —$S(O)_{0-2}C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl- $C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, —$C(=O)NR^{31}R^{32}$, —$C(=O)$ $NR^{34}R^{35}$, —$SO_2NR^{34}R^{35}$, —$SO_2NR^{31}R^{32}$, —$NR^{31}R^{32}$, or —$NR^{34}R^{35}$.

In some embodiments, $X_4$ is C—$R^9$. In other embodiments, $X_4$ is N.

The invention also provides a compound as defined above, wherein the compound is of Formula I-A:

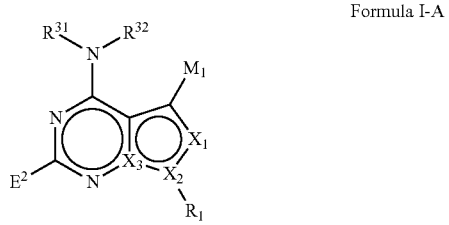

Formula I-A or a pharmaceutically acceptable salt thereof, and wherein the substituents are as defined above.

In some embodiments of the compounds of Formula I'-A' or I-A, $X_3$ is N.

In a second aspect, the invention provides a compound of Formula II-A-1:

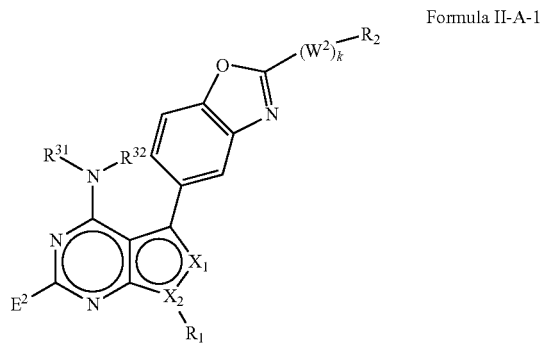

Formula II-A-1 or a pharmaceutically acceptable salt thereof, wherein:
$X_1$ is N or C-$E^1$ and $X_2$ is N; or $X_1$ is NH or CH-$E^1$ and $X_2$ is C;

$R_1$ is H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocyclyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, -L-heterocyclyl, each of which is unsubstituted or is substituted by one or more independent R³; and L is absent, —(C=O)—, —C(=O)O—, —C(=O)N(R³¹)—, —S—, —S(O)—, —S(O)₂—, —S(O)₂N(R³¹)—, or —N(R³¹);

k is 0 or 1;

E¹ and E² are independently —(W¹)ⱼ—R⁴;

j in E¹ or j in E², is independently 0 or 1;

W¹ is —O—, —NR⁷—, —S(O)₀₋₂—C(O)—, —C(O)N(R⁷)—, —N(R⁷)C(O)—, —N(R⁷)S(O), —N(R⁷)S(O)₂, —C(O)O—, —CH(R⁷)N(C(O)OR⁸)—, —CH(R⁷)N(C(O)R⁸)—, —CH(R⁷)N(SO₂R⁸)—, —CH(R⁷)N(R⁸)—, —CH(R⁷)C(O)N(R⁸)—, —CH(R⁷)N(R⁸)C(O)—, —CH(R⁷)N(R⁸)S(O)—, or —CH(R⁷)N(R⁸)S(O)₂—;

W² is —O—, —NR⁷—, —S(O)₀₋₂—, —C(O)—, —C(O)N(R⁷)—, —N(R⁷)C(O)—, —N(R⁷)C(O)N(R⁸)—, —N(R⁷)S(O)—, —N(R⁷)S(O)₂—, —C(O)O—, —CH(R⁷)N(C(O)OR⁸)—, —CH(R⁷)N(C(O)R⁸)—, —CH(R⁷)N(SO₂R⁸)—, —CH(R⁷)N(R⁸)—, —CH(R⁷)C(O)N(R⁸)—, —CH(R⁷)N(R⁸)C(O)—, —CH(R⁷)N(R⁸)S(O)—, or —CH(R⁷)N(R⁸)S(O)₂—;

R² is hydrogen, halogen, —OH, —R³¹, —CF₃, —OCF₃, —OR³¹, —NR³¹R³², —NR³⁴R³⁵, —C(O)R³¹, —CO₂R³¹, —C(=O)NR³¹R³², —C(=O)NR³⁴R³⁵, —NO₂, —CN, —S(O)₀₋₂R³¹, —SO₂NR³¹R³², —SO₂NR³⁴R³⁵, —NR³¹C(=O)R³², —NR³¹C(=O)OR³², —NR³¹C(=O)NR³²R³³, —NR³¹S(O)₀₋₂R³², —C(=S)OR³¹, —C(=O)SR³¹, —NR³¹C(=NR³²)NR³³R³², —NR³¹C(=NR³²)OR³³, —NR³¹C(=NR³²)SR³³, —OC(=O)OR³³, —OC(=O)NR³¹R³², —OC(=O)SR³¹, —SC(=O)OR³¹, —P(O)OR³¹OR³², —SC(=O)NR³¹R³², aryl (e.g. bicyclic aryl, unsubstituted aryl, or substituted monocyclic aryl), hetaryl, C₁₋₁₀alkyl, C₃₋₈cycloalkyl, C₁₋₁₀alkyl-C₃₋₈cycloalkyl, C₃₋₈cycloalkyl-C₁₋₁₀alkyl, C₃₋₈cycloalkyl-C₂₋₁₀alkenyl, C₃₋₈cycloalkyl-C₂₋₁₀alkynyl, C₁₋₁₀alkyl-C₂₋₁₀alkenyl, C₁₋₁₀alkyl-C₂₋₁₀alkynyl, C₁₋₁₀alkylaryl (e.g. C₂₋₁₀alkyl-monocyclic aryl, C₁₋₁₀alkyl-substituted monocyclic aryl, or C₁₋₁₀alkylbicycloaryl), C₁₋₁₀alkylhetaryl, C₁₋₁₀alkylheterocyclyl, C₂₋₁₀alkenyl, C₂₋₁₀alkynyl, C₂₋₁₀alkenyl-C₁₋₁₀alkyl, C₂₋₁₀alkynyl-C₁₋₁₀alkyl, C₂₋₁₀alkenylaryl, C₂₋₁₀alkenylhetaryl, C₂₋₁₀alkenylheteroalkyl, C₂₋₁₀-alkenylheterocyclcyl, C₂₋₁₀alkenyl-C₃₋₈cycloalkyl, C₂₋₁₀alkynylaryl, C₂₋₁₀alkynylhetaryl, C₂₋₁₀alkynylheteroalkyl, C₂₋₁₀alkynylheterocylyl, C₂₋₁₀alkynyl-C₃₋₈cycloalkenyl, C₁₋₁₀alkoxy C₁₋₁₀alkyl, C₁₋₁₀alkoxy-C₂₋₁₀alkenyl, C₁₋₁₀alkoxy-C₂₋₁₀alkynyl, heterocyclyl, heteroalkyl, heterocyclyl-C₁₋₁₀alkyl, heterocyclyl-C₂₋₁₀alkenyl, heterocyclyl-C₂₋₁₀alkynyl, aryl-C₁₋₁₀alkyl (e.g. monocyclic aryl-C₁₋₁₀alkyl, substituted monocyclic aryl-C₁₋₁₀alkyl, or bicycloaryl-C₁₋₁₀alkyl), aryl-C₂₋₁₀alkenyl, aryl-C₂₋₁₀alkynyl, aryl-heterocyclyl, hetaryl-C₁₋₁₀alkyl, hetaryl-C₂₋₁₀alkenyl, hetaryl-C₂₋₁₀alkynyl, hetaryl-C₃₋₈cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R³¹, —CF₃, —OCF₃, —OR³¹, —NR³¹R³², —NR³⁴R³⁵, —C(O)R³¹, —CO₂R³¹, —C(=O)NR³¹R³², —C(=O)NR³⁴R³⁵, —NO₂, —CN, —S(O)₀₋₂R³¹, —SO₂NR³¹R³², —SO₂NR³⁴R³⁵, —NR³¹C(=O)R³², —NR³¹C(=O)OR³², —NR³¹C(=O)NR³²R³³, —NR³¹S(O)₀₋₂R³², —C(=S)OR³¹, —C(=O)SR³¹, —NR³¹C(=NR³²)NR³³R³², —NR³¹C(=NR³²)OR³³, —NR³¹C(=NR³²)SR³³, —OC(=O)OR³³, —OC(=O)NR³¹R³², —OC(=O)SR³¹, —SC(=O)OR³¹, —P(O)OR³¹OR³², or —SC(=O)NR³¹R³², and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R³¹, —CF₃, —OCF₃, —OR³¹, —O-aryl, —NR³¹R³², —NR³⁴R³⁵, —C(O)R³¹, —CO₂R³¹, —C(=O)NR³⁴R³⁵, or —C(=O)NR³¹R³²;

R³ and R⁴ are independently hydrogen, halogen, —OH, —R³¹, —CF₃, —OCF₃, —OR³¹, —NR³¹R³², —NR³⁴R³⁵, —C(O)R³¹, —CO₂R³¹, —C(=O)NR³¹R³², —C(=O)NR³⁴R³⁵, —NO₂, —CN, —S(O)₀₋₂R³¹, —SO₂NR³¹R³², —SO₂NR³⁴R³⁵, —NR³¹C(=O)R³², —NR³¹C(=O)OR³², —NR³¹C(=O)NR³²R³³, —NR³¹S(O)₀₋₂R³², —C(=S)OR³¹, —C(=O)SR³¹, —NR³¹C(=NR³²)NR³³R³², —NR³¹C(=NR³²)OR³³, —NR³¹C(=NR³²)SR³³, —OC(=O)OR³³, —OC(=O)NR³¹R³², —OC(=O)SR³¹, —SC(=O)OR³¹, —P(O)OR³¹OR³², —SC(=O)NR³¹R³², aryl, hetaryl, C₁₋₁₀alkyl, C₃₋₈cycloalkyl, C₁₋₁₀alkyl-C₃₋₈cycloalkyl, C₃₋₈cycloalkyl-C₁₋₁₀alkyl, C₃₋₈cycloalkyl-C₂₋₁₀alkenyl, C₃₋₈cycloalkyl-C₂₋₁₀alkynyl, C₁₋₁₀alkyl-C₂₋₁₀alkenyl, C₁₋₁₀alkyl-C₂₋₁₀alkynyl, C₁₋₁₀alkylaryl, C₁₋₁₀alkylhetaryl, C₁₋₁₀alkylheterocyclyl, C₂₋₁₀alkenyl, C₂₋₁₀alkynyl, C₂₋₁₀alkenyl-C₁₋₁₀alkyl, C₂₋₁₀alkynyl-C₁₋₁₀alkyl, C₂₋₁₀alkenylaryl, C₂₋₁₀alkenylhetaryl, C₂₋₁₀alkenylheteroalkyl, C₂₋₁₀alkenylheterocyclcyl, C₂₋₁₀alkenyl-C₃₋₈cycloalkyl, C₂₋₁₀alkynyl-C₃₋₈cycloalkyl, C₂₋₁₀alkynylaryl, C₂₋₁₀alkynylhetaryl, C₂₋₁₀alkynylheteroalkyl, C₂₋₁₀alkynylheterocyclyl, C₂₋₁₀alkynyl-C₃₋₈cycloalkyl, C₁₋₁₀alkoxy C₁₋₁₀alkyl, C₁₋₁₀alkoxy-C₂₋₁₀alkenyl, C₁₋₁₀alkoxy-C₂₋₁₀alkynyl, heterocyclyl, heterocyclyl-C₁₋₁₀alkyl, heterocyclyl-C₂₋₁₀alkenyl, heterocyclyl-C₂₋₁₀alkynyl, aryl-C₁₋₁₀alkyl, aryl-C₂₋₁₀alkenyl, aryl-C₂₋₁₀alkynyl, aryl-heterocyclyl, hetaryl-C₁₋₁₀alkyl, hetaryl-C₂₋₁₀alkenyl, hetaryl-C₂₋₁₀alkynyl, hetaryl-C₃₋₈cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —R³¹, —CF₃, —OCF₃, —OR³¹, —NR³¹R³², —NR³⁴R³⁵, —C(O)R³¹, —CO₂R³¹, —C(=O)NR³¹R³², —C(=O)NR³⁴R³⁵, —NO₂, —CN, —S(O)₀₋₂R³¹, —SO₂NR³¹R³², —SO₂NR³⁴R³⁵, —NR³¹C(=O)R³², —NR³¹C(=O)OR³², —NR³¹C(=O)NR³²R³³, —NR³¹S(O)₀₋₂R³², —C(=S)OR³¹, —C(=O)SR³¹, —NR³¹C(=NR³²)NR³³R³², —NR³¹C(=NR³²)OR³³, —NR³¹C(=NR³²)SR³³, —OC(=O)OR³³, —OC(=O)NR³¹R³², —OC(=O)SR³¹, —SC(=O)OR³¹, —P(O)OR³¹OR³², or —SC(=O)NR³¹R³², and wherein each of said alkyl, cycloalkyl, heterocyclyl, or heteroalkyl moiety is unsubstituted or is substituted with one or more halo, —OH, —R³¹, —CF₃, —OCF₃, —OR³¹, —O-aryl, —NR³¹R³², —NR³⁴R³⁵, —C(O)R³¹, —CO₂R³¹, —C(=O)NR³⁴R³⁵, or —C(=O)NR³¹R³²;

each of R³¹, R³², and R³³ is independently H or C₁₋₁₀alkyl, wherein the C₁₋₁₀alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —C₁₋₁₀alkyl, —CF₃, —O-aryl, —OCF₃, —OC₁₋₁₀alkyl, —NH₂, —N(C₁₋₁₀alkyl)(C₁₋₁₀alkyl), —NH(C₁₀₋₁₀alkyl), —NH(aryl), —NR³⁴R³⁵, —C(O)(C₁₋₁₀alkyl), —C(O)(C₁₋₁₀alkyl-aryl), —C(O)(aryl), —CO₂—C₁₋₁₀alkyl, —CO₂—C₁₋₁₀alkylaryl, —CO₂-aryl, —C(=O)N(C₁₋₁₀alkyl)(C₁₋₁₀alkyl), —C(=O)NH(C₁₋₁₀alkyl), —C(=O)NR³⁴R³⁵, —C(=O)NH₂, —OCF₃, —O(C₁₋₁₀alkyl), —O-aryl, —N(aryl)(C₁₋₁₀alkyl), —NO₂, —CN, —S(O)₂C₁₋₁₀alkyl, —S(O)₀₋₂C₁₋₁₀alkylaryl, —S(O)₀₋₂ aryl, —SO₂N(C₁₋₁₀alkyl) (C₁₋₁₀alkyl), —SO₂NH(C₁₋₁₀alkyl) or —SO₂NR³⁴R³⁵;

R³⁴ and R³⁵ in —NR³⁴R³⁵, —C(=O)NR³⁴R³⁵, or —SO₂NR³⁴R³⁵, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, hetaryl, C$_{1-6}$alkyl, or O-aryl, and wherein said 3-10 membered saturated or unsaturated ring independently contains 0, 1, or 2 more heteroatoms in addition to the nitrogen atom;

each of R$^7$ and R$^8$ is independently hydrogen, C$_{1-10}$alkyl, C$_{2-10}$alkenyl, aryl, heteroaryl, heterocyclyl or C$_{3-10}$cycloalkyl, each of which except for hydrogen is unsubstituted or is substituted by one or more independent R$^6$; and R$^6$ is halo, —OR$^{31}$, —SH, —NH$_2$, —NR$^{34}$R$^{35}$, —NR$^{31}$R$^{32}$, —CO$_2$R$^{31}$, —CO$_2$aryl, —C(=O)NR$^{31}$R$^{32}$, —C(=O)NR$^{34}$R$^{35}$, —NO$_2$, —CN, —S(O)$_{0-2}$C$_{1-10}$alkyl, —S(O)$_{0-2}$aryl, —SO$_2$NR$^{34}$R$^{35}$, —SO$_2$NR$^{31}$R$^{32}$, C$_{1-10}$alkyl, C$_{2-10}$alkenyl, C$_{2-10}$alkynyl; or R$^6$ is aryl- C$_{1-10}$alkyl, aryl-C$_{2-10}$alkenyl, aryl-C$_{2-10}$alkynyl, hetaryl-C$_{1-10}$alkyl, hetaryl-C$_{2-10}$alkenyl, hetaryl-C$_{2-10}$alkynyl, each of which is unsubstituted or is substituted with one or more independent halo, cyano, nitro, —OC$_{1-10}$alkyl, C$_{1-10}$alkyl, C$_{2-10}$alkenyl, C$_{2-10}$alkynyl, haloC$_{1-10}$alkyl, haloC$_{2-10}$alkenyl, halo C$_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$.

In a third aspect, the invention provides a compound of Formula III:

Formula III or a pharmaceutically acceptable salt thereof, wherein:

X$_1$ is N or C-E$^1$ and X$_2$ is N; or X$_1$ is NH or CH-E$^1$ and X$_2$ is C;

R$_1$ is —H, -L-C$_{1-10}$alkyl, -L-C$_{3-8}$cycloalkyl, -L-C$_{1-10}$alkyl-C$_{3-8}$cycloalkyl, -L-aryl, -L-heteroaryl, -L-C$_{1-10}$alkylaryl, -L-C$_{1-10}$alkylhetaryl, -L-C$_{1-10}$alkylheterocylyl, -L-C$_{2-10}$alkenyl, -L-C$_{2-10}$alkynyl, -L-C$_{2-10}$alkenyl-C$_{3-8}$cycloalkyl, -L-C$_{2-10}$alkynyl-C$_{3-8}$cycloalkyl, -L-heteroalkyl, -L-heteroalkylaryl, -L-heteroalkylheteroaryl, -L-heteroalkyl-heterocylyl, -L-heteroalkyl-C$_{3-8}$cycloalkyl, -L-aralkyl, -L-heteroaralkyl, or -L-heterocyclyl, each of which is unsubstituted or is substituted by one or more independent R$^3$;

L is absent, —(C=O)—, —C(=O)O—, —C(=O)N(R$^{31}$)—, —S—, —S(O)—, —S(O)$_2$—, —S(O)$_2$N(R$^{31}$)—, or —N(R$^{31}$)—;

M$_1$ is benzoxazolyl substituted with —(W$^2$)$_k$—R$^2$;
k is 0 or 1;
E$^1$ and E$^2$ are independently —(W$^1$)$_j$—R$^4$;
j in E$^1$ or j in E$^2$, is independently 0 or 1;

W$^1$ is —O—, —NR$^7$—, —S(O)$_{0-2}$—, —C(O)—, —C(O)N(R$^7$)—, —N(R$^7$)C(O)—, —N(R$^7$)S(O)—, —N(R$^7$)S(O)$_2$—, —C(O)O—, —CH(R$^7$)N(C(O)OR)—, —CH(R$^7$)N(C(O)R$^8$)—, —CH(R$^7$)N(SO$_2$R$^8$)—, —CH(R$^7$)N(R$^8$)—, —CH(R$^7$)C(O)N(R$^8$)—, —CH(R$^7$)N(R$^8$)C(O)—, —CH(R$^7$)N(R$^8$)S(O)—, or —CH(R$^7$)N(R$^8$)S(O)$_2$—;

W$^2$ is —O—, —NR$^7$—, —S(O)$_{0-2}$—, —C(O)—, —C(O)N(R$^7$)—, —N(R$^7$)C(O)—, —N(R$^7$)C(O)N(R$^8$)—, —N(R$^7$)S(O)—, —N(R$^7$)S(O)$_2$—, —C(O)O—, —CH(R$^7$)N(C(O)OR)—, —CH(R$^7$)N(C(O)R$^8$)—, —CH(R$^7$)N(SO$_2$R$^8$)—, —CH(R$^7$)N(R$^8$)—, —CH(R$^7$)C(O)N(R$^8$)—, —CH(R$^7$)N(R$^8$)C(O)—, —CH(R$^7$)N(R$^8$)S(O)—, or —CH(R$^7$)N(R$^8$)S(O)$_2$—;

R$^2$ is hydrogen, halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, —SC(=O)NR$^{31}$R$^{32}$, aryl (e.g. bicyclic aryl, unsubstituted aryl, or substituted monocyclic aryl), hetaryl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{1-10}$alkyl-C$_{2-10}$alkenyl, C$_{1-10}$alkyl-C$_{2-10}$alkynyl, C$_{1-10}$alkylaryl (e.g. C$_{2-10}$alkyl-monocyclic aryl, C$_{1-10}$alkyl-substituted monocyclic aryl, or C$_{1-10}$alkylbicycloaryl), C$_{1-10}$alkylhetaryl, C$_{1-10}$alkylheterocyclyl, C$_{2-10}$alkenyl, C$_{2-10}$alkynyl, C$_{2-10}$alkenyl-C$_{1-10}$alkyl, C$_{2-10}$alkynyl-C$_{1-10}$alkyl, C$_{2-10}$alkenylaryl, C$_{2-10}$alkenylhetaryl, C$_{2-10}$alkenylheteroalkyl, C$_{2-10}$alkenylheterocyclyl, C$_{2-10}$alkenyl-C$_{3-8}$cycloalkyl, C$_{2-10}$alkynylaryl, C$_{2-10}$alkynylhetaryl, C$_{2-10}$alkynylheteroalkyl, C$_{2-10}$alkynylheterocylyl, C$_{2-10}$alkynyl-C$_{3-8}$cycloalkyl, C$_{1-10}$alkoxy C$_{1-10}$alkyl, C$_{1-10}$alkoxy-C$_{2-10}$alkenyl, C$_{1-10}$alkoxy-C$_{2-10}$alkynyl, heterocyclyl, heteroalkyl, heterocyclyl-C$_{1-10}$alkyl, heterocyclyl-C$_{2-10}$alkenyl, heterocyclyl-C$_{2-10}$alkynyl, aryl-C$_{1-10}$alkyl (e.g. monocyclic aryl-C$_{2-10}$alkyl, substituted monocyclic aryl-C$_{1-10}$alkyl, or bicycloaryl-C$_{1-10}$alkyl), aryl-C$_{2-10}$alkenyl, aryl-C$_{2-10}$alkynyl, aryl-heterocyclyl, hetaryl-C$_{1-10}$alkyl, hetaryl-C$_{2-10}$alkenyl, hetaryl-C$_{2-10}$alkynyl, hetaryl-C$_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

R$^3$ and R$^4$ are independently hydrogen, halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, —SC(=O)NR$^{31}$R$^{32}$, aryl, hetaryl, $C_{1-10}$alkyl, $C_{3-8}$cycloalkyl, $C_{1-10}$alkyl$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl—$C_{1-10}$alkyl, $C_{2-10}$alkenylaryl, $C_{2-10}$alkenylhetaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{2-10}$alkyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —C(=S)$OR^{31}$, —C(=O)$SR^{31}$, —$NR^{31}C(=NR^{32})NR^{33}R^{32'}$, $NR^{31}C(=NR^{32})OR^{33}$, —$NR^{31}C(=NR^{32})SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

each of $R^{31}$, $R^{32}$, and $R^{33}$ is are independently H or $C_{1-10}$alkyl, wherein the $C_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —$C_{1-10}$alkyl, —$CF_3$, —O-aryl, $OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —S(O)$_{0-2}C_{1-10}$alkyl, —S(O)$_{0-2}C_{1-10}$alkylaryl, —S(O)$_{0-2}$ aryl, —$SO_2$N(aryl), —$SO_2$N($C_{1-10}$alkyl)($C_{1-10}$alkyl), —$SO_2NH(C_{1-10}$alkyl) or $SO_2NR^{34}R^{35}$;

$R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom;

each of $R^7$ and $R^8$ is independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, —C(=O)$NR^{34}R^{35}$, —$NO_2$, CN, —S(O)$_{0-2}C_{1-10}$alkyl, —S(O)$_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)$NR^{31}R^{32}$, —C(=O)$NR^{34}R^{35}$, —$SO_2NR^{34}R^{35}$, —$SO_2NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, —C(=O)$NR^{34}R^{35}$, —$NO_2$, —CN, —S(O)$_{0-2}C_{1-10}$alkyl, —S(O)$_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl- $C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, —C(=O)$NR^{31}R^{32}$, —C(=O)$NR^{34}R^{35}$, —$SO_2NR^{34}R^{35}$, —$SO_2NR^{31}R^{32}$, —$NR^{31}R^{32}$, or —$NR^{34}R^{35}$.

In yet another aspect, the invention provides a compound of Formula IV-A-1:

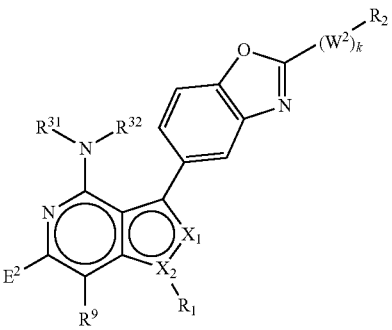

Formula IV-A-1 or a pharmaceutically acceptable salt thereof wherein:

$X_1$ is N or C-$E^1$ and $X_2$ is N; or $X_1$ is NH or CH-$E^1$ and $X_2$ is C;

$R_1$ is —H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocyclyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;

$E^1$ and $E^2$ are independently —(W$^1$)$_j$—$R^4$;

j in $E^1$ or j in $E^2$, is independently 0 or 1;

$W^1$ is —O—, —$NR^7$—, —S(O)$_{0-2}$—, —C(O)—, C(O)N($R^7$)—, —N($R^7$)C(O)—, —N($R^7$)S(O)—, —N($R^7$)S(O)$_2$—, —C(O)O—, —CH($R^7$)N(C(O)$OR^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$W^2$ is —O—, —NR$^7$—, —S(O)$_{0-2}$—, —C(O)—, C(O)N(R$^7$)—, —N(R$^7$)C(O)—, —N(R$^7$)C(O)N(R$^8$)—, —N(R$^7$)S(O)—, —N(R$^7$)S(O)$_2$—, —C(O)O—, —CH(R$^7$)N(C(O)OR$^8$)—, —CH(R$^7$)N(C(O)R$^8$)—, —CH(R$^7$)N(SO$_2$R$^8$)—, —CH(R$^7$)N(R$^8$)—, —CH(R$^7$)C(O)N(R$^8$)—, —CH(R$^7$)N(R$^8$)C(O)—, —CH(R$^7$)N(R$^8$)S(O)—, or —CH(R$^7$)N(R$^8$)S(O)$_2$—;

k is 0 or 1;

$R^2$, $R^3$ and $R^4$ are independently hydrogen, halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, —SC(=O)NR$^{31}$R$^{32}$, aryl (e.g. bicyclic aryl, unsubstituted aryl, or substituted monocyclic aryl), hetaryl, C$_{1-10}$alkyl, C$_{3-8}$cycloalkyl, C$_{1-10}$alkyl C$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{1-10}$alkyl-C$_{2-10}$alkenyl, C$_{1-10}$alkyl-C$_{2-10}$alkynyl, C$_{1-10}$alkylaryl (e.g. C$_{2-10}$alkyl-monocyclic aryl, C$_{1-10}$alkyl-substituted monocyclic aryl, or C$_{1-10}$alkylbicycloaryl), C$_{1-10}$alkylhetaryl, C$_{1-10}$alkylheterocyclyl, C$_{2-10}$alkenyl, C$_{2-10}$alkynyl, C$_{2-10}$alkenyl-C$_{1-10}$alkyl, C$_{2-10}$alkynyl-C$_{1-10}$alkyl, C$_{2-10}$alkenylaryl, C$_{2-10}$alkenylhetaryl, C$_{2-10}$alkenylheteroalkyl, C$_{2-10}$alkenylheterocyclyl, C$_{2-10}$alkenyl-C$_{3-8}$cycloalkyl, C$_{2-10}$alkynylaryl, C$_{2-10}$alkynylhetaryl, C$_{2-10}$alkynylheteroalkyl, C$_{2-10}$alkynylheterocyclyl, C$_{2-10}$alkynyl-C$_{3-8}$cycloalkenyl, C$_{1-10}$alkoxy C$_{1-10}$alkyl, C$_{1-10}$alkoxy-C$_{2-10}$alkenyl, C$_{1-10}$alkoxy-C$_{2-10}$alkynyl, heterocyclyl, heteroalkyl, heterocyclyl-C$_{1-10}$alkyl, heterocyclyl-C$_{2-10}$alkenyl, heterocyclyl-C$_{2-10}$alkynyl, aryl-C$_{1-10}$alkyl (e.g. monocyclic aryl-C$_{2-10}$alkyl, substituted monocyclic aryl-C$_{1-10}$alkyl, or bicycloaryl-C$_{1-10}$alkyl), arylC$_{2-10}$alkenyl, arylC$_{2-10}$alkynyl, aryl-heterocyclyl, hetaryl-C$_{1-10}$alkyl, hetaryl-C$_{2-10}$alkenyl, hetaryl-C$_{2-10}$alkynyl, hetaryl-C$_{3-8}$cycloalkyl, hetaryl-heteroalkyl, or hetaryl-heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_2$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_2$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

each of R$^{31}$, R$^{32}$, and R$^{33}$ is are independently H or C$_{1-10}$alkyl, wherein the C$_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —C$_{1-10}$alkyl, —CF$_3$, —O-aryl, —OCF$_3$, OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$C$_{1-10}$alkyl, —S(O)$_{0-2}$C$_{1-10}$alkylaryl, —S(O)$_{0-2}$ aryl, —SO$_2$N(aryl), —SO$_2$N(C$_{1-10}$alkyl)(C$_{1-10}$alkyl), —SO$_2$NH(C$_{1-10}$alkyl) or SO$_2$NR$^{34}$R$^{35}$;

R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, hetaryl, C$_{1-6}$alkyl, or O-aryl, and wherein said 3-10 membered saturated or unsaturated ring independently contains 0, 1, or 2 more heteroatoms in addition to the nitrogen atom;

each of R$^7$ and R$^8$ is independently hydrogen, C$_{1-10}$alkyl, C$_{2-10}$alkenyl, aryl, heteroaryl, heterocyclyl or C$_{3-10}$cycloalkyl, each of which except for hydrogen is unsubstituted or is substituted by one or more independent R$^6$;

R$^6$ is halo, —OR$^{31}$, —SH, —NH$_2$, —NR$^{34}$R$^{35}$, —NR$^{31}$R$^{32}$, —CO$_2$R$^{31}$, —CO$_2$aryl, —C(=O)NR$^{31}$R$^{32}$, —C(=O)NR$^{34}$R$^{35}$, —NO$_2$, —CN, —S(O)$_{0-2}$C$_{1-10}$alkyl, —S(O)$_{0-2}$aryl, —SO$_2$NR$^{34}$R$^{35}$, —SO$_2$NR$^{31}$R$^{32}$, C$_{1-10}$alkyl, C$_{2-10}$alkenyl, C$_{2-10}$alkynyl; aryl-C$_{1-10}$alkyl, aryl-C$_{2-10}$alkenyl, aryl-C$_{2-10}$alkynyl, hetaryl-C$_{1-10}$alkyl, hetaryl-C$_{2-10}$alkenyl, hetaryl-C$_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —OC$_{1-10}$alkyl, C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$; and R$^9$ is H, halo, —OR$^{31}$, —SH, —NH$_2$, —NR$^{34}$R$^{35}$, —NR$^{31}$R$^{32}$, —CO$_2$R$^{31}$, —CO$_2$aryl, —C(=O)NR$^{31}$R$^{32}$, —C(=O)NR$^{34}$R$^{35}$, —NO$_2$, —CN, —S(O)$_{0-2}$C$_{1-10}$alkyl, —S(O)$_{0-2}$aryl, —SO$_2$NR$^{34}$R$^{35}$, —SO$_2$NR$^{31}$R$^{32}$, C$_{1-10}$alkyl, C$_{2-10}$alkenyl, C$_{2-10}$alkynyl; aryl-C$_{1-10}$alkyl, aryl-C$_{2-10}$alkenyl, aryl-C$_{2-10}$alkynyl, hetaryl-C$_{1-10}$alkyl, hetaryl-C$_{2-10}$alkenyl, hetaryl-C$_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —OC$_{1-10}$alkyl, C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$.

In another aspect, the invention provides a compound of Formula IV-A or Formula IV-B:

Formula IV-A

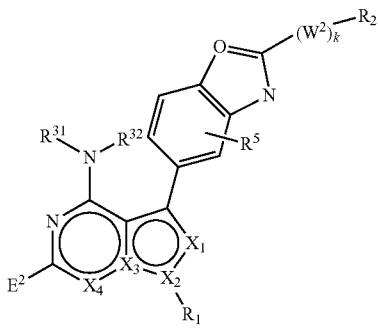

Formula IV-B

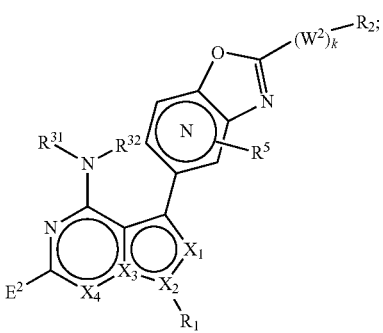

or pharmaceutically acceptable salt thereof, wherein:

$X_1$ is N or C-$E^1$, $X_2$ is N, $X_3$ is C, and $X_4$ is C$R^9$ or N; or $X_1$ is N or C-$E^1$, $X_2$ is C, $X_3$ is N, and $X_4$ is C$R^9$ or N;

$R_1$ is —H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;

k is 0 or 1;

$E^1$ and $E^2$ are independently —(W$^1$)$_j$—$R^4$;

j in $E^1$ or j in $E^2$, is independently 0 or 1;

$W^1$ is —O—, —N$R^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$W^2$ is —O—, —N$R^7$—, —S(O)$_{0-2}$—, —C(O)—, —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R^3$ and $R^4$ are independently hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_2R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{34}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, —SC(=O)N$R^{31}R^{32}$, aryl, hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocylcyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetarylC$_{2-10}$alkynyl, hetaryl $C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_2R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{34}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, or —SC(=O)N$R^{31}R^{32}$, and wherein each of said alkyl, cycloalkyl, heterocyclyl, or heteroalkyl moiety is unsubstituted or is substituted with one or more halo, —OH, —$R^{31}$, —CF$_3$, —OCF$_3$, —O$R^{31}$, —O-aryl, —N$R^{31}R^{32}$, —N$R^{34}R^{35}$, —C(O)$R^{31}$, —CO$_2R^{31}$, —C(=O)N$R^{34}R^{35}$, or —C(=O)N$R^{31}R^{32}$;

$R^2$ is hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_2R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, —SC(=O)N$R^{31}R^{32}$, aryl (e.g. bicyclic aryl, unsubstituted aryl, or substituted monocyclic aryl), hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocylcyl, $C_{2-10}$alkenyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —$CN$, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, $C(O)_2R^{31}$, —$CO_2R^{31}$, —$C(=O)NR^{34}R^{35}$, or —$C(=O)NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —$CN$, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$;

each of $R^{31}$, $R^{32}$, and $R^{33}$ is independently H or $C_{1-10}$alkyl, wherein the $C_{1-10}$alkyl is unsubstituted or is substituted with one or more aryl, heteroalkyl, heterocyclyl, or hetaryl group, wherein each of said alkyl, aryl, heteroalkyl, heterocyclyl, or hetaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl)($C_{1-10}$alkyl), —NH($C_{1-10}$alkyl), —NH(aryl), —$NR^{34}R^{35}$, —$C(O)(C_{1-10}$alkyl), —$C(O)(C_{1-10}$alkyl-aryl), —$C(O)(aryl)$, —$CO_2$—$C_{1-10}$alkyl, —$CO_2$—$C_{1-10}$alkylaryl, —$CO_2$-aryl, —$C(=O)N(C_{1-10}$alkyl)($C_{1-10}$alkyl), —$C(=O)NH(C_{1-10}$alkyl), —$C(=O)NR^{34}R^{35}$, —$C(=O)NH_2$, —$OCF_3$, —$O(C_{1-10}$alkyl), —O-aryl, —N(aryl)($C_{1-10}$alkyl), —$NO_2$, —$CN$, —$S(O)_{0-2}C_{1-10}$alkyl, —$S(O)_{0-2}C_{1-10}$alkylaryl, —$S(O)_{0-2}$ aryl, —$SO_2N(aryl)$, —$SO_2N(C_{1-10}$alkyl)($C_{1-10}$alkyl), —$SO_2NH(C_{1-10}$alkyl) or —$SO_2NR^{34}R^{35}$;

$R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom;

each of $R^7$ and $R^8$ is independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, —$C(=O)NR^{34}R^{35}$, —$NO_2$, —$CN$, —$S(O)_{0-2}C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, —$C(=O)NR^{34}R^{35}$, —$NO_2$, —$CN$, —$S(O)_{0-2}C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$.

In one embodiment of the compounds of the invention, $X_4$ is $CR^9$. In another embodiment, $X_4$ is N.

In some embodiments of the compounds of the invention, $E^2$ is —H. In some embodiments of the compounds of the invention, $X_1$ is N and $X_2$ is N. In other embodiments of the compounds of the invention, $X_1$ is C-$E^1$ and $X_2$ is N. In one embodiment of the compounds of the invention, $X_1$ is NH and $X_2$ is C.

In some embodiments of the compounds of the invention, $R_{31}$ and $R_{32}$ are —H.

In some embodiments of the compounds of Formula I'-A', I-A, I-B, III (including III-A and III-B), C, or C", $M_1$ is a benzoxazolyl moiety, substituted at the 2-position with —$(W_2)_k$—$R_2$. In some embodiments, $M_1$ is either a 5-benzoxazolyl or a 6-benzoxazolyl moiety, optionally substituted with —$(W_2)_k$—$R_2$. In some embodiments, $M_1$ is either a 5-benzoxazolyl or a 6-benzoxazolyl moiety, optionally substituted at its 2-position with —$(W_2)_k$—$R_2$.

In some embodiments of the compounds of the invention, $M_1$ is a moiety having one of the following structures:

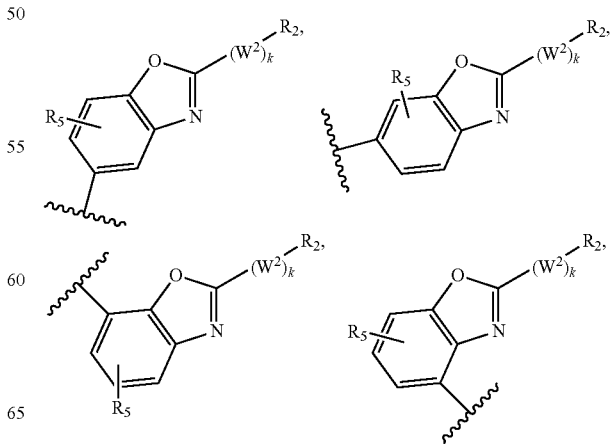

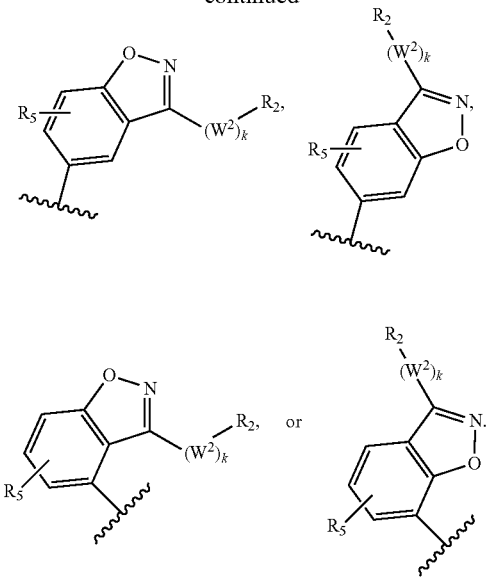

In some embodiments of the compounds of the invention, —(W$^2$)$_k$— is —NR$^7$—, —N(R$^7$)C(O)—, —N(R$^7$)C(O)N(R$^8$)—, or —N(R$^7$)S(O)$_2$—. In other embodiments of the compounds of the invention, —(W$^2$)$_k$— is —NH—. In another embodiment of the compounds of the invention, —(W$^2$)$_k$— is —(CH)$_2$—. In yet another embodiment of the compounds of the invention, —(W$^2$)$_k$— is —NHC(O)—. In yet another embodiment of the compounds of the invention, —(W$^2$)$_k$— is —N(R$^7$)C(O)N(R$^8$)—. In a further embodiment of the compounds of the invention, —(W$^2$)$_k$— is —NHS(O)$_2$—.

In some embodiments of the compounds of the invention, R$_1$ is -L-C$_{1-10}$alkyl, -L-C$_{3-8}$cycloalkyl, -L-C$_{1-10}$alkylheterocylyl, or -L-heterocyclyl, each of which is unsubstituted or is substituted by one or more independent R$^3$, wherein R$^3$ is hydrogen, —OH, —OR$^{31}$, C(O)R$^{31}$, C(=O)NR$^{31}$R$^{32}$, —C(=O)NR$^{34}$R$^{35}$, aryl, hetaryl, C$_{1-10}$alkyl, C$_{3-8}$cycloalkyl, or heterocyclyl, wherein each of said aryl, heteroaryl, alkyl, cycloalkyl, or heterocyclyl moiety is unsubstituted or is substituted with one or more alkyl or OH. In some embodiments of the compounds of the invention, R$_1$ is unsubstituted or is substituted with C$_{1-10}$alkyl or cycloC$_{3-10}$alkyl.

In some embodiments of the compounds of the invention, R$^2$ is H. In other embodiments of the compounds of the invention, R$^2$ is alkyl. In yet other embodiments of the compounds of the invention, R$^2$ is methyl. In other embodiments of the compounds of the invention, R$^2$ is isopropyl. In some embodiments of the compounds of the invention, R$^2$ is cycloalkyl. In other embodiments of the compounds of the invention, R$^2$ is cyclopropyl.

In some embodiments of the compounds of the invention, E$^2$ is H; X$_1$ and X$_2$ are N; R$_1$ is -L-C$_{1-10}$alkyl, -L-C$_{3-8}$cycloalkyl, -L-C$_{1-10}$alkylheterocylyl, or -L-heterocyclyl, each of which is unsubstituted or is substituted by one or more independent R$^3$; R$^3$ is hydrogen, —OH, —OR$^{31}$, —NR$^{31}$R$^{32}$, —C(O)R$^{31}$, —C(=O)NR$^{31}$R$^{32}$, —C(=O)NR$^{34}$R$^{35}$, aryl, hetaryl, C$_{1-4}$alkyl, C$_{1-10}$alkyl, C$_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_2$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, SC(=O)OR$^{31}$, —P(O)OR$^{31}$OR$^{32}$, or SC(=O)NR$^{31}$R$^{32}$ s, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$; and wherein —(W$^2$)$_k$— is —NR$^7$—, —N(R$^7$)C(O)— or —N(R$^7$)S(O)$_2$—.

The invention also provides a process for synthesizing a compound of Formula C:

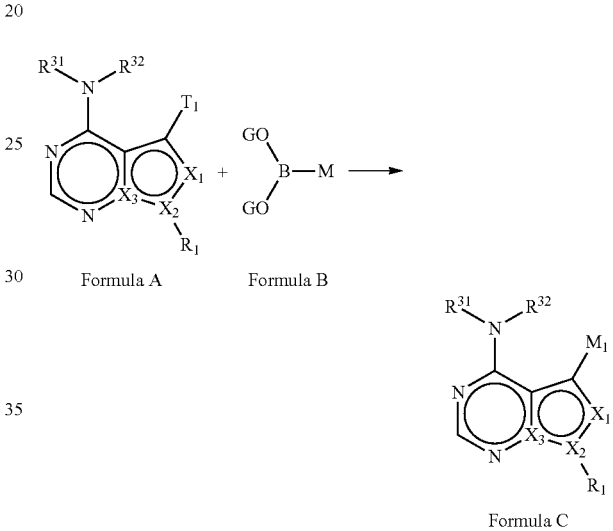

comprising the step of allowing a compound of Formula A to react with a compound of Formula B under conditions that are effective for synthesizing a compound of Formula C; wherein:

T$_1$ is halo;

X$_1$ is N or C-E$^1$, X$_2$ is N, and X$_3$ is C; or X$_1$ is N or C-E$^1$, X$_2$ is C, and X$_3$ is N; wherein no more than two ring nitrogen atoms of the compound of Formula A are adjacent; and wherein no more than two ring nitrogen atoms of the compound of Formula C are adjacent;

R$_1$ is hydrogen, -L-C$_{10-10}$alkyl, -L-C$_{3-8}$cycloalkyl, -L-C$_{1-10}$alkyl-C$_{3-8}$cycloalkyl, -L-aryl, -L-heteroaryl, -L-C$_{1-10}$alkylaryl, -L-C$_{1-10}$alkylhetaryl, -L-C$_{1-10}$alkylheterocylyl, -L-C$_{2-10}$alkenyl, -L-C$_{2-10}$alkynyl, -L-C$_{2-10}$alkenyl-C$_{3-8}$cycloalkyl, -L-C$_{2-10}$alkynyl-C$_{3-8}$cycloalkyl, -L-heteroalkyl, -L-heteroalkylaryl, -L-heteroalkylheteroaryl, -L-heteroalkyl-heterocylyl, -L-heteroalkyl-C$_{3-8}$cycloalkyl, -L-aralkyl, -L-heteroaralkyl, or -L-heterocyclyl, each of which is unsubstituted or is substituted by one or more independent R$^3$;

L is absent, —(C=O)—, —C(=O)O—, —C(=O)N(R$^{31}$)—, —S—, —S(O)—, —S(O)$_2$—, —S(O)$_2$N(R$^{31}$)—, or —N(R$^{31}$)—; each of G is independently H or R$_{G1}$; and R$_{G1}$ is alkyl, alkenyl, or aryl;

or the G groups of

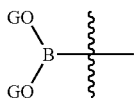

join together to form a 5- or 6-membered cyclic moiety;

M of Formula B is a $M_1$ moiety, and wherein $M_1$ moiety of Formula B and $M_1$ moiety of Formula C are identical, having one of the following structures:

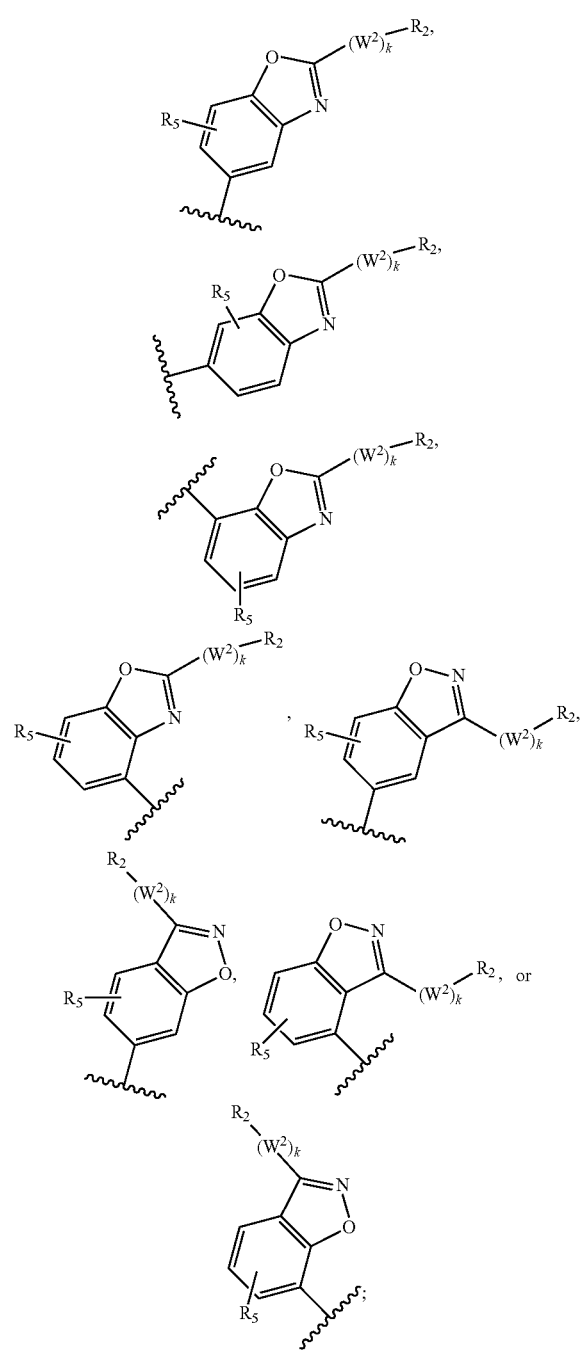

$W^1$ is —O—, —$NR^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$), CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

k is 0 or 1;

$W^2$ is —O—, —$NR^7$—, —S(O)$_{0-2}$—, —C(O)—, C(O)N($R^7$)—, —N($R^7$)C(O)—, —N($R^7$)C(O)N($R^8$)—, N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R^2$ is hydrogen, halogen, —OH, —$R^{31}$, —CF$_3$, —OCF$_3$, —O$R^{31}$, —$NR^{31}R^{32}$, —$NR^{34}R^{35}$, —C(O)$R^{31}$, —CO$_2R^{31}$, —C(=O)$NR^{31}R^{32}$, —C(=O)$NR^{34}R^{35}$, —NO$_2$, —CN, —S(O)$_{0-2}R^{31}$, —SO$_2NR^{31}R^{32}$, —SO$_2NR^{34}R^{35}$, —$NR^{31}$C(=O)$R^{32}$, —$NR^{31}$C(=O)O$R^{32}$, —$NR^{31}$C(=O)$NR^{32}R^{33}$, —$NR^{31}$S(O)$_{0-2}R^{32}$, —C(=S)O$R^{31}$, —C(=O)S$R^{31}$, —$NR^{31}$C(=$NR^{32}$)$NR^{33}R^{32}$, —$NR^{31}$C(=$NR^{32}$)O$R^{33}$, —$NR^{31}$C(=$NR^{32}$)S$R^{33}$, —OC(=O)O$R^{33}$, —OC(=O)$NR^{31}R^{32}$, —OC(=O)S$R^{31}$, SC(=O)O$R^{31}$, —P(O)O$R^{31}$O$R^{32}$, —SC(=O)$NR^{31}R^{32}$ bicyclic aryl, substituted monocyclic aryl, hetaryl, $C_{1-10}$alkyl, $C_{3-8}$cycloalkyl, $C_{1-10}$alkyl $C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{2-10}$alkyl-monocyclic aryl, monocyclic aryl-$C_{2-10}$alkyl, $C_{1-10}$alkylbicycloaryl, bicycloaryl-$C_{1-10}$alkyl, substituted $C_{1-10}$alkylaryl, substituted aryl-$C_{1-10}$alkyl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy$C_{2-10}$alkenyl, $C_{1-10}$alkoxy$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl $C_{2-10}$alkenyl, aryl-$C_{2-10}$alkynyl, aryl-heterocyclyl, or hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —$R^{31}$, —CF$_3$, —OCF$_3$, —O$R^{31}$, —$NR^{31}R^{32}$, —$NR^{34}R^{35}$, —C(O)$R^{31}$, —CO$_2R^{31}$, —C(=O)$NR^{31}R^{32}$, —C(=O)$NR^{34}R^{35}$, —NO$_2$, —CN, —S(O)$_2R^{31}$, —SO$_2NR^{31}R^{32}$, —SO$_2NR^{34}R^{35}$, —$NR^{31}$C(=O)$R^{32}$, —$NR^{31}$C(=O)O$R^{32}$, —$NR^{31}$C(=O)$NR^{32}R^{33}$, —$NR^{31}$S(O)$_{0-2}R^{32}$, —C(=S)O$R^{31}$, —C(=O)S$R^{31}$, —$NR^{31}$C(=$NR^{32}$)$NR^{33}R^{32}$, —$NR^{31}$C(=$NR^{32}$)O$R^{33}$, —$NR^{31}$C(=$NR^{32}$)S$R^{33}$, —OC(=O)O$R^{33}$, —OC(=O)$NR^{31}R^{32}$, —OC(=O)S$R^{31}$, —SC(=O)$R^{31}$, —P(O)O$R^{31}$O$R^3$, or —SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —CF$_3$, —OCF$_3$, —O$R^{31}$, —O-aryl, —$NR^{31}R^{32}$, —$NR^{34}R^{35}$, —C(O)$R^{31}$, —CO$_2R^{31}$, —C(=O)$NR^{34}R^{35}$, or —C(=O)$NR^{31}R^{32}$;

$R^3$ and $R^4$ are independently hydrogen, halogen, —OH, —$R^{31}$, —CF$_3$, —OCF$_3$, —O$R^{31}$, —$NR^{31}R^{32}$, —$NR^{34}R^{35}$, —C(O)$R^{31}$, —CO$_2R^{31}$, —C(=O)$NR^{31}R^{32}$, —C(=O)$NR^{34}R^{35}$, —NO$_2$, —CN, —S(O)$_{0-2}R^{31}$, —SO$_2NR^{31}R^{32}$, —SO$_2NR^{34}R^{35}$, —$NR^{31}$C(=O)$R^{32}$, —$NR^{31}$C(=O)O$R^{32}$, —$NR^{31}$C(=O)$NR^{32}R^{33}$, —$NR^{31}$S(O)$_2R^{32}$, —C(=S)O$R^{31}$, —C(=O)S$R^{31}$, —$NR^{31}$C(=$NR^{32}$)$NR^{33}R^{32}$, —$NR^{31}$C(=$NR^{32}$)O$R^{33}$, —$NR^{31}$C(=$NR^{32}$)S$R^{33}$, —OC(=O)O$R^{33}$, —OC(=O)NR³¹R³², —OC(=O)SR³¹, SC(=O)OR³¹, —P(O)OR³¹OR³², —SC(=O)NR³¹R³², aryl, hetaryl, C₁₋₁₀alkyl, C₃₋₈cycloalkyl, C₁₋₁₀alkylC₃₋₈cycloalkyl, C₃₋₈cycloalkyl-C₁₋₁₀alkyl, C₃₋₈cycloalkyl-C₂₋₁₀alkenyl, C₃₋₈cycloalkyl-C₂₋₁₀alkynyl, C₁₋₁₀alkyl-C₂₋₁₀alkenyl, C₁₋₁₀alkyl-C₂₋₁₀alkynyl, C₁₋₁₀alkylaryl, C₁₋₁₀alkylhetaryl, C₁₋₁₀alkylheterocyclyl, C₂₋₁₀alkenyl, C₂₋₁₀alkynyl, C₂₋₁₀alkenyl-C₁₋₁₀alkyl, C₂₋₁₀alkynyl-C₁₋₁₀alkyl, C₂₋₁₀alkenylaryl, C₂₋₁₀alkenylhetaryl, C₂₋₁₀alkenylheteroalkyl, C₂₋₁₀alkenyl-heterocyclyl, C₂₋₁₀alkenyl-C₃₋₈cycloalkyl, C₂₋₁₀alkynyl-C₃₋₈cycloalkyl, C₂₋₁₀alkynylaryl, C₂₋₁₀alkynylhetaryl, C₂₋₁₀alkynylheteroalkyl, C₂₋₁₀alkynylheterocyclyl, C₂₋₁₀alkynyl-C₃₋₈cycloalkenyl, C₁₋₁₀alkoxy C₁₋₁₀alkyl, C₁₋₁₀alkoxy-C₂₋₁₀alkenyl, C₁₋₁₀alkoxy-C₂₋₁₀alkynyl, heterocyclyl, heterocyclyl-C₁₋₁₀alkyl, heterocyclyl-C₂₋₁₀alkenyl, heterocyclyl-C₂₋₁₀alkynyl, aryl-C₁₋₁₀alkyl, aryl-C₂₋₁₀alkenyl, aryl-C₂₋₁₀alkynyl, aryl-heterocyclyl, hetaryl-C₁₋₁₀alkyl, hetaryl-C₂₋₁₀alkenyl, hetaryl-C₂₋₁₀alkynyl, hetaryl-C₃₋₈cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —R³¹, —CF₃, —OCF₃, —OR³¹, —NR³¹R³², —NR³⁴R³⁵, —C(O)R³¹, —CO₂R³¹, —C(=O)NR³¹R³², —C(=O)NR³⁴R³⁵, —NO₂, —CN, —S(O)₀₋₂R³¹, —SO₂NR³¹R³², —SO₂NR³⁴R³⁵, —NR³¹C(=O)R³², —NR³¹C(=O)OR³², —NR³¹C(=O)NR³²R³³, —NR³¹S(O)₀₋₂R³², —C(=S)OR³¹, —C(=O)SR³¹, —NR³¹C(=NR³²)NR³³R³², —NR³¹C(=NR³²)OR³³, —NR³¹C(=NR³²)SR³³, —OC(=O)OR³³, —OC(=O)NR³¹R³², —OC(=O)SR³¹, —SC(=O)OR³¹, —P(O)OR³¹OR³², or —SC(=O)NR³¹R³², and wherein each of said alkyl, cycloalkyl, heterocyclyl, or heteroalkyl moiety is unsubstituted or is substituted with one or more halo, —OH, —R³¹, —CF₃, —OCF₃, —OR³¹, —O-aryl, —NR³¹R³², —NR³⁴R³⁵, —C(O)R³¹, —CO₂R³¹, —C(=O)NR³⁴R³⁵, or —C(=O)NR³¹R³²;

$R^5$ is hydrogen;

each of $R^{31}$, $R^{32}$, and $R^{33}$ is independently H or $C_{1-10}$alkyl, wherein the $C_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —C₁₋₁₀alkyl, —CF₃, —O-aryl, —OCF₃, —OC₁₋₁₀alkyl, —NH₂, —N(C₁₋₁₀alkyl)(C₁₋₁₀alkyl), —NH(C₁₋₁₀alkyl), —NH(aryl), —NR³⁴R³⁵, —C(O)(C₁₋₁₀alkyl), —C(O)(C₁₋₁₀alkyl-aryl), —C(O)(aryl), —CO₂—C₁₋₁₀alkyl, —CO₂—C₁₋₁₀alkylaryl, —CO₂-aryl, —C(=O)N(C₁₋₁₀alkyl)(C₁₋₁₀alkyl), —C(=O)NH(C₁₋₁₀alkyl), —C(=O)NR³⁴R³⁵, —C(=O)NH₂, —OCF₃, —O(C₁₋₁₀alkyl), —O-aryl, —N(aryl)(C₁₋₁₀alkyl), —NO₂, —CN, —S(O)₀₋₂C₁₋₁₀alkyl, —S(O)₀₋₂C₁₋₁₀alkylaryl, —S(O)₀₋₂ aryl, —SO₂N(aryl), —SO₂N(C₁₋₁₀alkyl)(C₁₋₁₀alkyl), —SO₂NH(C₁₋₁₀alkyl) or —SO₂NR³⁴R³⁵;

$R^{34}$ and $R^{35}$ in —NR³⁴R³⁵, —C(=O)NR³⁴R³⁵, or —SO₂NR³⁴R³⁵, are taken together with the nitrogen atom to which they are attached to form a 3-10 membered saturated or unsaturated ring; wherein said ring is independently unsubstituted or is substituted by one or more —NR³¹R³², hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom; each of $R^7$ and $R^8$ is independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$; and $R^6$ is halo, —OR³¹, —SH, —NH₂, —NR³⁴R³⁵, —NR³¹R³², —CO₂R³¹, —CO₂aryl, —C(=O)NR³¹R³², —C(=O)NR³⁴R³⁵, —NO₂, —CN, —S(O)₀₋₂C₁₋₁₀alkyl, —S(O)₀₋₂aryl, —SO₂NR³⁴R³⁵, —SO₂NR³¹R³², C₁₋₁₀alkyl, C₂₋₁₀alkenyl, C₂₋₁₀alkynyl, aryl-C₁₋₁₀alkyl, aryl-C₂₋₁₀alkenyl, aryl-C₂₋₁₀alkynyl, hetaryl-C₁₋₁₀alkyl, hetaryl-C₂₋₁₀alkenyl, or hetaryl-C₂₋₁₀alkynyl, each of which is unsubstituted or is substituted with one or more independent halo, cyano, nitro, —OC₁₋₁₀alkyl, C₁₋₁₀alkyl, C₂₋₁₀alkenyl, C₂₋₁₀alkynyl, haloC₂₋₁₀alkyl, haloC₂₋₁₀alkenyl, haloC₂₋₁₀alkynyl, —COOH, —C(=O)NR³¹R³², —C(=O)NR³⁴R³⁵, —SO₂NR³⁴R³⁵, —SO₂NR³¹R³², —NR³¹R³², or —NR³⁴R³⁵; and $M_1$ of Formula B and $M_1$ of Formula C are the same; $R_1$ of Formula A and $R_1$ of Formula C are the same; $R_{31}$ of Formula A and $R_{31}$ of Formula C are the same; $R_{32}$ of Formula A and $R_{32}$ of Formula C are the same; $X_1$ of Formula A and $X_1$ of Formula C are the same; $X_2$ of Formula A and $X_2$ of Formula C are the same; and $X_3$ of Formula A and $X_3$ of Formula C are the same.

In some embodiments of the process for synthesizing a compound of Formula C, $T_1$ is iodo or bromo.

In other embodiments of the process for synthesizing a compound of Formula C, the compound of Formula B is a compound having one of the following formulae:

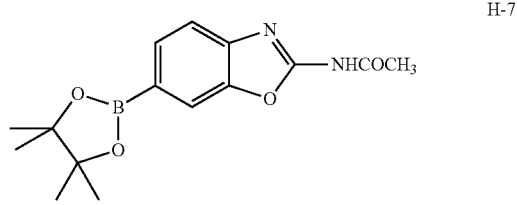

H-7

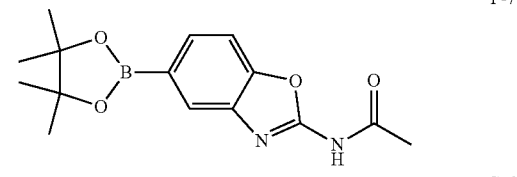

F-7

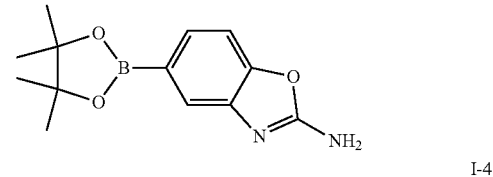

G-6

I-4

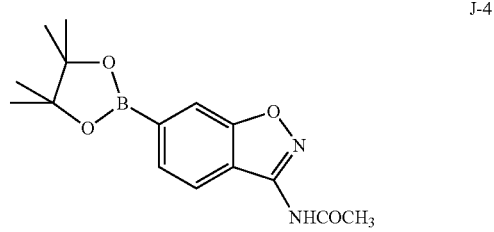

J-4

-continued

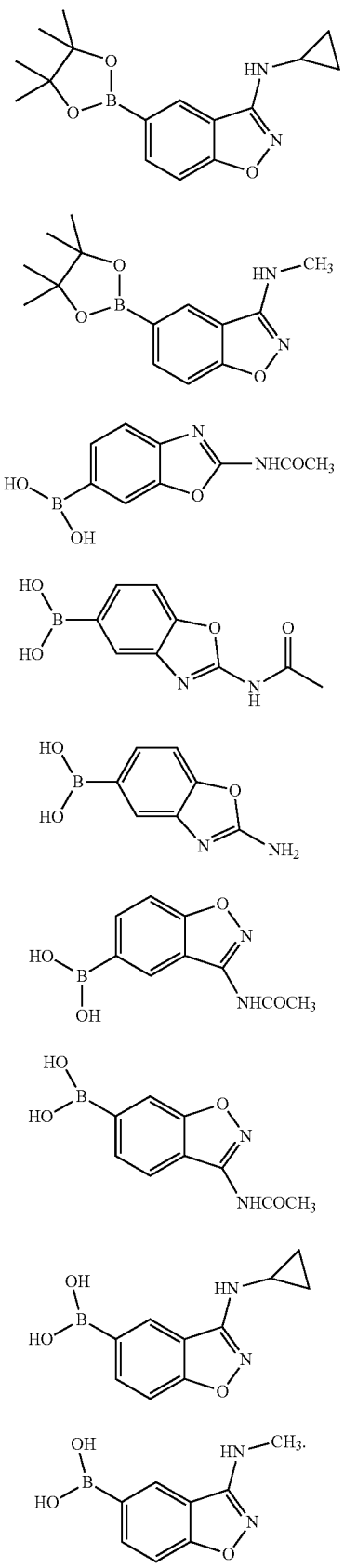

In some embodiments of the process for synthesizing a compound of Formula C, each of the compound of Formula B and the compound of Formula C is the compound wherein:

$X_1$ and $X_2$ are N;

$R_1$ is -L-$C_{1-10}$alkyl, -L-$C_{3-8}$cycloalkyl, -L-$C_{3-10}$alkylheterocylyl, or -L-heterocyclyl, each of which is unsubstituted or is substituted by one or more independent $R^3$ substituents;

$R^3$ is hydrogen, —OH, —$OR^{31}$, —$NR^{31}R^{32}$, —$C(O)R^{31}$, —$C(=O)NR^{31}R^{32}$, —$C(=O)NR^{34}R^{35}$, aryl, hetaryl, $C_{1-10}$alkyl, $C_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, $SC(=O)OR^{31}$, —$P(O)OR^{31}OR^{32}$, or —$SC(=O)NR^{31}R^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$; and wherein —$(W^2)_k$— is —$NR^7$—, —$N(R^7)C(O)$— or —$N(R^7)S(O)_2$—.

In some embodiments, the compound of Formula A reacts with the compound of Formula B in the presence of palladium tetrakis(triphenylphosphine). In some embodiments, when the compound of Formula A reacts with the compound of Formula B in the presence of palladium tetrakis(triphenylphosphine), the palladium tetrakis(triphenylphosphine) is present in an amount from about 0.07 molar equivalents to about 0.15 molar equivalents of the compound of Formula A.

In another aspect, the invention provides a composition comprising a compound of Formula A and a compound of Formula B:

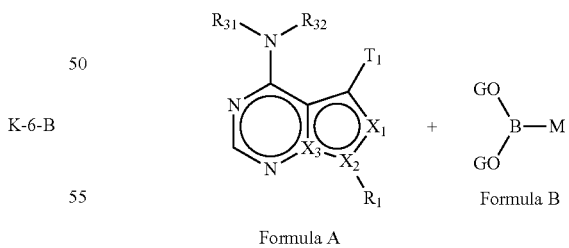

Formula A   Formula B or a salt thereof, wherein: T is halo; $X_1$ is N or C-$E^1$, $X_2$ is N, and $X_3$ is C; or $X_1$ is N or C-$E^1$, $X_2$ is C, and $X_3$ is N; wherein no more than two ring nitrogen atoms of the compound of Formula A are adjacent; and wherein no more than two ring nitrogen atoms of the compound of Formula C are adjacent;

each of G is independently H or $R_{G1}$; and $R_{G1}$ is alkyl, alkenyl, or aryl;

or the G groups of

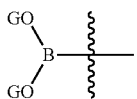

join together to form a 5- or 6-membered cyclic moiety;

M of Formula B is a $M_1$ moiety, and wherein $M_1$ of Formula B has one of the following structures:

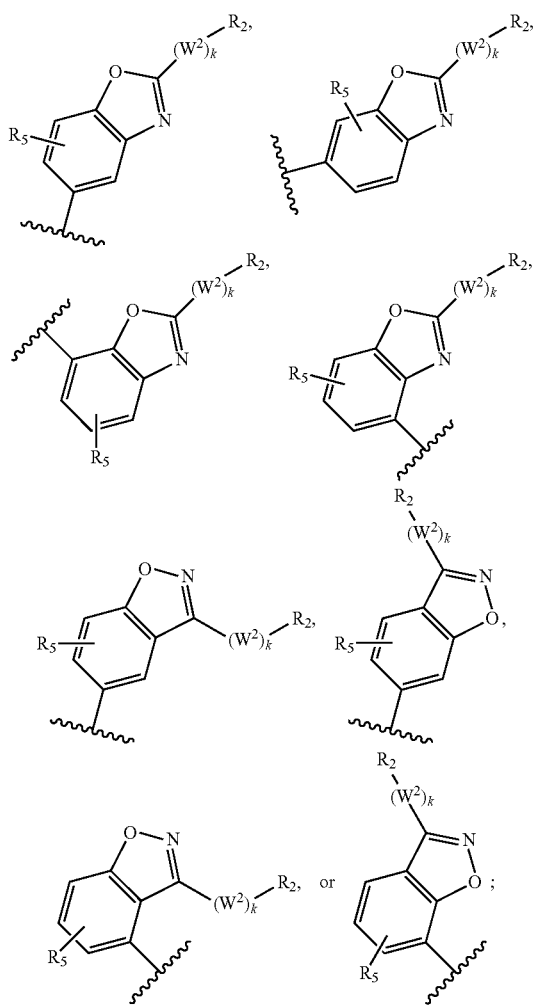

$E^1$ is —$(W^1)_j$—$R^4$ wherein j is 0 or 1;

$W^1$ is —O—, —$NR^7$—, —$S(O)_{0-2}$—, —C(O)—, —C(O)N($R^7$)—, —N($R^7$)C(O)—, —N($R^7$)S(O), —N($R^7$)S(O)$_2$, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

k is 0 or 1;

$W^2$ is —O—, —$NR^7$—, S(O)$_{0-2}$—, —C(O)—, —C(O)N($R^7$)—, —N($R^7$)C(O)—, —N($R^7$)C(O)N($R^8$)—, N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)C(O)—, —CH($R^7$)N($R^8$)S(O)—, or —CH($R^7$)N($R^8$)S(O)$_2$—;

$R_1$ is hydrogen, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_3$-cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C═O)—, —C(═O)O—, —C(═O)N($R^{31}$)—, —S—, —S(O)—, —S(O)$_2$—, —S(O)$_2$N($R^{31}$)—, or —N($R^{31}$)—;

$R^2$ is hydrogen, halogen, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(═O)$NR^{31}R^{32}$, —C(═O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(═O)$R^{32}$, —$NR^{31}$C(═O)O$R^{32}$, —$NR^{31}$C(═O)$NR^{32}R^{33}$, —$NR^{31}$S(O)$_2R^{32}$, —C(═S)O$R^{31}$, —C(═O)S$R^{31}$, —$NR^{31}$C(═$NR^{32}$)$NR^{33}R^{32'}$, $NR^{31}$C(═$NR^{32}$)O$R^{33}$, —$NR^{31}$C(═$NR^{32}$)S$R^{33}$, —OC(═O)O$R^{33}$, —OC(═O)$NR^{31}R^{32}$, —OC(═O)S$R^{31}$, —SC(═O)O$R^{31}$, —P(O)O$R^{31}$O$R^{32}$, —SC(═O)$NR^{31}R^{32}$, bicyclic aryl, substituted monocyclic aryl, hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{2-10}$alkyl-monocyclic aryl, monocyclic aryl-$C_{2-10}$alkyl, $C_{1-10}$alkylbicycloaryl, bicycloaryl-$C_{1-10}$alkyl, substituted $C_{1-10}$alkylaryl, substituted aryl-$C_{1-10}$alkyl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy$C_{2-10}$alkenyl, $C_{1-10}$alkoxy$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{2-10}$alkenyl, aryl-$C_{2-10}$alkynyl, aryl-heterocyclyl, or hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —$R^{31}$, —$CF_3$, —$OCF_3$, —O$R^{31}$, —$NR^{31}R^{32}$, —$NR^{34}R^{35}$, —C(O)$R^{31}$, —$CO_2R^{31}$, —C(═O)$NR^{31}R^{32}$, —C(═O)$NR^{34}R^{35}$, —$NO_2$, —CN, —S(O)$_2R^{31}$, —$SO_2NR^{31}R^{32}$, —$SO_2NR^{34}R^{35}$, —$NR^{31}$C(═O)$R^{32}$, —$NR^{31}$C(═O)O$R^{32}$, —$NR^{31}$C(═O)$NR^{32}R^{33}$, —$NR^{31}$S(O)$_2R^{32}$, —C(═S)O$R^{31}$, —C(═O)S$R^{31}$, —$NR^{31}$C(═$NR^{32}$)$NR^{33}R^{32}$, —$NR^{31}$C(═$NR^{32}$)O$R^{33}$, —$NR^{31}$C(═$NR^{32}$)S$R^{33}$, —OC(═O)O$R^{33}$, —OC(═O)$NR^{31}R^{32}$, —OC(═O)S$R^{31}$, —SC(═O)O$R^{31}$, —P(O)O$R^{31}$O$R^{32}$, or —SC(═O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —O$R^{31}$, —O-aryl, —$NR^{31}R^{32}$, —$NR^{34}R^{35}$, —C(O)$R^{31}$, —$CO_2R^{31}$, —C(═O)$NR^{34}R^{35}$, or —C(═O)$NR^{31}R^{32}$;

$R^3$ and $R^4$ are independently hydrogen, halogen, —OH, —$R^{31}$, —$CF_3$, —$OCF_3$, —O$R^{31}$, —$NR^{31}R^{32}$, —$NR^{34}R^{35}$, —C(O)$R^{31}$, —$CO_2R^{31}$, —C(═O)$NR^{31}R^{32}$, —C(═O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(═O)$R^{32}$, —$NR^{31}$C(═O)O$R^{32}$, —$NR^{31}$C(═O)$NR^{32}R^{33}$, —$NR^{31}$S(O)$_{0-2}R^{32}$, —C(═S)O$R^{31}$, —C(═O)S$R^{31}$, —$NR^{31}$C(═$NR^{32}$)$NR^{33}R^{32}$, —$NR^{31}$C(═$NR^{32}$)O$R^{33}$, —$NR^{31}$C(═$NR^{32}$)S$R^{33}$, —OC(═O)O$R^{33}$, —OC(═O)$NR^{31}R^{32}$, —OC(═O)S$R^{31}$, —SC $-C(=O)OR^{31}$, $-P(O)OR^{31}OR^{32}$, $-SC(=O)NR^{31}R^{32}$, aryl, hetaryl, $C_{1-10}$alkyl, $C_{3-8}$cycloalkyl, $C_{1-10}$alkyl$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, $-OH$, $-R^{31}$, $-CF_3$, $-OCF_3$, $-OR^{31}$, $-NR^{31}R^{32}$, $-NR^{34}R^{35}$, $-C(O)R^{31}$, $-CO_2R^{31}$, $-C(=O)NR^{31}R^{32}$, $-C(=O)NR^{34}R^{35}$, $-NO_2$, $-CN$, $-S(O)_{0-2}R^{31}$, $-SO_2NR^{31}R^{32}$, $-SO_2NR^{34}R^{35}$, $-NR^{31}C(=O)R^{32}$, $-NR^{31}C(=O)OR^{32}$, $-NR^{31}C(=O)NR^{32}R^{33}$, $-NR^{31}S(O)_{0-2}R^{32}$, $-C(=S)OR^{31}$, $-C(=O)SR^{31}$, $-NR^{31}C(=NR^{32})NR^{33}R^{32}$, $-NR^{31}C(=NR^{32})OR^{33}$, $-NR^{31}C(=NR^{32})SR^{33}$, $-OC(=O)OR^{33}$, $-OC(=O)NR^{31}R^{32}$, $-OC(=O)SR^{31}$, $-SC(=O)OR^{31}$, $-P(O)OR^{31}OR^{32}$, or $-SC(=O)NR^{31}R^{32}$, and wherein each of said alkyl, cycloalkyl, heterocyclyl, or heteroalkyl moiety is unsubstituted or is substituted with one or more halo, $-OH$, $-R^{31}$, $-CF_3$, $-OCF_3$, $-OR^{31}$, $-O$-aryl, $-NR^{31}R^{32}$, $-NR^{34}R^{35}$, $-C(O)R^{31}$, $-CO_2R^{31}$, $-C(=O)NR^{34}R^{35}$, or $-C(=O)NR^{31}R^{32}$;

$R^5$ is hydrogen;

each of $R^7$ and $R^8$ is independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, $-OR^{31}$, $-SH$, $-NH_2$, $-NR^{34}R^{35}$, $-NR^{31}R^{32}$, $-CO_2R^{31}$, $-CO_2$aryl, $-C(=O)NR^{31}R^{32}$, $-C(=O)NR^{34}R^{35}$, $-NO_2$, $-CN$, $-S(O)_{0-2}C_{1-10}$alkyl, $-S(O)_{0-2}$aryl, $-SO_2NR^{34}R^{35}$, $-SO_2NR^{31}R^{32}$, $C_{1-10}$alkyl, $C_{2-10}$alkenyl, $C_{2-10}$alkynyl, aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, or hetaryl-$C_{2-10}$alkynyl, each of which is unsubstituted or is substituted with one or more independent halo, cyano, nitro, $-OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $-C(=O)NR^{31}R^{32}$, $-C(=O)NR^{34}R^{35}$, $-SO_2NR^{34}R^{35}$, $-SO_2NR^{31}R^{32}$, $-NR^{31}R^{32}$, or $-NR^{34}R^{35}$;

each of $R^{31}$, $R^{32}$, and $R^{33}$ is independently H or $C_{1-10}$alkyl, wherein the $C_{1-10}$alkyl is unsubstituted or is substituted with one or more aryl, heteroalkyl, heterocyclyl, or hetaryl group, wherein each of said alkyl, aryl, heteroalkyl, heterocyclyl, or hetaryl group is unsubstituted or is substituted with one or more halo, $-OH$, $-C_{1-10}$alkyl, $-CF_3$, $-O$-aryl, $-OCF_3$, $-OC_{1-10}$alkyl, $-NH_2$, $-N(C_{1-10}$alkyl$)(C_{1-10}$alkyl$)$, $-NH(C_{1-10}$alkyl$)$, $-NH$(aryl), $-NR^{34}R^{35}$, $-C(O)(C_{1-10}$alkyl$)$, $-C(O)(C_{1-10}$alkyl-aryl$)$, $-C(O)$(aryl), $-CO_2-C_{1-10}$alkyl, $-CO_2-C_{1-10}$alkylaryl, $-CO_2$-aryl, $-C(=O)N(C_{1-10}$alkyl$)(C_{1-10}$alkyl$)$, $-C(=O)NH(C_{1-10}$alkyl$)$, $-C(=O)NR^{34}R^{35}$, $-C(=O)NH_2$, $-OCF_3$, $-O(C_{1-10}$alkyl$)$, $-O$-aryl, $-N$(aryl)$(C_{1-10}$alkyl$)$, $-NO_2$, $-CN$, $-S(O)_{0-2}C_{1-10}$alkyl, $-S(O)_{0-2}C_{1-10}$alkylaryl, $-S(O)_2$ aryl, $-SO_2N$(aryl), $-SO_2N(C_{1-10}$alkyl$)(C_{1-10}$alkyl$)$, $-SO_2NH(C_{1-10}$alkyl$)$ or $-SO_2NR^{34}R^{35}$; and $R^{34}$ and $R^{35}$ in $-NR^{34}R^{35}$, $-C(=O)NR^{34}R^{35}$, or $-SO_2NR^{34}R^{35}$, are taken together with the nitrogen atom to which they are attached to form a 3-10 membered saturated or unsaturated ring; wherein said ring is independently unsubstituted or is substituted by one or more $-NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom.

In some embodiments of the compositions of the invention, each of the compound of Formula A and the compound of Formula B is the compound wherein:

$X_1$ and $X_2$ are N; $R_1$ is -L-$C_{1-10}$alkyl, -L-$C_{3-8}$cycloalkyl, -L-$C_{1-10}$alkylheterocyclyl, or -L-heterocyclyl, each of which is unsubstituted or is substituted by one or more independent $R^3$ substituents; $R^3$ is hydrogen, $-OH$, $-OR^{31}$, $-NR^{31}R^{32}$; $-C(O)R^{31}$, $-C(=O)NR^{31}R^{32}$, $-C(=O)NR^{34}R^{35}$, aryl, hetaryl, $C_{1-10}$alkyl, $C_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, $-OH$, $-R^{31}$, $-CF_3$, $-OCF_3$, $-OR^{31}$, $-NR^{31}R^{32}$, $-NR^{34}R^{35}$, $-C(O)R^{31}$, $-CO_2R^{31}$, $-C(=O)NR^{31}R^{32}$, $-C(=O)NR^{34}R^{35}$, $-NO_2$, $-CN$, $-S(O)_{0-2}R^{31}$, $-SO_2NR^{31}R^{32}$, $-SO_2NR^{34}R^{35}$, $-NR^{31}C(=O)R^{32}$, $-NR^{31}C(=O)OR^{32}$, $-NR^{31}C(=O)NR^{32}R^{33}$, $-NR^{31}S(O)_{0-2}R^{32}$, $-C(=S)OR^{31}$, $-C(=O)SR^{31}$, $-NR^{31}C(=NR^{32})NR^{33}R^{32}$, $-NR^{31}C(=NR^{32})OR^{33}$, $-NR^{31}C(=NR^{32})SR^{33}$, $-OC(=O)OR^{33}$, $-OC(=O)NR^{31}R^{32}$, $-OC(=O)SR^{31}$, $-SC(=O)OR^{31}$, $-P(O)OR^{31}OR^{32}$, or $-SC(=O)NR^{31}R^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, $-OH$, $-R^{31}$, $-CF_3$, $-OCF_3$, $-OR^{31}$, $-O$-aryl, $-NR^{31}R^{32}$, $-NR^{34}R^{35}$, $-C(O)R^{31}$, $-CO_2R^{31}$, $-C(=O)NR^{34}R^{35}$, or $-C(=O)NR^{31}R^{32}$; and wherein $-(W^2)_k-$ is $-NR^7-$, $-N(R^7)C(O)-$ or $-N(R^7)S(O)_2-$.

In some embodiments of the compositions of the invention, the composition further comprises a compound of Formula C:

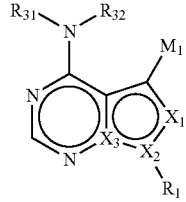

Formula C or a salt thereof, wherein:

$M_1$ of Formula B and $M_1$ of Formula C are the same; $R_1$ of Formula A and $R_1$ of Formula C are the same; $R_{31}$ of Formula A and $R_{31}$ of Formula C are the same; $R_{32}$ of Formula A and $R_{32}$ of Formula C are the same; $X_1$ of Formula A and $X_1$ of Formula C are the same; $X_2$ of Formula A and $X_2$ of Formula C are the same; and $X_3$ of Formula A and $X_3$ of Formula C are the same.

In some embodiments of the compositions of the invention, the composition further comprises an organic solvent.

In another aspect, the invention provides a process for synthesizing a compound of Formula G-6-B:

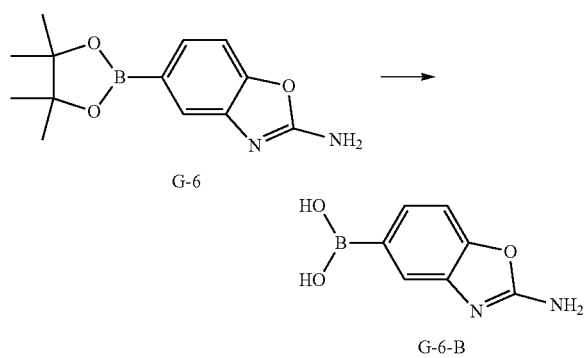

G-6

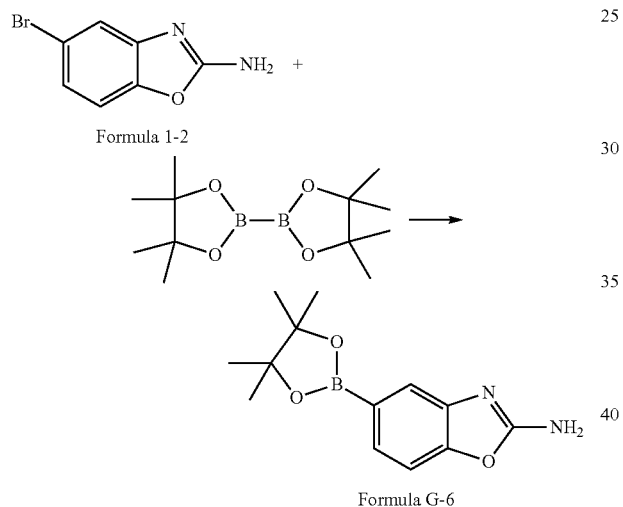

comprising the step of allowing a compound of Formula G-6 to react with an acid under conditions effective for synthesizing a compound of Formula G-6-B.

In some embodiments of the process for synthesizing a compound of Formula G-6-B, the acid is hydrochloric acid.

In another aspect, the invention provides a process for synthesizing a compound of Formula G-6:

comprising the step of allowing a compound of Formula 1-2 to react with bis(pinacolato)diboron under conditions effective for synthesis of the compound of Formula G-6.

In yet another aspect, the invention provides a process for synthesizing a compound of Formula 1-2:

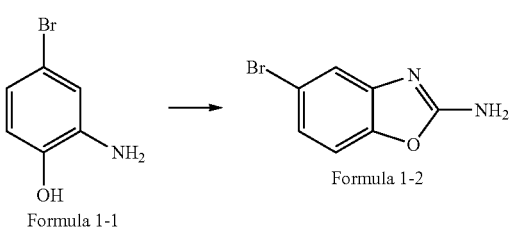 [SMILES: Nc1cc(Br)ccc1O ; Nc1nc2cc(Br)ccc2o1]

comprising the step of allowing a compound of Formula 1-1 to react with a cyanogen halide under conditions effective to synthesize the compound of Formula 1-2.

In some embodiments of the process for synthesizing a compound of Formula 1-2, the cyanogen halide is cyanogen bromide.

In a further aspect, the invention provides a process for synthesizing a compound of Formula B:

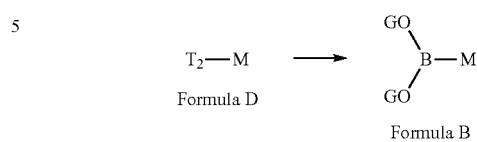

comprising the step of allowing a compound of Formula D to react with a base and a trialkyl borate under conditions effective to synthesize a compound of Formula B; wherein: G is alkyl; $T_2$ is halo, triflate, tosylate or mesylate; each of M of Formula D and M of Formula B is a $M_1$ moiety, and wherein $M_1$ moiety of Formula D and $M_1$ moiety of Formula B are identical, having one of the following structures:

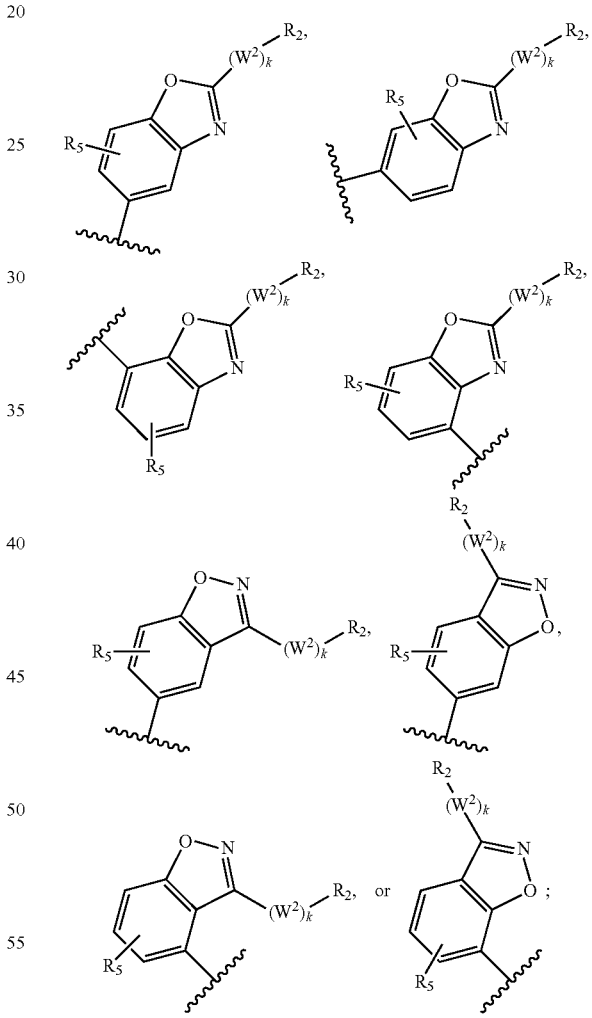

$R^5$ is hydrogen; k is 1; —$W^2$—$R^2$ is —NH-$G_p$;

$G_p$ is acetyl, tert-butyl carbamate (Boc), carbobenzyloxy (Cbz), benzyl (Bz), fluorenylmethyloxycarbonyl (FMOC), or p-methoxybenzyl (PMB); and wherein $G_p$ of Formula D and $G_p$ of Formula B are the same.

In other embodiments of the process for synthesizing a compound of Formula B, the base is n-butyllithium. In yet other embodiments, the trialkyl borate is triisopropyl borate.

In some embodiments of the process for synthesizing a compound of Formula B, each of the compound of Formula D and the compound of Formula B is the compound wherein —$(W^2)_k$— is —$NR^7$—, —$N(R^7)C(O)$— or —$N(R^7)S(O)_2$—.

In some embodiments, the process further comprises the step of allowing the compound of Formula B wherein —$W^2$—$R^2$ is —$NH$-$G_p$ and $G_p$ is tert-butyl carbamate to react with a reagent under conditions effective to yield a compound of Formula B, wherein —$W^2$—$R^2$ is $NH_2$. In some embodiments, the reagent is hydrochloric acid.

In yet another aspect, the invention provides a process for synthesizing a compound of Formula 3-4:

Formula 3-3

Formula 3-4 comprising the step of allowing a compound of Formula 3-3 to react with a cyanogen halide under conditions effective for synthesizing a compound of Formula 3-4; wherein:

$X_1$ is N or C-$E^1$, $X_2$ is N, and $X_3$ is C; or $X_1$ is N or C-$E^1$, $X_2$ is C, and $X_3$ is N; wherein no more than two ring nitrogen atoms of the compound of Formula 3-3 are adjacent; and wherein no more than two ring nitrogen atoms of the compound of Formula 3-4 are adjacent;

$E^1$ is —$(W^1)_j$—$R^4$ wherein j is 0 or 1;

$W^1$ is —O—, —$NR^7$—, —$S(O)_{0-2}$—, —$C(O)$—, $C(O)N(R^7)$—, —$N(R^7)C(O)$—, —$N(R^7)S(O)$—, —$N(R^7)S(O)_2$—, —$C(O)O$—, —$CH(R^7)N(C(O)OR^8)$—, —$CH(R^7)N(C(O)R^8)$—, —$CH(R^7)N(SO_2R^8)$—, —$CH(R^7)N(R^8)$—, —$CH(R^7)C(O)N(R^8)$—, —$CH(R^7)N(R^8)C(O)$—, —$CH(R^7)N(R^8)S(O)$—, or —$CH(R^7)N(R^8)S(O)_2$—;

$R_1$ is hydrogen, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;

$R^3$ and $R^4$ are independently hydrogen, halogen, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=N$R^{32}$)$NR^{33}R^{32}$, —$NR^{31}$C(=N$R^{32}$)$OR^{33}$, —$NR^{31}$C(=N$R^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, —SC(=O)$NR^{31}R^{32}$, aryl, hetaryl, $C_{1-10}$alkyl, $C_{3-8}$cycloalkyl, $C_{1-10}$alkyl$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_2$10 alkenylheterocyclcyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{2-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl $C_{2-10}$alkynyl, hetaryl $C_{3-8}$cycloalkyl, heteroalkyl, or hetaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

each of $R^{31}$, $R^{32}$, and $R^{33}$ is independently H or $C_{1-10}$alkyl, wherein the $C_{1-10}$alkyl is unsubstituted or is substituted with one or more aryl, heteroalkyl, heterocyclyl, or hetaryl group, wherein each of said alkyl, aryl, heteroalkyl, heterocyclyl, or hetaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, N(aryl)($C_{1-10}$alkyl), —$NO_2$, —CN, —S(O)$_{0-2}C_{1-10}$alkyl, —S(O)$_{0-2}C_{1-10}$alkylaryl, —S(O)$_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$;

$R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, hetaryl, C$_{1-6}$alkyl, or O-aryl, and wherein said 3-10 membered saturated or unsaturated ring independently contains 0, 1, or 2 more heteroatoms in addition to the nitrogen atom; each of R$^7$ and R$^8$ is independently hydrogen, C$_{1-10}$alkyl, C$_{2-10}$alkenyl, aryl, heteroaryl, heterocyclyl or C$_{3-10}$cycloalkyl, each of which except for hydrogen is unsubstituted or is substituted by one or more independent R$^6$; and R$^6$ is halo, —OR$^{31}$, —SH, —NH$_2$, —NR$^{34}$R$^{35}$, —NR$^{31}$R$^{32}$, —CO$_2$R$^{31}$, —CO$_2$aryl, —C(═O)NR$^{31}$R$^{32}$, —C(═O)NR$^{34}$R$^{35}$, —NO$_2$, —CN, —S(O)$_{0-2}$C$_{1-10}$alkyl, —S(O)$_{0-2}$aryl, —SO$_2$NR$^{34}$R$^{35}$, —SO$_2$NR$^{31}$R$^{32}$, C$_{1-10}$alkyl, C$_{2-10}$alkenyl, C$_{2-10}$alkynyl, aryl-C$_{1-10}$alkyl, aryl-C$_{2-10}$alkenyl, aryl-C$_{2-10}$alkynyl, hetaryl-C$_{1-10}$alkyl, hetaryl-C$_{2-10}$alkenyl, or hetaryl-C$_{2-10}$alkynyl, each of which is unsubstituted or is substituted with one or more independent halo, cyano, nitro, —OC$_{1-10}$alkyl, C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, —C(═O)NR$^{31}$R$^{32}$, —C(═O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$; and wherein R$_1$ of Formula 3-3 and R$_1$ of Formula 3-4 are the same; R$_{31}$ of Formula 3-3 and R$_{31}$ of Formula 3-4 are the same; R$_{32}$ of Formula 3-3 and R$_{32}$ of Formula 3-4 are the same; X$_1$ of Formula 3-3 and X$_1$ of Formula 3-4 are the same; X$_2$ of Formula 3-3 and X$_2$ of Formula 3-4 are the same; and X$_3$ of Formula 3-3 and X$_3$ of Formula 3-4 are the same.

In some embodiments of the process of the invention, each of the compound of Formula 3-3 and the compound of Formula 3-4 is the compound wherein:

X$_1$ and X$_2$ are N;

R$_1$ is -L-C$_{1-10}$alkyl, -L-C$_{3-8}$cycloalkyl, -L-C$_{1-10}$alkylheterocylyl, or -L-heterocyclyl, each of which is unsubstituted or is substituted by one or more independent R$^3$ substituents; and wherein R$^3$ is hydrogen, —OH, —OR$^{31}$, —NR$^{31}$R$^{32}$, —C(O)R$^{31}$, —C(═O)NR$^{31}$R$^{32}$, —C(═O)NR$^{34}$R$^{35}$, aryl, hetaryl, C$_{1-10}$alkyl, C$_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(═O)NR$^{31}$R$^{32}$, —C(═O)NR$^{34}$R$^{35}$, —NO$_2$, —CN, —S(O)$_2$R$^{31}$, —SO$_2$NR$^{31}$R$^{32}$, —SO$_2$NR$^{34}$R$^{35}$, —NR$^{31}$C(═O)R$^{32}$, —NR$^{31}$C(═O)OR$^{32}$, —NR$^{31}$C(═O) NR$^{32}$R$^{33}$, —NR$^{31}$S(O)$_{0-2}$R$^{32}$, —C(═S)OR$^{31}$, —C(═O) SR$^{31}$, —NR$^{31}$C(═NR$^{32}$)NR$^{33}$R$^{32}$, —NR$^{31}$C(═NR$^{32}$) OR$^{33}$, —NR$^{31}$C(═NR$^{32}$)SR$^{33}$, —OC(═O)OR$^{33}$, —OC(═O)NR$^{31}$R$^{31}$R$^{32}$, —OC(═O)SR$^{31}$, —SC(═O)OR$^{31}$, —P(O)OR$^{31}$OR$^{32}$, or —SC(═O)NR$^{31}$R$^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(═O)NR$^{34}$R$^{35}$, or —C(═O)NR$^{31}$R$^{32}$;

In some embodiments for synthesizing a compound of Formula 3-4, the cyanogen halide is cyanogen bromide.

In another aspect, the invention provides a process for synthesizing a compound of Formula 3-3:

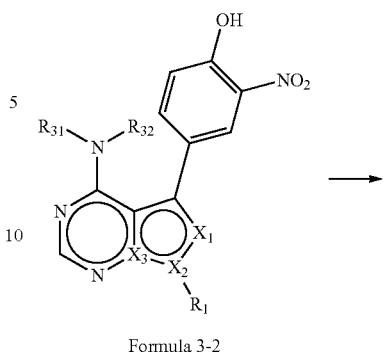

Formula 3-2

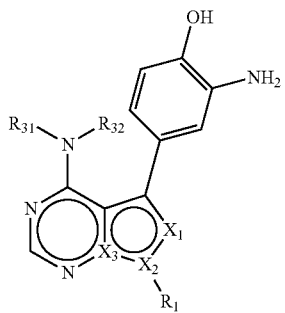

Formula 3-3 comprising the step of allowing a compound of Formula 3-2 to react with a reagent under conditions effective to synthesize a compound of Formula 3-3; wherein;

X$_1$ is N or C-E$^1$, X$_2$ is N, and X$_3$ is C; or X$_1$ is N or C-E$^1$, X$_2$ is C, and X$_3$ is N; wherein no more than two ring nitrogen atoms of the compound of Formula 3-3 are adjacent; and wherein no more than two ring nitrogen atoms of the compound of Formula 3-4 are adjacent;

E$^1$ is —(W)$_j$—R$^4$ wherein j is 0 or 1;

W$^1$ is —O—, —NR$^7$—, —S(O)$_{0-2}$—, —C(O)—, —C(O) N(R$^7$)—, —N(R$^7$)C(O)—, —N(R$^7$)S(O)—, —N(R$^7$) S(O)$_2$—, —C(O)O—, —CH(R$^7$)N(C(O)OR)—, —CH(R$^7$) N(C(O)R$^8$)—, —CH(R$^7$)N(SO$_2$R$^8$)—, —CH(R$^7$)N(R$^8$)—, —CH(R$^7$)C(O)N(R$^8$)—, —CH(R$^7$)N(R$^8$)C(O)—, —CH (R$^7$)N(R$^8$)S(O)—, or —CH(R$^7$)N(R$^8$)S(O)$_2$—;

R$_1$ is hydrogen, -L-C$_{1-10}$alkyl, -L-C$_{3-8}$cycloalkyl, -L-C$_{1-10}$alkyl-C$_{3-8}$cycloalkyl, -L-aryl, -L-heteroaryl, -L-C$_{1-10}$alkylaryl, -L-C$_{1-10}$alkylhetaryl, -L-C$_{1-10}$alkylheterocylyl, -L-C$_{2-10}$alkenyl, -L-C$_{2-10}$alkynyl, -L-C$_{2-10}$alkenyl-C$_{3-8}$cycloalkyl, -L-C$_{2-10}$alkynyl-C$_{3-8}$cycloalkyl, -L-heteroalkyl, -L-heteroalkylaryl, -L-heteroalkylheteroaryl, -L-heteroalkyl-heterocyclyl, -L-heteroalkyl-C$_{3-8}$cycloalkyl, -L-aralkyl, -L-heteroaralkyl, or -L-heterocyclyl, each of which is unsubstituted or is substituted by one or more independent R$^3$;

L is absent, —(C═O)—, —C(═O)O—, —C(═O)N (R$^{31}$)—, —S—, —S(O)—, —S(O)$_2$—, —S(O)$_2$N(R$^{31}$)—, or —N(R$^{31}$)—;

R$^3$ and R$^4$ are independently hydrogen, halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(═O)NR$^{31}$R$^{32}$, —C(═O) NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(═O)R$^{32}$, —NR$^{31}$C(═O)OR$^{32}$, —NR$^{31}$C(═O)NR$^{32}$R$^{33}$, —NR$^{31}$S(O)$_2$R$^{32}$, —C(═S)OR$^{31}$, —C(═O)SR$^{31}$, —NR$^{31}$C(═NR$^{32}$)NR$^{33}$R$^{32}$, —NR$^{31}$C (═NR$^{32}$)OR$^{33}$, —NR$^{31}$C(═NR$^{32}$)SR$^{33}$, —OC(═O)OR$^{33}$, —OC(═O)NR$^{31}$R$^{32}$, —OC(═O)SR$^{31}$, —SC(═O)OR$^{31}$, —P(O)OR$^{31}$OR$^{32}$, —SC(═O)NR$^{31}$R$^{32}$, aryl, hetaryl, C$_{1-10}$alkyl, C$_{3-8}$cycloalkyl, C$_{1-10}$alkylC$_{3-8}$cycloalkyl, C$_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylhetaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_2R^{31}$, —$SO_2NR^{31}R^{32}$, —$SO_2NR^{34}R^{35}$, —$NR^{31}C$(=O)$R^{32}$, —$NR^{31}C$(=O)$OR^{32}$, —$NR^{31}C$(=O)$NR^{32}R^{33}$, —$NR^{31}S$(O)$_{0-2}R^{32}$, —C(=S)$OR^{31}$, —C(=O)$SR^{31}$, —$NR^{31}C$(=$NR^{32}$)$NR^{33}R^{32}$, —$NR^{31}C$(=$NR^{32}$)$OR^{33}$, —$NR^{31}C$(=$NR^{32}$)$SR^{33}$, —OC(=O)$OR^{33}$, —OC(=O)$NR^{31}R^{32}$, —OC(=O)$SR^{31}$, —SC(=)$OR^{31}$, —P(O)$OR^{31}R^{32}$, or —SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

each of $R^{31}$, $R^{32}$, and $R^{33}$ is independently H or $C_{1-10}$alkyl, wherein the $C_{1-10}$alkyl is unsubstituted or is substituted with one or more aryl, heteroalkyl, heterocyclyl, or hetaryl group, wherein each of said alkyl, aryl, heteroalkyl, heterocyclyl, or hetaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NH_2$, —C(=O)$NR^{34}R^{35}$, —$OCF_3$, —O($C_{1-10}$alkyl), —O-aryl, —N(aryl)($C_{1-10}$alkyl), —$NO_2$, —CN, —S(O)$_{0-2}C_{1-10}$alkyl, —S(O)$_{0-2}C_{1-10}$alkylaryl, —S(O)$_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$;

$R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom; each of $R^7$ and $R^8$ is independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$; and $R^6$ is halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, —C(=O)$NR^{34}R^{35}$, —$NO_2$, —CN, —S(O)$_{0-2}C_{1-10}$alkyl, —S(O)$_{0-2}$aryl, $SO_2NR^{34}R^{35}$, $SO_2NR^{31}R^{32}$, $C_{1-10}$alkyl, $C_{2-10}$alkenyl, $C_{2-10}$alkynyl, aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, or hetaryl-$C_{2-10}$alkynyl, each of which is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)$NR^{31}R^{32}$, —C(=O)$NR^{34}R^{35}$, —$SO_2NR^{34}R^{35}$, —$SO_2NR^{31}R^{32}$, —$NR^{31}R^{32}$, or —$NR^{34}R^{35}$; and wherein $R_1$ of Formula 3-2 and $R_1$ of Formula 3-3 are the same; $R_{31}$ of Formula 3-2 and $R_{31}$ of Formula 3-3 are the same; $R_{32}$ of Formula 3-2 and $R_{32}$ of Formula 3-3 are the same; $X_1$ of Formula 3-2 and $X_1$ of Formula 3-3 are the same; $X_2$ of Formula 3-2 and $X_2$ of Formula 3-3 are the same; and $X_3$ of Formula 3-2 and $X_3$ of Formula 3-3 are the same.

In some embodiments of the process for synthesizing a compound of Formula 3-3, the reagent is (a) sodium dithionite or (b) palladium on carbon in the presence of hydrogen gas.

In some embodiments of the process for synthesizing a compound of Formula 3-3, each of the compound of Formula 3-2 and the compound of Formula 3-3 is a compound wherein: $X_1$ and $X_2$ are N; $R_1$ is -L-$C_{1-10}$alkyl, -L-$C_{3-8}$cycloalkyl, -L-$C_{1-10}$alkylheterocylyl, or -L-heterocyclyl, each of which is unsubstituted or is substituted by one or more independent $R^3$ substituents; and wherein $R^3$ is hydrogen, —OH, —$OR^{31}$, —$NR^{31}R^{32}$, —C(O)$R^{31}$, —C(=O)$NR^{31}R^{32}$, —C(=O)$NR^{34}R^{35}$, aryl, hetaryl, $C_{1-10}$alkyl, $C_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_2R^{31}$, —$SO_2NR^{31}R^{32}$, —$SO_2NR^{34}R^{35}$, —$NR^{31}C$(=O)$R^{32}$, —$NR^{31}C$(=O)$OR^{32}$, —$NR^{31}C$(=O)$NR^{32}R^{33}$, —$NR^{31}S$(O)$_{0-2}R^{32}$, —C(=S)$OR^{31}$, —C(=O)$SR^{31}$, —$NR^{31}C$(=$NR^{32}$)$NR^{33}R^{32}$, —$NR^{31}C$(=$NR^{32}$)$OR^{33}$, —$NR^{31}C$(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

In another aspect, the invention provides a process for synthesizing a compound of Formula 3-2:

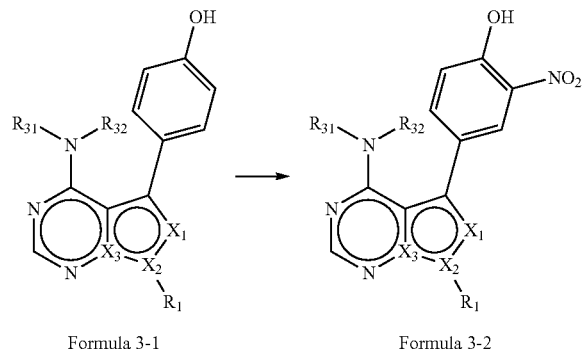

Formula 3-1 → Formula 3-2 comprising the step of allowing a compound of Formula 3-1 to react with a reagent under conditions effective to synthesize the compound of Formula 3-2; wherein:

$X_1$ is N or C-$E^1$, $X_2$ is N, and $X_3$ is C; or $X_1$ is N or C-$E^1$, $X_2$ is C, and $X_3$ is N; wherein no more than two ring nitrogen atoms of the compound of Formula 3-1 are adjacent; and wherein no more than two ring nitrogen atoms of the compound of Formula 3-2 are adjacent;

$E^1$ is —(W)$_j$—$R^4$ wherein j is 0 or 1;

$W^1$ is —O—, —N$R^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^7$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R_1$ is hydrogen, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;

$R^3$ and $R^4$ are independently hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, —SC(=O)N$R^{31}R^{32}$, aryl, hetaryl, $C_{1-10}$alkyl, $C_{3-8}$cycloalkyl, $C_{1-10}$alkyl$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocylcyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{2-10}$alkyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, or —SC(=O)N$R^{31}R^{32}$, and wherein each of said alkyl, cycloalkyl, heterocyclyl, or heteroalkyl moiety is unsubstituted or is substituted with one or more halo, —OH, —$R^{31}$, —CF$_3$, —OCF$_3$, —O$R^{31}$, —O-aryl, —N$R^{31}R^{32}$, —N$R^{34}R^{35}$, —C(O)$R^{31}$, —CO$_2R^{31}$, —C(=O)N$R^{34}R^{35}$, or —C(=O)N$R^{31}R^{32}$;

each of $R^{31}$, $R^{32}$, and $R^{33}$ is independently H or $C_{1-10}$alkyl, wherein the $C_{1-10}$alkyl is unsubstituted or is substituted with one or more aryl, heteroalkyl, heterocyclyl, or hetaryl group, wherein each of said alkyl, aryl, heteroalkyl, heterocyclyl, or hetaryl group is unsubstituted or is substituted with one or more halo, —OH, —$C_{1-10}$alkyl, —CF$_3$, —O-aryl, —OCF$_3$, —O$C_{1-10}$alkyl, —NH$_2$, —N($C_{1-10}$alkyl)($C_{1-10}$alkyl), —NH($C_{1-10}$alkyl), —NH(aryl), —N$R^{34}R^{35}$, —C(O)($C_{1-10}$alkyl), —C(O)($C_{1-10}$alkyl-aryl), —C(O)(aryl), —CO$_2$—$C_{1-10}$alkyl, —CO$_2$—$C_{1-10}$alkylaryl, —CO$_2$-aryl, —C(=O)N($C_{1-10}$alkyl)($C_{1-10}$alkyl), —C(=O)NH($C_{1-10}$alkyl), —C(=O)N$R^{34}R^{35}$, —C(=O)NH$_2$, —OCF$_3$, —O($C_{1-10}$alkyl), —O-aryl, —N(aryl)($C_{1-10}$alkyl), —NO$_2$, —CN, —S(O)$_{0-2}C_{1-10}$alkyl, —S(O)$_{0-2}C_{1-10}$alkylaryl, —S(O)$_{0-2}$ aryl, —SO$_2$N(aryl), —SO$_2$N($C_{1-10}$alkyl)($C_{1-10}$alkyl), —SO$_2$NH($C_{1-10}$alkyl) or —SO$_2$N$R^{34}R^{35}$;

$R^{34}$ and $R^{35}$ in —N$R^{34}R^{35}$, —C(=O)N$R^{34}R^{35}$, or —SO$_2$N$R^{34}R^{35}$, are taken together with the nitrogen atom to which they are attached to form a 3-10 membered saturated or unsaturated ring; wherein said ring is independently unsubstituted or is substituted by one or more —N$R^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom;

each of $R^7$ and $R^8$ is independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$; and $R^6$ is halo, —O$R^{31}$, —SH, —NH$_2$, —N$R^{34}R^{35}$, —N$R^{31}R^{32}$, —CO$_2R^{31}$, —CO$_2$aryl, —C(=O)N$R^{31}R^{32}$, —C(=O)N$R^{34}R^{35}$, —NO$_2$, —CN, —S(O)$_{0-2}C_{1-10}$alkyl, —S(O)$_{0-2}$aryl, SO$_2$N$R^{34}R^{35}$, SO$_2$N$R^{31}R^{32}$, $C_{1-10}$alkyl, $C_{2-10}$alkenyl, $C_{2-10}$alkynyl, aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, or hetaryl-$C_{2-10}$alkynyl, each of which is unsubstituted or is substituted with one or more independent halo, cyano, nitro, —O$C_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)N$R^{31}R^{32}$, —C(=O)N$R^{34}R^{35}$, —SO$_2$N$R^{34}R^{35}$, —SO$_2$N$R^{31}R^{32}$, —N$R^{31}R^{32}$, or —N$R^{34}R^{35}$; and wherein $R_1$ of Formula 3-1 and $R_1$ of Formula 3-23 are the same; $R_{31}$ of Formula 3-1 and $R_{31}$ of Formula 3-2 are the same; $R_{32}$ of Formula 3-1 and $R_{32}$ of Formula 3-2 are the same; $X_1$ of Formula 3-1 and $X_1$ of Formula 3-2 are the same; $X_2$ of Formula 3-1 and $X_2$ of Formula 3-2 are the same; and $X_3$ of Formula 3-1 and $X_3$ of Formula 3-2 are the same.

In some embodiments of the process for synthesizing a compound of Formula 3-2, the reagent is nitric acid.

In some embodiments of the process for synthesizing a compound of Formula 3-2, each of the compound of Formula 3-1 and the compound of Formula 3-2 is a compound wherein:

$X_1$ and $X_2$ are N; $R_1$ is -L-$C_{1-10}$alkyl, -L-$C_{3-8}$cycloalkyl, -L-$C_{1-10}$alkylheterocylyl, or -L-heterocyclyl, each of which is unsubstituted or is substituted by one or more independent $R^3$ substituents; and wherein $R^3$ is hydrogen, —OH, —O$R^{31}$, —N$R^{31}R^{32}$, —C(O)$R^{31}$, —C(=O)N$R^{31}R^{32}$, —C(=O)N$R^{34}R^{35}$, aryl, hetaryl, $C_{1-10}$alkyl, $C_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —C(=O)$NR^{31}R^{32}$, —C(=O)$NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}S(O)_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, $NR^{31}R^{32}$, —$NR^{34}R^{35}$, —$C(O)R^{31}$, —$CO_2R^{31}$, —C(=O)$NR^{34}R^{35}$, or —C(=O)$NR^{31}R^{32}$.

The invention also provides a compound of Formula E:

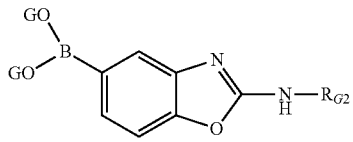

Formula E or a salt thereof, wherein:

G is H or $R_{G1}$; and $R_{G1}$ is alkyl, alkenyl, or aryl; or the G groups of

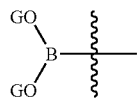

join together to form a 5- or 6-membered cyclic moiety; and $R_{G2}$ is H, acetyl, tert-butyl carbamate (Boc), carbobenzyloxy (Cbz), benzyl (Bz), fluorenylmethyloxycarbonyl (FMOC), or p-methoxybenzyl (PMB).

In some embodiments, the compound of Formula E is:

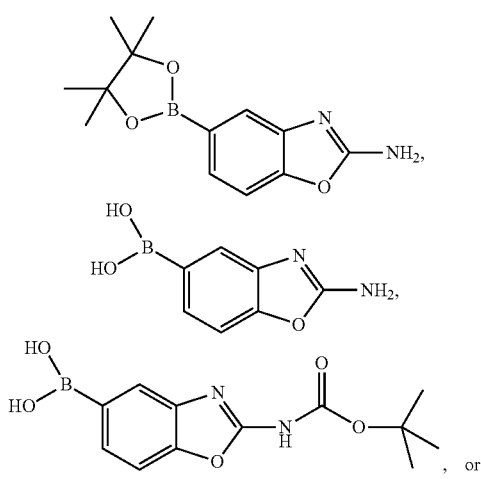

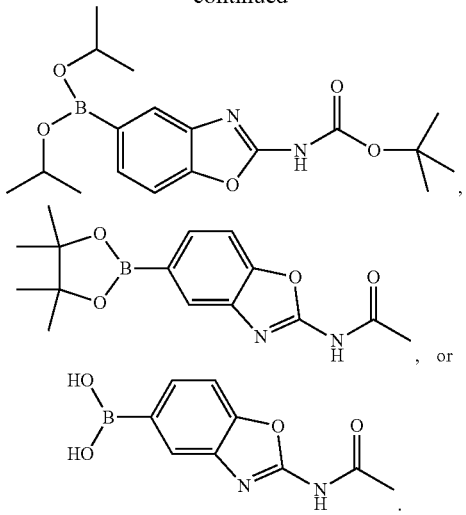

In some embodiments, a compound of the invention is a compound of Formula F:

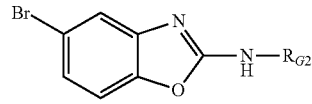

or a salt thereof, wherein $R_{G2}$ is H, tert-butyl carbamate, acetyl, tert-butyl carbamate (Boc), carbobenzyloxy (Cbz), benzyl (Bz), fluorenylmethyloxycarbonyl (FMOC), or p-methoxybenzyl (PMB).

In some embodiments, the invention provides a compound of Formula 3-3':

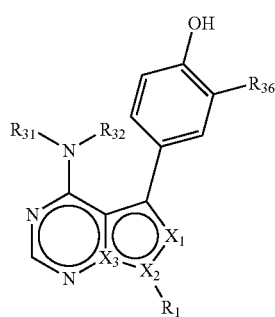

Formula 3-3' or a salt thereof wherein:

$X_1$ is N or C-$E^1$, $X_2$ is N, and $X_3$ is C; or $X_1$ is N or C-$E^1$, $X_2$ is C, and $X_3$ is N;

wherein no more than two ring nitrogen atoms are adjacent;

$E^1$ is —($W^1$)$_j$—$R^4$ wherein j is 0 or 1;

$W^1$ is —O—, —$NR^7$—, —$S(O)_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)OR)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R_1$ is hydrogen, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-C$_{2-10}$alkenyl, -L-C$_{2-10}$alkynyl, -L-C$_{2-10}$alkenyl-C$_{3-8}$cycloalkyl, -L-C$_{2-10}$alkynyl-C$_{3-8}$cycloalkyl, -L-heteroalkyl, -L-heteroalkylaryl, -L-heteroalkylheteroaryl, -L-heteroalkyl-heterocylyl, -L-heteroalkyl-C$_{3-8}$cycloalkyl, -L-aralkyl, -L-heteroaralkyl, or -L-heterocyclyl, each of which is unsubstituted or is substituted by one or more independent R$^3$;

L is absent, —(C═O)—, —C(═O)O—, —C(═O)N(R$^{31}$)—, —S—, —S(O)—, —S(O)$_2$—, —S(O)$_2$N(R$^{31}$)—, or —N(R$^{31}$)—;

R$^3$ and R$^4$ are independently hydrogen, halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(═O)NR$^{31}$R$^{32}$, —C(═O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(═O)R$^{32}$, —NR$^{31}$C(═O)OR$^{32}$, —NR$^{31}$C(═O)NR$^{32}$R$^{33}$, —NR$^{31}$S(O)R$^{32}$, —C(═S)OR$^{31}$, —C(═O)SR$^{31}$, —NR$^{31}$C(═NR$^{32}$)NR$^{33}$R$^{32}$, —NR$^{31}$C(═NR$^{32}$)OR$^{33}$, —NR$^{31}$C(═NR$^{32}$)SR$^{33}$, —OC(═O)OR$^{33}$, —OC(═O)NR$^{31}$R$^{32}$, —OC(═O)SR$^{31}$, —SC(═O)OR$^{31}$, —P(O)OR$^{31}$OR$^{32}$, —SC(═O)NR$^{31}$R$^{32}$, aryl, hetaryl, C$_{1-10}$alkyl, C$_{3-8}$cycloalkyl, C$_{1-10}$alkylC$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{1-10}$alkyl-C$_{2-10}$alkenyl, C$_{1-10}$alkyl-C$_{2-10}$alkynyl, C$_{1-10}$alkylaryl, C$_{1-10}$alkylhetaryl, C$_{1-10}$alkylheterocyclyl, C$_{2-10}$alkenyl, C$_{2-10}$alkynyl, C$_{2-10}$alkenyl-C$_{1-10}$alkyl, C$_{2-10}$alkynyl-C$_{1-10}$alkyl, C$_{2-10}$alkenylaryl, C$_{2-10}$alkenylhetaryl, C$_{2-10}$alkenylheteroalkyl, C$_2$10 alkenylheterocylcyl, C$_{2-10}$alkenyl-C$_{3-8}$cycloalkyl, C$_{2-10}$alkynyl-C$_{3-8}$cycloalkyl, C$_{2-10}$alkynylaryl, C$_{2-10}$alkynylhetaryl, C$_{2-10}$alkynylheteroalkyl, C$_{2-10}$alkynylheterocyclyl, C$_{2-10}$alkynyl-C$_{3-8}$cycloalkenyl, C$_{1-10}$alkoxy C$_{1-10}$alkyl, C$_{1-10}$alkoxy-C$_{2-10}$alkenyl, C$_{1-10}$alkoxy-C$_{2-10}$alkynyl, heterocyclyl, heterocyclyl-C$_{1-10}$alkyl, heterocyclyl-C$_{2-10}$alkenyl, heterocyclyl-C$_{2-10}$alkynyl, aryl-C$_{1-10}$alkyl, aryl-C$_{2-10}$alkenyl, aryl-C$_{2-10}$alkynyl, aryl-heterocyclyl, hetaryl-C$_{1-10}$alkyl, hetaryl-C$_{2-10}$alkenyl, hetaryl-C$_{2-10}$alkynyl, hetaryl-C$_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(═O)NR$^{31}$R$^{32}$, —C(═O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(═O)R$^{32}$, —NR$^{31}$C(═O)OR$^{32}$, —NR$^{31}$C(═O)NR$^{32}$R$^{33}$, —NR$^{31}$S(O)$_2$R$^{32}$, —C(═S)OR$^{31}$, —C(═O)SR$^{31}$, —NR$^{31}$C(═NR$^{32}$)NR$^{33}$R$^{32}$, —NR$^{31}$C(═NR$^{32}$)OR$^{33}$, —NR$^{31}$C(═NR$^{32}$)SR$^{33}$, —OC(═O)OR$^{33}$, —OC(═O)NR$^{31}$R$^{32}$, —OC(═O)SR$^{31}$, —SC(═O)OR$^{31}$, —P(O)OR$^{31}$OR$^{32}$, or —SC(═O)NR$^{31}$R$^{32}$, and wherein each of said alkyl, cycloalkyl, heterocyclyl, or heteroalkyl moiety is unsubstituted or is substituted with one or more halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(═O)NR$^{34}$R$^{35}$, or —C(═O)NR$^{31}$R$^{32}$;

each of R$^{31}$, R$^{32}$, and R$^{33}$ is independently H or C$_{1-10}$alkyl, wherein the C$_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(═O)N(C$_{1-10}$alkyl)(C$_{1-10}$alkyl), —C(═O)NH(C$_{1-10}$alkyl), —C(═O)NR$^{34}$R$^{35}$, —C(═O)NH$_2$, —OCF$_3$, —O(C$_{1-10}$alkyl), —O-aryl, N(aryl)(C$_{1-10}$alkyl), —NO$_2$, —CN, —S(O)$_{0-2}$C$_{1-10}$alkyl, —S(O)$_{0-2}$C$_{1-10}$alkylaryl, —S(O)$_{0-2}$ aryl, —SO$_2$N(aryl), —SO$_2$N(C$_{1-10}$alkyl)(C$_{1-10}$alkyl), —SO$_2$NH(C$_{1-10}$alkyl) or —SO$_2$NR$^{34}$R$^{35}$;

R$^{34}$ and R$^{35}$ in —NR$^{34}$R$^{35}$, —C(═O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, hetaryl, C$_{1-6}$alkyl, or O-aryl, and wherein said 3-10 membered saturated or unsaturated ring independently contains 0, 1, or 2 more heteroatoms in addition to the nitrogen atom; each of R$^7$ and R$^8$ is independently hydrogen, C$_{1-10}$alkyl, C$_{2-10}$alkenyl, aryl, heteroaryl, heterocyclyl or C$_{3-10}$cycloalkyl, each of which except for hydrogen is unsubstituted or is substituted by one or more independent R$^6$;

R$^6$ is halo, —OR$^{31}$, —SH, —NH$_2$, —NR$^{34}$R$^{35}$, —NR$^{31}$R$^{32}$, —CO$_2$R$^{31}$, —CO$_2$aryl, —C(═O)NR$^{31}$R$^{32}$, —C(═O)NR$^{34}$R$^{35}$, —NO$_2$, —CN, —S(O)$_{0-2}$C$_{1-10}$alkyl, —S(O)$_{0-2}$aryl, —SO$_2$NR$^{34}$R$^{35}$, —SO$_2$NR$^{31}$R$^{32}$, C$_{1-10}$alkyl, C$_{2-10}$alkenyl, C$_{2-10}$alkynyl, aryl-C$_{1-10}$alkyl, aryl-C$_{2-10}$alkenyl, aryl-C$_{2-10}$alkynyl, hetaryl-C$_{1-10}$alkyl, hetaryl-C$_{2-10}$alkenyl, or hetaryl-C$_{2-10}$alkynyl, each of which is unsubstituted or is substituted with one or more independent halo, cyano, nitro, —OC$_{1-10}$alkyl, C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, —C(═O)NR$^{31}$R$^{32}$, —C(═O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$; and R$^{36}$ is NH$_2$ or NO$_2$.

In some embodiments, the compound of Formula 3-3' is the compound wherein:

X$_1$ and X$_2$ are N;

R$_1$ is -L-C$_{1-10}$alkyl, -L-C$_{3-8}$cycloalkyl, -L-C$_{1-10}$alkylheterocylyl, or -L-heterocyclyl, each of which is unsubstituted or is substituted by one or more independent R$^3$ substituents;

R$^3$ is hydrogen, —OH, —OR$^{31}$, —NR$^{31}$R$^{32}$, —C(O)R$^{31}$, —C(═O)NR$^{31}$R$^{32}$, —C(═O)NR$^{34}$R$^{35}$, aryl, hetaryl, C$_{1-10}$alkyl, C$_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(═O)NR$^{31}$R$^{32}$, —C(═O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(═O)R$^{32}$, —NR$^{31}$C(═O)OR$^{32}$, —NR$^{31}$C(═O)NR$^{32}$R$^{33}$, —NR$^{31}$S(O)$_{0-2}$R$^{32}$, —C(═S)OR$^{31}$, —C(═O)SR$^{31}$, —NR$^{31}$C(═NR$^{32}$)NR$^{33}$R$^{32}$, —NR$^{31}$C(═NR$^{32}$)OR$^{33}$, —NR$^{31}$C(═NR$^{32}$)SR$^{33}$, —OC(═O)OR$^{33}$, —OC(═O)NR$^{31}$R$^{32}$, —OC(═O)SR$^{31}$, —SC(═O)OR$^{31}$, —P(O)OR$^{31}$OR$^{32}$, or —SC(═O)NR$^{31}$R$^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(═O)NR$^{34}$R$^{35}$, or —C(═O)NR$^{31}$R$^{32}$; and wherein —(W$^2$)$_k$— is —NR$^7$—, —N(R$^7$)C(O)— or —N(R$^7$)S(O)$_2$—.

In another aspect, the invention provides a composition comprising a compound of Formula 3-3:

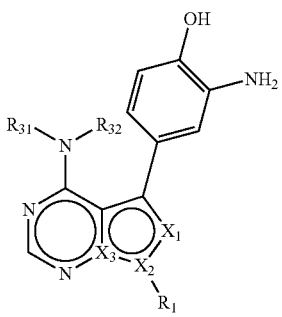

Formula 3-3 or a salt thereof, and a cyanogen halide wherein:

$X_1$ is N or C-$E^1$, $X_2$ is N, and $X_3$ is C; or $X_1$ is N or C-$E^1$, $X_2$ is C, and $X_3$ is N;

wherein no more than two nitrogen ring atoms are adjacent;

$E^1$ is —$(W^1)_j$—$R^4$ wherein j is 0 or 1;

$W^1$ is —O—, —$NR^7$—, —$S(O)_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(S$O_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R_1$ is hydrogen, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;

$R^3$ and $R^4$ are independently hydrogen, halogen, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —C(=S)$OR^{31}$, —C(=O)$SR^{31}$, —$NR^{31}C(=NR^{32})NR^{33}R^{32}$, —$NR^{31}C(=NR^{32})OR^{33}$, —$NR^{31}C(=NR^{32})SR^{33}$, —OC(=O)$OR^{33}$, —OC(=O)$NR^{31}R^{32}$, —OC(=O)$SR^{31}$, SC(=O)$OR^{31}$, —P(O)$OR^{31}OR^{32}$, —SC(=O)$NR^{31}R^{32}$, aryl, hetaryl, $C_{1-10}$alkyl, $C_{3-8}$cycloalkyl, $C_{1-10}$alkyl$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_2$10 alkenylheterocyclyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl $C_{2-10}$alkynyl, hetaryl $C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —C(=S)$OR^{31}$, —C(=O)$SR^{31}$, —$NR^{31}C(=NR^{32})NR^{33}R^{32}$, —$NR^{31}C(=NR^{32})OR^{33}$, —$NR^{31}C(=NR^{32})SR^{33}$, —OC(=O)$OR^{33}$, —OC(=O)$NR^{31}R^{32}$, —OC(=O)$SR^{31}$, SC(=O)$OR^{31}$, —P(O)$OR^{31}OR^{32}$, or SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, $NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

each of $R^7$ and $R^8$ is independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, —C(=O)$NR^{34}R^{35}$, —$NO_2$, —CN, —$S(O)_{0-2}C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl, aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, or hetaryl-$C_{2-10}$alkynyl, each of which is unsubstituted or is substituted with one or more independent halo, cyano, nitro, —O$C_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)$NR^{31}R^{32}$, —C(=O)$NR^{34}R^{35}$, —$SO_2NR^{34}R^{35}$, —$SO_2NR^{31}R^{32}$, —$NR^{31}R^{32}$, or —$NR^{34}R^{35}$;

each of $R^{31}$, $R^{32}$, and $R^{33}$ is independently H or $C_{1-10}$alkyl, wherein the $C_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —$C_{1-10}$alkyl, —$CF_3$, —O-aryl, —$OCF_3$, —O$C_{1-10}$alkyl, —$NH_2$, —N($C_{1-10}$alkyl)($C_{1-10}$ alkyl), —NH($C_{10-10}$alkyl), —NH(aryl), —$NR^{34}R^{35}$, —C(O)($C_{1-10}$alkyl), —C(O)($C_{1-10}$alkyl-aryl), C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}$—$C_{1-10}$alkyl, —$S(O)_{0-2}C_{1-10}$alkylaryl, —$S(O)_{0-2}$aryl, —$SO_2N$(aryl), —$SO_2N(C_{1-10}$alkyl)($C_{1-10}$alkyl), —$SO_2NH(C_{1-10}$alkyl) or —$SO_2NR^{34}R^{35}$; and $R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom.

In some embodiments of the composition comprising a compound of Formula 3-3 and cyanogen halide, the cyanogen halide is cyanogen bromide.

In some embodiments of the composition comprising a compound of Formula 3-3 and cyanogen halide, the compound of Formula 3-3 is the compound wherein:

$X_1$ and $X_2$ are N;

$R_1$ is -L-$C_{1-10}$alkyl, -L-$C_{3-8}$cycloalkyl, -L-$C_{1-10}$alkylheterocylyl, or -L-heterocyclyl, each of which is unsubstituted or is substituted by one or more independent $R^3$ substituents; and wherein $R^3$ is hydrogen, —OH, —$OR^{31}$, —$NR^{31}R^{32}$, —$C(O)R^{31}$, —$C(=O)NR^{31}R^{32}$, —$C(=O)NR^{34}R^{35}$, aryl, hetaryl, $C_{1-10}$alkyl, $C_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, OR, $NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_2R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$.

In some embodiments of the composition comprising a compound of Formula 3-3 and cyanogen halide, the composition further comprises a compound of Formula 3-4:

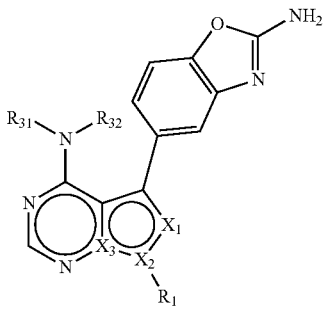

Formula 3-4 or a salt thereof, wherein: $R_1$ of Formula 3-3 and $R_1$ of Formula 3-4 are the same; $R_{31}$ of Formula 3-3 and $R_{31}$ of Formula 3-4 are the same; $R_{32}$ of Formula 3-3 and $R_{32}$ of Formula 3-4 are the same; $X_1$ of Formula 3-3 and $X_1$ of Formula 3-4 are the same; $X_2$ of Formula 3-3 and $X_2$ of Formula 3-4 are the same; and $X_3$ of Formula 3-3 and $X_3$ of Formula 3-4 are the same.

In another aspect, the invention provides a composition comprising a compound of Formula 3-1:

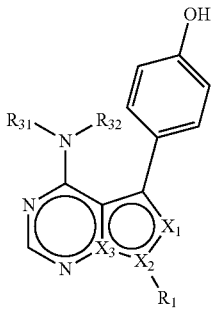

Formula 3-1 or a salt thereof, and a nitrating reagent wherein:

$X_1$ is N or C-$E^1$, $X_2$ is N, and $X_3$ is C; or $X_1$ is N or C-$E^1$, $X_2$ is C, and $X_3$ is N;

wherein no more than two nitrogen ring atoms are adjacent;

$E^1$ is —($W^1$)$_j$—$R^4$ wherein j is 0 or 1;

$W^1$ is —O—, —$NR^7$—, —$S(O)_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)OR)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R_1$ is hydrogen, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{1-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;

$R^3$ and $R^4$ are independently hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, —$SC(=O)NR^{31}R^{32}$, aryl, hetaryl, $C_{1-10}$alkyl, $C_{3-8}$cycloalkyl, $C_{1-10}$alkyl$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{2-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{2-10}$alkyl, aryl-$C_{2-10}$alkenyl, aryl-$C_{2-10}$alkynyl, aryl-heterocyclyl, hetaryl-$C_{1-10}$alkyl, hetaryl-$C_{1-10}$alkenyl, hetaryl-$C_{2-10}$alkynyl, hetaryl-$C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

each of $R^7$ and $R^8$ is independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, —$C(=O)NR^{34}R^{35}$, —$NO_2$, —CN, —$S(O)_{0-2}C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl, aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, or hetaryl-$C_{2-10}$alkynyl, each of which is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$;

each of $R^{31}$, $R^{32}$, and $R^{33}$ is independently H or $C_{1-10}$alkyl, wherein the $C_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl$)(C_{1-10}$alkyl$)$, —NH($C_{1-10}$alkyl), —NH(aryl), —$NR^{34}R^{35}$, —$C(O)(C_{1-10}$alkyl), —$C(O)(C_{1-10}$alkyl-aryl), —$C(O)$(aryl), —$CO_2$—$C_{1-10}$alkyl, —$CO_2$—$C_{1-10}$alkylaryl, —$CO_2$-aryl, —$C(=O)N(C_{1-10}$alkyl$)(C_{1-10}$alkyl$)$, —$C(=O)NH(C_{1-10}$alkyl$)$, —$C(=O)NR^{34}R^{35}$, —$C(=O)NH_2$, —$OCF_3$, —$O(C_{1-10}$alkyl), —O-aryl, —N(aryl)($C_{1-10}$alkyl), —$NO_2$, —CN, —$S(O)_2C_{1-10}$alkyl, —$S(O)_{0-2}C_{1-10}$alkylaryl, —$S(O)_{0-2}$ aryl, —$SO_2N$(aryl), —$SO_2N(C_{1-10}$alkyl$)(C_{1-10}$alkyl$)$, —$SO_2NH(C_{1-10}$alkyl$)$ or —$SO_2NR^{34}R^{35}$; and $R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom.

In some embodiments of the composition comprising a compound of Formula 3-1 and a nitrating agent, the compound of Formula 3-1 is the compound wherein:

$X_1$ and $X_2$ are N;

$R_1$ is -L-$C_{1-10}$alkyl, -L-$C_{3-8}$cycloalkyl, -L-$C_{1-10}$alkylheterocylyl, or -L-heterocyclyl, each of which is unsubstituted or is substituted by one or more independent $R^3$ substituents;

$R^3$ is hydrogen, —OH, —$OR^{31}$, —$NR^{31}R^{32}$, —$C(O)R^{31}$, —$C(=O)NR^{31}R^{32}$, —$C(=O)NR^{34}R^{35}$, aryl, hetaryl, $C_{1-10}$alkyl, $C_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, CN, —$S(O)_2R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$; and wherein —$(W^2)_k$— is —$NR^7$—, —$N(R^7)C(O)$— or —$N(R^7)S(O)_2$—.

In some embodiments, the nitrating agent is nitric acid.

In some embodiments of the composition comprising a compound of Formula 3-1 and a nitrating agent, the composition further comprises a compound of Formula 3-2:

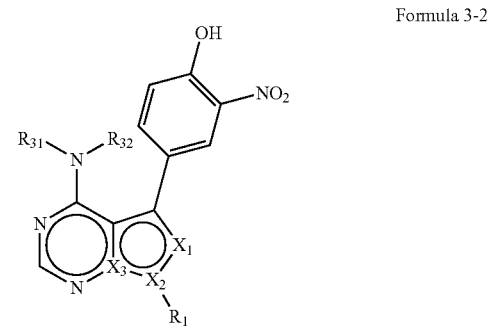

Formula 3-2 or a salt thereof, wherein:

$R_1$ of Formula 3-1 and $R_1$ of Formula 3-2 are the same; $R_{31}$ of Formula 3-1 and $R_{31}$ of Formula 3-2 are the same; $R_{32}$ of Formula 3-1 and $R_{32}$ of Formula 3-2 are the same; $X_1$ of Formula 3-1 and $X_1$ of Formula 3-2 are the same; $X_2$ of Formula 3-1 and $X_2$ of Formula 3-2 are the same, and $X_3$ of Formula 3-1 and $X_3$ of Formula 3-2 are the same.

In another aspect, the invention provides a process for synthesizing a compound of Formula C:

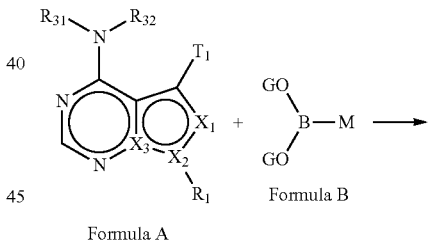

Formula A          Formula B

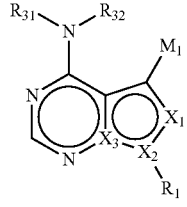

Formula C comprising the step of allowing a compound of Formula A to react with a compound of Formula B under conditions that are effective for synthesizing a compound of Formula C; wherein;

$T_1$ is halo;

$X_1$ is N or C-$E^1$, $X_2$ is N, and $X_3$ is C; or $X_1$ is N or C-$E^1$, $X_2$ is C, and $X_3$ is N; wherein no more than two ring nitrogen atoms of the compound of Formula A are adjacent; and wherein no more than two ring nitrogen atoms of the compound of Formula C are adjacent;

$R_1$ is hydrogen, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—; each of G is independently H or $R_{G1}$; and $R_{G1}$ is alkyl, alkenyl, or aryl;

or the G groups of join together to form a 5- or 6-membered cyclic moiety;

M of Formula B is a $M_1$ moiety, and wherein $M_1$ moiety of Formula B and $M_1$ moiety of Formula C are identical, having one of the following structures:

$E^1$ is —($W^1$)$_j$—$R^4$ wherein j is 0 or 1;

$W^1$ is —O—, —NR$^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)OR)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

k is 0 or 1;

$W^2$ is —O—, —NR$^7$—, —S(O)$_{0-2}$—, —C(O)—, —C(O)N($R^7$)—, —N($R^7$)C(O)—, —N($R^7$)C(O)N($R^7$)—, —N($R^7$)S(O)—, —N($R^7$)S(O)$_2$—, —C(O)O—, —CH($R^7$)N(C(O)OR)—, —CH($R^7$)N(C(O)$R^8$)—, —CH($R^7$)N(SO$_2R^8$)—, —CH($R^7$)N($R^8$)—, —CH($R^7$)C(O)N(RB)—, —CH($R^7$)N($R^8$)C(O)—, —CH($R^7$)N($R^8$)S(O)—, or —CH($R^7$)N($R^8$)S(O)$_2$—;

$R^2$ is hydrogen, halogen, —OH, —$R^{31}$, —CF$_3$, —OCF$_3$, —OR$^{31}$, —NR$^{31}R^{32}$, —NR$^{34}R^{35}$, —C(O)R$^{31}$, —CO$_2R^{31}$, —C(=O)NR$^{31}R^{32}$, —C(=O)NR$^{34}R^{35}$, —NO$_2$, —CN, —S(O)$_{0-2}R^{31}$, —SO$_2$NR$^{31}R^{32}$, —SO$_2$NR$^{34}R^{35}$, —NR$^{31}$C(=O)R$^{32}$, —NR$^{31}$C(=O)OR$^{32}$, —NR$^{31}$C(=O)NR$^{32}R^{33}$, —NR$^{31}$S(O)$_2R^{32}$, —C(=S)OR$^{31}$, —C(=O)SR$^{31}$, —NR$^{31}$C(=NR$^{32}$)NR$^{33}R^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}R^{32}$, —OC(=O)SR$^{31}$, —SC(=O)OR$^{31}$, —P(O)OR$^{31}$OR$^{32}$, —SC(=O)NR$^{31}R^{32}$, bicyclic aryl, substituted monocyclic aryl, hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{2-10}$alkyl-monocyclic aryl, monocyclic aryl-$C_{2-10}$alkyl, $C_{1-10}$alkylbicycloaryl, bicycloaryl-$C_{1-10}$alkyl, substituted $C_{1-10}$alkylaryl, substituted aryl-$C_{1-10}$alkyl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxyC$_{2-10}$alkenyl, $C_{1-10}$alkoxyC$_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{2-10}$alkenyl, aryl-$C_{2-10}$alkynyl, aryl-heterocyclyl, or hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —$R^{31}$, —CF$_3$, —OCF$_3$, —OR$^{31}$, —NR$^{31}R^{32}$, —NR$^{34}R^{35}$, —C(O)R$^{31}$, —CO$_2R^{31}$, —C(=O)NR$^{31}R^{32}$, —C(=O)NR$^{34}R^{35}$, —NO$_2$, —CN, —S(O)$_2R^{31}$, —SO$_2$NR$^{31}R^{32}$, —SO$_2$NR$^{34}R^{35}$, —NR$^{31}$C(=O)R$^{32}$, —NR$^{31}$C(=O)OR$^{32}$, —NR$^{31}$C(=O)NR$^{32}R^{33}$, —NR$^{31}$S(O)$_{0-2}R^{32}$, —C(=S)OR$^{31}$, —C(=O)SR$^{31}$, —NR$^{31}$C(=NR$^{32}$)NR$^{33}R^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}R^{32}$, —OC(=O)SR$^{31}$, —SC(=O)OR$^{31}$, —P(O)OR$^{31}$OR$^{32}$, or —SC(=O)NR$^{31}R^{32}$, and wherein each of said alkyl, cycloalkyl, heterocyclyl, or heteroalkyl moiety is unsubstituted or is substituted with one or more halo, —OH, —$R^{31}$, —CF$_3$, —OCF$_3$, —OR$^{31}$, —O-aryl, —NR$^{31}R^{32}$, —NR$^{34}R^{35}$, —C(O)R$^{31}$, —CO$_2R^{31}$, —C(=O)NR$^{34}R^{35}$, or —C(=O)NR$^{31}R^{32}$;

$R^3$ and $R^4$ are independently hydrogen, halogen, —OH, —$R^{31}$, —CF$_3$, —OCF$_3$, —OR$^{31}$, —NR$^{31}R^{32}$, —NR$^{34}R^{35}$, —C(O)R$^{31}$, —CO$_2R^{31}$, —C(=O)NR$^{31}R^{32}$, —C(=O)NR$^{34}R^{35}$, —NO$_2$, —CN, —S(O)$_{0-2}R^{31}$, —SO$_2$NR$^{31}R^{32}$, —SO$_2$NR$^{34}R^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, —SC(=O)NR$^{31}$R$^{32}$, aryl, hetaryl, C$_{1-10}$alkyl, C$_{3-8}$cycloalkyl, C$_{1-10}$alkylC$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{1-10}$alkyl-C$_{2-10}$alkenyl, C$_{1-10}$alkyl-C$_{2-10}$alkynyl, C$_{1-10}$alkylaryl, C$_{1-10}$alkylhetaryl, C$_{1-10}$alkylheterocyclyl, C$_{2-10}$alkenyl, C$_{2-10}$alkynyl, C$_{2-10}$alkenyl-C$_{1-10}$alkyl, C$_{2-10}$alkynyl-C$_{1-10}$alkyl, C$_{2-10}$alkenylaryl, C$_{2-10}$alkenylhetaryl, C$_{2-10}$alkenylheteroalkyl, C$_{2}$10 alkenylheterocyclcyl, C$_{2-10}$alkenyl-C$_{3-8}$cycloalkyl, C$_{2-10}$alkynyl-C$_{3-8}$cycloalkyl, C$_{2-10}$alkynylaryl, C$_{2-10}$alkynylhetaryl, C$_{2-10}$alkynylheteroalkyl, C$_{2-10}$alkynylheterocylyl, C$_{2-10}$alkynyl-C$_{3-8}$cycloalkenyl, C$_{1-10}$alkoxy C$_{1-10}$alkyl, C$_{1-10}$alkoxy-C$_{2-10}$alkenyl, C$_{1-10}$alkoxy-C$_{2-10}$alkynyl, heterocyclyl, heterocyclyl-C$_{1-10}$alkyl, heterocyclyl-C$_{2-10}$alkenyl, heterocyclyl-C$_{2-10}$alkynyl, aryl-C$_{1-10}$alkyl, aryl-C$_{2-10}$alkenyl, aryl-C$_{2-10}$alkynyl, aryl-heterocyclyl, hetaryl-C$_{1-10}$alkyl, hetaryl-C$_{2-10}$alkenyl, hetaryl-C$_{2-10}$alkynyl, hetaryl-C$_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

R$^5$ is halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$;

each of R$^{31}$, R$^{32}$, and R$^{33}$ is independently H or C$_{1-10}$alkyl, wherein the C$_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{10-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$C$_{1-10}$alkyl, —S(O)$_{0-2}$C$_{1-10}$alkylaryl, —S(O)$_{0-2}$ aryl, —SO$_2$N(aryl), —SO$_2$N(C$_{1-10}$alkyl)(C$_{1-10}$alkyl), —SO$_2$NH(C$_{1-10}$alkyl) or —SO$_2$NR$^{34}$R$^{35}$;

R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, hetaryl, C$_{1-6}$alkyl, or O-aryl, and wherein said 3-10 membered saturated or unsaturated ring independently contains 0, 1, or 2 more heteroatoms in addition to the nitrogen atom; each of R$^7$ and R$^8$ is independently hydrogen, C$_{1-10}$alkyl, C$_{2-10}$alkenyl, aryl, heteroaryl, heterocyclyl or C$_{3-10}$cycloalkyl, each of which except for hydrogen is unsubstituted or is substituted by one or more independent R$^6$; and R$^6$ is halo, —OR$^{31}$, —SH, —NH$_2$, —NR$^{34}$R$^{35}$, —NR$^{31}$R$^{32}$, —CO$_2$R$^{31}$, —CO$_2$aryl, —C(=O)NR$^{31}$R$^{32}$, —C(=O)NR$^{34}$R$^{35}$, —NO$_2$, —CN, —S(O)$_{0-2}$C$_{1-10}$alkyl, —S(O)$_{0-2}$aryl, —SO$_2$NR$^{34}$R$^{35}$, —SO$_2$NR$^{31}$R$^{32}$, C$_{1-10}$alkyl, C$_{1-10}$alkenyl, C$_{2-10}$alkynyl, aryl-C$_{1-10}$alkyl, aryl-C$_{2-10}$alkenyl, aryl-C$_{2-10}$alkynyl, hetaryl-C$_{1-10}$alkyl, hetaryl-C$_{2-10}$alkenyl, or hetaryl-C$_{2-10}$alkynyl, each of which is unsubstituted or is substituted with one or more independent halo, cyano, nitro, —OC$_{1-10}$alkyl, C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$; and M$_1$ of Formula B and M$_1$ of Formula C are the same; R$_5$ of Formula B and R$_5$ of Formula C are the same; R$_1$ of Formula A and R$_1$ of Formula C are the same; R$_{31}$ of Formula A and R$_{31}$ of Formula C are the same; R$_{32}$ of Formula A and R$_{32}$ of Formula C are the same; X$_1$ of Formula A and X$_1$ of Formula C are the same; X$_2$ of Formula A and X$_2$ of Formula C are the same; and X$_3$ of Formula A and X$_3$ of Formula C are the same.

In some of the embodiments of the process for synthesizing a compound of Formula C, each of the compound of Formula A and the compound of Formula C is the compound wherein:

X$_1$ and X$_2$ are N;

R$_1$ is -L-C$_{1-10}$alkyl, -L-C$_{3-8}$cycloalkyl, -L-C$_{1-10}$alkylheterocylyl, or -L-heterocyclyl, each of which is unsubstituted or is substituted by one or more independent R$^3$ substituents;

R$^3$ is hydrogen, —OH, —OR$^{31}$, —NR$^{31}$R$^{32}$, —C(O)R$^{31}$, —C(=O)NR$^{31}$R$^{32}$, —C(=O)NR$^{34}$R$^{35}$, aryl, hetaryl, C$_{1-10}$alkyl, C$_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=)R$^{32}$, NR$^{31}$C(=O)OR$^{32}$, —NR$^{31}$C(=O)NR$^{32}$R$^{33}$, —NR$^{31}$S(O)$_2$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$; and wherein —(W$^2$)$_k$— is —NR$^7$—, —N(R$^7$)C(O)— or —N(R$^7$)S(O)$_2$—.

In some of the embodiments of the process for synthesizing a compound of Formula C, the compound of Formula B has one of the following structures:

H-7
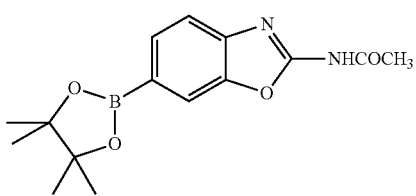

F-7
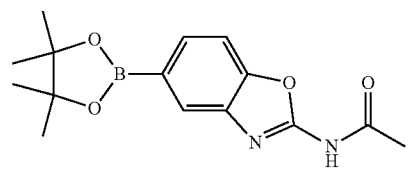

G-6
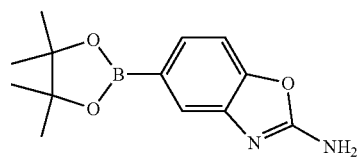

I-4
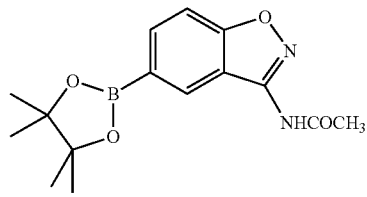

J-4
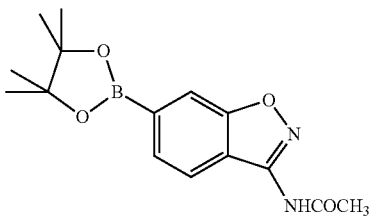

K-6
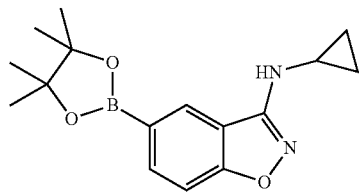

L-6
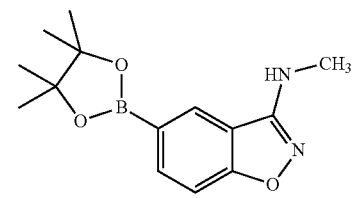

H-7-B
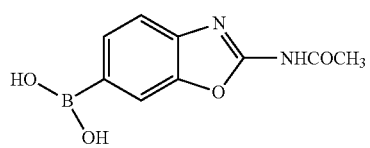

F-7-B
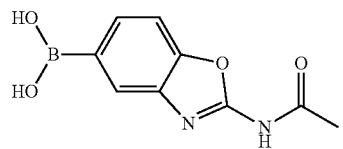

G-6-B
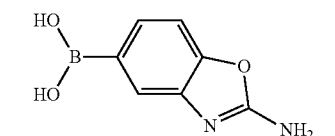

I-4-B
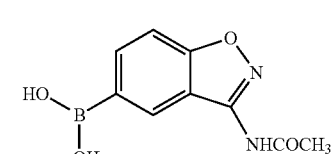

J-4-B
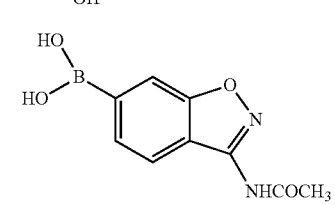

K-6-B
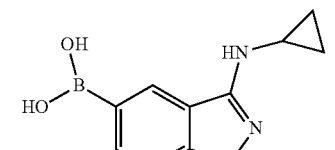

L-6-B
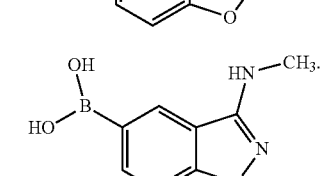

In another aspect, the invention provides a composition comprising a compound of Formula A and a compound of Formula B:

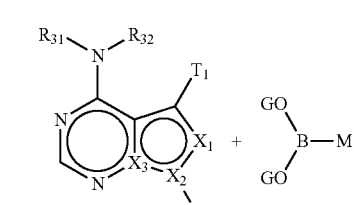

Formula A       Formula B or a salt thereof, wherein:

T is halo;

$X_1$ is N or C-$E^1$, $X_2$ is N, and $X_3$ is C; or $X_1$ is N or C-$E^1$, $X_2$ is C, and $X_3$ is N; wherein no more than two ring nitrogen atoms of the compound of Formula A are adjacent; and wherein no more than two ring nitrogen atoms of the compound of Formula C are adjacent;

each of G is independently H or $R_{G1}$; and $R_{G1}$ is alkyl, alkenyl, or aryl;

or the G groups of

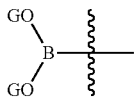

join together to form a 5- or 6-membered cyclic moiety;

M of Formula B is a $M_1$ moiety, and wherein $M_1$ moiety of Formula B has one of the following structures:

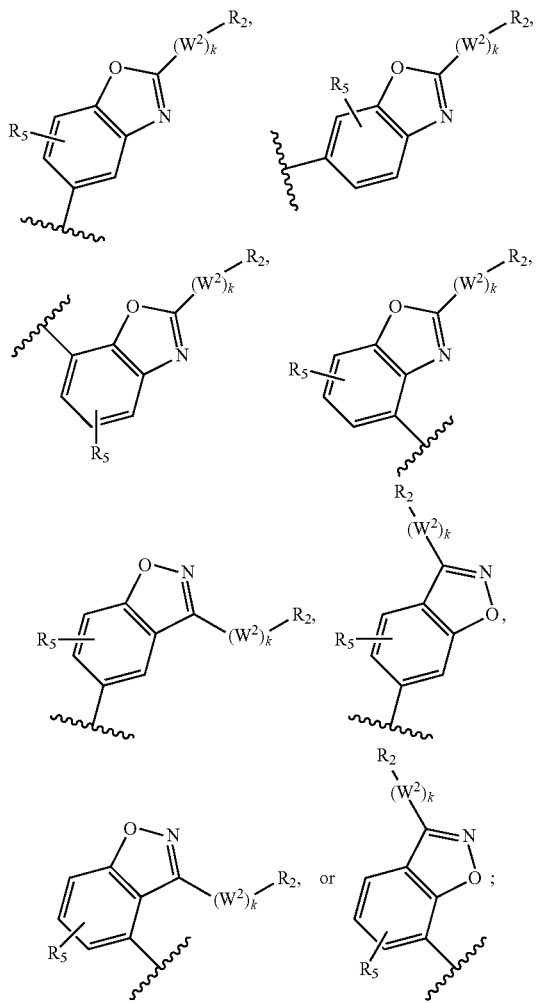

$E^1$ is —$(W^1)_j$—$R^4$ wherein j is 0 or 1;

$W^1$ is —O—, —$NR^7$—, —$S(O)_{0-2}$—, —C(O)—, —C(O)N($R^7$)—, —N($R^7$)C(O)—, —N($R^7$)S(O), —N($R^7$)S(O)$_2$, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

k is 0 or 1;

$W^2$ is —O—, —$NR^7$—, —$S(O)_{0-2}$—, —C(O)—, C(O)N($R^7$), —N($R^7$)C(O)—, —N($R^7$)C(O)N($R^8$)—, —N($R^7$)S(O)—, N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R_1$ is hydrogen, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C═O)—, —C(═O)O—, —C(═O)N($R^{31}$)—, —S—, —S(O)—, —S(O)$_2$—, —S(O)$_2$N($R^{31}$)—, or —N($R^{31}$)—;

$R^2$ is hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(═O)NR^{31}R^{32}$, —$C(═O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(═O)R^{32}$, —$NR^{31}C(═O)OR^{32}$, —$NR^{31}C(═O)NR^{32}R^{33}$, —$NR^{31}S(O)_{0-2}R^{32}$, —$C(═S)OR^{31}$, —$C(═O)SR^{31}$, —$NR^{31}C(═NR^{32})NR^{33}R^{32'}$, $NR^{31}C(═NR^{32})OR^{33}$, —$NR^{31}C(═NR^{32})SR^{33}$, —$OC(═O)OR^{33}$, —$OC(═O)NR^{31}R^{32}$, —$OC(═O)SR^{31}$, $SC(═O)OR^{31}$, —$P(O)OR^{31}OR^{32}$, —$SC(═O)NR^{31}R^{32}$, bicyclic aryl, substituted monocyclic aryl, hetaryl, $C_{1-10}$alkyl, $C_{3-8}$cycloalkyl, $C_{1-10}$alkyl $C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{2-10}$alkyl-monocyclic aryl, monocyclic aryl-$C_{2-10}$alkyl, $C_{1-10}$alkylbicycloaryl, bicycloaryl-$C_{1-10}$alkyl, substituted $C_{1-10}$alkylaryl, substituted aryl-$C_{1-10}$alkyl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynylaryl, $C_{1-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy$C_{2-10}$alkenyl, $C_{1-10}$alkoxy$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl$C_{2-10}$alkenyl, aryl-$C_{2-10}$alkynyl, aryl-heterocyclyl, or hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —$R^{31}$, —$CF_3$, $OCF_3$, —$OR^{31}$, —$NR^{31}R^{32}$, —$NR^{34}R^{35}$, —$C(O)R^{31}$, —$CO_2R^{31}$, —$C(═O)NR^{31}R^{32}$, —$C(═O)NR^{34}R^{35}$, —$NO_2$, —CN, —$S(O)_2R^{31}$, —$SO_2NR^{31}R^{32}$, —$SO_2NR^{34}R^{35}$, —$NR^{31}C(═O)R^{32}$, —$NR^{31}C(═O)OR^{32}$, —$NR^{31}C(═O)NR^{32}R^{33}$, —$NR^{31}S(O)_{0-2}R^{32}$, —$C(═S)OR^{31}$, —$C(═O)SR^{31}$, —$NR^{31}C(═NR^{32})NR^{33}R^{32}$, —$NR^{31}C(═NR^{32})OR^{33}$, —$NR^{31}C(═NR^{32})SR^{33}$, —$OC(═O)OR^{33}$, —$OC(═O)NR^{31}R^{32}$, —$OC(═O)SR^{31}$, —$SC(═O)OR^{31}$, —$P(O)OR^{31}OR^{32}$, or —$SC(═O)NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(═O)NR^{34}R^{35}$, or —$C(═O)NR^{31}R^{32}$;

$R^3$ and $R^4$ are independently hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(═O)NR^{31}R^{32}$, —$C(═O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(═O)R^{32}$, —$NR^{31}C(═O)OR^{32}$, —$NR^{31}C(═O)NR^{32}R^{33}$, —$NR^{31}S(O)_{0-2}R^{32}$, —$C(═S)OR^{31}$, —$C(═O)SR^{31}$, —$NR^{31}C(═NR^{32})NR^{31}R^{32}$, —$NR^{31}C(═NR^{32})OR^{33}$, —$NR^{31}C(═NR^{32})SR^{33}$, —$OC(═O)OR^{33}$, —$OC(═O)NR^{31}R^{32}$, —$OC(═O)SR^{31}$, —SC =O)OR$^{31}$, —P(O)OR$^{31}$OR$^{32}$, —SC(=O)NR$^{31}$R$^{32}$, aryl, hetaryl, C$_{1-10}$alkyl, C$_{3-8}$cycloalkyl, C$_{1-10}$alkylC$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{1-10}$alkyl-C$_{2-10}$alkenyl, C$_{1-10}$alkyl-C$_{2-10}$alkynyl, C$_{1-10}$alkylaryl, C$_{1-10}$alkylhetaryl, C$_{1-10}$alkylheterocyclyl, C$_{2-10}$alkenyl, C$_{2-10}$alkynyl, C$_{2-10}$alkenyl-C$_{1-10}$alkyl, C$_{2-10}$alkynyl-C$_{1-10}$alkyl, C$_{2-10}$alkenylaryl, C$_{2-10}$alkenylhetaryl, C$_{2-10}$alkenylheteroalkyl, C$_{2-10}$alkenylheterocyclyl, C$_{2-10}$alkenyl-C$_{3-8}$cycloalkyl, C$_{2-10}$alkynyl-C$_{3-8}$cycloalkyl, C$_{2-10}$alkynylaryl, C$_{2-10}$alkynylhetaryl, C$_{2-10}$alkynylheteroalkyl, C$_{2-10}$alkynylheterocylyl, C$_{2-10}$alkynyl-C$_{3-8}$cycloalkenyl, C$_{1-10}$alkoxy C$_{1-10}$alkyl, C$_{1-10}$alkoxy-C$_{2-10}$alkenyl, C$_{1-10}$alkoxy-C$_{2-10}$alkynyl, heterocyclyl, heterocyclyl-C$_{1-10}$alkyl, heterocyclyl-C$_{2-10}$alkenyl, heterocyclyl-C$_{2-10}$alkynyl, aryl-C$_{1-10}$alkyl, aryl-C$_{2-10}$alkenyl, aryl-C$_{2-10}$alkynyl, aryl-heterocyclyl, hetaryl-C$_{1-10}$alkyl, hetaryl-C$_{1-10}$alkenyl, hetaryl-C$_{2-10}$alkynyl, hetaryl-C$_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

R$^5$ is halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$; each of R$^7$ and R$^8$ is independently hydrogen, C$_{1-10}$alkyl, C$_{2-10}$alkenyl, aryl, heteroaryl, heterocyclyl or C$_{3-10}$cycloalkyl, each of which except for hydrogen is unsubstituted or is substituted by one or more independent R$^6$;

R$^6$ is halo, —OR$^{31}$, —SH, —NH$_2$, —NR$^{34}$R$^{35}$, —NR$^{31}$R$^{32}$, —CO$_2$R$^{31}$, —CO$_2$aryl, —C(=O)NR$^{31}$R$^{32}$, —C(=O)NR$^{34}$R$^{35}$, —NO$_2$, CN, —S(O)$_{0-2}$C$_{1-10}$alkyl, —S(O)$_{0-2}$aryl, —SO$_2$NR$^{34}$R$^{35}$, —SO$_2$NR$^{31}$R$^{32}$, C$_{1-10}$alkyl, C$_{2-10}$alkenyl, C$_{2-10}$alkynyl, aryl-C$_{1-10}$alkyl, aryl-C$_{2-10}$alkenyl, aryl-C$_{2-10}$alkynyl, hetaryl-C$_{1-10}$alkyl, hetaryl-C$_{2-10}$alkenyl, or hetaryl-C$_{2-10}$alkynyl, each of which is unsubstituted or is substituted with one or more independent halo, cyano, nitro, —OC$_{1-10}$alkyl, C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$;

each of R$^{31}$, R$^{32}$, and R$^{33}$ is independently H or C$_{1-10}$alkyl, wherein the C$_{1-10}$alkyl is unsubstituted or is substituted with one or more aryl, heteroalkyl, heterocyclyl, or hetaryl group, wherein each of said alkyl, aryl, heteroalkyl, heterocyclyl, or hetaryl group is unsubstituted or is substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$C$_{1-10}$alkyl, —S(O)$_{0-2}$C$_{1-10}$alkylaryl, —S(O)$_{0-2}$ aryl, —SO$_2$N(aryl), —SO$_2$N(C$_{1-10}$alkyl)(C$_{1-10}$alkyl), —SO$_2$NH(C$_{1-10}$alkyl) or —SO$_2$NR$^{34}$R$^{35}$; and R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, hetaryl, C$_{1-6}$alkyl, or O-aryl, and wherein said 3-10 membered saturated or unsaturated ring independently contains 0, 1, or 2 more heteroatoms in addition to the nitrogen atom.

In some embodiments of the composition comprising a compound of Formula A and a compound of Formula B, the compound of Formula A is the compound wherein:

$X_1$ and $X_2$ are N;

$R_1$ is -L-C$_{1-10}$alkyl, -L-C$_{3-8}$cycloalkyl, -L-C$_{1-10}$alkylheterocylyl, or -L-heterocyclyl, each of which is unsubstituted or is substituted by one or more independent R$^3$ substituents;

R$^3$ is hydrogen, —OH, —OR$^{31}$, —NR$^{31}$R$^{32}$, —C(O)R$^{31}$, —C(=O)NR$^{31}$R$^{32}$, —C(=O)NR$^{34}$R$^{35}$, aryl, hetaryl, C$_{1-10}$alkyl, C$_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$; and wherein —(W$^2$)$_k$— is —NR$^7$—, —N(R$^7$)C(O)— or —N(R$^7$)S(O)$_2$—.

In some embodiments of the composition comprising a compound of Formula A and a compound of Formula B, the compound of Formula B is a compound having one of the following formulae:

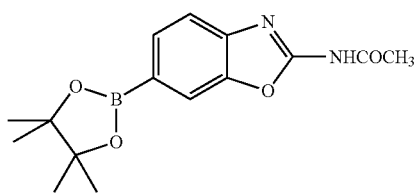

H-7

-continued

F-7
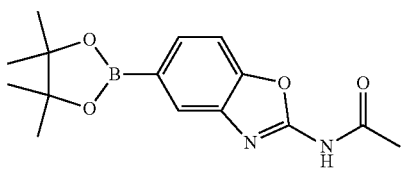

G-6
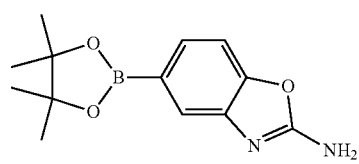

I-4
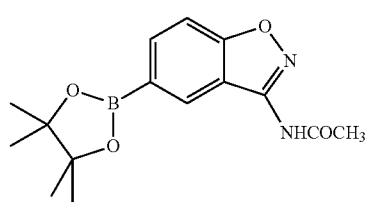

J-4
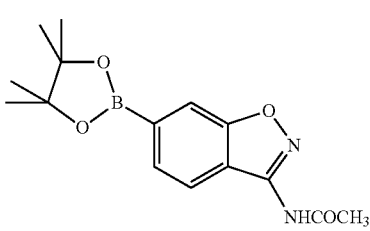

K-6
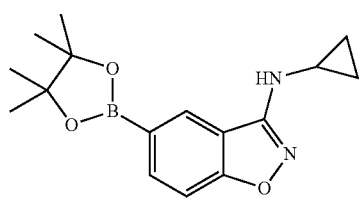

L-6
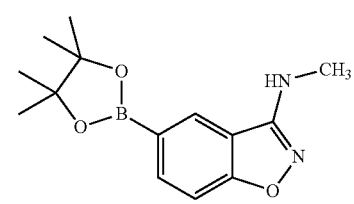

H-7-B
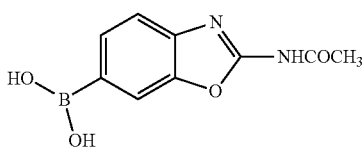

F-7-B
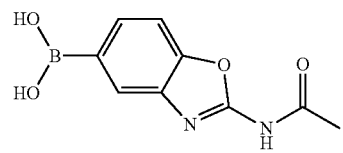

-continued

G-6-B
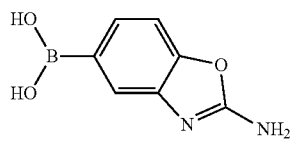

I-4-B
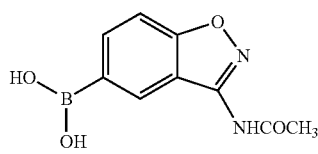

J-4-B
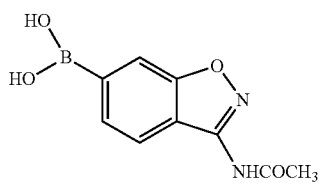

K-6-B

L-6-B
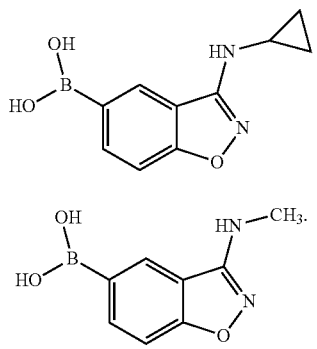

In some embodiments of the composition comprising a compound of Formula A and a compound of Formula B, the composition further comprises a compound of Formula C:

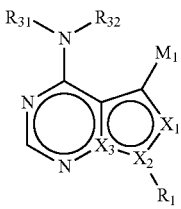

Formula C or a salt thereof, wherein:

$M_1$ of Formula B and $M_1$ of Formula C are the same; $R_5$ of Formula B and $R_5$ of Formula C are the same; $R_1$ of Formula A and $R_1$ of Formula C are the same; $R_1$ of Formula A and $R_1$ of Formula C are the same; $R_{31}$ of Formula A and $R_{31}$ of Formula C are the same; $R_{32}$ of Formula A and $R_{32}$ of Formula C are the same; $X_1$ of Formula A and $X_1$ of Formula C are the same; $X_2$ of Formula A and $X_2$ of Formula C are the same; and $X_3$ of Formula A and $X_3$ of Formula C are the same.

In a further aspect the invention provides a compound of Formula I-B:

Formula I-B

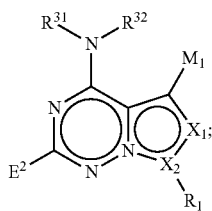

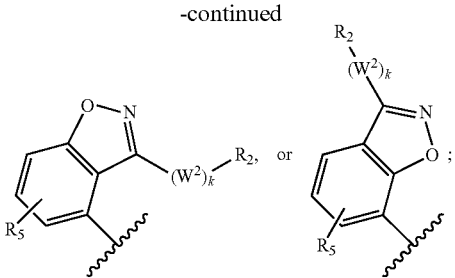

or a pharmaceutically acceptable salt thereof, wherein:

$X_1$ is N and $X_2$ is C, or $X_1$ is C-$E^1$ and $X_2$ is C;

$R_1$ is hydrogen, L-$C_{2-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{1-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;

$M_1$ is a moiety having one of the following structures:

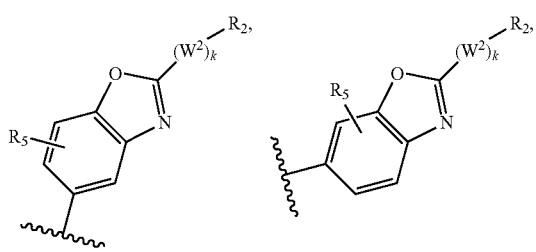

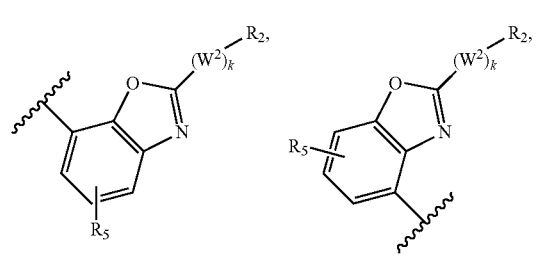

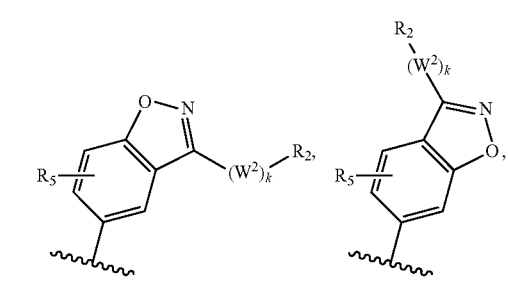

k is 0 or 1;

$E^1$ and $E^2$ are independently —($W^1$)$_j$—$R^4$;

j in $E^1$ or j in $E^2$, is independently 0 or 1;

$W^1$ is —O—, —N$R^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$W^2$ is —O—, —N$R^7$—, —S(O)$_{0-2}$—, —C(O)—, —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R^3$ and $R^4$ are independently hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, —SC(=O)N$R^{31}R^{32}$, aryl, hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC (=O)OR³¹, —P(O)OR³¹OR³², or —SC(=O)NR³¹R³², and wherein each of said alkyl, cycloalkyl, heterocyclyl, or heteroalkyl moiety is unsubstituted or is substituted with one or more halo, —OH, —R³¹, —CF₃, —OCF₃, —OR³¹, —O-aryl, —NR³¹R³², —NR³⁴R³⁵, —C(O)R³¹, —CO₂R³¹, —C(=O)NR³⁴R³⁵, or —C(=O)NR³¹R³²;

R⁵ is hydrogen, halogen, —OH, —R³¹, —CF₃, —OCF₃, —OR³¹, —NR³¹R³², —NR³⁴R³⁵, —C(O)R³¹, —CO₂R³¹, —C(=O)NR³¹R³², —C(=O)NR³⁴R³⁵, —NO₂, —CN, —S(O)₀₋₂R³¹, —SO₂NR³¹R³², —SO₂NR³⁴R³⁵, —NR³¹C(=O)R³², —NR³¹C(=O)OR³², —NR³¹C(=O)NR³²R³³, —NR³¹S(O)₀₋₂R³², —C(=S)OR³¹, —C(=O)SR³¹, —NR³¹C(=NR³²)NR³³R³², —NR³¹C(=NR³²)OR³³, —NR³¹C(=NR³²)SR³³, —OC(=O)OR³³, —OC(=O)NR³¹R³², —OC(=O)SR³¹, —SC(=O)OR³¹, —P(O)OR³¹OR³², or —SC(=O)NR³¹R³²;

R² is hydrogen, halogen, —OH, —R³¹, —CF₃, —OCF₃, —OR³¹, —NR³¹R³², —NR³⁴R³⁵, —C(O)R³¹, —CO₂R³¹, —C(=O)NR³¹R³², —C(=O)NR³⁴R³⁵, —NO₂, —CN, —S(O)₀₋₂R³¹, —SO₂NR³¹R³², —SO₂NR³⁴R³⁵, —NR³¹C(=O)R³², —NR³¹C(=O)OR³², —NR³¹C(=O)NR³²R³³, —NR³¹S(O)₀₋₂R³², —C(=S)OR³¹, —C(=O)SR³¹, —NR³¹C(=NR³²)NR³³R³², —NR³¹C(=NR³²)OR³³, —NR³¹C(=NR³²)SR³³, —OC(=O)OR³³, —OC(=O)NR³¹R³², —OC(=O)SR³¹, —SC(=O)OR³¹, —P(O)OR³¹OR³², —SC(=O)NR³¹R³², bicyclic aryl, substituted monocyclic aryl, hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{2-10}$alkyl-monocyclic aryl, monocyclic aryl-$C_{2-10}$alkyl, $C_{1-10}$alkylbicycloaryl, bicycloaryl-$C_{1-10}$alkyl, substituted $C_{1-10}$alkylaryl, substituted aryl-$C_{1-10}$alkyl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclyl, $C_{2-10}$alkenyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy$C_{2-10}$alkenyl, $C_{1-10}$alkoxy$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{2-10}$alkenyl, aryl-$C_{2-10}$alkynyl, aryl-heterocyclyl, or hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —R³¹, —CF₃, —OCF₃, —OR³¹, —NR³¹R³², —NR³⁴R³⁵, —C(O)R³¹, —CO₂R³¹, —C(=O)NR³¹R³², —C(=O)NR³⁴R³⁵, —NO₂, —CN, —S(O)₂R³¹, —SO₂NR³¹R³², —SO₂NR³⁴R³⁵, —NR³¹C(=O)R³², —NR³¹C(=O)OR³², —NR³¹C(=O)NR³²R³³, —NR³¹S(O)₂R³², —C(=S)OR³¹, —C(=O)SR³¹, —NR³¹C(=NR³²)NR³³R³², —NR³¹C(=NR³²)OR³³, —NR³¹C(=NR³²)SR³³, —OC(=O)OR³³, —OC(=O)NR³¹R³², —OC(=O)SR³¹, —SC(=O)OR³¹, —P(O)OR³¹OR³², or —SC(=O)NR³¹R³², and wherein each of said alkyl, cycloalkyl, heterocyclyl, or heteroalkyl moiety is unsubstituted or is substituted with one or more halo, —OH, —R³¹, —CF₃, —OCF₃, —OR³¹, —O-aryl, —NR³¹R³², —NR³⁴R³⁵, —C(O)R³¹, —CO₂R³¹, —C(=O)NR³⁴R³⁵, or —C(=O)NR³¹R³²;

each of R³¹, R³², and R³³ is independently H or $C_{1-10}$alkyl, wherein the $C_{1-10}$alkyl is unsubstituted or is substituted with one or more aryl, heteroalkyl, heterocyclyl, or hetaryl group, wherein each of said alkyl, aryl, heteroalkyl, heterocyclyl, or hetaryl group is unsubstituted or is substituted with one or more halo, —OH, —$C_{1-10}$alkyl, —CF₃, —O-aryl, —OCF₃, —O$C_{1-10}$alkyl, —NH₂, —N($C_{1-10}$alkyl)($C_{1-10}$alkyl), —NH($C_{1-10}$alkyl), —NH(aryl), —NR³⁴R³⁵, —C(O)($C_{1-10}$alkyl), —C(O)($C_{1-10}$alkyl-aryl), —C(O)(aryl), —CO₂—$C_{1-10}$alkyl, —CO₂—$C_{1-10}$alkylaryl, —CO₂-aryl, —C(=O)N($C_{1-10}$alkyl)($C_{1-10}$alkyl), —C(=O)NH($C_{1-10}$alkyl), —C(=O)NR³⁴R³⁵, —C(=O)NH₂, —OCF₃, —O($C_{1-10}$alkyl), —O-aryl, —N(aryl)($C_{1-10}$alkyl), —NO₂, —CN, —S(O)₀₋₂$C_{1-10}$alkyl, —S(O)₀₋₂$C_{1-10}$alkylaryl, —S(O)₀₋₂ aryl, —SO₂N(aryl), —SO₂N($C_{1-10}$alkyl)($C_{1-10}$alkyl), —SO₂NH($C_{1-10}$alkyl) or —SO₂NR³⁴R³⁵ s;

R³⁴ and R³⁵ in —NR³⁴R³⁵, —C(=O)NR³⁴R³⁵, or —SO₂NR³⁴R³⁵, are taken together with the nitrogen atom to which they are attached to form a 3-10 membered saturated or unsaturated ring; wherein said ring is independently unsubstituted or is substituted by one or more —NR³¹R³², hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom;

each of R⁷ and R⁸ is independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent R⁶; and R⁶ is halo, —OR³¹, —SH, —NH₂, —NR³⁴R³⁵, —NR³¹R³², —CO₂R³¹, —CO₂aryl, —C(=O)NR³¹R³², —C(=O)NR³⁴R³⁵, —NO₂, —CN, —S(O)₀₋₂$C_{1-10}$alkyl, —S(O)₀₋₂aryl, —SO₂NR³⁴R³⁵, —SO₂NR³¹R³², $C_{1-10}$alkyl, $C_{2-10}$alkenyl, $C_{2-10}$alkynyl, aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, or hetaryl-$C_{2-10}$alkynyl, each of which is unsubstituted or is substituted with one or more independent halo, cyano, nitro, —O$C_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)NR³¹R³², —C(=O)NR³⁴R³⁵, —SO₂NR³⁴R³⁵, —SO₂NR³¹R³², —NR³¹R³², or —NR³⁴R³⁵.

In some embodiments the compound Formula I-B, is the compound wherein M₁ is:

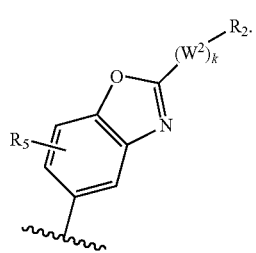

In yet another aspect, the invention provides a compound of Formula IV-A or Formula IV-B:

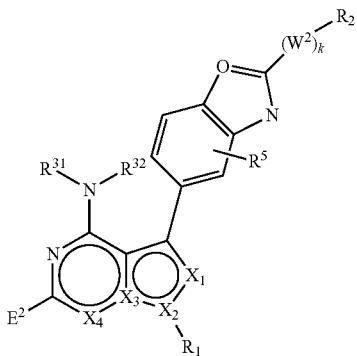

Formula IV-A

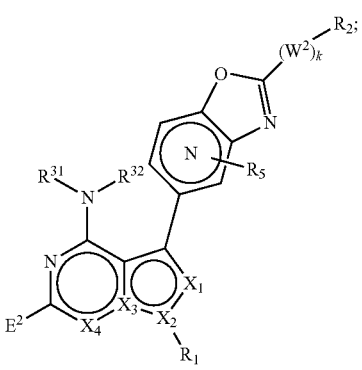

Formula IV-B or a pharmaceutically acceptable salt thereof, wherein:

$X_1$ is N or C-$E^1$, $X_2$ is N, and $X_3$ is C; or $X_1$ is N or C-$E^1$, $X_2$ is C, $X_3$ is N, and $X_4$ is C$R^9$ or N;

$R_1$ is —H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocyclyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;

k is 0 or 1;

$E^1$ and $E^2$ are independently —($W^1$)$_j$—$R^4$;

j in $E^1$ or j in $E^2$, is independently 0 or 11;

$W^1$ is —O—, —N$R^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2$$R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$W^2$ is —O—, —N$R^7$—, —S(O)$_{0-2}$—, C(O), —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2$$R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R^3$ and $R^4$ are independently hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2$$R^{31}$, —C(=O)N$R^{31}R^{32}$, —C(=O)N$R^{34}R^{35}$, —NO$_2$, —CN, —S(O)$_{0-2}$$R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}$$R^{32}$, —C(=S)O$R^{31}$, —C(=O)S$R^{31}$, —N$R^{31}$C(=N$R^{32}$)N$R^{33}R^{34}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, SC(=O)O$R^{31}$, —P(O)O$R^{31}$O$R^{32}$, —SC(=O)N$R^{31}R^{32}$, aryl, hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl $C_{2-10}$alkynyl, hetaryl $C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2$$R^{31}$, —C(=O)N$R^{31}R^{32}$, —C(=O)N$R^{34}R^{35}$, —NO$_2$, —CN, —S(O)$_2$$R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}$$R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, or —SC(=O)N$R^{31}R^{32}$, and wherein each of said alkyl, cycloalkyl, heterocyclyl, or heteroalkyl moiety is unsubstituted or is substituted with one or more halo, —OH, —$R^{31}$, —CF$_3$, —OCF$_3$, —O$R^{31}$, —O-aryl, —N$R^{31}R^{32}$, —N$R^{34}R^{35}$, —C(O)$R^{31}$, —CO$_2$$R^{31}$, —C(=O)N$R^{34}R^{35}$, or —C(=O)N$R^{31}R^{32}$;

$R^2$ is hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2$$R^{31}$, —C(=O)N$R^{31}R^{32}$, —C(=O)N$R^{34}R^{35}$, —NO$_2$, —CN, —S(O)$_2$$R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}$$R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, —SC(=O)N$R^{31}R^{32}$, bicyclic aryl, substituted monocyclic aryl, hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{2-10}$alkyl-monocyclic aryl, monocyclic aryl-$C_{2-10}$alkyl, $C_{1-10}$alkylbicycloaryl, bicycloaryl-$C_{1-10}$alkyl, substituted $C_{1-10}$alkylaryl, substituted aryl-$C_{1-10}$alkyl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy$C_{2-10}$alkenyl, $C_{1-10}$alkoxy$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{2-10}$alkenyl, aryl-$C_{2-10}$alkynyl, aryl-heterocyclyl, or hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_2R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_2R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, $NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_2R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$;

each of $R^{31}$, $R^{32}$, and $R^{33}$ is independently H or $C_{1-10}$alkyl, wherein the $C_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —S(O)$_{0-2}C_{1-10}$alkyl, —S(O)$_{0-2}C_{1-10}$alkylaryl, —S(O)$_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$;

$R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom;

each of $R^7$ and $R^8$ is independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, —C(=O)$NR^{34}R^{35}$, —$NO_2$, —CN, —S(O)$_{0-2}C_{1-10}$alkyl, —S(O)$_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)$NR^{31}R^{32}$, —C(=O)$NR^{34}R^{35}$, —$SO_2NR^{34}R^{35}$, —$SO_2NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, —C(=O)$NR^{34}R^{35}$, —$NO_2$, —CN, —S(O)$_{0-2}C_{1-10}$ alkyl, —S(O)$_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)$NR^{31}R^{32}$, —C(=O)$NR^{34}R^{35}$, —$SO_2NR^{34}R^{35}$, —$SO_2NR^{31}R^{32}$, —$NR^{31}R^{32}$, or —$NR^{34}R^{35}$.

In some embodiments of the compound of Formula IV-A or Formula IV-B, $X_4$ is $CR^9$. In other embodiments, $X_4$ is N.

The compounds of the invention inhibit a protein kinase. In some embodiments of the compounds of the invention, the compound inhibits a lipid kinase. In other embodiments of the compounds of the invention, the compound inhibits a protein kinase and a lipid kinase. In some embodiments of the compounds of the invention, the compound inhibits a kinase selected from the group consisting of PI3 kinase α, PI3 kinase β, PI3 kinase γ, PI3 kinase δ, DNA-PK, mTorC (including mTorC1 and mTorC2), Abl. VEGFR, EphB4, Tie2, Flt3, PDGFR, RET, InsR, ATM, ATR, hSmg-1, and IGFR.

In some embodiments, a compound of the invention or a pharmaceutically acceptable salt thereof inhibits mTor at an IC50 value of less than about 100 nM. In other embodiments, a compound of the invention or a pharmaceutically acceptable salt thereof inhibits mTor at an IC50 value of less than about 10 nM.

In a further aspect, the invention provides a composition comprising a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof and a pharmaceutically acceptable carrier.

In some embodiments of the compositions of the invention, a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof, is a compound wherein $E^2$ is —H; $X_1$ and $X_2$ are N; $R_1$ is -L-$C_{1-10}$alkyl, -L-$C_{3-8}$cycloalkyl, -L-$C_{1-10}$alkylheterocyclyl, or -L-heterocyclyl, each of which is unsubstituted or is substituted by one or more independent $R^3$; $R^3$ is hydrogen, —OH, —$OR^{31}$, —$NR^{31}R^{32}$, —C(O)$R^{31}$, —C(=O)$NR^{31}R^{32}$, —C(=O)$NR^{34}R^{35}$, aryl, hetaryl, $C_{1-4}$alkyl, $C_{1-10}$alkyl, $C_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)

$NR^{32}R^{33}$, $-NR^{31}S(O)_{0-2}R^{32}$, $-C(=S)OR^{31}$, $-C(=O)SR^{31}$, $-NR^{31}C(=NR^{32})NR^{33}R^{32}$, $-NR^{31}C(=NR^{32})OR^{33}$, $-NR^{31}C(=NR^{32})SR^{33}$, $-OC(=O)OR^{33}$, $-OC(=O)NR^{31}R^{32}$, $-OC(=O)SR^{31}$, $-SC(=O)OR^{31}$, $-P(O)OR^{31}OR^{32}$, or $-SC(=O)NR^{31}R^{32}$ s, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, $-OH$, $-R^{31}$, $-CF_3$, $-OCF_3$, $-OR^{31}$, $-O$-aryl, $-NR^{31}R^{32}$, $-NR^{34}R^{35}$, $-C(O)R^{31}$, $-CO_2R^{31}$, $-C(=O)NR^{34}R^{35}$, or $-C(=O)NR^{31}R^{32}$; and wherein $-(W^2)_k-$ is $-NR^7-$, $-N(R^7)C(O)-$ or $-N(R^7)S(O)_2-$.

In some embodiments of the compositions of the invention, a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof, is a compound wherein $X_4$ is $CR^9$. In another embodiment, $X_4$ is N.

In some embodiments of the compositions of the invention, a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof, is a compound wherein $E^2$ is $-H$. In some embodiments of the compounds of the invention, $X_1$ is N and $X_2$ is N. In other embodiments of the compounds of the invention, $X_1$ is $C-E^1$ and $X_2$ is N. In one embodiment of the compounds of the invention, $X_1$ is NH and $X_2$ is C.

In some embodiments of the compositions of the invention, a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof, is a compound wherein $R_{31}$ and $R_{32}$ are $-H$.

In some embodiments of the compositions of the invention, a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof, is a compound wherein $-(W^2)_k-$ is $-NR^7-$, $-N(R^7)C(O)-$, $-N(R^7)C(O)N(R^8)-$, or $-N(R^7)S(O)_2-$. In other embodiments, $-(W^2)_k-$ is $-NH-$. In another embodiment, $-(W^2)_k-$ is $-(CH)_2-$. In yet another embodiment, $-(W^2)_k-$ is $NHC(O)-$. In a further embodiment of the compounds of the invention, $-(W^2)_k-$ is $-N(R^7)C(O)N(R^8)-$. In another embodiment of the compounds of the invention, $-(W^2)_k-$ is $-NHS(O)_2-$.

In some embodiments of the compositions of the invention, a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof, is a compound wherein $R_1$ is -L-$C_{1-10}$alkyl, -L-$C_{3-8}$cycloalkyl, -L-$C_{1-10}$alkylheterocylyl, or -L-heterocyclyl, each of which is unsubstituted or is substituted by one or more independent $R^3$, wherein $R^3$ is hydrogen, $-OH$, $-OR^{31}$, $-C(O)R^{31}$, $-C(=O)NR^{31}R^{32}$, $-C(=O)NR^{34}R^{35}$, aryl, hetaryl, $C_{1-10}$alkyl, $C_{3-8}$cycloalkyl, or heterocyclyl, wherein each of said aryl, heteroaryl, alkyl, cycloalkyl, or heterocyclyl moiety is unsubstituted or is substituted with one or more alkyl or $-OH$. In some embodiments of the compounds of the invention, $R_1$ is unsubstituted or is substituted with $C_{1-10}$alkyl or cyclo$C_{3-10}$alkyl.

In some embodiments of the compositions of the invention, a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof, is a compound wherein $R^2$ is alkyl. In yet other embodiments, $R^2$ is methyl. In other embodiments of the compounds of the invention, $R^2$ is isopropyl. In some embodiments, $R^2$ is cycloalkyl. In other embodiments, $R^2$ is cyclopropyl.

In another aspect of the invention, a method is provided of inhibiting activity of a protein kinase and/or a lipid kinase present in a cell, comprising contacting said cell with an effective amount of a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3.

In some embodiments of the methods of the invention, a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof, is a compound wherein $E^2$ is $-H$; $X_1$ and $X_2$ are N; $R_1$ is -L-$C_{1-10}$alkyl, -L-$C_{3-8}$cycloalkyl, -L-$C_{1-10}$alkylheterocylyl, or -L-heterocyclyl, each of which is unsubstituted or is substituted by one or more independent $R^3$; $R^3$ is hydrogen, $-OH$, $-OR^{31}$, $-NR^{31}R^{32}$, $-C(O)R^{31}$, $-C(=O)NR^{31}R^{32}$, $-C(=O)NR^{34}R^{35}$, aryl, hetaryl, $C_{1-4}$alkyl, $C_{2-10}$alkyl, $C_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, $-OH$, $-R^{31}$, $-CF_3$, $-OCF_3$, $-OR^{31}$, $-NR^{31}R^{32}$, $-NR^{34}R^{35}$, $-C(O)R^{31}$, $-CO_2R^{31}$, $-C(=O)NR^{31}R^{32}$, $-C(=O)NR^{34}R^{35}$, $-NO_2$, $-CN$, $-S(O)_{0-2}R^{31}$, $-SO_2NR^{31}R^{32}$, $-SO_2NR^{34}R^{35}$, $-NR^{31}C(=O)R^{32}$, $-NR^{31}C(=O)OR^{32}$, $-NR^{31}C(=O)NR^{32}R^{33}$, $-NR^{31}S(O)_{0-2}R^{32}$, $-C(=S)OR^{31}$, $-C(=O)SR^{31}$, $-NR^{31}C(=NR^{32})NR^{33}R^{32}$, $-NR^{31}C(=NR^{32})OR^{33}$, $-NR^{31}C(=NR^{32})SR^{33}$, $-OC(=O)OR^{33}$, $-OC(=O)NR^{31}R^{32}$, $-OC(=O)SR^{31}$, $-SC(=O)OR^{31}$, $-P(O)OR^{31}OR^{32}$, or $-SC(=O)NR^{31}R^{32}$ s, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, $-OH$, $-R^{31}$, $-CF_3$, $-OCF_3$, $-OR^{31}$, $-O$-aryl, $-NR^{31}R^{32}$, $-NR^{34}R^{35}$, $-C(O)R^{31}$, $-CO_2R^{31}$, $-C(=O)NR^{34}R^{35}$, or $-C(=O)NR^{31}R^{32}$; and wherein $-(W^2)_k-$ is $-NR^7-$, $-N(R^7)C(O)-$ or $N(R^7)S(O)_2-$.

In some embodiments of the methods of the invention, a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof, is a compound wherein $X_4$ is $CR^9$. In another embodiment, $X_4$ is N.

In some embodiments of the methods of the invention, a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof, is a compound wherein $E^2$ is —H. In some embodiments of the compounds of the invention, $X_1$ is N and $X_2$ is N. In other embodiments of the compounds of the invention, $X_1$ is C-$E^1$ and $X_2$ is N. In one embodiment of the compounds of the invention, $X_1$ is NH and $X_2$ is C.

In some embodiments of the methods of the invention, a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof, is a compound wherein $R_{31}$ and $R_{32}$ are —H.

In some embodiments of the methods of the invention, a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof, is a compound wherein —$(W^2)_k$— is —$NR^7$—, —$N(R^7)C(O)$—, —$N(R^7)C(O)N(R^8)$—, or —$N(R^7)S(O)_2$—. In other embodiments, —$(W^2)_k$— is —NH—. In another embodiment, —$(W^2)_k$— is —$(CH)_2$—. In yet another embodiment, —$(W^2)_k$— is —NHC(O)—. In a further embodiment of the compounds of the invention, —$(W^2)_k$— is —$N(R^7)C(O)N(R^8)$—. In another embodiment of the compounds of the invention, —$(W^2)_k$— is —$NHS(O)_2$—.

In some embodiments of the methods of the invention, a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof, is a compound wherein $R_1$ is -L-$C_{1-10}$alkyl, -L-$C_{3-8}$cycloalkyl, -L-$C_{3-10}$alkylheterocylyl, or -L-heterocyclyl, each of which is unsubstituted or is substituted by one or more independent $R^3$, wherein $R^3$ is hydrogen, —OH, —$OR^{31}$, —$C(O)R^{31}$, —$C(=O)NR^{31}R^{32}$, —$C(=O)NR^{34}R^{35}$, aryl, hetaryl, $C_{1-10}$ alkyl, $C_{3-8}$cycloalkyl, or heterocyclyl, wherein each of said aryl, heteroaryl, alkyl, cycloalkyl, or heterocyclyl moiety is unsubstituted or is substituted with one or more alkyl or —OH. In some embodiments of the compounds of the invention, $R_1$ is unsubstituted or is substituted with $C_{1-10}$alkyl or cyclo$C_{3-10}$alkyl.

In some embodiments of the compositions of the invention, a compound of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, or N-3, or a pharmaceutically acceptable salt thereof, is a compound wherein $R^2$ is alkyl. In yet other embodiments, $R^2$ is methyl. In other embodiments of the compounds of the invention, $R^2$ is isopropyl. In some embodiments, $R^2$ is cycloalkyl. In other embodiments, $R^2$ is cyclopropyl.

In some of the embodiments of the methods of the invention, the inhibiting takes place in a subject suffering from a disorder selected from the group consisting of cancer, bone disorder, inflammatory disease, immune disease, nervous system disease, metabolic disease, respiratory disease, and cardiac disease. Further, in some embodiments of the method of the invention a second therapeutic agent is administered.

In some embodiments, one or more compounds of the invention yield selective inhibition of mTor-mediated signal transduction as compared to PI3K. In some other embodiments, the compounds provided herein can inhibit mTor-mediated activity more effectively than rapamycin, hence providing an alternative treatment for rapamycin-resistant conditions.

In some embodiments, one or more compounds of the invention selectively inhibits both mTorC1 and mTorC2 activity relative to all type I phosphatidylinositol 3-kinases (PI3-kinase) consisting of PI3-kinase α, PI3-kinase β, PI3-kinase γ, and PI3-kinase δ. In some embodiments, one or more compounds of the invention selectively inhibits both mTor activity with an IC50 value of about 100 nM, 50 nM, 10 nM, 5 nM, 100 pM, 10 pM or even 1 pM, or less as ascertained in an in vitro kinase assay. In some embodiments, one or more compounds of the invention is substantially ineffective in inhibiting a type I PI3-kinase at a concentration of 100 nM, 200 nM, 500 nM, or 1 uM, 5 uM or 10 uM, or higher in an in vitro kinase assay.

In some embodiments, one or more compounds of the invention inhibits phosphorylation of Akt (S473) and Akt (T308) more effectively than rapamycin when tested at a comparable molar concentration in an in vitro kinase assay.

In some embodiments, one or more compounds of the invention competes with ATP for binding to ATP-binding site on mTorC1 and/or mTorC2.

In some embodiments, one or more compounds of the invention causes apoptosis of said cell or cell cycle arrest.

The present invention provides methods and composition for inhibiting cell proliferation. In one embodiment, the method comprises contacting a cell with one or more compounds of the invention that selectively inhibits mTorC1 and/or mTorC2 activity relative to one or more type I phosphatidylinositol 3-kinases (PI3-kinase) ascertained by an in vitro kinase assay, wherein the one or more type I PI3-kinase is selected from the group consisting of PI3-kinase α, PI3-kinase β, PI3-kinase γ, and PI3-kinase δ. In some embodiment, the inhibition of cell-proliferation is evidenced by an assay selected from the group consisting of an MTS cell proliferation assay, a resazurin assay, a colony formation assay, flow cytometry, and a cell division tracker dye assay.

In a separate and related embodiment, the present invention provides a method of inhibiting phosphorylation of both Akt (S473) and Akt (T308) in a cell, comprising contacting a cell with an effective amount of one or more compounds of the invention that selectively inhibits both mTorC1 and mTorC2 activity relative to one or more type I phosphatidylinositol 3-kinases (PI3-kinase) as ascertained by a cell-based assay or an in vitro kinase assay, wherein the one or more type I PI3-kinase is selected from the group consisting of PI3-kinase α, PI3-kinase β, PI3-kinase γ, and PI3-kinase δ, thereby Akt phosphorylation at residues S473 and T308 is simultaneously inhibited.

In another embodiment, the present invention provides a method of substantially inhibiting proliferation of a neoplastic cell comprising contacting the cell with an effective amount of one or more compounds of the invention that inhibits full activation of Akt in a cell and an anti-cancer agent, wherein said inhibition of cell proliferation is enhanced through a synergistic effect of said compound and said anti-cancer agent.

In yet another embodiment, the present invention provides a method of ameliorating a medical condition mediated by mTorC1 and/or mTorC2, comprising administering to a subject in need thereof a therapeutically effective amount of one or more compounds of the invention that selectively inhibits mTorC1 and/or mTorC2 activity relative to one or more type I phosphatidylinositol 3-kinases (PI3-kinase) as ascertained in a cell-based assay or an in vitro kinase assay, wherein the one or more type I PI3-kinase is selected from the group consisting of PI3-kinase α, PI3-kinase β, PI3-kinase γ, and PI3-kinase δ.

Also provided in the present invention is a combination treatment for a subject diagnosed with or at risk of a neoplastic condition, comprising administering to said subject a therapeutically effective amount of one or more compounds of the invention that substantially inhibits full activation of Akt in a cell and an anti-cancer agent, wherein the efficacy of said treatment is enhanced through a synergistic effect of said compound and said anti-cancer agent.

In some embodiment, the compound utilized in the subject methods is a compound that selectively inhibits both mTorC1 and mTORC2 activity relative to all type I phosphatidylinositol 3-kinases (PI3-kinase) consisting of PI3-kinase α, PI3-kinase β, PI3-kinase γ, and PI3-kinase δ.

In some other embodiments, the anti-cancer agent utilized in the subject methods can include but are not limited to rapamycin, Gleevec, or derivative thereof, which inhibits a mammalian target of rapamycin or Gleevec.

A wide variety of neoplastic conditions can be treated using one or more of the subject compositions. Such conditions include but are not limited to neoplastic condition such as restenosis, cancer selected from B cell lymphoma, T cell lymphoma, non small cell lung carcinoma, and leukemia, or an autoimmune disorder.

The compound of the invention and/or the anti-cancer agent can be administered parenterally, orally, intraperitoneally, intravenously, intraarterially, transdermally, intramuscularly, liposomally, via local delivery by catheter or stent, subcutaneously, intraadiposally, or intrathecally.

INCORPORATION BY REFERENCE

All publications and patent applications mentioned in this specification are herein incorporated by reference in their entirety as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A-1B summarizes the results of cell proliferation inhibition assays performed with a wide range of neoplastic cell lines in vitro using conventional anti-cancer drugs or a compound of the present invention such as a compound of Table 1. The experimental procedure is described herein, e.g., in Example 17. The degree of inhibition is reported in the Figure herein as +, ++, +++, ++++, or +++++ in the order of increased magnitude in inhibiting cell proliferation. The results demonstrate that one or more compounds of the invention yields 50% inhibition of cell proliferation at a concentration that is one or two orders of magnitude less than that of the conventional anti-cancer drugs when tested under the same condition.

FIG. 6 depicts the effects of a compound of Table 1 of the present invention on PC3 cell proliferation, PC3 pAKT activation, and primary tumor cell line proliferation. Additionally, the specificity of a compound of Table 1 was tested by culturing Jurakt cells in whole blood to test for non-specific binding/inactivation of the one or more compounds by components of whole blood.

FIG. 7A-7B depict the effect of a compound of Table 1 of the present invention on cellular proliferation and PI3K pathway activation as compared to rapamycin. FIG. 7A depicts a graph showing the dose response curve of PC3 cell proliferation in response to rapamycin and a compound of the invention from Table 1. FIG. 7B depicts a western blot analysis of inhibition of phosphorylation of PI3K pathway targets by one or more compounds selected from Table 1 as compared to rapamycin.

FIG. 8A-8B depicts a comparison of the effect of a compound of Table 1 of the present invention on the proliferation of the indicated cell lines. FIG. 8A depicts the IC$_{50}$ of the compound for inhibition of cell lines derived from lung and colon and lists the respective proliferation activating mutations associated with those cell lines. FIG. 8B depicts the effects of a compound of Table 1 of the present invention on proliferation of cell lines comprising the various activating mutations indicated in comparison to the inhibition provided by a Pan PI3 kinase inhibitor or a Pan PI3 kinase inhibitor that also inhibits mTOR.

FIG. 9A-9B depict the effects of a compound of Table 1 of the present invention on cell cycle progression in HCT116 and SW620 cells as compared to various other compounds. FIG. 9A depicts the inhibiting effect of the compound at 500 nM on cell cycle progression as compared to DMSO vehicle control and as compared to 10 uM doxorubicin. FIG. 9B depicts the effect of the indicated compounds on the population of cells residing in $G_0/G_1$ phase during culture for two different cell lines.

FIG. 12 further depicts the size of the excised U87 tumors which decreases with an increasing dose of a compound of the present invention.

DETAILED DESCRIPTION OF THE INVENTION

Figure 2:
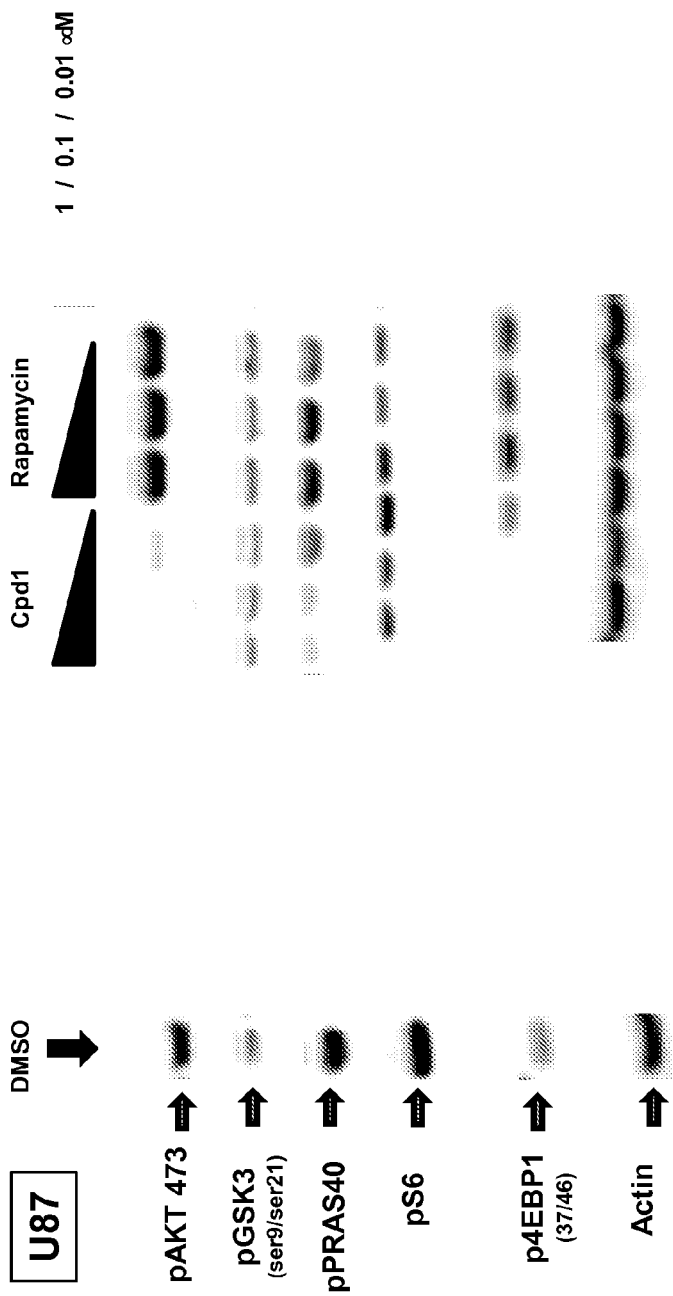
FIG. 2 is a western blot illustrating the dose dependent effect of a compound of Table 1 in inhibiting pAKT phosphorylation at residue 47 as well as other signalling molecules downstream of mTOR including p4EBP1 and pRAS40. The results demonstrate that the subject mTOR inhibitor of the invention is more effective in inhibiting Akt phosphorylation as compared to rapamycin.

While preferred embodiments of the present invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" include plural references unless the context clearly dictates otherwise.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating," or "palliating" or "ameliorating" is used interchangeably herein. These terms refer to an approach for obtaining beneficial or desired results including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal so that both agents and/or their metabolites are present in the subject at the same time. Co-administration includes simultaneous administration in separate compositions, administration at different times in separate compositions, or administration in a composition in which both agents are present.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like, when the molecule contains an acidic functionality; and when the molecule contains a basic functionality, salts of organic or inorganic acids, such as hydrochloride, hydrobromide, tartrate, mesylate (methane sulfonate), ethane sulfonate, acetate, maleate, oxalate, phosphate, and the like. In a compound with more than one basic moiety, more than one of the basic moieties may be converted to the salt form, including but not limited to a bis- or tris-salt.

Alternatively, a compound having more than one basic moiety may form a salt at only one of the basic moieties.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" refers to a biologically active agent refers to the agent's ability to preferentially reduce the target signaling activity as compared to off-target signaling activity, via direct or indirect interaction with the target.

"mTorC1 and/or mTorC2 activity" as applied to a biologically active agent refers to the agent's ability to modulate signal transduction mediated by mTorC1 and/or mTorC2. For example, modulation of mTorC1 and/or mTorC2 activity is evidenced by alteration in signaling output from the PI3K/Akt/mTor pathway.

The term "B-ALL" as used herein refers to B-cell Acute Lymphoblastic Leukemia.

"Subject" refers to an animal, such as a mammal, for example a human. The methods described herein can be useful in both human therapeutics and veterinary applications. In some embodiments, the subject is a mammal, and in some embodiments, the subject is human.

"Radiation therapy" means exposing a subject, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

Unless otherwise stated, the connections of compound name moieties are at the rightmost recited moiety. That is, the substituent name starts with a terminal moiety, continues with any linking moieties, and ends with the linking moiety. For example, hetarylthio $C_{1-4}$ alkyl has a heteroaryl group connected through a thio sulfur to a $C_{1-4}$ alkyl radical that connects to the chemical species bearing the substituent. This condition does not apply where a formula such as, for example "-L-$C_{1-10}$ alkyl-$C_{3-8}$ cycloalkyl" is represented. In such case, the terminal group is a $C_{3-8}$ cycloalkyl group attached to a linking $C_{1-10}$ alkyl moiety which is attached to an element L, which is itself connected to the chemical species bearing the substituent.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present invention, whether radioactive or not, are encompassed within the scope of the present invention.

As used herein, for example, "$C_{1-4}$alkyl" is used to mean an alkyl having 1-4 carbons—that is, 1, 2, 3, or 4 carbons in a straight or branched configuration. In all embodiments of this invention, the term "alkyl" includes both branched and straight chain alkyl groups, or cyclic hydrocarbon groups, or a combination thereof. Alkyl groups are fully saturated, unsubstituted or substituted, and can include di- and multivalent radicals, having the number of carbon atoms designated (i.e. $C_1$-$C_{10}$ means one to ten carbons and $C_2$-$C_{10}$ means two to ten carbons). Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl, and the like.

The term "halo" or "halogen" refers to fluoro, chloro, bromo, or iodo.

The term "haloalkyl" refers to an alkyl group substituted with one or more halo groups, for example chloromethyl, 2-bromoethyl, 3-iodopropyl, trifluoromethyl, perfluoropropyl, 8-chlorononyl, and the like.

The term "acyl" refers to the structure —C(=O)—R, in which R is a general substituent variable such as, for example $R^1$ described above. Examples include, but are not limited to, alkylketo, (bi)(cyclo)alkylketo, (cyclo)alkenylketo, alkynylketo, arylketo, hetarylketo, heterocyclylketo, heterobicycloalkylketo, spiroalkylketo. An acyl moiety is unsubstituted or is substituted on R.

Unless otherwise specified, the term "cycloalkyl" refers to a 3-8 carbon cyclic aliphatic ring structure that is unsubstituted or substituted with, for example, alkyl, hydroxy, oxo, or halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl, and the like.

The term "$C_{1-10}$alkyl-$C_{3-8}$cycloalkyl" is used to describe an alkyl group, branched or straight chain and containing 1 to 10 carbon atoms, attached to a linking cycloalkyl group which contains 3 to 8 carbons, such as for example, 2-methyl cyclopropyl, and the like. Either portion of the moiety is unsubstituted or substituted.

The term "bicycloalkyl" refers to a structure consisting of two cycloalkyl moieties, unsubstituted or substituted, that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[3.2.1]heptyl ("norbornyl"), bicyclo[2.2.2]octyl, and the like.

As used herein, the term "heteroatom" or "ring heteroatom" is meant to include oxygen (O), nitrogen (N), sulfur (S), phosphorus (P), and silicon (Si).

The term "heteroalkyl," by itself or in combination with another term, means, unless otherwise stated, a straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. The alkyl portion of the moiety is unsubstituted or substituted. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR, and/or —$SO_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The term "heteroalkylaryl" refers to a heteroalkyl group as defined above which is attached to an aryl group, and may be attached at a terminal point or through a branched portion of the heteroalkyl, for example, an benzyloxymethyl moiety. Either portion of the moiety is unsubstituted or substituted.

The term "heteroalkylheteroaryl" refers likewise to a heteroalkyl group which is attached to a hetaryl moiety, for example, an ethoxymethylpyridyl group. Either portion of the moiety is unsubstituted or substituted.

The term "heteroalkyl-heterocylyl" refers to a heteroalkyl group as defined above, which is attached to a heterocyclic group, for example, 4(3-aminopropyl)-N-piperazinyl. Either portion of the moiety is unsubstituted or substituted.

The term "heteroalkyl-$C_{3-8}$cycloalkyl" refers to a heteroalkyl group as defined above, which is attached to a cyclic alkyl containing 3 to 8 carbons, for example, 1-aminobutyl-4-cyclohexyl. Either portion of the moiety is unsubstituted or substituted.

The term "heterobicycloalkyl" refers to a bicycloalkyl structure, which is unsubstituted or substituted, in which at least one carbon atom is replaced with a heteroatom independently selected from oxygen, nitrogen, and sulfur.

The term "heterospiroalkyl" refers to a spiroalkyl structure, which is unsubstituted or substituted, in which at least one carbon atom is replaced with a heteroatom independently selected from oxygen, nitrogen, and sulfur.

"Alkenyl" refers to a straight or branched hydrocarbon chain radical group consisting solely of carbon and hydrogen atoms, containing at least one double bond, and having from two to ten carbon atoms (ie. $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. The alkenyl is unsubstituted or substituted. The term "$C_{2-10}$ alkenyl-$C_{3-8}$cycloalkyl" refers to a group containing an alkenyl group, containing 2 to 10 carbons and branched or straight chain, which is attached to a linking cycloalkyl group containing 3 to 8 carbons, such as, for example 3-prop-3-enyl-cyclopent-1yl, and the like. Either portion of the moiety is unsubstituted or substituted.

The term "$C_{2-10}$ alkenyl-heteroalkyl" refers to a group having an alkenyl moiety, containing 2 to 10 carbon atoms and is branched or straight chain, which is attached to a linking heteroalkyl group, such as, for example, allyloxy, and the like. Either portion of the moiety is unsubstituted or substituted.

The term "$C_{2-10}$ alkynyl-heteroalkyl" refers to a group having an alkynyl moiety, which is unsubstituted or substituted, containing 2 to 10 carbon atoms and is branched or straight chain, which is attached to a linking heteroalkyl group, such as, for example, 4-but-1-ynoxy, and the like. Either portion of the moiety is unsubstituted or substituted.

The term "haloalkenyl" refers to an alkenyl group substituted with one or more halo groups.

Unless otherwise specified, the term "cycloalkenyl" refers to a cyclic aliphatic 3 to 8 membered ring structure, optionally substituted with alkyl, hydroxy and halo, having 1 or 2 ethylenic bonds such as methylcyclopropenyl, trifluoromethylcyclopropenyl, cyclopentenyl, cyclohexenyl, 1,4-cyclohexadienyl, and the like.

"Alkynyl" refers to a straight or branched hydrocarbon chain radical group consisting solely of carbon and hydrogen atoms, containing at least one triple bond, having from two to ten carbon atoms (ie. $C_2$-$C_{10}$ alkynyl). Whenever it appears herein, a numerical range such as "2 to 10" refers to each integer in the given range; e.g., "2 to 10 carbon atoms" means that the alkynyl group may consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the rest of the molecule by a single bond, for example, ethynyl, propynyl, butynyl, pentynyl, hexynyl, and the like. The alkynyl is unsubstituted or substituted.

The term $C_{2-10}$ alkynyl-$C_{3-8}$ cycloalkyl refers to a group containing an alkynyl group, containing 2 to 10 carbons and branched or straight chain, which is attached to a linking cycloalkyl group containing 3 to 8 carbons, such as, for example 3-prop-3-ynyl-cyclopent-1yl, and the like. Either portion of the moiety is unsubstituted or substituted.

The term, "haloalkynyl" refers to an alkynyl group substituted with one or more independent halo groups.

"Amino" or "amine" refers to a —NR'R" moiety, where each R is independently hydrogen, alkyl, fluoroalkyl, cycloalkyl, cycloalkylalkyl, aryl, aralkyl, heterocyclyl, heterocyclylalkyl, heteroaryl or heteroarylalkyl, unless stated otherwise specifically in the specification. When both R' and R" of a —NR'R" moiety are not hydrogen, R' and R" can be combined with the nitrogen atom to form a 4-, 5-, 6-, or 7-membered ring. For example, —NR'R" is meant to include, but not be limited to, 1-pyrrolidinyl and 4-morpholinyl. Unless stated otherwise specifically in the specification, an amino group is optionally substituted by one or more substituent which independently is: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR', —SR', —OC(O)—R', —N(R')$_2$, —C(O)R', —C(O)OR', —OC(O)N(R')$_2$, —C(O)N(R')$_2$, —N(R')C(O)OR', —N(R')C(O)R', —N(R')C(O)N(R')$_2$, N(R')C(NR)N(R')$_2$, —N(R')S(O)$_t$R' (where t is 1 or 2), —S(O)$_t$OR' (where t is 1 or 2), —S(O)$_t$N(R')$_2$ (where t is 1 or 2), or PO$_3$(R')$_2$, where each R is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Amide" or "amido" refers to a chemical moiety with formula —C(O)N(R')$_2$ or —NHC(O)R', where R' is selected from the group consisting of hydrogen, alkyl, cycloalkyl, aryl, heteroaryl (bonded through a ring carbon) and heteroalicyclic (bonded through a ring carbon). In some embodiments it is a $C_1$-$C_4$ amido or amide radical, which includes the amide carbonyl in the total number of carbons in the radical. The R'$_2$ of —N(R')$_2$ of the amide may optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocyclyl. An amide may be an amino acid or a peptide molecule attached to a compound of Formula (I'-A'), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety.

"Aromatic" or "aryl" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Examples of aryl include, but are not limited to, phenyl, 4-chlorophenyl, 4-fluorophenyl, 4-bromophenyl, 3-nitrophenyl, 2-methoxyphenyl, 2-methylphenyl, 3-methylphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, and 2-iodo-4-methylphenyl. An aryl moiety is unsubstituted or substituted.

"Heteroaryl" or, alternatively, "heteroaromatic", "hetaryl", "heteroar" or "hetar" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). A heteroaryl moiety is unsubstituted or substituted.

The terms "aryl-alkyl", "arylalkyl" and "aralkyl" are used to describe a group wherein the alkyl chain can be branched or straight chain forming a linking portion with the terminal aryl, as defined above, of the aryl-alkyl moiety.

Examples of aryl-alkyl groups include, but are not limited to, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl)propyl, 3-(2-methylphenyl)propyl, 3-(4-methoxyphenyl)propyl, 3-(4-(trifluoromethyl)phenyl)propyl, 3-(2,4-dichlorophenyl)propyl, 4-phenylbutyl, 4-(4-chlorophenyl)butyl, 4-(2-methylphenyl)butyl, 4-(2,4-dichlorophenyl)butyl, 4-(2-methoxphenyl)butyl, and 10-phenyldecyl. Either portion of the moiety is unsubstituted or substituted.

The term "$C_{1-10}$alkylaryl" as used herein refers to an alkyl group, as defined above, containing 1 to 10 carbon atoms, branched or unbranched, wherein the aryl group replaces one hydrogen on the alkyl group, for example, 3-phenylpropyl. Either portion of the moiety is unsubstituted or substituted.

The term $C_{2-10}$ alkyl monocycloaryl" refers to a group containing a terminal alkyl group, branched or straight chain and containing 2 to 10 atoms attached to a linking aryl group which has only one ring, such as for example, 2-phenyl ethyl. Either portion of the moiety is unsubstituted or substituted.

The term $C_{1-10}$ alkyl bicycloaryl" refers to a group containing a terminal alkyl group, branched or straight chain and containing 2 to 10 atoms attached to a linking aryl group which is bicyclic, such as for example, 2-(1-naphthyl)-ethyl. Either portion of the moiety is unsubstituted or substituted.

The terms "aryl-cycloalkyl" and "arylcycloalkyl" are used to describe a group wherein the terminal aryl group is attached to a cycloalkyl group, for example phenylcyclopentyl and the like. Either portion of the moiety is unsubstituted or substituted.

The terms "hetaryl-$C_{3-8}$cycloalkyl" and "heteroaryl-$C_{3-8}$cycloalkyl" are used to describe a group wherein the terminal hetaryl group is attached to a cycloalkyl group, which contains 3 to 8 carbons, for example pyrid-2-yl-cyclopentyl and the like. Either portion of the moiety is unsubstituted or substituted.

The term "hetaryl-heteroalkyl" refers to a group wherein the terminal hetaryl group is attached to a linking heteroalkyl group, such as for example, pyrid-2-yl methylenoxy, and the like. Either portion of the moiety is unsubstituted or substituted.

The terms "aryl-alkenyl", "arylalkenyl" and "aralkenyl" are used to describe a group wherein the alkenyl chain can be branched or straight chain forming a linking portion of the aralkenyl moiety with the terminal aryl portion, as defined above, for example styryl(2-phenylvinyl), phenpropenyl, and the like. Either portion of the moiety is unsubstituted or substituted.

The term "aryl-$C_{2-10}$alkenyl" means an arylalkenyl as described above wherein the alkenyl moiety contains 2 to 10 carbon atoms such as for example, styryl(2-phenylvinyl), and the like. Either portion of the moiety is unsubstituted or substituted.

The term "$C_{2-10}$alkenyl-aryl" is used to describe a group wherein the terminal alkenyl group, which contains 2 to 10 carbon atoms and can be branched or straight chain, is attached to the aryl moiety which forms the linking portion of the alkenyl-aryl moiety, such as for example, 3-propenyl-naphth-1-yl, and the like. Either portion of the moiety is unsubstituted or substituted.

The terms "aryl-alkynyl", "arylalkynyl" and "aralkynyl" are used to describe a group wherein the alkynyl chain can be branched or straight chain forming a linking portion of the aryl-alkynyl moiety with the terminal aryl portion, as defined above, for example 3-phenyl-1-propynyl, and the like. Either portion of the moiety is unsubstituted or substituted.

The term "aryl-$C_{2-10}$alkynyl" means an arylalkynyl as described above wherein the alkynyl moiety contains two to ten carbons, such as, for example 3-phenyl-1-propynyl, and the like. Either portion of the moiety is unsubstituted or substituted.

The term "$C_{2-10}$alkynyl-aryl" means a group containing an alkynyl moiety attached to an aryl linking group, both as defined above, wherein the alkynyl moiety contains two to ten carbons, such as, for example 3-propynyl-naphth-1-yl. Either portion of the moiety is unsubstituted or substituted.

The terms "aryl-oxy", "aryloxy" and "aroxy" are used to describe a terminal aryl group attached to a linking oxygen atom. Typical aryl-oxy groups include phenoxy, 3,4-dichlorophenoxy, and the like. Either portion of the moiety is unsubstituted or substituted.

The terms "aryl-oxyalkyl", "aryloxyalkyl" and "aroxyalkyl" are used to describe a group wherein an alkyl group is substituted with a terminal aryl-oxy group, for example pentafluorophenoxymethyl and the like. Either portion of the moiety is unsubstituted or substituted.

The term "$C_{1-10}$alkoxy-$C_{1-10}$alkyl" refers to a group wherein an alkoxy group, containing 1 to 10 carbon atoms and an oxygen atom within the branching or straight chain, is attached to a linking alkyl group, branched or straight chain which contains 1 to 10 carbon atoms, such as, for example methoxypropyl, and the like. Either portion of the moiety is unsubstituted or substituted.

The term "$C_{1-10}$alkoxy-$C_{2-10}$alkenyl" refers to a group wherein an alkoxy group, containing 1 to 10 carbon atoms and an oxygen atom within the branching or straight chain, is attached to a linking alkenyl group, branched or straight chain which contains 1 to 10 carbon atoms, such as, for example 3-methoxybut-2-en-1-yl, and the like. Either portion of the moiety is unsubstituted or substituted.

The term "$C_{2-10}$alkoxy-$C_{2-10}$alkynyl" refers to a group wherein an alkoxy group, containing 1 to 10 carbon atoms and an oxygen atom within the branching or straight chain, is attached to a linking alkynyl group, branched or straight chain which contains 1 to 10 carbon atoms, such as, for example 3-methoxybut-2-in-1-yl, and the like. Either portion of the moiety is unsubstituted or substituted.

The term "heterocycloalkenyl" refers to a cycloalkenyl structure, which is unsubstituted or substituted in which at least one carbon atom is replaced with a heteroatom selected from oxygen, nitrogen, and sulfur.

The terms "hetaryl-oxy", "heteroaryl-oxy", "hetaryloxy", "heteroaryloxy", "hetaroxy" and "heteroaroxy" are used to describe a terminal hetaryl group, which is unsubstituted or substituted, attached to a linking oxygen atom. Typical hetaryl-oxy groups include 4,6-dimethoxypyrimidin-2-yloxy and the like.

The terms "hetarylalkyl", "heteroarylalkyl", "hetarylalkyl", "heteroaryl-alkyl", "hetaralkyl" and "heteroaralkyl" are used to describe a group wherein the alkyl chain can be branched or straight chain forming a linking portion of the heteroaralkyl moiety with the terminal heteroaryl portion, as defined above, for example 3-furylmethyl, thenyl, furfuryl, and the like. Either portion of the moiety is unsubstituted or substituted.

The term "hetaryl-$C_{1-10}$alkyl" is used to describe a hetaryl alkyl group as described above where the alkyl group contains 1 to 10 carbon atoms. Either portion of the moiety is unsubstituted or substituted.

The term "$C_{1-10}$alkyl-hetaryl" is used to describe a alkyl attached to a hetaryl group as described above where the alkyl group contains 1 to 10 carbon atoms. Either portion of the moiety is unsubstituted or substituted.

The terms "hetarylalkenyl", "heteroarylalkenyl", "hetarylalkenyl", "heteroaryl-alkenyl", "hetaralkenyl" and "heteroaralkenyl" are used to describe a hetarylalkenyl group wherein the alkenyl chain can be branched or straight chain forming a linking portion of the heteroaralkenyl moiety with the terminal heteroaryl portion, as defined above, for example 3-(4-pyridyl)-1-propenyl. Either portion of the moiety is unsubstituted or substituted.

The term "hetaryl-$C_{2-10}$alkenyl" group is used to describe a group as described above wherein the alkenyl group contains 2 to 10 carbon atoms. Either portion of the moiety is unsubstituted or substituted.

The term "$C_{2-10}$alkenyl-hetaryl" is used to describe a group containing an alkenyl group, which is branched or straight chain and contains 2 to 10 carbon atoms, and is attached to a linking hetaryl group, such as, for example 2-styryl-4-pyridyl, and the like. Either portion of the moiety is unsubstituted or substituted.

The terms "hetarylalkynyl", "heteroarylalkynyl", "hetarylalkynyl", "heteroaryl-alkynyl", "hetaralkynyl" and "heteroaralkynyl" are used to describe a group wherein the alkynyl chain can be branched or straight chain forming a linking portion of the heteroaralkynyl moiety with the heteroaryl portion, as defined above, for example 4-(2-thienyl)-1-butynyl, and the like. Either portion of the moiety is unsubstituted or substituted.

The term "hetaryl-$C_{2-10}$alkynyl" is used to describe a hetarylalkynyl group as described above wherein the alkynyl group contains 2 to 10 carbon atoms. Either portion of the moiety is unsubstituted or substituted.

The term "$C_{2-10}$alkynyl-hetaryl" is used to describe a group containing an alkynyl group which contains 2 to 10 carbon atoms and is branched or straight chain, which is attached to a linking hetaryl group such as, for example, 4(but-1-ynyl) thien-2-yl, and the like. Either portion of the moiety is unsubstituted or substituted.

The term "heterocyclyl", "hetcyclyl", or "heterocycloalkyl" refers to a substituted or unsubstituted 3-, 4-, 5-, or 6-membered saturated or partially unsaturated ring containing one, two, or three heteroatoms, preferably one or two heteroatoms independently selected from oxygen, nitrogen and sulfur; or to a bicyclic ring system containing up to 10 atoms including at least one heteroatom independently selected from oxygen, nitrogen, and sulfur wherein the ring containing the heteroatom is saturated. Examples of heterocyclyls include, but are not limited to, tetrahydrofuranyl, tetrahydrofuryl, pyrrolidinyl, piperidinyl, 4-pyranyl, tetrahydropyranyl, thiolanyl, morpholinyl, piperazinyl, dioxolanyl, dioxanyl, indolinyl, and 5-methyl-6-chromanyl.

The terms "heterocyclylalkyl", "heterocyclyl-alkyl", "hetcyclylalkyl", and "hetcyclyl-alkyl" are used to describe a group wherein the alkyl chain can be branched or straight chain forming a linking portion of the heterocyclylalkyl moiety with the terminal heterocyclyl portion, as defined above, for example 3-piperidinylmethyl and the like. The term "heterocycloalkylene" refers to the divalent derivative of heterocycloalkyl.

The term "$C_{1-10}$alkyl-heterocycyl" refers to a group as defined above where the alkyl moiety contains 1 to 10 carbon atoms. Either portion of the moiety is unsubstituted or substituted.

The term "heterocycyl-$C_{1-10}$alkyl" refers to a group containing a terminal heterocyclic group attached to a linking alkyl group which contains 1 to 10 carbons and is branched or straight chain, such as, for example, 4-morpholinyl ethyl, and the like. Either portion of the moiety is unsubstituted or substituted.

The terms "heterocyclylalkenyl", "heterocyclyl-alkenyl", "hetcyclylalkenyl" and "hetcyclyl-alkenyl" are used to describe a group wherein the alkenyl chain can be branched or straight chain forming a linking portion of the heterocyclylalkenyl moiety with the terminal heterocyclyl portion, as defined above, for example 2-morpholinyl-1-propenyl and the like. The term "heterocycloalkenylene" refers to the divalent derivative of heterocyclylalkenyl. Either portion of the moiety is unsubstituted or substituted.

The term "heterocycyl-$C_{2-10}$ alkenyl" refers to a group as defined above where the alkenyl group contains 2 to 10 carbon atoms and is branched or straight chain, such as, for example, 4-(N-piperazinyl)-but-2-en-1-yl, and the like. Either portion of the moiety is unsubstituted or substituted.

The terms "heterocyclylalkynyl", "heterocyclyl-alkynyl", "hetcyclylalkynyl" and "hetcyclyl-alkynyl" are used to describe a group wherein the alkynyl chain can be branched or straight chain forming a linking portion of the heterocyclylalkynyl moiety with the terminal heterocyclyl portion, as defined above, for example 2-pyrrolidinyl-1-butynyl and the like. Either portion of the moiety is unsubstituted or substituted.

The term "heterocycyl-$C_{2-10}$ alkynyl" refers to a group as defined above where the alkynyl group contains 2 to 10 carbon atoms and is branched or straight chain, such as, for example, 4-(N-piperazinyl)-but-2-yn-1-yl, and the like.

The term "aryl-heterocycyl" refers to a group containing a terminal aryl group attached to a linking heterocyclic group, such as for example, N4-(4-phenyl)-piperazinyl, and the like. Either portion of the moiety is unsubstituted or substituted.

The term "hetaryl-heterocycyl" refers to a group containing a terminal hetaryl group attached to a linking heterocyclic group, such as for example, N4-(4-pyridyl)-piperazinyl, and the like. Either portion of the moiety is unsubstituted or substituted.

The term "carboxylalkyl" refers to a terminal carboxyl (—COOH) group attached to branched or straight chain alkyl groups as defined above.

The term "carboxylalkenyl" refers to a terminal carboxyl (—COOH) group attached to branched or straight chain alkenyl groups as defined above.

The term "carboxylalkynyl" refers to a terminal carboxyl (—COOH) group attached to branched or straight chain alkynyl groups as defined above.

The term "carboxylcycloalkyl" refers to a terminal carboxyl (—COOH) group attached to a cyclic aliphatic ring structure as defined above.

The term "carboxylcycloalkenyl" refers to a terminal carboxyl (—COOH) group attached to a cyclic aliphatic ring structure having ethylenic bonds as defined above.

The terms "cycloalkylalkyl" and "cycloalkyl-alkyl" refer to a terminal cycloalkyl group as defined above attached to an alkyl group, for example cyclopropylmethyl, cyclohexylethyl, and the like. Either portion of the moiety is unsubstituted or substituted.

The terms "cycloalkylalkenyl" and "cycloalkyl-alkenyl" refer to a terminal cycloalkyl group as defined above attached to an alkenyl group, for example cyclohexylvinyl, cycloheptylallyl, and the like. Either portion of the moiety is unsubstituted or substituted.

The terms "cycloalkylalkynyl" and "cycloalkyl-alkynyl" refer to a terminal cycloalkyl group as defined above attached to an alkynyl group, for example cyclopropylpropargyl, 4-cyclopentyl-2-butynyl, and the like. Either portion of the moiety is unsubstituted or substituted.

The terms "cycloalkenylalkyl" and "cycloalkenyl-alkyl" refer to a terminal cycloalkenyl group as defined above attached to an alkyl group, for example 2-(cyclopenten-1-yl) ethyl and the like. Either portion of the moiety is unsubstituted or substituted.

The terms "cycloalkenylalkenyl" and "cycloalkenyl-alkenyl" refer to terminal a cycloalkenyl group as defined above attached to an alkenyl group, for example 1-(cyclohexen-3-yl)allyl and the like.

The terms "cycloalkenylalkynyl" and "cycloalkenyl-alkynyl" refer to terminal a cycloalkenyl group as defined above attached to an alkynyl group, for example 1-(cyclohexen-3-yl)propargyl and the like. Either portion of the moiety is unsubstituted or substituted.

The term "alkoxy" includes both branched and straight chain terminal alkyl groups attached to a linking oxygen atom. Typical alkoxy groups include methoxy, ethoxy, n-propoxy, isopropoxy, tert-butoxy and the like. An alkoxy moiety is unsubstituted or substituted.

The term "haloalkoxy" refers to an alkoxy group substituted with one or more halo groups, for example chloromethoxy, trifluoromethoxy, difluoromethoxy, perfluoroisobutoxy, and the like.

The term "alkoxyalkoxyalkyl" refers to an alkyl group substituted with an alkoxy moiety which is in turn is substituted with a second alkoxy moiety, for example methoxymethoxymethyl, isopropoxymethoxyethyl, and the like. This moiety is substituted with further substituents or not substituted with other substituents.

The term "alkylthio" includes both branched and straight chain alkyl groups attached to a linking sulfur atom, for example methylthio and the like.

The term "alkoxyalkyl" refers to an alkyl group substituted with an alkoxy group, for example isopropoxymethyl and the like. Either portion of the moiety is unsubstituted or substituted.

The term "alkoxyalkenyl" refers to an alkenyl group substituted with an alkoxy group, for example 3-methoxyallyl and the like. Either portion of the moiety is unsubstituted or substituted.

The term "alkoxyalkynyl" refers to an alkynyl group substituted with an alkoxy group, for example 3-methoxypropargyl and the like. Either portion of the moiety is unsubstituted or substituted.

The term "$C_{2-10}$alkenyl$C_{3-8}$cycloalkyl" refers to an alkenyl group as defined above substituted with a three to eight membered cycloalkyl group, for example, 4-(cyclopropyl)-2-butenyl and the like. Either portion of the moiety is unsubstituted or substituted.

The term "$C_{2-10}$alkynyl$C_{3-8}$cycloalkyl" refers to an alkynyl group as defined above substituted with a three to eight membered cycloalkyl group, for example, 4-(cyclopropyl)-2-butynyl and the like. Either portion of the moiety is unsubstituted or substituted.

The term "heterocyclyl-$C_{1-10}$alkyl" refers to a heterocyclic group as defined above substituted with an alkyl group as defined above having 1 to 10 carbons, for example, 4-(N-methyl)-piperazinyl, and the like. Either portion of the moiety is unsubstituted or substituted.

The term "heterocyclyl-$C_{2-10}$alkenyl" refers to a heterocyclic group as defined above, substituted with an alkenyl group as defined above, having 2 to 10 carbons, for example, 4-(N-allyl) piperazinyl, and the like. Moieties wherein the heterocyclic group is substituted on a carbon atom with an alkenyl group are also included. Either portion of the moiety is unsubstituted or substituted.

The term "heterocyclyl-$C_{2-10}$alkynyl" refers to a heterocyclic group as defined above, substituted with an alkynyl group as defined above, having 2 to 10 carbons, for example, 4-(N-propargyl) piperazinyl, and the like. Moieties wherein the heterocyclic group is substituted on a carbon atom with an alkenyl group are also included. Either portion of the moiety is unsubstituted or substituted.

The term "oxo" refers to an oxygen that is double bonded to a carbon atom. One in the art understands that an "oxo" requires a second bond from the atom to which the oxo is attached. Accordingly, it is understood that oxo cannot be substituted onto an aryl or heteroaryl ring, unless it forms part of the aromatic system as a tautomer.

The term "oligomer" refers to a low-molecular weight polymer, whose number average molecular weight is typically less than about 5000 g/mol, and whose degree of polymerization (average number of monomer units per chain) is greater than one and typically equal to or less than about 50.

"Sulfonamidyl" or "sulfonamido" refers to a —S(=O)$_2$—NR'R' radical, where each R' is selected independently from the group consisting of hydrogen, alkyl, cycloalkyl, aryl, heteroaryl (bonded through a ring carbon) and heteroalicyclic (bonded through a ring carbon). The R' groups in —NR'R' of the —S(=O)$_2$—NR'R' radical may be taken together with the nitrogen to which it is attached to form a 4-, 5-, 6-, or 7-membered ring. A sulfonamido group is optionally substituted by one or more of the substituents described for alkyl, cycloalkyl, aryl, heteroaryl respectively.

Compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The present invention includes all manner of rotamers and conformationally restricted states of a compound of the invention.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: alkyl, heteroalkyl, alkenyl, alkynyl, cycloalkyl, heterocycloalkyl, aryl, arylalkyl, heteroaryl, heteroarylalkyl, —OR', =O, =NR', =N—OR', —NR'R'', —SR', -halogen, —SiR'R''R''', —OC(O)R', —C(O)R', —CO$_2$R', —C(O)NR'R'', —OC(O)NR'R'', —NR''C(O)R', —NR'—C(O)NR''R''', —NR''C(O)OR', —NR—C(NR'R'')=NR''', —S(O)R', —S(O)$_2$R', —S(O)$_2$NR'R'', —NRSO$_2$R', —CN and —NO$_2$ in a number ranging from zero to (2m'+1), where m' is the total number of carbon atoms in such radical. R', R'', R''' and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R'', R''' and R'''' groups when more than one of these groups is present.

When R' and R'' or R'' and R''' are attached to the same nitrogen atom, they can be combined with the nitrogen atom to form a 4-, 5-, 6-, or 7-membered ring. For example, —NR'R'' is meant to include, but not be limited to, 1-pyrrolidinyl, 4 piperazinyl, and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, alkyl, heteroalkyl, alkenyl, alkynyl, cycloalkyl, heterocycloalkyl, aryl, arylalkyl, heteroaryl, heteroarylalkyl, —OR', —NR'R'', —SR', -halogen, —SiR'R''R''', —OC(O)R', —C(O)R', —CO$_2$R', —C(O)NR'R'', —OC(O)NR'R'', —NR''C(O)R', —NR'—C(O)NR''R''', —NR''C(O)OR', —NR—C(NR'R''R''')=NR'''', —NR—C(NR'R'')=NR''', —S(O)R', —S(O)$_2$R', —S(O)$_2$NR'R'', —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R'', R''' and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R'', R''' and R'''' groups when more than one of these groups is present.

As used herein, 0-2 in the context of —S(O)$_{(0-2)}$— are integers of 0, 1, and 2.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3.

Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C''R''')$_d$—, where s and d are independently integers of from 0 to 3, and X' is —O—, —NR'—, —S—, —S(O)—, —S(O)$_2$—, or —S(O)$_2$NR'—. The substituents R, R', R'' and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

A. GENERIC FORMULAS AND DETAILED DESCRIPTION

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

A compound or a pharmaceutically acceptable salt thereof is provided, wherein the compound has the Formula I'-A':

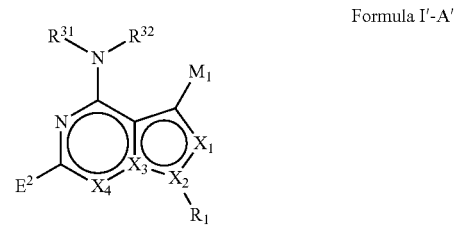

Formula I'-A' or a pharmaceutically acceptable salt thereof, wherein:
X$_1$ is N or C-E$^1$, X$_2$ is N, X$_3$ is C, and X$_4$ is C—R$^9$ or N; or
X$_1$ is N or C-E$^1$, X$_2$ is C, X$_3$ is N, and X$_4$ is C—R$^9$ or N;
wherein no more than two nitrogen ring atoms are adjacent;

R₁ is —H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{1-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —C(=O)—, —C(=O)O—, —C(=O)N($R^{31}$)—, —S—, —S(O)—, —S(O)₂—, —S(O)₂N($R^{31}$)—, or —N($R^{31}$)—;

$M_1$ is a moiety having the structure of Formula A-1 or Formula A-2:

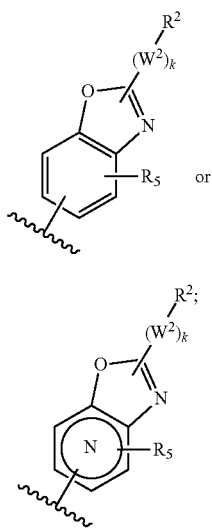

Formula A-1

Formula A-2 k is 0 or 1;

$E^1$ and $E^2$ are independently —(W¹)$_j$—$R^4$;

j, in each instance (i.e., in $E^1$ or j in $E^2$), is independently 0 or 1

$W^1$ is —O—, —NR⁷—, —S(O)$_{0-2}$—, —C(O)—, —C(O)N(R⁷)—, —N(R⁷)C(O)—, —N(R⁷)S(O)—, —N(R⁷)S(O)₂—, —C(O)O—, —CH(R⁷)N(C(O)OR⁸)—, —CH(R⁷)N(C(O)R⁸)—, —CH(R⁷)N(SO₂R⁸)—, —CH(R⁷)N(R⁸)—, —CH(R⁷)C(O)N(R⁸)—, —CH(R⁷)N(R⁸)C(O)—, —CH(R⁷)N(R⁸)S(O)—, or —CH(R⁷)N(R⁸)S(O)₂—;

$W^2$ is —O—, —NR⁷—, —S(O)$_{0-2}$—, —C(O)—, —C(O)N(R⁷)—, —N(R⁷)C(O)—, —N(R⁷)C(O)N(R⁸)—, —N(R⁷)S(O)—, —N(R⁷)S(O)₂—, —C(O)O—, —CH(R⁷)N(C(O)OR⁸)—, —CH(R⁷)N(C(O)R⁸)—, —CH(R⁷)N(SO₂R⁸)—, —CH(R⁷)N(R⁸)—, —CH(R⁷)C(O)N(R⁸)—, —CH(R⁷)N(R⁸)C(O)—, —CH(R⁷)N(R⁸)S(O)—, or —CH(R⁷)N(R⁸)S(O)₂—;

$R^2$ is hydrogen, halogen, —OH, —$R^{31}$, —CF₃, —OCF₃, —$OR^{31}$, —$NR^{31}R^{32}$, —$NR^{34}R^{35}$, —C(O)$R^{31}$, —CO₂$R^{31}$, —C(=O)$NR^{31}R^{32}$, —C(=O)$NR^{34}R^{35}$, —NO₂, —CN, —S(O)$_{0-2}R^{31}$, —SO₂$NR^{31}R^{32}$, —SO₂$NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, SC(=O)$OR^{31}$, —P(O)$OR^{31}OR^{32}$, or —SC(=O)$NR^{31}R^{32}$, aryl (e.g. bicyclic aryl, unsubstituted aryl, or substituted monocyclic aryl), hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenyl-hetaryl, $C_{2-10}$alkenylheteroalkyl, $C_{2-10}$alkenylheterocyclyl, $C_{2-10}$alkenyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF₃, —OCF₃, —$OR^{31}$, —$NR^{31}R^{32}$, —$NR^{34}R^{35}$, C(O)$R^{31}$, —CO₂$R^{31}$, —C(=O)$NR^{31}R^{32}$, —C(=O)$NR^{34}R^{35}$, —NO₂, —CN, —S(O)$_{0-2}R^{31}$, —SO₂$NR^{31}R^{32}$, —SO₂$NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF₃, —OCF₃, —$OR^{31}$, —O-aryl, $NR^{31}R^{32}$, —$NR^{34}R^{35}$, —C(O)$R^{31}$, —CO₂$R^{31}$, —C(=O)$NR^{34}R^{35}$, or —C(=O)$NR^{31}R^{32}$;

$R^3$ and $R^4$ are independently hydrogen, halogen, —OH, —$R^{31}$, —CF₃, —OCF₃, —$OR^{31}$, —$NR^{31}R^{32}$, —$NR^{34}R^{35}$, —C(O)$R^{31}$, —CO₂$R^{31}$, —C(=O)$NR^{31}R^{32}$, —C(=O)$NR^{34}R^{35}$, —NO₂, —CN, —S(O)$_{0-2}R^{31}$, —SO₂$NR^{31}R^{32}$, —SO₂$NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, SC(=O)$OR^{31}$, —P(O)$OR^{31}OR^{32}$, —SC(=O)$NR^{31}R^{32}$, aryl, hetaryl, $C_{1-4}$alkyl, $C_{1-10}$alkyl, $C_{3-8}$cycloalkyl, $C_{1-10}$alkyl-$C_{3-8}$cycloalkyl, $C_{3-8}$cycloalkyl —$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_2$-$C_{10}$alkenylhetaryl, $C_{2-10}$alkenylheteroalkyl, $C_{2-10}$alkenylheterocyclyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$;

$R^{31}$, $R^{32}$, and $R^{33}$, in each instance, are independently H or $C_{1-10}$alkyl, wherein the $C_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —$C_{1-10}$alkyl, —$CF_3$, —O-aryl, $OCF_3$, —$OC_{1-10}$alkyl, —$NH_2$, —N($C_{1-10}$alkyl)($C_{1-10}$alkyl), —NH($C_{10-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH ($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —S(O)$_{0-2}C_{1-10}$alkyl, —S(O)$_{0-2}C_{1-10}$alkylaryl, —S(O)$_{0-2}$ aryl, —$SO_2$N(aryl), —$SO_2$N($C_{1-10}$alkyl) ($C_{1-10}$alkyl), —$SO_2$NH($C_{1-10}$alkyl) or $SO_2NR^{34}R^{35}$;

$R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom;

$R^7$ and $R^8$ are each independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, —C(=O)$NR^{34}R^{35}$, —$NO_2$, —CN, —S(O)$_{0-2}C_{1-10}$alkyl, —S(O)$_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)$NR^{31}R^{32}$, —C(=O)$NR^{34}R^{35}$, —$SO_2NR^{34}R^{35}$, —$SO_2NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, —C(=O)$NR^{34}R^{35}$, —$NO_2$, —CN, —S(O)$_{0-2}C_{1-10}$alkyl, —S(O)$_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl- $C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)$NR^{31}R^{32}$, —C(=O)$NR^{34}R^{35}$, —$SO_2NR^{34}R^{35}$, —$SO_2NR^{31}R^{32}$, —$NR^{31}R^{32}$, or —$NR^{34}R^{35}$.

In some embodiments, $X_4$ is C—$R^9$.

The invention also provides a compound as defined above, wherein the compound is of Formula I:

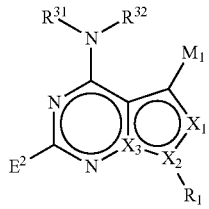

Formula I or a pharmaceutically acceptable salt thereof, and wherein the substituents are as defined above.

In various embodiments the compound of Formula I or its pharmaceutically acceptable salt thereof, is a compound having the structure of Formula I-A or Formula I-B:

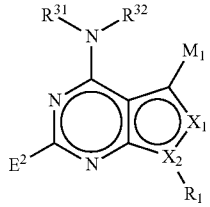

Formula I-A

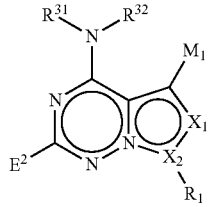

Formula I-B or a pharmaceutically acceptable salt thereof.

In various embodiments of Formula I-A, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C.

In various embodiments of Formula I-B, $X_1$ is N and $X_2$ is C. In further embodiments, $X_1$ is C-$E^1$ and $X_2$ is C.

In various embodiments, $X_1$ is C—($W^1$)$_j$—$R^4$, where j is 0.

In another embodiment, $X_1$ is CH. In yet another embodiment, $X_1$ is C-halogen, where halogen is Cl, F, Br, or I.

In various embodiments of $X_1$, it is C—$(W^1)_j$—$R^4$. In various embodiments of $X_1$, j is 1, and $W^1$ is —O—. In various embodiments of $X_1$, j is 1, and $W^1$ is —$NR^7$—. In various embodiments of $X_1$, j is 1, and $W^1$ is —NH—. In various embodiments of $X_1$, j is 1, and $W^1$ is —$S(O)_{0-2}$—. In various embodiments of $X_1$, j is 1, and $W^1$ is —C(O)—. In various embodiments of $X_1$, j is 1, and $W^1$ is —$C(O)N(R^7)$—. In various embodiments of $X_1$, j is 1, and $W^1$ is —$N(R^7)C(O)$—. In various embodiments of $X_1$, j is 1, and $W^1$ is —$N(R^7)S(O)$—. In various embodiments of $X_1$, j is 1, and $W^1$ is —$N(R^7)S(O)_2$—.

In various embodiments of $X_1$, j is 1, and $W^1$ is —C(O)O—. In various embodiments of $X_1$, j is 1, and $W^1$ is —$CH(R^7)N(C(O)OR)$—. In various embodiments of $X_1$, j is 1, and $W^1$ is —$CH(R^7)N(C(O)R)$—. In various embodiments of $X_1$, j is 1, and $W^1$ is —$CH(R^7)N(SO_2R^8)$—. In various embodiments of $X_1$, j is 1, and $W^1$ is —$CH(R^7)N(R^8)$—. In various embodiments of $X_1$, j is 1, and $W^1$ is —$CH(R^7)C(O)N(R^8)$—. In various embodiments of $X_1$, j is 1, and $W^1$ is —$CH(R^7)N(R^8)C(O)$—. In various embodiments of $X_1$, j is 1, and $W^1$ is —$CH(R^7)N(R^8)S(O)$—. In various embodiments of $X_1$, j is 1, and $W^1$ is —$CH(R^7)N(R^8)S(O)_2$—.

In various embodiments, $X_1$ is CH—$(W^1)_j$—$R^4$, where j is 0.

In another embodiment, $X_1$ is $CH_2$. In yet another embodiment, $X_1$ is CH-halogen, where halogen is Cl, F, Br, or I.

In various embodiments of $X_1$, it is CH—$(W^1)_j$—$R^4$. In various embodiments of $X_1$, j is 1, and $W^1$ is —O—. In various embodiments of $X_1$, j is 1, and $W^1$ is —$NR^7$—. In various embodiments of $X_1$, j is 1, and $W^1$ is —NH—. In various embodiments of $X_1$, j is 1, and $W^1$ is —$S(O)_{0-2}$—. In various embodiments of $X_1$, j is 1, and $W^1$ is —C(O)—. In various embodiments of $X_1$, j is 1, and $W^1$ is —$C(O)N(R^7)$—. In various embodiments of $X_1$, j is 1, and $W^1$ is —$N(R^7)C(O)$—. In various embodiments of $X_1$, j is 1, and $W^1$ is —$N(R^7)S(O)$—. In various embodiments of $X_1$, j is 1, and $W^1$ is —$N(R^7)S(O)_2$—.

In various embodiments of $X_1$, j is 1, and $W^1$ is —C(O)O—. In various embodiments of $X_1$, j is 1, and $W^1$ is $CH(R^7)N(C(O)OR)$—. In various embodiments of $X_1$, j is 1, and $W^1$ is —$CH(R^7)N(C(O)R)$—. In various embodiments of $X_1$, j is 1, and $W^1$ is —$CH(R^7)N(SO_2R^8)$—. In various embodiments of $X_1$, j is 1, and $W^1$ is —$CH(R^7)N(R^8)$—. In various embodiments of $X_1$, j is 1, and $W^1$ is —$CH(R^7)C(O)N(R^8)$—. In various embodiments of $X_1$, j is 1, and $W^1$ is —$CH(R^7)N(R^8)C(O)$—. In various embodiments of $X_1$, j is 1, and $W^1$ is —$CH(R^7)N(R^8)S(O)$—. In various embodiments of $X_1$, j is 1, and $W^1$ is —$CH(R^7)N(R^8)S(O)_2$—.

In another embodiment, $X_1$ is N.

In various embodiments, $X_2$ is N. In other embodiments, $X_2$ is C.

In various embodiments, $E^2$ is —$(W^1)_j$—$R^4$, where j is 0.

In another embodiment, $E^2$ is CH. In yet another embodiment, $E^2$ is C-halogen, where halogen is Cl, F, Br, or I.

In various embodiments of $E^2$, it is —$(W^1)_j$—$R^4$. In various embodiments of $E^2$, j is 1, and $W^1$ is —O—. In various embodiments of $E^2$, j is 1, and $W^1$ is —$NR^7$—. In various embodiments of $E^2$, j is 1, and $W^1$ is —NH—. In various embodiments of $E^2$, j is 1, and $W^1$ is —$S(O)_{0-2}$—. In various embodiments of $E^2$, j is 1, and $W^1$ is —C(O)—. In various embodiments of $E^2$, j is 1, and $W^1$ is —$C(O)N(R^7)$—. In various embodiments of $E^2$, j is 1, and $W^1$ is —$N(R^7)C(O)$—. In various embodiments of $E^2$, j is 1, and $W^1$ is —$N(R^7)S(O)$—. In various embodiments of $E^2$, j is 1, and $W^1$ is —$N(R^7)S(O)_2$—. In various embodiments of $E^2$, j is 1, and $W^1$ is —C(O)O—. In various embodiments of $E^2$, j is 1, and $W^1$ is $CH(R^7)N(C(O)OR)$—. In various embodiments of $E^2$, j is 1, and $W^1$ is —$CH(R^7)N(C(O)R)$—. In various embodiments of $E^2$, j is 1, and $W^1$ is —$CH(R^7)N(SO_2R^8)$—. In various embodiments of $E^2$, j is 1, and $W^1$ is —$CH(R^7)N(R^8)$—. In various embodiments of $E^2$, j is 1, and $W^1$ is —$CH(R^7)C(O)N(R^8)$—. In various embodiments of $E^2$, j is 1, and $W^1$ is —$CH(R^7)N(R^8)C(O)$—. In various embodiments of $E^2$, j is 1, and $W^1$ is —$CH(R^7)N(R^8)S(O)$—. In various embodiments of $E^2$, j is 1, and $W^1$ is —$CH(R^7)N(R^8)S(O)_2$—.

In various embodiments when $M_1$ is a moiety of Formula A-1, $M_1$ is benzoxazolyl substituted with —$(W_2)_k$—$R_2$. In some embodiments, $M_1$ is a benzoxazolyl substituted at the 2-position with —$(W^2)_j$—$R^2$. In some embodiments, $M_1$ is either a 5-benzoxazolyl or a 6-benzoxazolyl moiety, optionally substituted at the 2-position with —$(W^2)_j$—$R^2$. Exemplary Formula A-I $M_1$ moieties include but are not limited to the following:

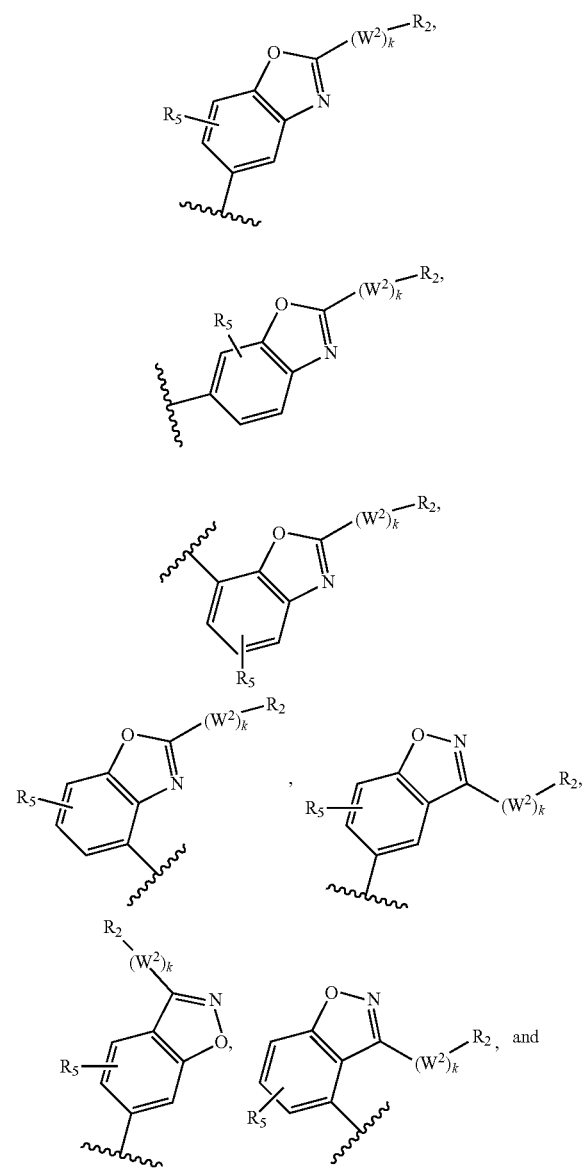

-continued

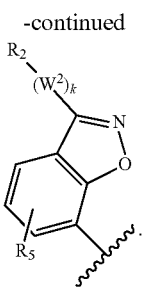

In various embodiments when $M_1$ is a moiety of Formula A-2, Formula A-2 is an aza-substituted benzoxazolyl moiety having a structure of one of the following formulae:

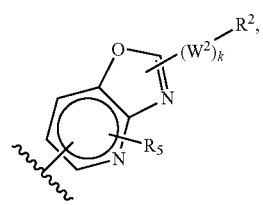 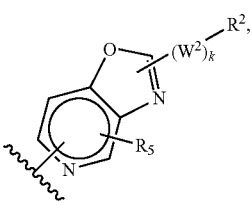

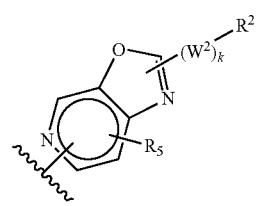 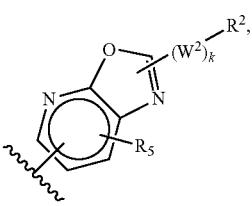

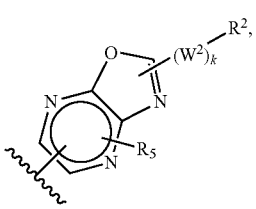 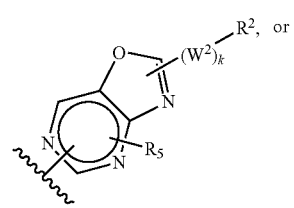

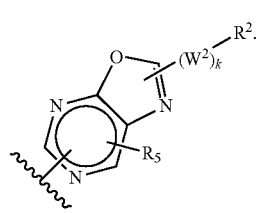

Exemplary Formula A-2 $M_1$ moieties include but are not limited to the following:

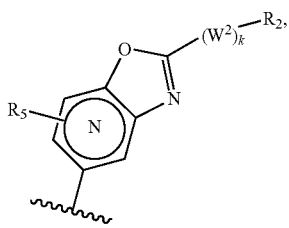

-continued

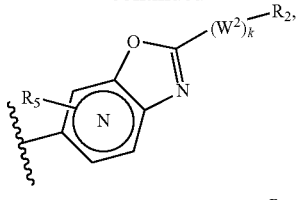

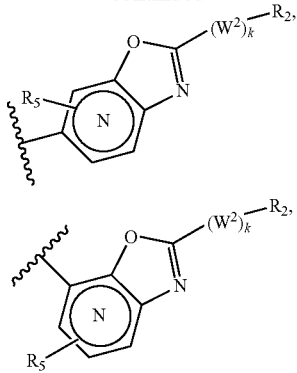

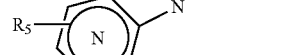

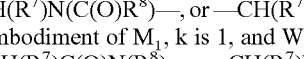

In various embodiments of $M_1$, k is 0. In other embodiments of $M_1$, k is 1, and $W^2$ is selected from one of the following: —O—, —NR$^7$—, —S(O)$_{0-2}$—, —C(O)—, —C(O)N(R$^7$)—, —N(R$^7$)C(O)—, or —N(R$^7$)C(O)N(R$^8$)—. In yet another embodiment of $M_1$, k is 1, and $W^2$ is —N(R$^7$)S(O)—, —N(R$^7$)S(O)$_2$—, —C(O)O—, —CH(R$^7$)N(C(O)OR$^8$)—, —CH(R$^7$)N(C(O)R$^8$)—, or —CH(R$^7$)N(SO$_2$R$^8$)—. In a further embodiment of $M_1$, k is 1, and $W^2$ is —CH(R$^7$)N(R$^8$)—, —CH(R$^7$)C(O)N(R$^8$)—, —CH(R$^7$)N(R$^8$)C(O)—, or —CH(R$^7$)N(R$^8$)S(O)—. In yet another embodiment of $M_1$, k is 1, and $W^2$ is —CH(R$^7$)N(R$^8$)S(O)$_2$—.

In some embodiments, the compound of Formula I'-A', I (including I-A and I-B), II-A (including II-A-1 and II-A-2), II-B (including II-B-1 and II-B-2), C, 3-6, C''', or 3-6''' is not a compound having one of the following structures:

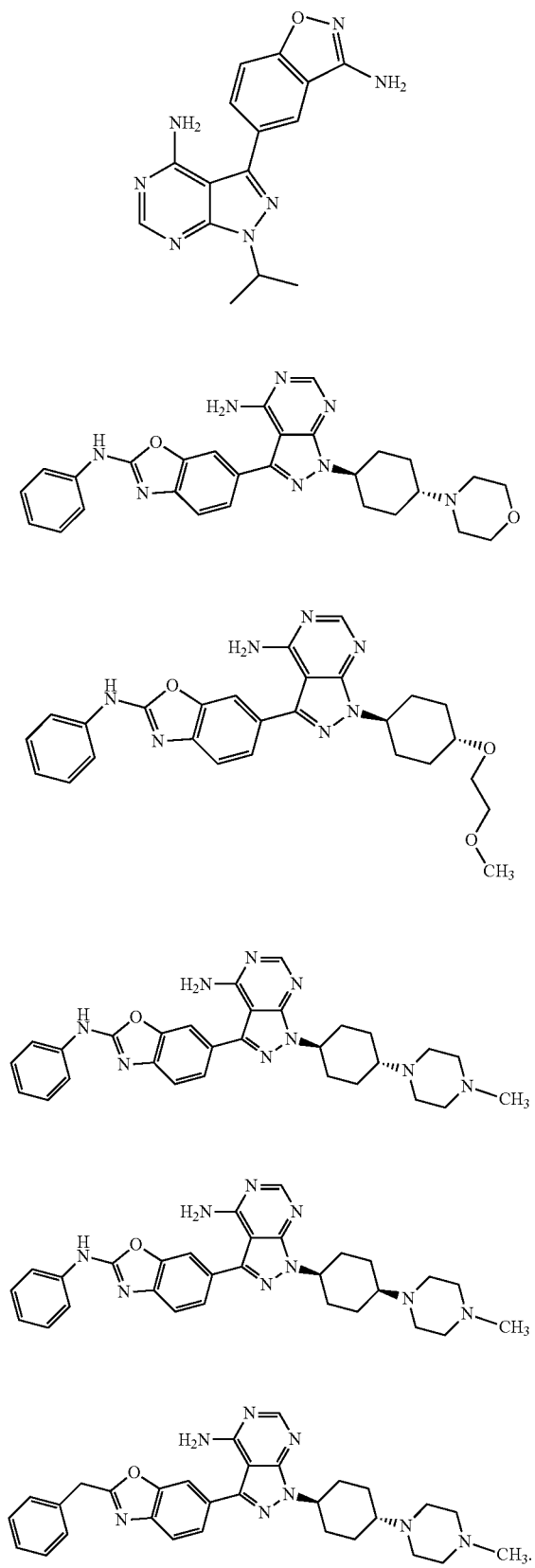

The invention provides a compound of Formula II-A or Formula II-B:

Formula II-A

Formula II-B or a pharmaceutically acceptable salt thereof, wherein $X_1$ is N or C-$E^1$, $X_2$ is N, and $X_3$ is C; or $X_1$ is N or C-$E^1$, $X_2$ is C, and $X_3$ is N;

$R_1$ is —H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;

$E^1$ and $E^2$ are independently —($W^1$)$_j$—$R^4$;

j in $E^1$ or j in $E^2$, is independently 0 or 1;

$W^1$ is —O—, —$NR^7$—, —S(O)$_{0-2}$—, —C(O)—, —C(O)N($R^7$)—, —N($R^7$)C(O)—, —N($R^7$)S(O)—, —N($R^7$)S(O)$_2$, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$W^2$ is —O—, —$NR^7$—, —S(O)$_{0-2}$—, —C(O)—, C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

k is 0 or 1;

$R^2$ is hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —NR³¹S(O)₀₋₂R³², —C(=S)OR³¹, —C(=O)SR³¹, —NR³¹C(=NR³²)NR³³R³², NR³¹C(=NR³²)OR³³, —NR³¹C(=NR³²)SR³³, —OC(=O)OR³³, —OC(=O)NR³¹R³², —OC(=O)SR³¹, SC(=O)OR³¹, —P(O)OR³¹OR³², —SC(=O)NR³¹R³² aryl (e.g. bicyclic aryl, unsubstituted aryl, or substituted monocyclic aryl), hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclyl, $C_{2-10}$alkenyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R³¹, —CF₃, —OCF₃, —OR³¹, —NR³¹R³², —NR³⁴R³⁵, —C(O)R³¹, —CO₂R³¹, —C(=O)NR³¹R³², —C(=O)NR³⁴R³⁵, —NO₂, —CN, —S(O)₀₋₂R³¹, —SO₂NR³¹R³², —SO₂NR³⁴R³⁵, —NR³¹C(=O)R³², —NR³¹C(=O)OR³², —NR³¹C(=O)NR³²R³³, —NR³¹S(O)₀₋₂R³², —C(=S)OR³¹, —C(=O)SR³¹, —NR³¹C(=NR³²)NR³³R³², —NR³¹C(=NR³²)OR³³, —NR³¹C(=NR³²)SR³³, —OC(=O)OR³³, —OC(=O)NR³¹R³², —OC(=O)SR³¹, —SC(=O)OR³¹, —P(O)OR³¹OR³², or —SC(=O)NR³¹R³² s, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R³¹, —CF₃, —OCF₃, —OR³¹, —O-aryl, —NR³¹R³², —NR³⁴R³⁵, —C(O)R³¹, —CO₂R³¹, —C(=O)NR³⁴R³⁵, or —C(=O)NR³¹R³²;

R³ and R⁴ are independently hydrogen, halogen, —OH, —R³¹, —CF₃, —OCF₃, —OR³¹, —NR³¹R³², —NR³⁴R³⁵, —C(O)R³¹, —CO₂R³¹, —C(=O)NR³¹R³², —C(=O)NR³⁴R³⁵, —NO₂, —CN, —S(O)₀₋₂R³¹, —SO₂NR³¹R³², —SO₂NR³⁴R³⁵, —NR³¹C(=O)R³², —NR³¹C(=O)OR³², —NR³¹C(=O)NR³²R³³, —NR³¹S(O)₀₋₂R³², —C(=S)OR³¹, —C(=O)SR³¹, —NR³¹C(=NR³²)NR³³R³², —NR³¹C(=NR³²)OR³³, —NR³¹C(=NR³²)SR³³, —OC(=O)OR³³, —OC(=O)NR³¹R³², —OC(=O)SR³¹, —SC(=O)OR³¹, —P(O)OR³¹OR³², —SC(=O)NR³¹R³², aryl, hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R³¹, —CF₃, —OCF₃, —OR³¹, —NR³¹R³², —NR³⁴R³⁵, —C(O)R³¹, —CO₂R³¹, —C(=O)NR³¹R³², —C(=O)NR³⁴R³⁵, —NO₂, —CN, —S(O)₀₋₂R³¹, —SO₂NR³¹R³², —SO₂NR³⁴R³⁵, —NR³¹C(=O)R³², —NR³¹C(=O)OR³², —NR³¹C(=O)NR³²R³³, —NR³¹S(O)₀₋₂R³², —C(=S)OR³¹, —C(=O)SR³¹, —NR³¹C(=NR³²)NR³³R³², —NR³¹C(=NR³²)OR³³, —NR³¹C(=NR³²)SR³³, —OC(=O)OR³³, —OC(=O)NR³¹R³², —OC(=O)SR³¹, —SC(=O)OR³¹, —P(O)OR³¹OR³², or —SC(=O)NR³¹R³², and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R³¹, —CF₃, —OCF₃, —OR³¹, —O-aryl, —NR³¹R³², —NR³⁴R³⁵, —C(O)R³¹, —CO₂R³¹, —C(=O)NR³⁴R³⁵, or —C(=O)NR³¹R³²;

R⁵ is hydrogen, halogen, —OH, —R³¹, —CF₃, —OCF₃, —OR³¹, —NR³¹R³², —NR³⁴R³⁵, —C(O)R³¹, —CO₂R³¹, —C(=O)NR³¹R³², —C(=O)NR³⁴R³⁵, —NO₂, —CN, —S(O)₀₋₂R³¹, —SO₂NR³¹R³², —SO₂NR³⁴R³⁵, —NR³¹C(=O)R³², —NR³¹C(=O)OR³², —NR³¹C(=O)NR³²R³³, —NR³¹S(O)₀₋₂R³², —C(=S)OR³¹, —C(=O)SR³¹, —NR³¹C(=NR³²)NR³³R³², —NR³¹C(=NR³²)OR³³, —NR³¹C(=NR³²)SR³³, —OC(=O)OR³³, —OC(=O)NR³¹R³², —OC(=O)SR³¹, —SC(=O)OR³¹, —P(O)OR³¹OR³², or —SC(=O)NR³¹R³²;

R³¹, R³², and R³³, in each instance, are independently H or $C_{1-10}$alkyl, wherein the $C_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —$C_{1-10}$alkyl, —CF₃, —O-aryl, —OCF₃, —O$C_{1-10}$alkyl, —NH₂, —N($C_{1-10}$alkyl)($C_{1-10}$alkyl), —NH($C_{1-10}$alkyl), —NH(aryl), —NR³⁴R³⁵, —C(O)($C_{1-10}$alkyl), —C(O)($C_{1-10}$alkyl-aryl), —C(O)(aryl), —CO₂—$C_{1-10}$alkyl, —CO₂—$C_{1-10}$alkylaryl, —CO₂-aryl, —C(=O)N($C_{1-10}$alkyl)($C_{1-10}$alkyl), —C(=O)NH($C_{1-10}$alkyl), —C(=O)NR³⁴R³⁵, —C(=O)NH₂, —OCF₃, —O($C_{1-10}$alkyl), —O-aryl, —N(aryl)($C_{1-10}$alkyl), —NO₂, —CN, —S(O)₀₋₂$C_{1-10}$alkyl, —S(O)₀₋₂$C_{1-10}$alkylaryl, —S(O)₀₋₂ aryl, —SO₂N(aryl), —SO₂N($C_{1-10}$alkyl)($C_{1-10}$alkyl), —SO₂NH($C_{1-10}$alkyl) or —SO₂NR³⁴R³⁵;

R³⁴ and R³⁵ in —NR³⁴R³⁵, —C(=O)NR³⁴R³⁵, or —SO₂NR³⁴R³⁵, are taken together with the nitrogen atom to which they are attached to form a 3-10 membered saturated or unsaturated ring; wherein said ring is independently unsubstituted or is substituted by one or more —NR³¹R³², hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom; and R⁷ and R⁸ are each independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent R⁶; and R⁶ is halo, —OR³¹, —SH, NH₂, —NR³⁴R³⁵, —NR³¹R³², —CO$_2$R$^{31}$, —CO$_2$aryl, —C(=O)NR$^{31}$R$^{32}$, —C(=O) NR$^{34}$R$^{35}$, —NO$_2$, —CN, —S(O)$_{0-2}$C$_{1-10}$alkyl, —S(O)$_{0-2}$aryl, —SO$_2$NR$^{34}$R$^{35}$, —SO$_2$NR$^{31}$R$^{32}$, C$_{1-10}$alkyl, C$_{2-10}$alkenyl, or C$_{2-10}$alkynyl; or R$^6$ is aryl-C$_{1-10}$alkyl, aryl-C$_{2-10}$alkenyl, aryl-C$_{2-10}$alkynyl, hetaryl-C$_{1-10}$alkyl, hetaryl-C$_{2-10}$alkenyl, hetaryl-C$_{2-10}$alkynyl, each of which is unsubstituted or is substituted with one or more independent halo, cyano, nitro, —OC$_{1-10}$alkyl, C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$.

In various embodiments of the compound of Formula II-A, the compound has a structure of Formula II-A-1 or Formula II-A-2:

Formula II-A-1

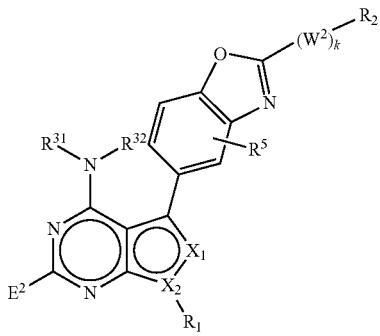

Formula II-A-2

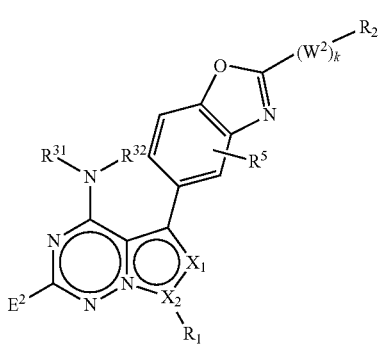

or a pharmaceutically acceptable salt thereof.

In some embodiments of Formula II-A-1, X$_1$ is N and X$_2$ is N. In other embodiments, X$_1$ is C-E$^1$ and X$_2$ is N. In yet other embodiments, X$_1$ is NH and X$_2$ is C. In further embodiments, X$_1$ is CH-E$^1$ and X$_2$ is C.

In several embodiments of Formula II-A-2, X$_1$ is N and X$_2$ is C. In yet other embodiments, X$_1$ is NH and X$_2$ is C.

In further embodiments, X$_1$ is CH-E$^1$ and X$_2$ is C.

In various embodiments of the compound of Formula II-B, the compound has a structure of Formula II-B-1 or Formula II-B-2:

Formula II-B-1

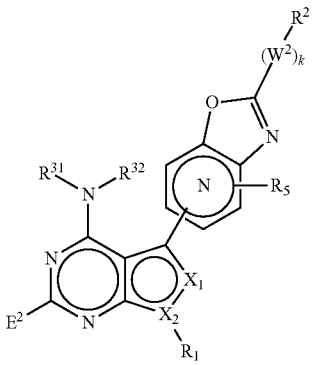

Formula II-B-2

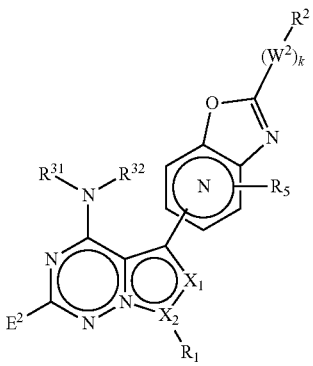

or a pharmaceutically acceptable salt thereof.

In some embodiments of Formula II-B-1, X$_1$ is N and X$_2$ is N. In other embodiments, X$_1$ is C-E$^1$ and X$_2$ is N. In yet other embodiments, X$_1$ is NH and X$_2$ is C. In further embodiments, X$_1$ is CH-E$^1$ and X$_2$ is C.

In several embodiments of Formula II-B-2, X$_1$ is N and X$_2$ is C. In further embodiments, X$_1$ is C-E$^1$ and X$_2$ is C.

In various embodiments, X$_1$ is C—(W$^1$)$_j$—R$^4$, where j is 0.

In another embodiment, X$_1$ is CH. In yet another embodiment, X$_1$ is C-halogen, where halogen is Cl, F, Br, or I.

In various embodiments of X$_1$, it is C—(W$^1$)$_j$—R$^4$. In various embodiments of X$_1$, j is 1, and W$^1$ is —O—. In various embodiments of X$_1$, j is 1, and W$^1$ is —NR$^7$—. In various embodiments of X$_1$, j is 1, and W$^1$ is —NH—. In various embodiments of X$_1$, j is 1, and W$^1$ is —S(O)$_{0-2}$—. In various embodiments of X$_1$, j is 1, and W$^1$ is —C(O). In various embodiments of X$_1$, j is 1, and W$^1$ is —C(O)N(R$^7$)—. In various embodiments of X$_1$, j is 1, and W$^1$ is —N(R$^7$)C(O)—. In various embodiments of X$_1$, j is 1, and W$^1$ is —N(R$^7$)S(O)—. In various embodiments of X$_1$, j is 1, and W$^1$ is —N(R$^7$)S(O)$_2$—. In various embodiments of X$_1$, j is 1, and W$^1$ is —C(O)O—. In various embodiments of X$_1$, j is 1, and W$^1$ is —CH(R$^7$)N(C(O)OR$^8$)—. In various embodiments of X$_1$, j is 1, and W$^1$ is —CH(R$^7$)N(C(O)R$^8$)—. In various embodiments of X$_1$, j is 1, and W$^1$ is —CH(R$^7$)N(SO$_2$R$^8$)—. In various embodiments of X$_1$, j is 1, and W$^1$ is —CH(R$^7$)N(R$^8$)—. In various embodiments of X$_1$, j is 1, and W$^1$ is —CH(R$^7$)C(O)N(R$^8$)—. In various embodiments of X$_1$, j is 1, and W$^1$ is —CH(R$^7$)N(R$^8$)C(O)—. In various embodiments of X$_1$, j is 1, and W$^1$ is —CH(R$^7$)N(R$^8$)S(O). In various embodiments of X$_1$, j is 1, and W$^1$ is —CH(R$^7$)N(R$^8$)S(O)$_2$—.

In various embodiments, X$_1$ is CH—(W$^1$)$_j$—R$^4$, where j is 0.

In another embodiment, $X_1$ is $CH_2$. In yet another embodiment, $X_1$ is CH-halogen, where halogen is Cl, F, Br, or I.

In various embodiments of $X_1$, it is $CH-(W^1)_j-R^4$. In various embodiments of $X_1$, j is 1, and $W^1$ is $-O-$. In various embodiments of $X_1$, j is 1, and $W^1$ is $-NR^7-$. In various embodiments of $X_1$, j is 1, and $W^1$ is $-NH-$. In various embodiments of $X_1$, j is 1, and $W^1$ is $-S(O)_{0-2}-$. In various embodiments of $X_1$, j is 1, and $W^1$ is $-C(O)$. In various embodiments of $X_1$, j is 1, and $W^1$ is $-C(O)N(R^7)-$. In various embodiments of $X_1$, j is 1, and $W^1$ is $-N(R^7)C(O)-$. In various embodiments of $X_1$, j is 1, and $W^1$ is $-N(R^7)S(O)$. In various embodiments of $X_1$, j is 1, and $W^1$ is $-N(R^7)S(O)_2-$.

In various embodiments of $X_1$, j is 1, and $W^1$ is $-C(O)O-$. In various embodiments of $X_1$, j is 1, and $W^1$ is $-CH(R^7)N(C(O)OR^8)-$. In various embodiments of $X_1$, j is 1, and $W^1$ is $-CH(R^7)N(C(O)R^8)-$. In various embodiments of $X_1$, j is 1, and $W^1$ is $-CH(R^7)N(SO_2R^8)-$. In various embodiments of $X_1$, j is 1, and $W^1$ is $-CH(R^7)N(R^8)-$. In various embodiments of $X_1$, j is 1, and $W^1$ is $-CH(R^7)C(O)N(R^8)-$. In various embodiments of $X_1$, j is 1, and $W^1$ is $-CH(R^7)N(R^8)C(O)-$. In various embodiments of $X_1$, j is 1, and $W^1$ is $-CH(R^7)N(R^8)S(O)-$. In various embodiments of $X_1$, j is 1, and $W^1$ is $-CH(R^7)N(R^8)S(O)_2-$.

In another embodiment, $X_1$ is N.

In various embodiments, $X_2$ is N. In other embodiments, $X_2$ is C.

In various embodiments, $E^2$ is $-(W^1)_j-R^4$, where j is 0.

In another embodiment, $E^2$ is CH. In yet another embodiment, $E^2$ is C-halogen, where halogen is Cl, F, Br, or I.

In various embodiments of $E^2$, it is $-(W^1)_j-R^4$. In various embodiments of $E^2$, j is 1, and $W^1$ is $-O-$. In various embodiments of $E^2$, j is 1, and $W^1$ is $-NR-$. In various embodiments of $E^2$, j is 1, and $W^1$ is $-NH-$. In various embodiments of $E^2$, j is 1, and $W^1$ is $-S(O)_{0-2}-$. In various embodiments of $E^2$, j is 1, and $W^1$ is $-C(O)-$. In various embodiments of $E^2$, j is 1, and $W^1$ is $-C(O)N(R^7)-$. In various embodiments of $E^2$, j is 1, and $W^1$ is $-N(R^7)C(O)-$. In various embodiments of $E^2$, j is 1, and $W^1$ is $-N(R^7)S(O)-$. In various embodiments of $E^2$, j is 1, and $W^1$ is $-N(R^7)S(O)_2-$. In various embodiments of $E^2$, j is 1, and $W^1$ is $-C(O)O-$. In various embodiments of $E^2$, j is 1, and $W^1$ is $CH(R^7)N(C(O)OR)-$. In various embodiments of $E^2$, j is 1, and $W^1$ is $-CH(R^7)N(C(O)R)-$. In various embodiments of $E^2$, j is 1, and $W^1$ is $-CH(R^7)N(SO_2R^8)-$. In various embodiments of $E^2$, j is 1, and $W^1$ is $-CH(R^7)N(R^8)-$. In various embodiments of $E^2$, j is 1, and $W^1$ is $-CH(R^7)C(O)N(R^8)-$. In various embodiments of $E^2$, j is 1, and $W^1$ is $-CH(R^7)N(R^8)C(O)-$. In various embodiments of $E^2$, j is 1, and $W^1$ is $-CH(R^7)N(R^8)S(O)-$. In various embodiments of $E^2$, j is 1, and $W^1$ is $-CH(R^7)N(R^8)S(O)_2-$.

In various embodiments, k is 0. In other embodiments, k is 1 and $W^2$ is $-O-$. In another embodiment, k is 1 and $W^2$ is $-NR^7-$. In yet another embodiment of, k is 1, and $W^2$ is $-S(O)_{0-2}-$. In another embodiment of, k is 1 and $W^2$ is $-C(O)-$. In a further embodiment, k is 1 and $W^2$ is $-C(O)N(R^7)-$. In another embodiment, k is 1, and $W^2$ is $-N(R^7)C(O)-$. In another embodiment, k is 1 and $W^2$ is $-N(R^7)C(O)N(R^8)-$. In yet another embodiment, k is 1 and $W^2$ is $-N(R^7)S(O)-$. In still yet another embodiment, k is 1 and $W^2$ is $-N(R^7)S(O)_2-$. In a further embodiment, k is 1 and $W^2$ is $-C(O)O-$. In another embodiment, k is 1 and $W^2$ is $-CH(R^7)N(C(O)OR)-$. In another embodiment, k is 1 and $W^2$ is $-CH(R^7)N(C(O)R^8)-$. In another embodiment, k is 1 and $W^2$ is $-CH(R^7)N(SO_2R^8)-$. In a further embodiment, k is 1 and $W^2$ is $-CH(R^7)N(R^8)-$. In another embodiment, k is 1 and $W^2$ is $-CH(R^7)C(O)N(R^8)-$. In yet another embodiment, k is 1 and $W^2$ is $-CH(R^7)N(R^8)C(O)-$. In another embodiment, k is 1 and $W^2$ is $-CH(R^7)N(R^8)S(O)-$. In yet another embodiment, k is 1 and $W^2$ is $-CH(R^7)N(R^8)S(O)_2-$.

The invention also provides a compound of Formula III:

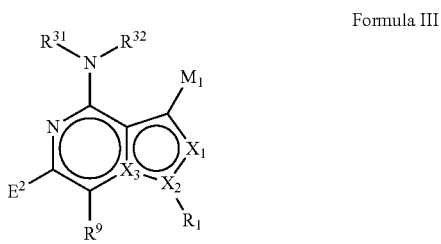

Formula III or a pharmaceutically acceptable salt thereof, wherein: $X_1$ is N or C-$E^1$, $X_2$ is N, and $X_3$ is C; or $X_1$ is N or C-$E^1$, $X_2$ is C, and $X_3$ is N;

$R_1$ is $-H$, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, $-(C=O)-$, $-C(=O)O-$, $-C(=O)N(R^{31})-$, $-S-$, $-S(O)-$, $-S(O)_2-$, $-S(O)_2N(R^{31})-$, or $-N(R^{31})-$;

$M_1$ is a moiety having the structure of Formula A-1 or Formula A-2:

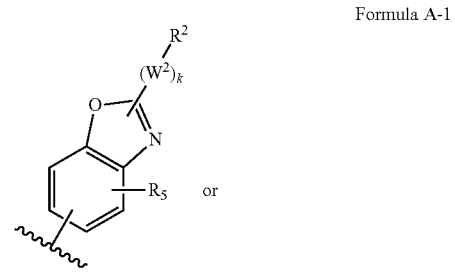

Formula A-1

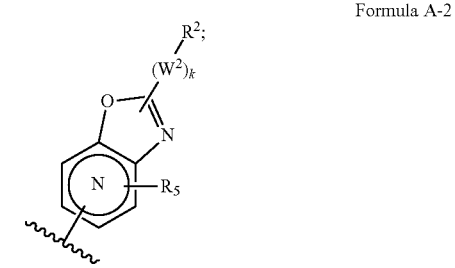

Formula A-2 k is 0 or 1;

$E^1$ and $E^2$ are independently $-(W^1)_j-R^4$;

j in $E^1$ or j in $E^2$, is independently 0 or 1;

$W^1$ is $-O-$, $-NR^7-$, $-S(O)_{0-2}-$, $-C(O)-$, $-C(O)N(R^7)-$, $-N(R^7)C(O)-$, $-N(R^7)S(O)-$, $-N(R^7)S(O)_2-$, $-C(O)O-$, $-CH(R^7)N(C(O)OR)-$, $-CH(R^7)N(C(O)R^8)-$, $-CH(R^7)N(SO_2R^8)-$, $-CH(R^7)N(R^8)-$,

—CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$W^2$ is —O—, —N$R^7$—, —S(O)$_{0-2}$—, —C(O)N($R^7$)—, —N($R^7$)C(O)—, —N($R^7$)C(O)N($R^7$)—, —N($R^7$)S(O)—, —N($R^7$)S(O)$_2$—, —C(O)O—, —CH($R^7$)N(C(O)OR)—, —CH($R^7$)N(C(O)$R^8$)—, —CH($R^7$)N(SO$_2R^8$)—, —CH($R^7$)N($R^8$)—, —CH($R^7$)C(O)N(RB)—, —CH($R^7$)N($R^8$)C(O)—, —CH($R^7$)N($R^8$)S(O)—, or —CH($R^7$)N($R^8$)S(O)$_2$—;

$R^2$ is hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32'}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, —SC(=O)N$R^{31}R^{32}$, aryl (e.g. bicyclic aryl, unsubstituted aryl, or substituted monocyclic aryl), hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclyl, $C_{2-10}$alkenyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, or —SC(=O)N$R^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —O-aryl, —N$R^{31}R^{32}$, —N$R^{34}R^{35}$, —C(O)$R^{31}$, —CO$_2R^{31}$, —C(=O)N$R^{34}R^{35}$, or —C(=O)N$R^{31}R^{32}$;

$R^3$ and $R^4$ are independently hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, —SC(=O)N$R^{31}R^{32}$, aryl, hetaryl, $C_{1-4}$alkyl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, or —SC(=O)N$R^{31}R^{32}$, and wherein each of said alkyl, cycloalkyl, heterocyclyl, or heteroalkyl moiety is unsubstituted or is substituted with one or more halo, —OH, —$R^{31}$, —CF$_3$, —OCF$_3$, —O$R^{31}$, —O-aryl, —N$R^{31}R^{32}$, —N$R^{34}R^{35}$, —C(O)$R^{31}$, —CO$_2R^{31}$, —C(=O)N$R^{34}R^{35}$, or —C(=O)N$R^{31}R^{32}$;

$R^5$ is hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, or —SC(=O)N$R^{31}R^{32}$;

$R^{31}$, $R^{32}$, and $R^{33}$, in each instance, are independently H or $C_{1-10}$alkyl, wherein the $C_{1-10}$alkyl is unsubstituted or is substituted with one or more aryl, heteroalkyl, heterocyclyl, or hetaryl group wherein each of said aryl, heteroalkyl, heterocyclyl, or hetaryl group is unsubstituted or is substituted with one or more halo, —OH, —$C_{1-10}$alkyl, —CF$_3$, —O-aryl, OCF$_3$, —O$C_{1-10}$alkyl, —NH$_2$, —N($C_{1-10}$alkyl)($C_{1-10}$alkyl), —NH($C_{1-10}$alkyl), —NH(aryl), —N$R^{34}R^{35}$, —C(O)($C_{1-10}$alkyl), —C(O)($C_{1-10}$alkyl-aryl), —C(O)(aryl), —CO$_2$—$C_{1-10}$alkyl, —CO$_2$—$C_{1-10}$alkylaryl, —CO$_2$-aryl, —C(=O)N($C_{1-10}$alkyl)($C_{1-10}$alkyl), —C(=O)NH($C_{1-10}$alkyl), —C(=O)N$R^{34}R^{35}$, —C(=O)NH$_2$, —OCF$_3$, —O($C_{1-10}$alkyl), —O-aryl, —N(aryl)($C_{1-10}$alkyl), —NO$_2$, —CN, —S(O)$_{0-2}C_{1-10}$alkyl, —S(O)$_{0-2}C_{1-10}$alkylaryl, —S(O)$_{0-2}$ aryl, —SO$_2$N(aryl), —SO$_2$N($C_{1-10}$alkyl)($C_{1-10}$alkyl), —SO$_2$NH($C_{1-10}$alkyl) or —SO$_2$N$R^{34}R^{35}$;

$R^{34}$ and $R^{35}$ in —N$R^{34}R^{35}$, —C(=O)N$R^{34}R^{35}$, or —SO$_2$N$R^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom;

$R^7$ and $R^8$ are each independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, —C(=O)$NR^{34}R^{35}$, —$NO_2$, —CN, —S(O)$_{0-2}C_{1-10}$alkyl, —S(O)$_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)$NR^{31}R^{32}$, —C(=O)$NR^{34}R^{35}$, —$SO_2NR^{34}R^{35}$, —$SO_2NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, —C(=O)$NR^{34}R^{35}$, —$NO_2$, —CN, —S(O)$_{0-2}C_{1-10}$alkyl, —S(O)$_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)$NR^{31}R^{32}$, —C(=O)$NR^{34}R^{35}$, —$SO_2NR^{34}R^{35}$, —$SO_2NR^{31}R^{32}$, —$NR^{31}R^{32}$, or —$NR^{34}R^{35}$.

In various embodiments of the compound of Formula III, the compound has a structure of Formula III-A or Formula III-B:

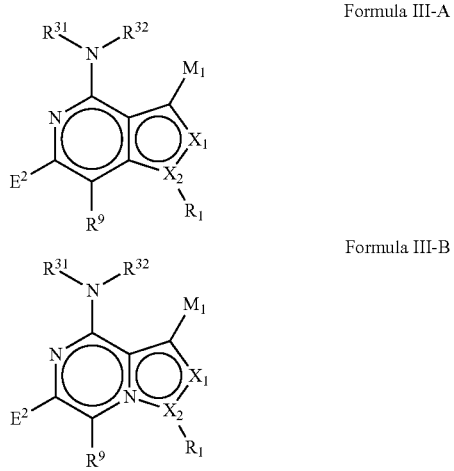

Formula III-A

Formula III-B or a pharmaceutically acceptable salt thereof.

In some embodiments of Formula III-A, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C.

In several embodiments of Formula III-B, $X_1$ is N and $X_2$ is C. In further embodiments, $X_1$ is C-$E^1$ and $X_2$ is C.

In various embodiments, $X_1$ is C—$(W^1)_j$—$R^4$, where j is 0. In another embodiment, $X_1$ is CH. In yet another embodiment, $X_1$ is C-halogen, where halogen is Cl, F, Br, or I.

In various embodiments of $X_1$, it is C—$(W^1)_j$—$R^4$. In various embodiments of $X_1$, j is 1, and $W^1$ is —O—. In various embodiments of $X_1$, j is 1, and $W^1$ is —$NR^7$—. In various embodiments of $X_1$, j is 1, and $W^1$ is —NH—. In various embodiments of $X_1$, j is 1, and $W^1$ is —S(O)$_{0-2}$—. In various embodiments of $X_1$, j is 1, and $W^1$ is —C(O)—. In various embodiments of $X_1$, j is 1, and $W^1$ is —C(O)N($R^7$)—. In various embodiments of $X_1$, j is 1, and $W^1$ is —N($R^7$)C(O)—. In various embodiments of $X_1$, j is 1, and $W^1$ is —N($R^7$)S(O)—. In various embodiments of $X_1$, j is 1, and $W^1$ is —N($R^7$)S(O)$_2$—. In various embodiments of $X_1$, j is 1, and $W^1$ is —C(O)O—. In various embodiments of $X_1$, j is 1, and $W^1$ is CH($R^7$)N(C(O)OR)—. In various embodiments of $X_1$, j is 1, and $W^1$ is —CH($R^7$)N(C(O)R)—. In various embodiments of $X_1$, j is 1, and $W^1$ is —CH($R^7$)N($SO_2R^8$)—. In various embodiments of $X_1$, j is 1, and $W^1$ is —CH($R^7$)N($R^8$)—. In various embodiments of $X_1$, j is 1, and $W^1$ is —CH($R^7$)C(O)N($R^8$)—. In various embodiments of $X_1$, j is 1, and $W^1$ is —CH($R^7$)N($R^8$)C(O)—. In various embodiments of $X_1$, j is 1, and $W^1$ is —CH($R^7$)N($R^8$)S(O)—. In various embodiments of $X_1$, j is 1, and $W^1$ is —CH($R^7$)N($R^8$)S(O)$_2$—.

In various embodiments, $X_1$ is CH—$(W^1)_j$—$R^4$, where j is 0.

In another embodiment, $X_1$ is $CH_2$. In yet another embodiment, $X_1$ is CH-halogen, where halogen is Cl, F, Br, or I.

In various embodiments of $X_1$, it is CH—$(W^1)_j$—$R^4$. In various embodiments of $X_1$, j is 1, and $W^1$ is —O—. In various embodiments of $X_1$, j is 1, and $W^1$ is —$NR^7$—. In various embodiments of $X_1$, j is 1, and $W^1$ is —NH—. In various embodiments of $X_1$, j is 1, and $W^1$ is —S(O)$_{0-2}$—. In various embodiments of $X_1$, j is 1, and $W^1$ is —C(O)—. In various embodiments of $X_1$, j is 1, and $W^1$ is —C(O)N($R^7$)—. In various embodiments of $X_1$, j is 1, and $W^1$ is —N($R^7$)C(O)—. In various embodiments of $X_1$, j is 1, and $W^1$ is —N($R^7$)S(O)—. In various embodiments of $X_1$, j is 1, and $W^1$ is —N($R^7$)S(O)$_2$—. In various embodiments of $X_1$, j is 1, and $W^1$ is —C(O)O—. In various embodiments of $X_1$, j is 1, and $W^1$ is —CH($R^7$)N(C(O)OR)—. In various embodiments of $X_1$, j is 1, and $W^1$ is —CH($R^7$)N(C(O)R)—. In various embodiments of $X_1$, j is 1, and $W^1$ is —CH($R^7$)N($SO_2R^8$)—. In various embodiments of $X_1$, j is 1, and $W^1$ is —CH($R^7$)N($R^8$)—. In various embodiments of $X_1$, j is 1, and $W^1$ is —CH($R^7$)C(O)N($R^8$)—. In various embodiments of $X_1$, j is 1, and $W^1$ is —CH($R^7$)N($R^8$)C(O)—. In various embodiments of $X_1$, j is 1, and $W^1$ is —CH($R^7$)N($R^8$)S(O)—. In various embodiments of $X_1$, j is 1, and $W^1$ is —CH($R^7$)N($R^8$)S(O)$_2$—.

In another embodiment, $X_1$ is N.

In various embodiments, $X_2$ is N. In other embodiments, $X_2$ is C.

In various embodiments, $E^2$ is —$(W^1)_j$—$R^4$, where j is 0.

In another embodiment, $E^2$ is CH. In yet another embodiment, $E^2$ is C-halogen, where halogen is Cl, F, Br, or I.

In various embodiments of $E^2$, it is —$(W^1)_j$—$R^4$. In various embodiments of $E^2$, j is 1, and $W^1$ is —O—. In various embodiments of $E^2$, j is 1, and $W^1$ is —$NR^7$—. In various embodiments of $E^2$, j is 1, and $W^1$ is —NH—. In various embodiments of $E^2$, j is 1, and $W^1$ is —S(O)$_{0-2}$—. In various embodiments of $E^2$, j is 1, and $W^1$ is —C(O)—. In various embodiments of $E^2$, j is 1, and $W^1$ is —C(O)N($R^7$)—. In various embodiments of $E^2$, j is 1, and $W^1$ is —N($R^7$)C(O)—.

In various embodiments of $E^2$, j is 1, and $W^1$ is —N($R^7$)S(O)—. In various embodiments of $E^2$, j is 1, and $W^1$ is —N($R^7$)S(O)$_2$—. In various embodiments of $E^2$, j is 1, and $W^1$ is —C(O)O—. In various embodiments of $E^2$, j is 1, and $W^1$ is CH($R^7$)N(C(O)OR)—. In various embodiments of $E^2$, j is 1, and $W^1$ is —CH($R^7$)N(C(O)R)—. In various embodiments of $E^2$, j is 1, and $W^1$ is —CH($R^7$)N(SO$_2R^8$)—. In various embodiments of $E^2$, j is 1, and $W^1$ is —CH($R^7$)N($R^8$)—. In various embodiments of $E^2$, j is 1, and $W^1$ is —CH($R^7$)C(O)N($R^8$)—. In various embodiments of $E^2$, j is 1, and $W^1$ is —CH($R^7$)N($R^8$)C(O)—. In various embodiments of $E^2$, j is 1, and $W^1$ is —CH($R^7$)N($R^8$)S(O)—. In various embodiments of $E^2$, j is 1, and $W^1$ is —CH($R^7$)N($R^8$)S(O)$_2$—.

In various embodiments when $M_1$ is a moiety of Formula A-1, $M_1$ is benzoxazolyl substituted with —(W$_2$)$_k$—$R_2$. In some embodiments, $M_1$ is a benzoxazolyl moiety, substituted at the 2-position with —(W$_2$)$_k$—$R_2$. In some embodiments, $M_1$ is either a 5-benzoxazolyl or a 6-benzoxazolyl moiety, optionally substituted with —(W$_2$)$_k$—$R_2$. Exemplary Formula A-1 $M_1$ moieties include but are not limited to the following:

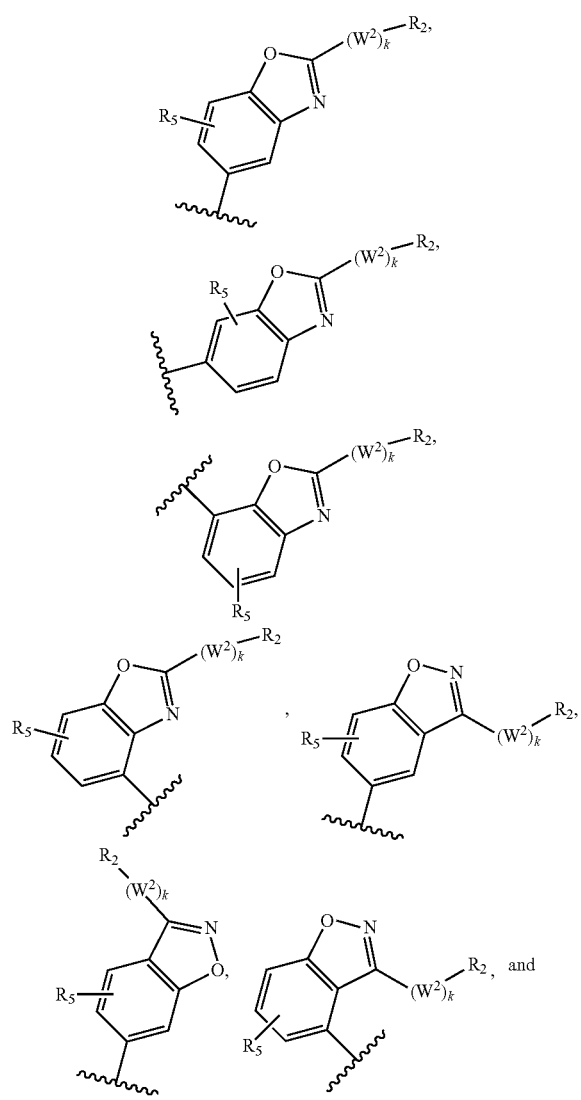

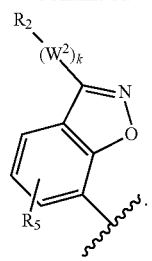

In various embodiments when $M_1$ is a moiety of Formula A-2, Formula A-2 is an aza-substituted benzoxazolyl moiety having a structure of one of the following formulae:

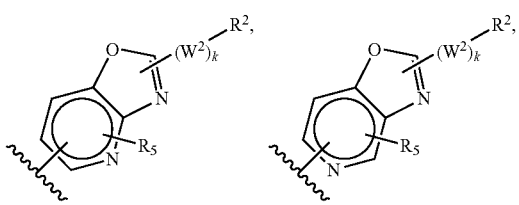

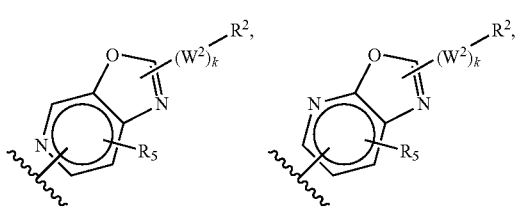

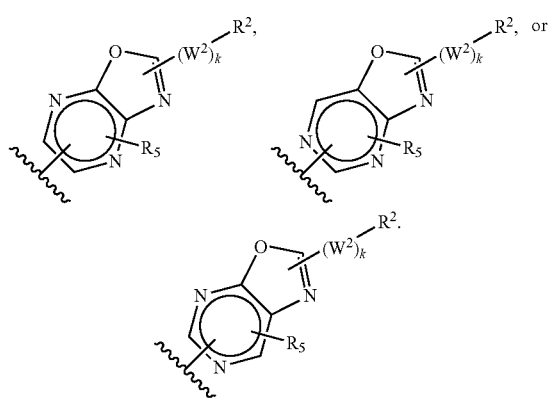

Exemplary Formula A-2 $M_1$ moieties include but are not limited to the following:

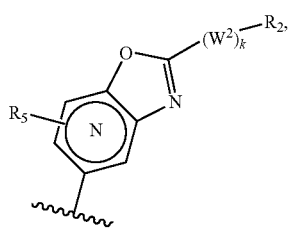

-continued

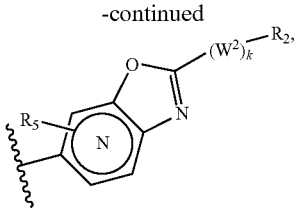

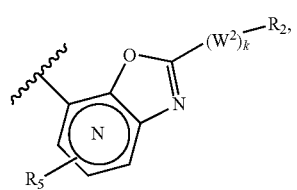

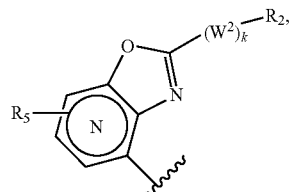

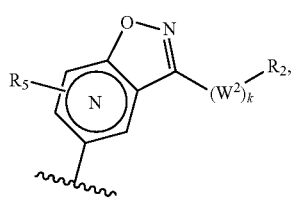

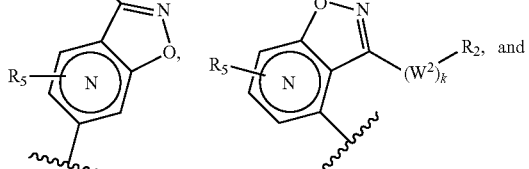

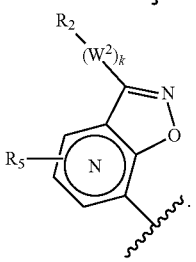

In various embodiments of $M_1$, k is 0. In other embodiments of $M_1$, k is 1 and $W^2$ is —O—. In another embodiment of $M_1$, k is 1 and $W^2$ is —NR$^7$—. In yet another embodiment of $M_1$, k is 1 and $W^2$ is —S(O)$_{0-2}$—. In another embodiment of $M_1$, k is 1 and $W^2$ is —C(O)—. In a further embodiment of $M_1$, k is 1 and $W^2$ is —C(O)N(R$^7$)—. In another embodiment of $M_1$, k is 1 and $W^2$ is —N(R$^7$)C(O)—. In another embodiment, k is 1 and $W^2$ is —N(R$^7$)C(O)N(R$^8$)—. In yet another embodiment of $M_1$, k is 1 and $W^2$ is —N(R$^7$)S(O)—. In still yet another embodiment of $M_1$, k is 1 and $W^2$ is —N(R$^7$)S(O)$_2$—. In a further embodiment of $M_1$, k is 1 and $W^2$ is —C(O)O—. In another embodiment of $M_1$, k is 1 and $W^2$ is —CH(R$^7$)N(C(O)OR$^8$)—. In another embodiment of $M_1$, k is 1 and $W^2$ is —CH(R$^7$)N(C(O)R$^8$)—. In another embodiment of $M_1$, k is 1 and $W^2$ is —CH(R$^7$)N(SO$_2$R$^8$)—. In a further embodiment of $M_1$, k is 1 and $W^2$ is —CH(R$^7$)N(R$^8$)—. In another embodiment of $M_1$, k is 1 and $W^2$ is —CH(R$^7$)C(O)N(R$^8$)—. In yet another embodiment of $M_1$, k is 1 and $W^2$ is —CH(R$^7$)N(R$^8$)C(O)—. In another embodiment of $M_1$, k is 1 and $W^2$ is —CH(R$^7$)N(R$^8$)S(O)—. In yet another embodiment of $M_1$, k is 1 and $W^2$ is —CH(R$^7$)N(R$^8$)S(O)$_2$—.

In some aspects of the invention, a compound of Formula I'-A' is a compound of Formula IV-A or Formula IV-B:

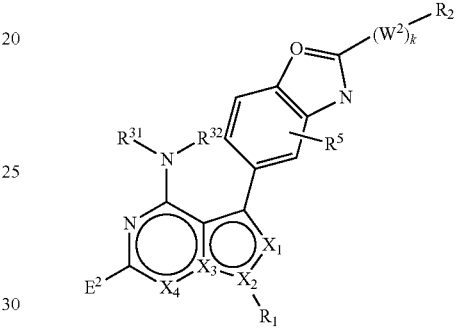

Formula IV-A

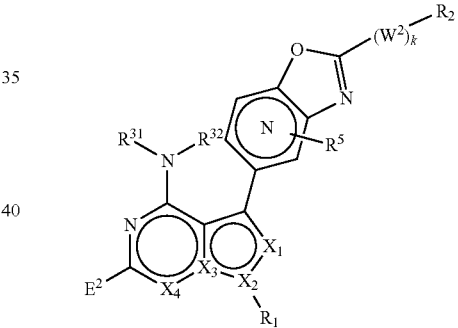

Formula IV-B or a pharmaceutically acceptable salt thereof.

In various embodiments of the compound of Formula IV-A, the compound has a structure of Formula IV-A-1 or Formula IV-A-2:

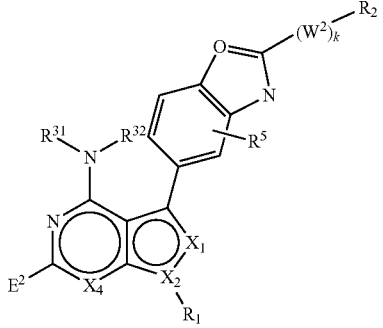

Formula IV-A-1

-continued

Formula IV-A-2

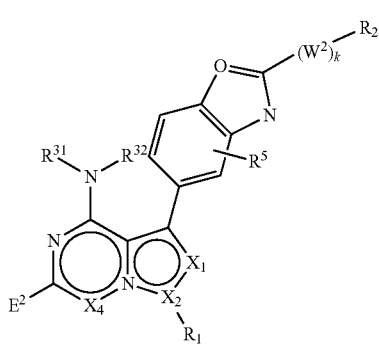

or a pharmaceutically acceptable salt thereof.

In some embodiments of Formula IV-A-1, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C. In several embodiments of Formula IV-A-2, $X_1$ is N and $X_2$ is C. In further embodiments, $X_1$ is C-$E^1$ and $X_2$ is C.

In some embodiments, $X_4$ is $CR^9$. In other embodiments, $X_4$ is N.

In various embodiments of the compound of Formula II-B, the compound has a structure of Formula II-B-1 or Formula II-B-2:

Formula IV-B-1

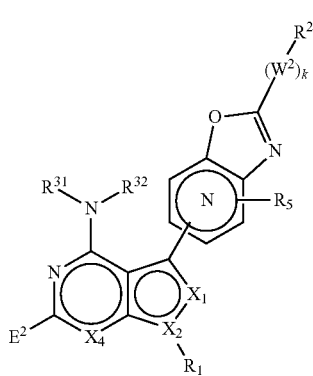

Formula IV-B-2

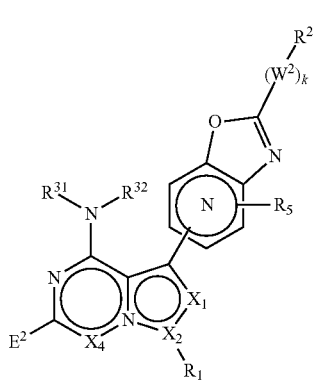

or a pharmaceutically acceptable salt thereof.

In some embodiments of Formula IV-B-1, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C.

In several embodiments of Formula IV-B-2, $X_1$ is N and $X_2$ is C. In further embodiments, $X_1$ is C-$E^1$ and $X_2$ is C.

In some embodiments, $X_4$ is $CR^9$. In other embodiments, $X_4$ is N.

Additional embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, B (including B' and B"), C, 3-1, 3-3, 3-4, 3-5, 3-6, C", 3-1", 3-3", 3-4", 3-5", 3-6", N-1, N-3, N-1", or N-3" are described below.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, C, 3-1, 3-3, 3-4, 3-5, 3-6, C", 3-1", 3-3", 3-4", 3-5", A, A", C, 3-1, 3-3, 3-4, 3-5, 3-6, C", 3-1", 3-3", 3-4", 3-5", 3-6", N-1, N-3, N-1", or N-3", L is absent. In another embodiment, L is —(C=O)—. In another embodiment, L is C(=O)O—. In a further embodiment, L is —C(=O)$NR^{31}$—. In yet another embodiment, L is —S—. In one embodiment, L is —S(O)—. In another embodiment, L is —S(O)$_2$—. In yet another embodiment, L is —S(O)$_2NR^{31}$—. In another embodiment, L is —$NR^{31}$—.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, C, 3-1, 3-3, 3-4, 3-5, 3-6, C", 3-1", 3-3", 3-4", 3-5", 3-6", N-1, N-3, N-1", or N-3", $R_1$ is -L-$C_{1-10}$alkyl, which is unsubstituted. In another embodiment, $R_1$ is -L-$C_{1-10}$alkyl, which is substituted by one or more independent $R^3$. In yet another embodiment, $R_1$ is -L-unsubstituted $C_{1-10}$alkyl, where L is absent. In another embodiment, $R_1$ is -L-$C_{1-10}$alkyl, which is substituted by one or more independent $R^3$, and L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, C, 3-1, 3-3, 3-4, 3-5, 3-6, C", 3-1", 3-3", 3-4", 3-5", 3-6", N-1, N-3, N-1", or N-3", $R_1$ is -L-$C_{3-8}$cycloalkyl, which is unsubstituted. In another embodiment, $R_1$ is -L-$C_{3-8}$cycloalkyl, which is substituted by one or more independent $R^3$. In yet another embodiment, $R_1$ is -L-$C_{3-8}$cycloalkyl, which is unsubstituted, and L is absent. In a further embodiment, $R_1$ is -L-$C_{3-8}$cycloalkyl which is substituted by one or more independent $R^3$, and L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, C, 3-1, 3-3, 3-4, 3-5, 3-6, C", 3-1", 3-3", 3-4", 3-5", 3-6", N-1, N-3, N-1", or N-3", $R_1$ is H.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (IV-B-1 and IV-B-2), A, C, 3-1, 3-3, 3-4, 3-5, 3-6, C", 3-1", 3-3", 3-4", 3-5", 3-6", N-1, N-3, N-1", or N-3", $R_1$ is -L-aryl, which is unsubstituted. In another embodiment, $R_1$ is -L-aryl, which is substituted by one or more independent $R^3$. In another embodiment, $R_1$ is -L-aryl which is unsubstituted, and L is absent. In yet another embodiment, $R_1$ is -L-aryl, which is substituted by one or more independent $R^3$, and L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, C, 3-1, 3-3, 3-4, 3-5, 3-6, C", 3-1", 3-3", 3-4", 3-5", 3-6", N-1, N-3, N-1", or N-3", $R_1$ is -L-heteroaryl, which is unsubstituted. In another embodiment, $R_1$ is -L-heteroaryl, which is substituted by one or more independent $R^3$. In a further embodiment, $R_1$ is -L-heteroaryl which is unsubstituted and L is absent. In yet another embodiment, $R_1$ is -L-heteroaryl, which is substituted by one or more independent $R^3$, and L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, C, 3-1, 3-3, 3-4, 3-5, 3-6, C", 3-1", 3-3", 3-4", 3-5", 3-6", N-1, N-3, N-1", or N-3", $R_1$ is -L-$C_{1-10}$alkyl-$C_{3-8}$cycloalkyl, which is unsubstituted. In another embodiment, $R_1$ is -L-$C_{1-10}$alkyl-$C_{3-8}$cycloalkyl, which is substituted by one or more independent $R^3$. In a further embodiment, $R_1$ is -L-$C_{1-10}$alkyl-$C_{3-8}$cycloalkyl which is unsubstituted and L is absent. In yet another embodiment, $R_1$ is -L-$C_{1-10}$alkyl-$C_{3-8}$cycloalkyl, which is substituted by one or more independent $R^3$, and L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, C, 3-1, 3-3, 3-4, 3-5, 3-6, C", 3-1", 3-3", 3-4", 3-5", 3-6", N-1, N-3, N-1", or N-3", $R_1$ is -L-$C_{1-10}$alkylaryl, which is unsubstituted. In another embodiment, $R_1$ is -L-$C_{1-10}$alkylaryl, which is substituted by one or more independent $R^3$. In a further embodiment, $R_1$ is -L-$C_{1-10}$alkylaryl which is unsubstituted and L is absent. In yet another embodiment, $R_1$ is -L-$C_{1-10}$alkylaryl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, C, 3-1, 3-3, 3-4, 3-5, 3-6, C", 3-1", 3-3", 3-4", 3-5", 3-6", N-1, N-3, N-1", or N-3", $R_1$ is -L-$C_{1-10}$alkylhetaryl, which is unsubstituted. In another embodiment, $R_1$ is -L-$C_{1-10}$alkylhetaryl, which is substituted by one or more independent $R^3$. In a further embodiment, $R_1$ is -L-$C_{1-10}$alkylhetaryl which is unsubstituted and L is absent. In yet another embodiment, $R_1$ is -L-$C_{1-10}$alkylhetaryl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, C, 3-1, 3-3, 3-4, 3-5, 3-6, C", 3-1", 3-3", 3-4", 3-5", 3-6", N-1, N-3, N-1", or N-3", $R_1$ is -L-$C_{1-10}$alkylheterocylyl, which is unsubstituted. In another embodiment, $R_1$ is -L-$C_{1-10}$alkylheterocylyl, which is substituted by one or more independent $R^3$. In a further embodiment, $R_1$ is -L-$C_{1-10}$alkylheterocylyl which is unsubstituted and L is absent. In yet another embodiment, $R_1$ is -L-$C_{1-10}$alkylheterocylyl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, C, 3-1, 3-3, 3-4, 3-5, 3-6, C", 3-1", 3-3", 3-4", 3-5", 3-6", N-1, N-3, N-1", or N-3", $R_1$ is -L-$C_{1-10}$alkenyl, which is unsubstituted. In another embodiment, $R_1$ is -L-$C_2$-$C_{10}$alkenyl which is substituted by one or more independent $R^3$. In a further embodiment, $R_1$ is -L-$C_{2-10}$alkenyl which is unsubstituted and L is absent. In yet another embodiment, $R_1$ is -L-$C_2$-$C_{10}$alkenyl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, C, 3-1, 3-3, 3-4, 3-5, 3-6, C", 3-1", 3-3", 3-4", 3-5", 3-6", N-1, N-3, N-1", or N-3", $R_1$ is -L-$C_{1-10}$alkynyl, which is unsubstituted. In another embodiment, $R_1$ is -L-$C_{1-10}$alkynyl which is substituted by one or more independent $R^3$. In a further embodiment, $R_1$ is -L-$C_{2-10}$alkynyl which is unsubstituted and L is absent. In yet another embodiment, $R_1$ is -L-$C_2$-$C_{10}$alkynyl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, C, 3-1, 3-3, 3-4, 3-5, 3-6, C", 3-1", 3-3", 3-4", 3-5", 3-6", N-1, N-3, N-1", or N-3", $R_1$ is -L-$C_{2-10}$alkenyl-$C_{3-8}$cycloalkyl, which is unsubstituted. In another embodiment, $R_1$ is -L-$C_{2-10}$alkenyl-$C_{3-8}$cycloalkyl which is substituted by one or more independent $R^3$. In a further embodiment, $R_1$ is -L-$C_{2-10}$alkenyl-$C_{3-8}$cycloalkyl which is unsubstituted and L is absent. In yet another embodiment, $R_1$ is -L-$C_{2-10}$alkenyl-$C_{3-8}$cycloalkyl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, C, 3-1, 3-3, 3-4, 3-5, 3-6, C", 3-1", 3-3", 3-4", 3-5", 3-6", N-1, N-3, N-1", or N-3", $R_1$ is -L-$C_{2-10}$alkynyl-$C_{3-8}$cycloalkyl, which is unsubstituted. In another embodiment, $R_1$ is -L-$C_{2-10}$alkynyl-$C_{3-8}$cycloalkyl which is substituted by one or more independent $R^3$. In a further embodiment, $R_1$ is -L-$C_{1-10}$alkynyl-$C_{3-8}$cycloalkyl which is unsubstituted and L is absent. In yet another embodiment, $R_1$ is -L-$C_{2-10}$alkynyl-$C_{3-8}$cycloalkyl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", $R_1$ is -L-$C_{1-10}$alkynyl-$C_{3-8}$cycloalkyl, which is unsubstituted. In another embodiment, $R_1$ is -L-$C_{2-10}$alkynyl-$C_{3-8}$cycloalkyl which is substituted by one or more independent $R^3$. In a further embodiment, $R_1$ is -L-$C_{2-10}$alkynyl-$C_{3-8}$cycloalkyl which is unsubstituted and L is absent. In yet another embodiment, $R_1$ is -L-$C_{2-10}$alkynyl-$C_{3-8}$cycloalkyl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", $R_1$ is -L-heteroalkyl, which is unsubstituted. In another embodiment, $R_1$ is -L-heteroalkyl which is substituted by one or more independent $R^3$. In a further embodiment, $R_1$ is -L-heteroalkyl which is unsubstituted and L is absent. In yet another embodiment, $R_1$ is -L-heteroalkyl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", $R_1$ is -L-heteroalkylaryl, which is unsubstituted. In another embodiment, $R_1$ is -L-heteroalkylaryl which is substituted by one or more independent $R^3$. In a further embodiment, $R_1$ is -L-heteroalkylaryl which is unsubstituted and L is absent. In yet another embodiment, $R_1$ is -L-heteroalkylaryl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", $R_1$ is -L-heteroalkylheteroaryl, which is unsubstituted. In another embodiment, $R_1$ is -L-heteroalkylheteroaryl, which is substituted by one or more independent $R^3$. In a further embodiment, $R_1$ is -L-heteroalkylheteroaryl which is unsubstituted and L is absent. In yet another embodiment, $R_1$ is -L-heteroalkylheteroaryl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", $R_1$ is -L-heteroalkyl-heterocylyl, which is unsubstituted. In another embodiment, $R_1$ is -L-heteroalkyl-heterocylyl, which is substituted by one or more independent $R^3$. In a further embodiment, $R_1$ is -L-heteroalkyl-heterocylyl which is unsubstituted, and L is absent. In yet another embodiment, $R_1$ is -L-heteroalkyl-heterocylyl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", $R_1$ is -L-heteroalkyl-$C_{3-8}$cycloalkyl, which is unsubstituted. In another embodiment, $R_1$ is -L-heteroalkyl-$C_{3-8}$cycloalkyl, which is substituted by one or more independent $R^3$. In a further embodiment, $R_1$ is -L-heteroalkyl-$C_{3-8}$cycloalkyl which is unsubstituted and L is absent. In yet another embodiment, $R_1$ is -L-heteroalkyl-$C_{3-8}$cycloalkyl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", $R_1$ is -L-aralkyl, which is unsubstituted. In another embodiment, $R_1$ is -L-aralkyl, which is substituted by one or more independent $R^3$. In a further embodiment, $R_1$ is -L-aralkyl which is unsubstituted. In yet another embodiment, $R_1$ is -L-aralkyl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", $R_1$ is -L-heteroaralkyl, which is unsubstituted. In another embodiment, $R_1$ is -L-heteroaralkyl, which is substituted by one or more independent $R^3$. In a further embodiment, $R_1$ is -L-heteroaralkyl which is unsubstituted and L is absent. In yet another embodiment, $R_1$ is -L-heteroaralkyl, which is substituted by one or more independent $R^3$, where L is absent.

In various embodiments of compounds of Formula I'-A', I (including I-A and I-B), II-A (including II-A-1 and II-A-2), II-B (including II-B-1 and II-B-2), III (including III-A and III-B), IV-A (including IV-A-1 and IV-A-2), IV-B (including IV-B-1 and IV-B-2), A, C, 3-1, 3-3, 3-4, 3-5, 3-6, C", 3-1", 3-3", 3-4", 3-5", 3-6", N-1, N-3, N-1", or N-3", $R_1$ is -L-heterocyclyl, which is unsubstituted. In another embodiment, $R_1$ is -L-heterocyclyl, which is substituted by one or more independent $R^3$. In a further embodiment, $R_1$ is -L-heterocyclyl which is unsubstituted and L is absent. In yet another embodiment, $R_1$ is -L-heterocyclyl, which is substituted by one or more independent $R^3$, where L is absent.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", $R_1$ is a substituent as shown below:

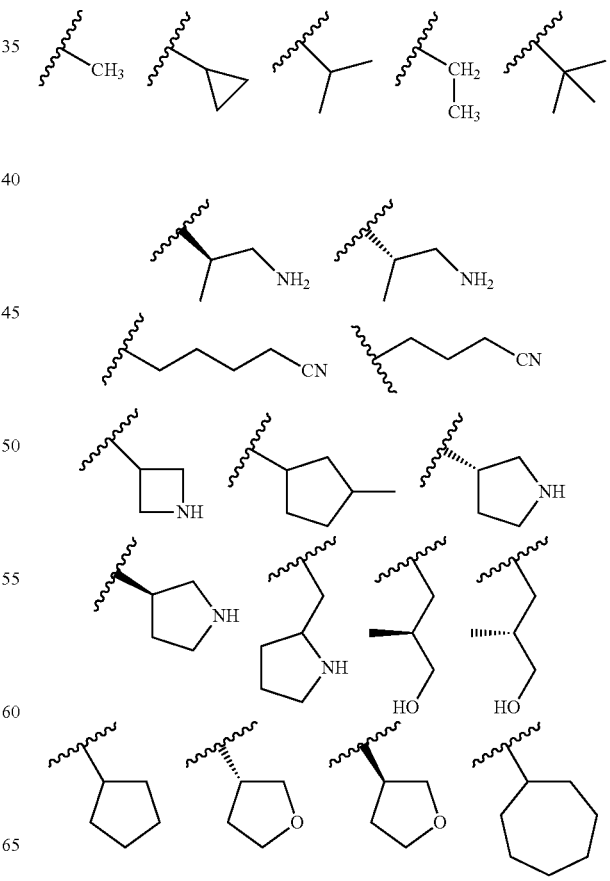

-continued
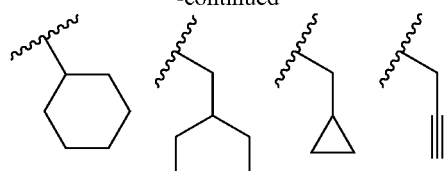
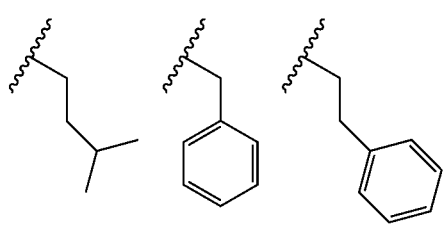
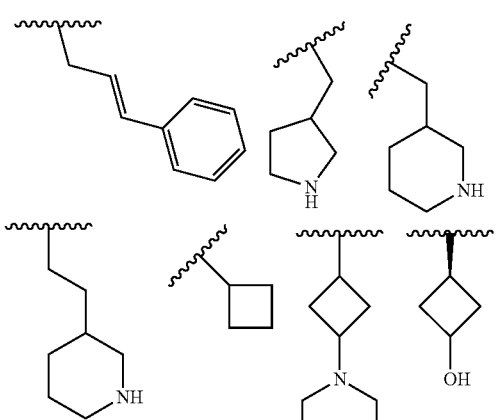
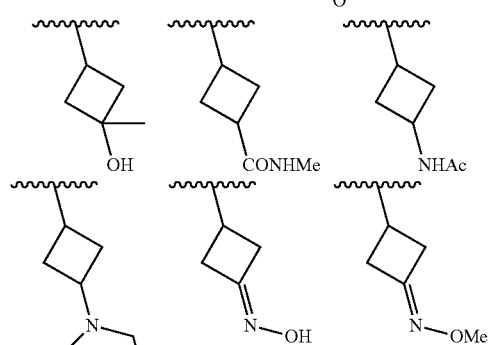
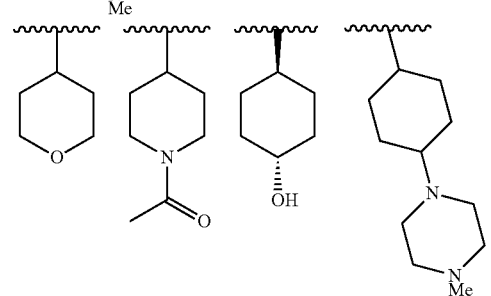
-continued
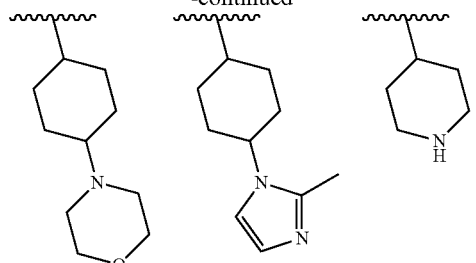
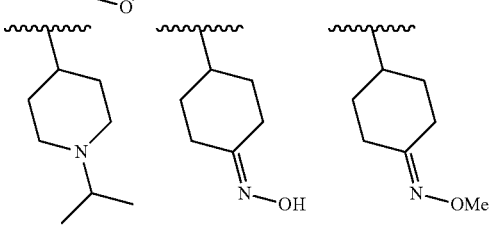
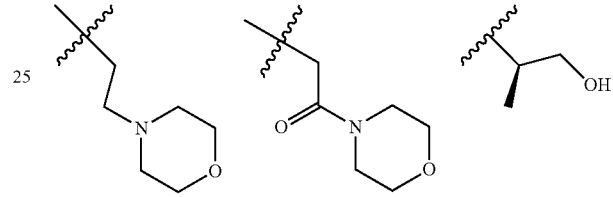
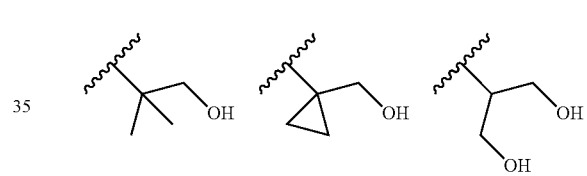
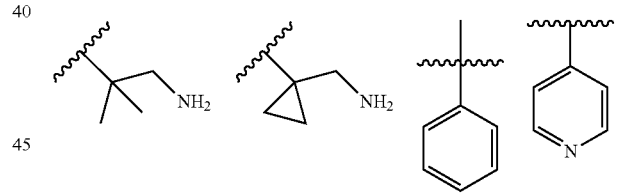
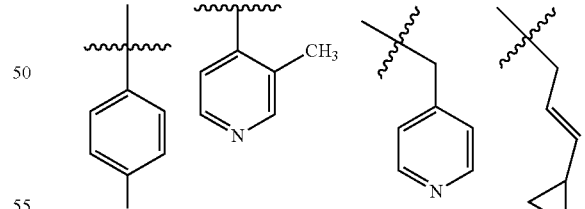
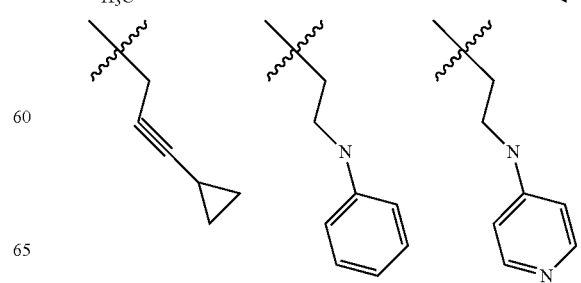

-continued

[Chemical structure: piperidine connected via N to a propyl chain with wavy bond indicating attachment point, and NH at bottom]

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), B (including B' and B"), C, 3-6, C", or 3-6", $R^2$ is hydrogen. In another embodiment, $R^2$ is halogen. In another embodiment, $R^2$ is —OH. In another embodiment, $R^2$ is —$R^{31}$. In another embodiment, $R^2$ is —$CF_3$. In another embodiment, $R^2$ is —$OCF_3$. In another embodiment, $R^2$ is —$OR^{31}$. In another embodiment, $R^2$ is —$NR^{31}R^{32}$. In another embodiment, $R^2$ is —$NR^{34}R^{35}$. In another embodiment, $R^2$ is —C(O)$R^{31}$. In another embodiment, $R^2$ is —$CO_2R^{31}$. In another embodiment, $R^2$ is —C(=O)$NR^{31}R^{32}$. In another embodiment, $R^2$ is —C(=O)$NR^{34}R^{35}$. In another embodiment, $R^2$ is —$NO_2$. In another embodiment, $R^2$ is —CN. In another embodiment, $R^2$ is —S(O)$_{0-2}R^{31}$. In another embodiment, $R^2$ is —$SO_2NR^{31}R^{32}$. In another embodiment, $R^2$ is —$SO_2NR^{34}R^{35}$. In another embodiment, $R^2$ is —$NR^{31}C(=O)R^{32}$. In another embodiment, $R^2$ is —$NR^{31}C(=O)OR^{32}$. In another embodiment, $R^2$ is —$NR^{31}C(=O)NR^{32}R^{33}$. In another embodiment, $R^2$ is —$NR^{31}S(O)_{0-2}R^{32}$. In another embodiment, $R^2$ is —C(=S)$OR^{31}$. In another embodiment, $R^2$ is —C(=O)$SR^{31}$. In another embodiment, $R^2$ is —$NR^{31}C(=NR^{32})NR^{33}R^{32}$. In another embodiment, $R^2$ is —$NR^{31}C(=NR^{32})OR^{33}$. In another embodiment, $R^2$ is —$NR^{31}C(=NR^{32})SR^{33}$. In another embodiment, $R^2$ is —OC(=O)$OR^{33}$. In another embodiment, $R^2$ is —OC(=O)$NR^{31}R^{32}$. In another embodiment, $R^2$ is —OC(=O)$SR^{31}$. In another embodiment, $R^2$ is —SC(=O)$OR^{31}$. In another embodiment, $R^2$ is —P(O)$OR^{31}OR^{32}$. In another embodiment, $R^2$ is —SC(=O)$NR^{31}R^{32}$. In another embodiment, $R^2$ is monocyclic aryl. In another embodiment, $R^2$ is bicyclic aryl. In another embodiment, $R^2$ is substituted monocyclic aryl. In another embodiment, $R^2$ is hetaryl. In another embodiment, $R^2$ is $C_{1-4}$alkyl. In another embodiment, $R^2$ is $C_{1-10}$alkyl. In another embodiment, $R^2$ is $C_{3-8}$cycloalkyl. In another embodiment, $R^2$ is $C_{3-8}$cycloalkyl-$C_{1-10}$alkyl. In another embodiment, $R^2$ is $C_{1-10}$alkyl-$C_{3-8}$cycloalkyl. In another embodiment, $R^2$ is $C_{1-10}$alkyl-monocyclic aryl. In another embodiment, $R^2$ is $C_{2-10}$alkyl-monocyclic aryl. In another embodiment, $R^2$ is monocyclic aryl-$C_{2-10}$alkyl. In another embodiment, $R^2$ is $C_{1-10}$alkyl-bicyclicaryl. In another embodiment, $R^2$ is bicyclicaryl-$C_{1-10}$alkyl. In another embodiment, $R^2$ is —$C_{1-10}$alkylhetaryl. In another embodiment, $R^2$ is $C_{1-10}$alkylheterocyclyl. In another embodiment, $R^2$ is $C_{2-10}$alkenyl. In another embodiment, $R^2$ is $C_{2-10}$alkynyl. In another embodiment, $R^2$ is $C_{2-10}$alkenylaryl. In another embodiment, $R^2$ is $C_{2-10}$alkenylhetaryl. In another embodiment, $R^2$ is $C_{2-10}$alkenylheteroalkyl. In another embodiment, $R^2$ is $C_{2-10}$alkenylheterocyclyl. In another embodiment, $R^2$ is —$C_{2-10}$alkynylaryl. In another embodiment, $R^2$ is —$C_{2-10}$alkynylhetaryl. In another embodiment, $R^2$ is —$C_{2-10}$alkynylheteroalkyl. In another embodiment, $R^2$ is —$C_{2-10}$alkynylheterocylyl. In another embodiment, $R^2$ is —$C_{2-10}$alkynyl$C_{3-8}$cycloalkyl. In another embodiment, $R^2$ is —$C_{2-10}$alkynyl$C_{3-8}$cycloalkenyl. In another embodiment, $R^2$ is —$C_{1-10}$alkoxy-$C_{1-10}$alkyl. In another embodiment, $R^2$ is —$C_{1-10}$alkoxy-$C_{2-10}$alkenyl. In another embodiment, $R^2$ is —$C_{1-10}$alkoxy-$C_{2-10}$alkynyl. In another embodiment, $R^2$ is -heterocyclyl $C_{1-10}$alkyl. In another embodiment, $R^2$ is heterocyclyl$C_{2-10}$alkenyl. In another embodiment, $R^2$ is heterocyclyl$C_{2-10}$alkynyl. In another embodiment, $R^2$ is aryl-$C_{2-10}$alkyl. In another embodiment, $R^2$ is aryl $C_{1-10}$alkyl. In another embodiment, $R^2$ is aryl-$C_{2-10}$alkenyl. In another embodiment, $R^2$ is aryl-$C_{2-10}$alkynyl. In another embodiment, $R^2$ is aryl-heterocyclyl. In another embodiment, $R^2$ is hetaryl-$C_{1-10}$alkyl. In another embodiment, $R^2$ is hetaryl-$C_{2-10}$alkenyl. In another embodiment, $R^2$ is hetaryl-$C_{2-10}$alkynyl. In another embodiment, $R^2$ is hetaryl-$C_{3-8}$cycloalkyl. In another embodiment, $R^2$ is hetaryl-heteroalkyl. In another embodiment, $R^2$ is hetaryl-heterocyclyl.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), C, 3-6, C", or 3-6", when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is unsubstituted. In various embodiments, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent halo. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —OH. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{3-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$R^{31}$. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$CF_3$. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —OCF. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$OR^{31}$. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}R^{32}$. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —NR$^{34}$R$^{35}$. In another embodiment, when R$^4$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —C(O)R$^{31}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —CO$_2$R$^{31}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —C(=O)NR$^{31}$R$^{32}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —C(=O)NR$^{34}$R$^{35}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —NO$_2$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —CN. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —S(O)$_{0-2}$R$^{31}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —SO$_2$NR$^{31}$R$^{32}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —SO$_2$NR$^{34}$R$^{35}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent NR$^{31}$C(=O)R$^{32}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —NR$^{31}$C(=O)OR$^{32}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —NR$^{31}$C(=O)NR$^{32}$R$^{33}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —NR$^{31}$S(O)$_{0-2}$R$^{32}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —C(=S)OR$^{31}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —C(=O)SR$^{31}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —NR$^{31}$C(=NR$^{32}$)NR$^{33}$R$^{32}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent, —NR$^{31}$C(=NR$^{32}$)OR$^{33}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —NR$^{31}$C(=NR$^{32}$)SR$^{33}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —OC(=O)OR$^{33}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —OC(=O)NR$^{31}$R$^{32}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —OC(=O)SR$^{31}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —SC(=O)OR$^{31}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —P(O)OR$^{31}$OR$^{32}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —SC(=O)NR$^{31}$R$^{32}$. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent alkyl. In another embodiment, when R$^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent heteroalkyl. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent alkenyl. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent alkynyl. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent cycloalkyl. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent heterocycloalkyl. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent aryl. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent arylalkyl. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent heteroaryl. In another embodiment, when $R^2$ is bicyclic aryl, monocyclic aryl, hetaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent heteroarylalkyl.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", $R^3$ is hydrogen. In another embodiment, $R^3$ is halogen. In another embodiment, $R^3$ is —OH. In another embodiment, $R^3$ is —$R^{31}$. In another embodiment, $R^3$ is —$CF_3$. In another embodiment, $R^3$ is —$OCF_3$. In another embodiment, $R^3$ is —$OR^{31}$. In another embodiment, $R^3$ is —$NR^{31}R^{32}$. In another embodiment, $R^3$ is —$NR^{34}R^{35}$. In another embodiment, $R^3$ is —C(O)$R^{31}$. In another embodiment, $R^3$ is —$CO_2R^{31}$. In another embodiment, $R^3$ is —C(=O)$NR^{31}R^{32}$. In another embodiment, $R^3$ is C(=O)$NR^{34}R^{35}$. In another embodiment, $R^3$ is —$NO_2$. In another embodiment, $R^3$ is —CN. In another embodiment, $R^3$ is —$S(O)_{0-2}R^3$. In another embodiment, $R^3$ is —$SO_2NR^{31}R^{32}$. In another embodiment, $R^3$ is —$SO_2NR^{34}R^{35}$. In another embodiment, $R^3$ is —$NR^{31}C(=O)R^{32}$. In another embodiment, $R^3$ is —$NR^{31}C(=O)OR^{32}$. In another embodiment, $R^3$ is —$NR^{31}C(=O)NR^{32}R^{33}$. In another embodiment, $R^3$ is —$NR^{31}S(O)_{0-2}R^{32}$. In another embodiment, $R^3$ is —C(=S)$OR^{31}$. In another embodiment, $R^3$ is —C(=O)$SR^{31}$. In another embodiment, $R^3$ is —$NR^{31}C(=NR^{32})NR^{33}R^{32}$. In another embodiment, $R^3$ is —$NR^{31}C(=NR^{32})OR^{33}$. In another embodiment, $R^3$ is —$NR^{31}C(=NR^{32})SR^{33}$. In another embodiment, $R^3$ is —OC(=O)$OR^{33}$. In another embodiment, $R^3$ is —OC(=O)$NR^{31}R^{32}$. In another embodiment, $R^3$ is —OC(=O)$SR^{31}$. In another embodiment, $R^3$ is —SC(=O)$OR^{31}$. In another embodiment, $R^3$ is —P(O)$OR^{31}OR^{32}$. In another embodiment, $R^3$ is —SC(=O)$NR^{31}R^{32}$. In another embodiment, $R^3$ is aryl. In another embodiment, $R^2$ is hetaryl. In another embodiment, $R^3$ is $C_{1-4}$alkyl. In another embodiment, $R^3$ is $C_{1-10}$alkyl. In another embodiment, $R^3$ is $C_{3-8}$cycloalkyl. In another embodiment, $R^3$ is $C_{3-8}$cycloalkyl-$C_{1-10}$alkyl. In another embodiment, $R^3$ is —$C_{1-10}$alkyl-$C_{3-8}$cycloalkyl. In another embodiment, $R^3$ is $C_{2-10}$alkyl-monocyclic aryl. In another embodiment, $R^3$ is monocyclic aryl-$C_{2-10}$alkyl. In another embodiment, $R^3$ is $C_{1-10}$alkyl-bicyclicaryl. In another embodiment, $R^3$ is bicyclicaryl-$C_{1-10}$alkyl. In another embodiment, $R^3$ is $C_{1-10}$alkylhetaryl. In another embodiment, $R^3$ is $C_{1-10}$alkylheterocyclyl. In another embodiment, $R^3$ is $C_{2-10}$alkenyl. In another embodiment, $R^3$ is $C_{2-10}$alkynyl. In another embodiment, $R^3$ is $C_{2-10}$alkenylaryl. In another embodiment, $R^3$ is $C_{2-10}$alkenylhetaryl. In another embodiment, $R^3$ is $C_{2-10}$alkenylheteroalkyl. In another embodiment, $R^3$ is $C_{2-10}$alkenylheterocyclcyl. In another embodiment, $R^3$ is —$C_{2-10}$alkynylaryl. In another embodiment, $R^3$ is —$C_{2-10}$alkynylhetaryl. In another embodiment, $R^3$ is —$C_{2-10}$alkynylheteroalkyl. In another embodiment, $R^3$ is $C_{2-10}$alkynylheterocylyl. In another embodiment, $R^3$ is —$C_{2-10}$alkynyl$C_{3-8}$cycloalkyl. In another embodiment, $R^3$ is $C_{2-10}$alkynyl$C_{3-8}$cycloalkenyl. In another embodiment, $R^3$ is —$C_{1-10}$alkoxy-$C_{1-10}$alkyl. In another embodiment, $R^3$ is $C_{1-10}$alkoxy-$C_{2-10}$alkenyl. In another embodiment, $R^3$ is —$C_{1-10}$alkoxy-$C_{2-10}$alkynyl. In another embodiment, $R^3$ is heterocyclyl-$C_{1-10}$alkyl. In another embodiment, $R^3$ is -heterocyclyl$C_{2-10}$alkenyl. In another embodiment, $R^3$ is heterocyclyl-$C_{2-10}$alkynyl. In another embodiment, $R^3$ is aryl-$C_{1-10}$alkyl. In another embodiment, $R^3$ is aryl-$C_{2-10}$alkenyl. In another embodiment, $R^3$ is aryl-$C_{2-10}$alkynyl. In another embodiment, $R^3$ is aryl-heterocyclyl. In another embodiment, $R^3$ is hetaryl-$C_{1-10}$alkyl. In another embodiment, $R^3$ is hetaryl-$C_{2-10}$alkenyl. In another embodiment, $R^3$ is hetaryl-$C_{2-10}$alkynyl. In another embodiment, $R^3$ is hetaryl-$C_{3-8}$cycloalkyl. In another embodiment, $R^3$ is hetaryl-heteroalkyl. In another embodiment, $R^3$ is hetaryl-heterocyclyl.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is unsubstituted. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent halo. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —OH. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$R^{31}$. In another embodiment, when $R^3$ is aryl, hetaryl, $C_{1-10}$alkyl, $C_{3-8}$cycloalkyl, $C_{3-8}$cycloalkyl- $C_{1-10}$alkyl, heterocyclyl, heterocyclyl $C_{1-10}$alkyl, or heteroalkyl, it is substituted with one or more independent —$CF_3$. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —OCF. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$OR^{31}$. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NR^{31}R^{32}$. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NR^{34}R^{35}$. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$C(O)R^{31}$. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$CO_2R^{31}$. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$C(=O)NR^{31}R^{32}$. In another embodiment, when $R^3$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$C(=O)NR^{34}R^{35}$. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NO_2$. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —CN. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$S(O)_{0-2}R^{31}$. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$SO_2NR^{31}R^{32}$. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$SO_2NR^{34}R^{35}$. In another embodiment, when $R^3$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent $NR^{31}C(=O)R^{32}$. In another embodiment, when $R^3$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=O)OR^{32}$. In another embodiment, when $R^3$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=O)NR^{32}R^{33}$. In another embodiment, when $R^3$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}S(O)_{0-2}R^{32}$. In another embodiment, when $R^3$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$C(=S)OR^{31}$. In another embodiment, when $R^3$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$C(=O)SR^{31}$. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NR^{31}C(=NR^{32})NR^{33}R^{32}$. In another embodiment, when $R^3$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent, —$NR^{31}C(=NR^{32})OR^{33}$. In another embodiment, when $R^3$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=NR^{32})SR^{33}$. In another embodiment, when $R^3$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$OC(=O)OR^{33}$. In another embodiment, when $R^3$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$OC(=O)NR^{31}R^{32}$. In another embodiment, when $R^3$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$OC(=O)SR^{31}$. In another embodiment, when $R^3$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$SC(=O)OR^{31}$. In another embodiment, when $R^3$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$P(O)OR^{31}OR^{32}$. In another embodiment, when $R^3$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$SC(=O)NR^{31}R^{32}$.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", $R^4$ is hydrogen. In another embodiment, $R^4$ is halogen. In another embodiment, $R^4$ is —OH. In another embodiment, $R^4$ is —$R^{31}$. In another embodiment, $R^4$ is $CF_3$. In another embodiment, $R^4$ is —$OCF_3$. In another embodiment, $R^4$ is $OR^{31}$. In another embodiment, $R^4$ is —$NR^{31}R^{32}$. In another embodiment, $R^4$ is —$NR^{34}R^{35}$. In another embodiment, $R^4$ is —$C(O)R^{31}$. In another embodiment, $R^4$ is $CO_2R^{31}$. In another embodiment, $R^4$ is —$C(=O)NR^{31}R^{32}$. In another embodiment, $R^4$ is —$C(=O)NR^{34}R^{35}$. In another embodiment, $R^4$ is —$NO_2$. In another embodiment, $R^4$ is —CN. In another embodiment, $R^4$ is $S(O)_{0-2}R^3$. In another embodiment, $R^4$ is —$SO_2NR^{31}R^{32}$. In another embodiment, $R^4$ is —$SO_2NR^{34}R^{35}$. In another embodiment, $R^4$ is —$NR^{31}C(=O)R^{32}$. In another embodiment, $R^4$ is —$NR^{31}C(=O)OR^{32}$. In another embodiment, $R^4$ is —$NR^{31}C(=O)NR^{32}R^{33}$. In another embodiment, $R^4$ is —$NR^{31}S(O)_{0-2}R^{32}$. In another embodiment, $R^4$ is —$C(=S)OR^{31}$. In another embodiment, $R^4$ is —$C(=O)SR^{31}$. In another embodiment, $R^4$ is —$NR^{31}C(=NR^{32})NR^{33}R^{32}$. In another embodiment, $R^4$ is —$NR^{31}C(=NR^{32})OR^{33}$. In another embodiment, $R^4$ is —$NR^{31}C(=NR^{32})SR^{33}$. In another embodiment, $R^4$ is —$OC(=O)OR^{33}$. In another embodiment, $R^4$ is —$OC(=O)NR^{31}R^{32}$. In another embodiment, $R^4$ is —$OC(=O)SR^{31}$. In another embodiment, $R^4$ is —$SC(=O)OR^{31}$. In another embodiment, $R^4$ is —$P(O)OR^{31}OR^{32}$. In another embodiment, $R^4$ is —$SC(=O)NR^{31}R^{32}$. In another embodiment, $R^4$ is aryl. In another embodiment, $R^4$ is hetaryl. In another embodiment, $R^4$ is $C_{1-4}$alkyl. In another embodiment, $R^4$ is $C_{1-10}$alkyl. In another embodiment, $R^4$ is $C_{3-8}$cycloalkyl. In another embodiment, $R^4$ is $C_{1-10}$alkyl-$C_{3-8}$cycloalkyl. In another embodiment, $R^4$ is $C_{1-10}$alkylaryl. In another embodiment, $R^4$ is $C_{1-10}$alkylhetaryl. In another embodiment, $R^4$ is $C_{1-10}$alkylheterocyclyl. In another embodiment, $R^4$ is $C_{2-10}$alkenyl. In another embodiment, $R^4$ is $C_{2-10}$alkynyl. In another embodiment, $R^4$ is $C_{1-10}$alkynyl-$C_{3-8}$cycloalkyl. $R^4$ is $C_{2-10}$alkenyl-$C_{3-8}$cycloalkyl. In another embodiment, $R^4$ is $C_{2-10}$alkenylaryl. In another embodiment, $R^4$ is $C_{2-10}$alkenyl-hetaryl. In another embodiment, $R^4$ is $C_{2-10}$alkenylheteroalkyl. In another embodiment, $R^4$ is $C_{2-10}$alkenylheterocylcyl. In another embodiment, $R^4$ is —$C_{2-10}$alkynylaryl. In another embodiment, $R^4$ is $C_{2-10}$alkynylhetaryl. In another embodiment, $R^4$ is $C_{2-10}$alkynylheteroalkyl. In another embodiment, $R^4$ is $C_{2-10}$alkynylheterocylyl. In another embodiment, $R^4$ is $C_{2-10}$alkynyl $C_{3-8}$cycloalkyl. In another embodiment, $R^4$ is heterocyclyl $C_{1-10}$alkyl. In another embodiment, $R^4$ is heterocyclyl $C_{2-10}$alkenyl. In another embodiment, $R^4$ is heterocyclyl-$C_{2-10}$alkynyl. In another embodiment, $R^4$ is aryl-$C_{1-10}$alkyl. In another embodiment, $R^4$ is aryl-$C_{2-10}$alkenyl. In another embodiment, $R^4$ is aryl-$C_{2-10}$alkynyl. In another embodiment, $R^4$ is aryl-heterocyclyl. In another embodiment, $R^4$ is hetaryl-$C_{1-10}$alkyl. In another embodiment, $R^4$ is hetaryl-$C_{2-10}$alkenyl. In another embodiment, $R^4$ is hetaryl-$C_{2-10}$alkynyl. In another embodiment, $R^4$ is $C_{3-8}$cycloalkyl-$C_{1-10}$alkyl. In another embodiment, $R^4$ is $C_{3-8}$cycloalkyl-$C_{2-10}$alkenyl. In another embodiment, $R^4$ is $C_{3-8}$cycloalkyl-$C_{2-10}$alkynyl.

In various embodiments of compounds of Formula I'-A', I (including I-A and I-B), II-A (including II-A-1, II-A-1a. and II-A-2), II-B (including II-B-1 and II-B-2), III (including III-A and III-B), IV-A (including IV-A-1 and IV-A-2), IV-B (including IV-B-1 and IV-B-2), A, A'', C, 3-1, 3-3, 3-4, 3-5, 3-6, C'', 3-1'', 3-3'', 3-4'', 3-5'', 3-6'', N-1, N-3, N-1'', or N-3'' when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is unsubstituted. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent halo. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —OH. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$R^{31}$. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$CF_3$. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —OCF. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$OR^{31}$. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NR^{31}R^{32}$. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NR^{34}R^{35}$. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$C(O)R^{31}$. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent $CO_2R^{31}$. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$C(=O)NR^{31}R^{32}$. In another embodiment, when $R^4$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$C(=O)NR^{34}R^{35}$. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NO_2$. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —CN. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$S(O)_{0-2}R^{31}$. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$SO_2NR^{31}R^{32}$. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$SO_2NR^{34}R^{35}$. In another embodiment, when $R^4$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent $NR^{31}C(=O)R^{32}$. In another embodiment, when $R^4$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=O)OR^{32}$. In another embodiment, when $R^4$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=O)NR^{32}R^{33}$. In another embodiment, when $R^4$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}S(O)_{0-2}R^{32}$. In another embodiment, when $R^4$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$C(=S)OR^{31}$. In another embodiment, when $R^4$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$C(=O)SR^{31}$. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NR^{31}C(=NR^{32})NR^{33}R^{32}$. In another embodiment, when $R^4$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent, —$NR^{31}C(=NR^{32})OR^{33}$. In another embodiment, when $R^4$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=NR^{32})SR^{33}$. In another embodiment, when $R^4$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$OC(=O)OR^{33}$. In another embodiment, when $R^4$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$OC(=O)NR^{31}R^{32}$. In another embodiment, when $R^4$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$OC(=O)SR^{31}$. In another embodiment, when $R^4$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$SC(=O)OR^{31}$. In another embodiment, when $R^4$ is aryl, hetaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$P(O)OR^{31}OR^{32}$. In another embodiment, when $R^4$ is aryl, hetaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$SC(=O)NR^{31}R^{32}$.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), B, C, or C", $R^5$ is hydrogen. In another embodiment, $R^5$ is halogen. In another embodiment, $R^5$ is —OH. In another embodiment, $R^5$ is —$R^{31}$. In another embodiment, $R^5$ is —$CF_3$. In another embodiment, $R^5$ is —$OCF_3$. In another embodiment, $R^5$ is —$OR^{31}$. In another embodiment, $R^5$ is —$NR^{31}R^{32}$. In another embodiment, $R^5$ is —$NR^{34}R^{35}$. In another embodiment, $R^5$ is —$C(O)R^{31}$. In another embodiment, $R^5$ is —$CO_2R^{31}$. In another embodiment, $R^5$ is —$C(=O)NR^{31}R^{32}$. In another embodiment, $R^5$ is —$C(=O)NR^{34}R^{35}$. In another embodiment, $R^5$ is —$NO_2$. In another embodiment, $R^5$ is —CN. In another embodiment, $R^5$ is —$S(O)_2R^{31}$. In another embodiment, $R^5$ is —$SO_2NR^{31}R^{32}$. In another embodiment, $R^5$ is —$SO_2NR^{34}R^{35}$. In another embodiment, $R^5$ is —$NR^{31}C(=O)R^{32}$. In another embodiment, $R^5$ is $NR^{31}C(=O)OR^{32}$. In another embodiment, $R^5$ is —$NR^{31}C(=O)NR^{32}R^{33}$. In another embodiment, $R^5$ is —$NR^{31}S(O)_{0-2}R^{32}$. In another embodiment, $R^5$ is —$C(=S)OR^{31}$. In another embodiment, $R^5$ is —$C(=O)SR^{31}$. In another embodiment, $R^5$ is —$NR^{31}C(=NR^{32})NR^{33}R^{32}$. In another embodiment, $R^5$ is —$NR^{31}C(=NR^{32})OR^{33}$. In another embodiment, $R^5$ is —$NR^{31}C(=NR^{32})SR^{33}$. In another embodiment, $R^5$ is —$OC(=O)OR^{33}$. In another embodiment, $R^5$ is —$OC(=O)NR^{31}R^{32}$. In another embodiment, $R^5$ is —$OC(=O)SR^{31}$. In another embodiment, $R^5$ is —$SC(=O)OR^{31}$. In another embodiment, $R^5$ is —$P(O)OR^{31}OR^{32}$. In another embodiment, $R^5$ is or —$SC(=O)NR^{31}R^{32}$.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", $R^7$ is hydrogen. In another embodiment, $R^7$ is unsubstituted $C_{1-10}$alkyl. In another embodiment, $R^7$ is unsubstituted $C_{2-10}$alkenyl. In another embodiment, $R^7$ is unsubstituted aryl. In another embodiment, $R^7$ is unsubstituted heteroaryl. In another embodiment, $R^7$ is unsubstituted heterocyclyl. In another embodiment, $R^7$ is unsubstituted $C_{3-10}$cycloalkyl. In another embodiment, $R^7$ is $C_{1-10}$alkyl substituted by one or more independent $R^6$. In another embodiment, $R^7$ is $C_{2-10}$alkenyl substituted by one or more independent $R^6$. In another embodiment, $R^7$ is aryl substituted by one or more independent $R^6$. In another embodiment, $R^7$ is heteroaryl substituted by one or more independent $R^6$. In another embodiment, $R^7$ is heterocycyl substituted by one or more independent $R^6$. In another embodiment, $R^7$ is $C_{3-10}$cycloalkyl substituted by one or more independent $R^6$.

In various embodiments of compounds of Formula I'-A', I (including I-A and I-B), II-A (including II-A-1, II-A-1a. and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", $R^8$ is hydrogen. In another embodiment, $R^8$ is unsubstituted $C_{1-10}$alkyl. In another embodiment, $R^8$ is unsubstituted $C_{2-10}$alkenyl. In another embodiment, $R^8$ is unsubstituted aryl. In another embodiment, $R^8$ is unsubstituted heteroaryl. In another embodiment, $R^8$ is unsubstituted heterocyclyl. In another embodiment, $R^8$ is unsubstituted $C_{3-10}$cycloalkyl. In another embodiment, $R^8$ is $C_{1-10}$alkyl substituted by one or more independent $R^6$. In another embodiment, $R^8$ is $C_{2-10}$alkenyl substituted by one or more independent $R^6$. In another embodiment, $R^8$ is aryl substituted by one or more independent $R^6$. In another embodiment, $R^8$ is heteroaryl substituted by one or more independent $R^6$. In another embodiment, $R^8$ is heterocyclyl substituted by one or more independent $R^6$. In another embodiment, $R^8$ is $C_{3-10}$cycloalkyl substituted by one or more independent $R^6$.

In various embodiments of compounds of Formula I'-A', I (including I-A and I-B), II-A (including II-A-1, II-A-1a, and II-A-2), II-B (including II-B-1 and II-B-2), III (including III-A and III-B), IV-A (including IV-A-1 and IV-A-2), IV-B (including IV-B-1 and IV-B-2), A, A", C, 3-1, 3-3, 3-4, 3-5, 3-6, C", 3-1", 3-3", 3-4", 3-5", 3-6", N-1, N-3, N-1", or N-3", $R^6$ is halo, In another embodiment, $R^6$ is —$OR^{31}$. In another embodiment, $R^6$ is —SH. In another embodiment, $R^6$ is $NH_2$. In another embodiment, $R^6$ is —$NR^{34}R^{35}$. In another embodiment, $R^6$ is —$NR^{31}R^{32}$. In another embodiment, $R^6$ is $CO_2R^{31}$. In another embodiment, $R^6$ is —$CO_2$aryl. In another embodiment, $R^6$ is —$C(=O)NR^{31}R^{32}$. In another embodiment, $R^6$ is —$C(=O)NR^{34}R^{35}$. In another embodiment, $R^6$ is —$NO_2$. In another embodiment, $R^6$ is —CN. In another embodiment, $R^6$ is —$S(O)_{0-2}C_{1-10}$alkyl. In another embodiment, $R^6$ is —$S(O)_{0-2}$aryl. In another embodiment, $R^6$ is —$SO_2NR^{34}R^{35}$. In another embodiment, $R^6$ is —$SO_2NR^{31}R^{32}$. In another embodiment, $R^6$ is $C_{1-10}$alkyl. In another embodiment, $R^6$ is $C_{2-10}$alkenyl. In another embodiment, $R^6$ is $C_{2-10}$alkynyl. In another embodiment, $R^6$ is unsubstituted aryl-$C_{1-10}$alkyl. In another embodiment, $R^6$ is unsubstituted aryl-$C_{2-10}$alkenyl. In another embodiment, $R^6$ is unsubstituted aryl-$C_{2-10}$alkynyl. In another embodiment, $R^6$ is unsubstituted hetaryl-$C_{1-10}$alkyl. In another embodiment, $R^6$ is unsubstituted hetaryl-$C_{2-10}$alkenyl. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent halo. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent cyano. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{1-10}$alkenyl substituted by one or more independent nitro. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{1-10}$alkenyl substituted by one or more independent —$OC_{1-10}$alkyl. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —$C_{1-10}$alkyl. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{1-10}$alkenyl substituted by one or more independent —$C_{3-10}$alkenyl. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —$C_{3-10}$alkynyl. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent -(halo)$C_{1-10}$alkyl. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent -(halo)$C_{1-10}$alkenyl. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent -(halo)$C_{2-10}$alkynyl. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —COOH. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —$C(=O)NR^{31}R^{32}$. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —$C(=O)NR^{34}R^{35}$. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —$SO_2NR^{34}R^{35}$. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —$SO_2NR^{31}R^{32}$. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{1-10}$alkenyl substituted by one or more independent —$NR^{31}R^{32}$. In another embodiment, $R^6$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{1-10}$alkenyl substituted by one or more independent —$NR^{34}R^{35}$.

In various embodiments of compounds of Formula I'-A', I (including I-A and I-B), III (including III-A and III-B), IV-A (including IV-A-1 and IV-A-2), or IV-B (including IV-B-1 and IV-B-2) A, A", C, 3-1, 3-3, 3-4, 3-5, 3-6, C", 3-1", 3-3", 3-4", 3-5", 3-6", N-1, N-3, N-1", or N-3", $R^9$ is H. In another embodiment, $R^9$ is halo. In another embodiment, $R^9$ is —$OR^{31}$. In another embodiment, $R^9$ is —SH. In another embodiment, $R^9$ is $NH_2$. In another embodiment, $R^9$ is —$NR^{34}R^{35}$. In another embodiment, $R^9$ is —$NR^{31}R^{32}$. In another embodiment, $R^9$ is —$CO_2R^{31}$. In another embodiment, $R^9$ is —$CO_2$aryl. In another embodiment, $R^9$ is —$C(=O)NR^{31}R^{32}$. In another embodiment, $R^9$ is —$C(=O)NR^{34}R^{35}$. In another embodiment, $R^9$ is $NO_2$. In another embodiment, $R^9$ is —CN. In another embodiment, $R^9$ is —$S(O)_{0-2}C_{1-10}$alkyl. In another embodiment, $R^9$ is —$S(O)_{0-2}$aryl. In another embodiment, $R^9$ is —$SO_2NR^{34}R^{35}$. In another embodiment, $R^9$ is —$SO_2NR^{31}R^{32}$. In another embodiment, $R^9$ is $C_{1-10}$alkyl. In another embodiment, $R^9$ is $C_{2-10}$alkenyl. In another embodiment, $R^9$ is $C_{2-10}$alkynyl. In another embodiment, $R^9$ is unsubstituted aryl-$C_{1-10}$alkyl. In another embodiment, $R^9$ is unsubstituted aryl-$C_{2-10}$alkenyl. In another embodiment, $R^9$ is unsubstituted aryl-$C_{2-10}$alkynyl. In another embodiment, $R^9$ is unsubstituted hetaryl-$C_{1-10}$alkyl. In another embodiment, $R^9$ is unsubstituted hetaryl-$C_{2-10}$alkenyl. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent halo. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent cyano. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent nitro. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —$OC_{1-10}$alkyl. In another embodiment, $R^9$ is aryl-$C_{1-10}$alkyl, aryl-$C_{2-10}$alkenyl, aryl-$C_{3-10}$alkynyl, hetaryl-$C_{1-10}$alkyl, or hetaryl-$C_{2-10}$alkenyl substituted by one or more independent —$C_{1-10}$alkyl. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{1-10}$alkenyl substituted by one or more independent —$C_{2-10}$alkenyl. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —$C_{2-10}$alkynyl. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent -(halo)$C_{1-10}$alkyl. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent -(halo)$C_{2-10}$alkenyl. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent -(halo)$C_{2-10}$alkynyl. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent COOH. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —$C(=O)NR^{31}R^{32}$. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —C(=O) $NR^{34}R^{35}$. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —$SO_2NR^{34}R^{35}$. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —$SO_2NR^{31}R^{32}$. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —$NR^{31}R^{32}$. In another embodiment, $R^9$ is aryl-$C_{1-10}$alkyl, aryl-$C_{2-10}$alkenyl, aryl-$C_{2-10}$alkynyl, hetaryl-$C_{1-10}$alkyl, or hetaryl-$C_{2-10}$alkenyl substituted by one or more independent —$NR^{34}R^{35}$.

In various embodiments of compounds of Formula I'-A', I (including I-A and I-B), II-A (including II-A-1 and II-A-2), II-B (including II-B-1 and II-B-2), III (including III-A and III-B), IV-A (including IV-A-1 and IV-A-2), IV-B (including IV-B-1 and IV-B-2), A, B (including B' and B"), C, C, 3-1, 3-3, 3-4, 3-5, 3-6, C", 3-1", 3-3", 3-4", 3-5", 3-6", N-1, N-3, N-1", or N-3", or N-3, $R^{31}$ is H. In some embodiments, $R^{31}$ is unsubstituted $C_{1-10}$alkyl. In some embodiments, $R^{31}$ is substituted $C_{1-10}$alkyl. In some embodiments, $R^{31}$ is $C_{1-10}$alkyl substituted with one or more aryl. In some embodiments, $R^{31}$ is $C_{1-10}$alkyl substituted with one or more heteroalkyl. In some embodiments, $R^{31}$ is $C_{1-10}$alkyl substituted with one or more heterocyclyl.

In some embodiments, $R^{31}$ is $C_{1-10}$alkyl substituted with one or more hetaryl. In some embodiments, when $R^{31}$ is $C_{1-10}$alkyl substituted with one or more aryl, each of said aryl substituents is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, O($C_{1-10}$alkyl), —O-aryl, —N(aryl)($C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$. In some embodiments, when $R^{31}$ is $C_{1-10}$alkyl substituted with one or more heteroalkyl, each of said heteroalkyl group is unsubstituted or substituted with one or more halo, —OH, —$C_{1-10}$alkyl, —$CF_3$, —O—, aryl, $OCF_3$, $OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$ substituents. In some embodiments, when $R^{31}$ is $C_{1-10}$alkyl substituted with one or more heterocyclyl, each of said heterocyclyl group is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH ($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$. In some embodiments, when $R^{31}$ is $C_{1-10}$alkyl substituted with one or more hetaryl, each of said hetaryl group is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$. In some embodiments, when $R^{31}$ is substituted $C_{1-10}$alkyl, it is substituted by a combination of aryl, heteroalkyl, heterocyclyl, or hetaryl groups.

In various embodiments of compounds of Formula I'-A', I (including I-A and I-B), II-A (including II-A-1 and II-A-2), II-B (including II-B-1 and II-B-2), III (including III-A and III-B), IV-A (including IV-A-1 and IV-A-2), IV-B (including IV-B-1 and IV-B-2), A, B (including B' and B"), C, 3-1, 3-2, 3-3, 3-4, 3-5, 3-6, N-1, or N-3, $R^{32}$ is H. In some embodiments, $R^{32}$ is unsubstituted $C_{1-10}$alkyl. In some embodiments, $R^{32}$ is substituted $C_{1-10}$alkyl. In some embodiments, $R^{32}$ is $C_{1-10}$alkyl substituted with one or more aryl. In some embodiments, $R^{32}$ is $C_{1-10}$alkyl substituted with one or more heteroalkyl. In some embodiments, $R^{32}$ is $C_{1-10}$alkyl substituted with one or more heterocyclyl. In some embodiments, $R^{32}$ is $C_{1-10}$alkyl substituted with one or more hetaryl. In some embodiments, when $R^{32}$ is $C_{1-10}$alkyl substituted with one or more aryl, each of said aryl group is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH (aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —CO—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$. In some embodiments, when $R^{32}$ is $C_{1-10}$alkyl substituted with one or more heteroalkyl, each of said heteroalkyl group is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH ($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$. In some embodiments, when $R^{32}$ is $C_{1-10}$alkyl substituted with one or more heterocyclyl, each of said heterocyclyl group is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —S(O)$_{0-2}$C$_{1-10}$alkyl, —S(O)$_{0-2}$C$_{1-10}$alkylaryl, —S(O)$_{0-2}$ aryl, —SO$_2$N(aryl), —SO$_2$N(C$_{1-10}$alkyl)(C$_{1-10}$alkyl), —SO$_2$NH(C$_{1-10}$alkyl) or —SO$_2$NR$^{34}$R$^{35}$. In some embodiments, when R$^{32}$ is C$_{1-10}$alkyl substituted with one or more hetaryl, each of said hetaryl group is unsubstituted or substituted with one or more halo, —OH, —C$_{1-10}$alkyl, —CF$_3$, —O-aryl, OCF$_3$, OC$_{1-10}$alkyl, —NH$_2$, —N(C$_1$-C$_{10}$alkyl)(C$_{1-10}$alkyl), —NH(C$_{1-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$C$_{1-10}$alkyl, —S(O)$_{0-2}$C$_{1-10}$alkylaryl, —S(O)$_{0-2}$ aryl, —SO$_2$N(aryl), —SO$_2$N(C$_{1-10}$alkyl)(C$_{1-10}$alkyl), —SO$_2$NH(C$_{1-10}$alkyl) or —SO$_2$NR$^{34}$R$^{35}$. In some embodiments, when R$^{32}$ is substituted C$_{1-10}$alkyl, it is substituted by a combination of aryl, heteroalkyl, heterocyclyl, or hetaryl groups.

In various embodiments of compounds of Formula I'-A', I (including I-A and I-B), II-A (including II-A-1 and II-A-2), II-B (including II-B-1 and II-B-2), III (including III-A and III-B), IV-A (including IV-A-1 and IV-A-2), IV-B (including IV-B-1 and IV-B-2), A, B (including B' and B"), C, 3-1, 3-3, 3-4, 3-5, 3-6, C", 3-1", 3-3", 3-4", 3-5", 3-6", N-1, N-3, N-1", or N-3", R$^{33}$ is unsubstituted C$_{1-10}$alkyl. In some embodiments, R$^{33}$ is substituted C$_{1-10}$alkyl. In some embodiments, R$^{33}$ is C$_{1-10}$alkyl substituted with one or more aryl. In some embodiments, R$^{33}$ is C$_{1-10}$alkyl substituted with one or more heteroalkyl. In some embodiments, R$^{33}$ is C$_{1-10}$alkyl substituted with one or more heterocyclyl. In some embodiments, R$^{33}$ is C$_{1-10}$alkyl substituted with one or more hetaryl. In some embodiments, when R$^{33}$ is C$_{1-10}$alkyl substituted with one or more aryl, each of said aryl group is unsubstituted or substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, N(aryl)(C$_{1-10}$alkyl), —NO$_2$, —CN, —S(O)$_2$C$_{1-10}$alkyl, —S(O)$_{0-2}$C$_{1-10}$alkylaryl, —S(O)$_{0-2}$ aryl, —SO$_2$N(aryl), —SO$_2$N(C$_{2-10}$alkyl)(C$_{1-10}$alkyl), —SO$_2$NH(C$_{2-10}$alkyl) or —SO$_2$NR$^{34}$R$^{35}$. In some embodiments, when R$^{33}$ is C$_{1-10}$alkyl substituted with one or more heteroalkyl, each of said heteroalkyl group is unsubstituted or substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), C(O)(C$_{1-10}$alkyl-aryl), C(O)(aryl), CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$C$_{1-10}$alkyl, —S(O)$_{0-2}$C$_{1-10}$alkylaryl, —S(O)$_{0-2}$ aryl, —SO$_2$N(aryl), —SO$_2$N(C$_{1-10}$alkyl)(C$_{1-10}$alkyl), —SO$_2$NH(C$_{1-10}$alkyl) or —SO$_2$NR$^{34}$R$^{35}$. In some embodiments, when R$^{33}$ is C$_{1-10}$alkyl substituted with one or more heterocyclyl, each of said heterocyclyl group is unsubstituted or substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$C$_{1-10}$alkyl, —S(O)$_{0-2}$C$_{1-10}$alkylaryl, —S(O)$_{0-2}$ aryl, —SO$_2$N(aryl), —SO$_2$N(C$_{1-10}$alkyl)(C$_{1-10}$alkyl), —SO$_2$NH(C$_{1-10}$alkyl) or —SO$_2$NR$^{34}$R$^{35}$. In some embodiments, when R$^{33}$ is C$_{1-10}$alkyl substituted with one or more hetaryl, each of said hetaryl group is unsubstituted or substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$C$_{1-10}$alkyl, —S(O)$_{0-2}$C$_{1-10}$alkylaryl, —S(O)$_{0-2}$ aryl, —SO$_2$N(aryl), —SO$_2$N(C$_{1-10}$alkyl)(C$_{1-10}$alkyl), —SO$_2$NH(C$_{1-10}$alkyl) or —SO$_2$NR$^{34}$R$^{35}$. In some embodiments, when R$^{33}$ is substituted C$_{1-10}$alkyl, it is substituted by a combination of aryl, heteroalkyl, heterocyclyl, or hetaryl groups.

In various embodiments of compounds of Formula I'-A', I (including I-A and I-B), II-A (including II-A-1 and II-A-2), II-B (including II-B-1 and II-B-2), III (including III-A and III-B), IV-A (including IV-A-1 and IV-A-2), IV-B (including IV-B-1 and IV-B-2), A, B (including B' and B"), C, 3-1, 3-3, 3-4, 3-5, 3-6, C", 3-1", 3-3", 3-4", 3-5", or 3-6", N-1, N-3, N-1", or N-3", R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, hetaryl, C$_{1-6}$alkyl, or O-aryl, and wherein said 3-10 membered saturated or unsaturated ring independently contains 0, 1, or 2 more heteroatoms in addition to the nitrogen.

In some embodiments, the R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form:

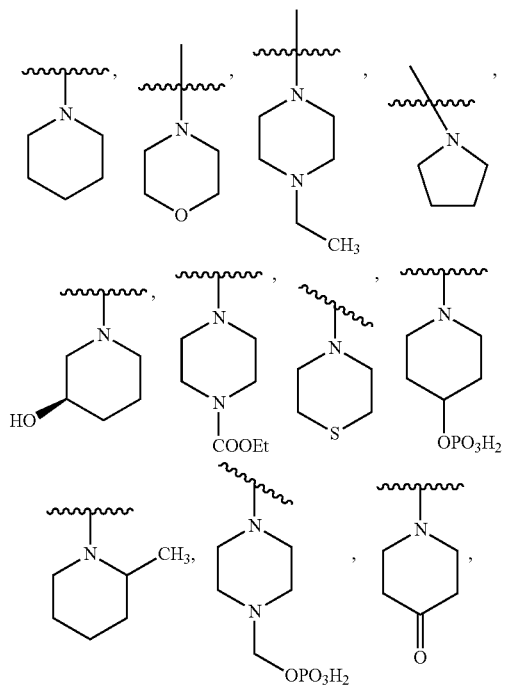

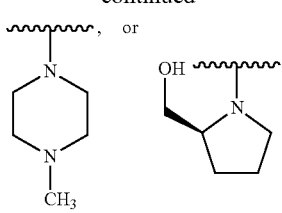

In another embodiment, $X_1$ is C—NH$_2$.

In various embodiments, $X_1$ is C—NH—R$^4$, where —NH—R$^4$ is:

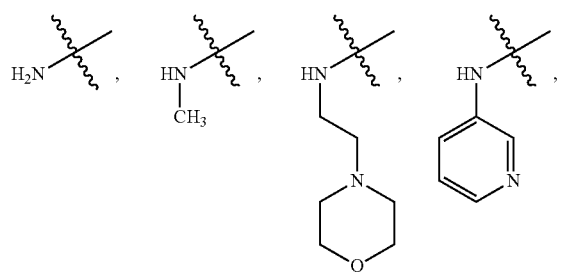

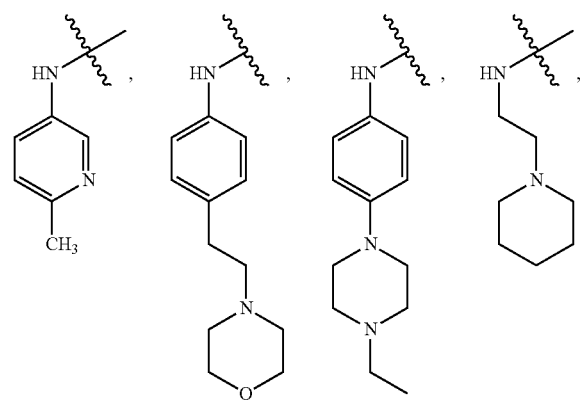

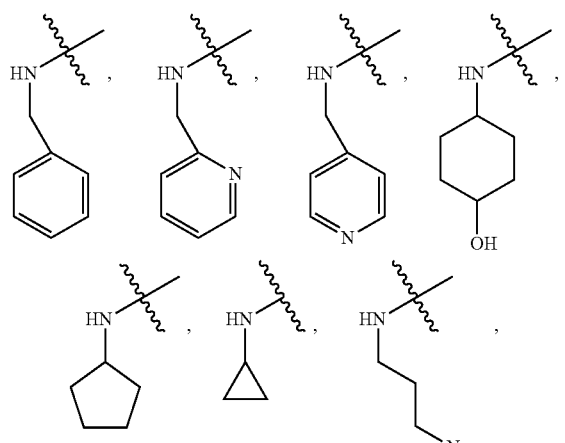

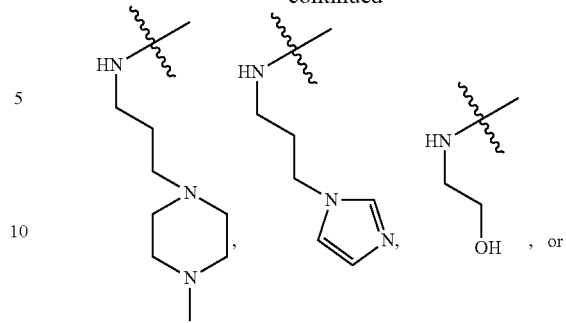

In one aspect, the invention provides a compound of Formula II-A-1:

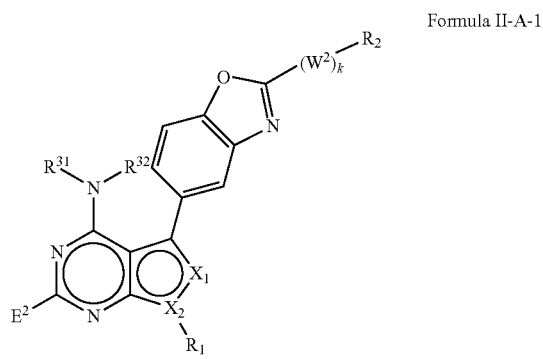

Formula II-A-1 or a pharmaceutically acceptable salt thereof, wherein:

$X_1$ is N or C-E$^1$ and $X_2$ is N; or $X_1$ is NH or CH-E$^1$ and $X_2$ is C;

$R_1$ is hydrogen, -L-C$_{1-10}$alkyl, -L-C$_{3-8}$cycloalkyl, -L-C$_{1-10}$alkyl-C$_{3-8}$cycloalkyl, -L-aryl, -L-heteroaryl, -L-C$_{1-10}$alkylaryl, -L-C$_{1-10}$alkylhetaryl, -L-C$_{1-10}$alkylheterocylyl, -L-C$_{2-10}$alkenyl, -L-C$_{2-10}$alkenyl-C$_{3-8}$cycloalkyl, -L-C$_{2-10}$alkynyl-C$_{3-8}$cycloalkyl, -L-heteroalkyl, -L-heteroalkylaryl, -L-heteroalkylheteroaryl, -L-heteroalkyl-heterocylyl, -L-heteroalkyl-C$_{3-8}$cycloalkyl, -L-aralkyl, -L-heteroaralkyl, or -L-heterocyclyl, each of which is unsubstituted or substituted by one or more independent R$^3$;

L is absent, —(C═O)—, —C(═O)O—, —C(═O)N(R$^{31}$)—, —S—, —S(O)—, —S(O)$_2$—, —S(O)$_2$N(R$^{31}$)—, or —N(R$^{31}$)—;

M$_1$ is benzoxazolyl substituted with (W$^2$)$_k$—R$^2$;

k is 0 or 1;

E$^1$ and E$^2$ are independently —(W$^1$)$_j$—R$^4$;

j in E$^1$ or j in E$^2$, is independently 0 or 11;

W$^1$ is —O—, —NR$^7$—, —S(O)$_{0-2}$—, —C(O), —C(O)N(R$^7$)—, —N(R$^7$)C(O)—, —N(R$^7$)S(O)—, N(R$^7$)S(O)$_2$, —C(O)O—, —CH(R$^7$)N(C(O)OR$^8$)—, —CH(R$^7$)N(C(O)R$^8$)—, —CH(R$^7$)N(SO$_2$R$^8$)—, —CH(R$^7$)N(R$^8$)—, —CH(R$^7$)C(O)N(R$^8$)—, —CH(R$^7$)N(R$^8$)C(O)—, —CH(R$^7$)N(R$^8$)S(O)—, or —CH(R$^7$)N(R$^8$)S(O)$_2$—;

W$^2$ is —O—, —NR$^7$—, —S(O)$_{0-2}$—, —C(O)—, —C(O)N(R$^7$)—, —N(R$^7$)C(O)—, —N(R$^7$)C(O)N(R$^8$)—, N(R$^7$)S(O)—, —N(R$^7$)S(O)$_2$—, —C(O)O—, —CH(R$^7$)N(C(O)

$OR^8$)—, —CH($R^7$)N(C(O)$R^8$)—, —CH($R^7$)N($SO_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R^3$ and $R^4$ are independently hydrogen, halogen, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, SC(=O)$OR^{31}$, P(O)$OR^{31}OR^{32}$, —SC(=O)$NR^{31}R^{32}$, aryl, hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkynyl-$C_{3-8}$cycloalkyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl $C_{2-10}$alkynyl, hetaryl $C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_2R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, SC(=O)$OR^{31}$, —P(O)$OR^{31}OR^{32}$, or SC(=O)$NR^{31}R^{32}$, and wherein each of said alkyl, cycloalkyl, heterocyclyl, or heteroalkyl moiety is unsubstituted or substituted with one or more halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^2$ is hydrogen, halogen, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}C_2R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, SC(=O)$OR^{31}$, —P(O)$OR^{31}OR^{32}$, —SC(=O)$NR^{31}R^{32}$, bicyclic aryl, substituted monocyclic aryl, hetaryl, $C_{1-10}$alkyl, $C_{3-8}$cycloalkyl, $C_{1-10}$alkyl $C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{2-10}$alkyl-monocyclic aryl, monocyclic aryl-$C_{2-10}$alkyl, $C_{1-10}$alkylbicycloaryl, bicycloaryl-$C_{1-10}$alkyl, $C_{1-10}$alkylaryl, substituted aryl-$C_{1-10}$alkyl, $C_{1-10}$alkylhetaryl, $C_{1-10}$alkylheterocyclyl, $C_{2-10}$alkenyl, $C_{2-10}$alkynyl, $C_{2-10}$alkenylaryl, $C_{2-10}$alkenylhetaryl, $C_{2-10}$alkenylheteroalkyl, $C_{2-10}$alkenylheterocyclyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkenyl-$C_{3-8}$cycloalkyl, $C_{2-10}$alkynyl-$C_{3-8}$cycloalkenyl, $C_{1-10}$alkoxy $C_{1-10}$alkyl, $C_{1-10}$alkoxy$C_{2-10}$alkenyl, $C_{1-10}$alkoxy$C_{2-10}$alkynyl, heterocyclyl, heterocyclyl $C_{1-10}$alkyl, heterocyclyl$C_{2-10}$alkenyl, heterocyclyl-$C_{2-10}$alkynyl, aryl-$C_{1-10}$alkyl, aryl $C_{2-10}$alkynyl, aryl-heterocyclyl, hetaryl $C_{1-10}$alkyl, hetaryl-$C_{2-10}$alkenyl, hetaryl-$C_{2-10}$alkynyl, hetaryl $C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —$R^{31}$, —$CF_3$, $OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_2R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_2R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=)$OR^{33}$, —OC(=O)$NR^{31}R^{32}$, —OC(=O)$SR^{31}$, —SC(=)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^{31}$, $R^{32}$, and $R^{33}$, in each instance, are independently H or $C_{1-10}$alkyl, wherein the $C_{1-10}$alkyl is unsubstituted or is substituted with one or more aryl, heteroalkyl, heterocyclyl, or hetaryl group, wherein each of said, aryl, heteroalkyl, heterocyclyl, or hetaryl group is unsubstituted or is substituted with one or more halo, —OH, —$C_{1-10}$alkyl, —$CF_3$, —O-aryl, OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —$NR^{34}R^{35}$, —C(O)(C$_{1-10}$alkyl), —C(O)(C$_{1-10}$alkyl-aryl), —C(O)(aryl), —$CO_2$—C$_{1-10}$alkyl, —$CO_2$—C$_{1-10}$alkylaryl, —$CO_2$-aryl, —C(=O)N(C$_{1-10}$alkyl)(C$_{1-10}$alkyl), —C(=O)NH(C$_{1-10}$alkyl), —C(=O)$NR^{34}R^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$C$_{1-10}$alkyl, —S(O)$_{0-2}$C$_{1-10}$alkylaryl, —S(O)$_{0-2}$ aryl, —SO$_2$N(aryl), —SO$_2$N(C$_{1-10}$alkyl) (C$_{1-10}$alkyl), —SO$_2$NH(C$_{1-10}$alkyl) or SO$_2$NR$^{34}$R$^{35}$;

$R^{34}$ and $R^{35}$ in —$NR^{34}R^{35}$, —C(=O)$NR^{34}R^{35}$, —SO$_2$NR$^{34}$R$^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, C$_{1-6}$alkyl, or O-aryl, and wherein said 3-10 membered saturated or unsaturated ring independently contains 0, 1, or 2 more heteroatoms in addition to the nitrogen;

$R^7$ and $R^8$ are each independently hydrogen, C$_{1-10}$alkyl, C$_{2-10}$alkenyl, aryl, heteroaryl, heterocyclyl or C$_{3-10}$cycloalkyl, each of which except for hydrogen is unsubstituted or is substituted by one or more independent $R^6$; and $R^6$ is halo, —$OR^{31}$, —SH, —NH$_2$, —$NR^{34}R^{35}$, —$NR^{31}R^{32}$, —$CO_2R^{31}$, CO$_2$aryl-C(=O)$NR^{31}R^{32}$, C(=O)NR$^{34}$R$^{35}$, —NO$_2$, —CN, —S(O)$_{0-2}$C$_{1-10}$alkyl, —S(O)$_{0-2}$aryl, —SO$_2$NR$^{34}$R$^{35}$, —SO$_2$NR$^{31}$R$^{32}$, C$_{1-10}$alkyl, C$_{2-10}$alkenyl, C$_{2-10}$alkynyl, aryl-C$_{1-10}$alkyl, aryl-C$_{2-10}$alkenyl, aryl-C$_{2-10}$alkynyl, hetaryl-C$_{1-10}$alkyl, hetaryl-C$_{2-10}$alkenyl, or hetaryl-C$_{2-10}$alkynyl, each of which is unsubstituted or is substituted with one or more independent halo, cyano, nitro, —OC$_{1-10}$alkyl, C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$.

In another aspect, the invention provides a compound of Formula II-A-1 or a pharmaceutically acceptable salt thereof wherein:

$E^2$ is —H; $X_1$ and $X_2$ are N;

$R_1$ is -L-C$_{1-10}$alkyl, -L-C$_{3-8}$cycloalkyl, -L-C$_{1-10}$alkylheterocylyl, or -L-heterocyclyl, each of which is unsubstituted or is substituted by one or more independent $R^3$;

L is absent, —(C=O)—, —C(=O)O—, —C(=O)N (R$^{31}$)—, —S—, —S(O)—, —S(O)$_2$—, —S(O)$_2$N(R$^{31}$)—, or —N(R$^{31}$)—;

$R^3$ is hydrogen, —OH, —OR$^{31}$, —NR$^{31}$R$^{32}$, —C(O)R$^{31}$, —C(=O)NR$^{31}$R$^{32}$, —C(=O)NR$^{34}$R$^{35}$, aryl, hetaryl, C$_{1-4}$alkyl, C$_{1-10}$alkyl, C$_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_2$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_2$R$^{32}$, —C(=S)OR$^{31}$, —C(=O)SR$^{31}$, —NR$^{31}$C(=NR$^{32}$)NR$^{33}$R$^{32}$, —NR$^{31}$C (=NR$^2$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

—(W$^2$)$_k$— is —NR$^7$—, —N(R$^7$)C(O)— or N(R$^7$)S(O)$_2$—;

k is 0 or 1;

$R^2$ is hydrogen, halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_2$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, —SC(=O)NR$^{31}$R$^{32}$, bicyclic aryl, substituted monocyclic aryl, hetaryl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{2-10}$alkyl-monocyclic aryl, monocyclic aryl-C$_{2-10}$alkyl, C$_{1-10}$alkylbicycloaryl, bicycloaryl-C$_{1-10}$alkyl, substituted C$_{1-10}$alkylaryl, substituted aryl-C$_{1-10}$alkyl, C$_{1-10}$alkylhetaryl, C$_{1-10}$alkylheterocyclyl, C$_{2-10}$alkenyl, C$_{2-10}$alkynyl, C$_{2-10}$alkenylaryl, C$_{2-10}$alkenylhetaryl, C$_{2-10}$alkenylheteroalkyl, C$_{2-10}$alkenylheterocyclcyl, C$_{2-10}$alkynylaryl, C$_{2-10}$alkynylhetaryl, C$_{2-10}$alkynylheteroalkyl, C$_{2-10}$alkynylheterocyclyl, C$_{2-10}$alkenyl-C$_{3-8}$cycloalkyl, C$_{2-10}$alkynyl-C$_{3-8}$cycloalkyl, C$_{1-10}$alkoxy C$_{10-10}$alkyl, C$_{1-10}$alkoxyC$_{2-10}$alkenyl, C$_{1-10}$alkoxyC$_{2-10}$alkynyl, heterocyclyl, heterocyclyl C$_{1-10}$alkyl, heterocyclylC$_{2-10}$alkenyl, heterocyclyl-C$_{2-10}$alkynyl, aryl-C$_{2-10}$alkenyl, aryl-C$_{2-10}$alkynyl, aryl-heterocyclyl, hetaryl-C$_{1-10}$alkyl, hetaryl-C$_{2-10}$alkenyl, hetaryl-C$_{2-10}$alkynyl, hetaryl-C$_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=)OR$^{31}$, —P(O)OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more halo, —OH, —R$^{31}$, —CF$_3$, —OCF$_3$, —OR$^{31}$, —O-aryl, NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

$R^{31}$, $R^{32}$, and $R^{33}$, in each instance, are independently H or C$_{1-10}$alkyl, wherein the C$_{1-10}$alkyl is unsubstituted or is substituted with one or more aryl, heteroalkyl, heterocyclyl, or hetaryl group, wherein each of said alkyl, aryl, heteroalkyl, heterocyclyl, or hetaryl group is unsubstituted or is substituted with one or more halo, —C$_{1-10}$alkyl, —CF$_3$, —O-aryl, —OCF$_3$, —OC$_{1-10}$alkyl, —NH$_2$, —N(C$_{1-10}$alkyl) (C$_{1-10}$ alkyl), —NH(C$_{1-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH (C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$C$_{1-10}$alkyl, —S(O)$_{0-2}$C$_{1-10}$alkylaryl, —S(O)$_{0-2}$ aryl, —SO$_2$N(aryl), —SO$_2$N(C$_{1-10}$alkyl) (C$_{1-10}$alkyl), —SO$_2$NH(C$_{1-10}$alkyl) or SO$_2$NR$^{34}$R$^{35}$;

$R^{34}$ and $R^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, hetaryl, C$_{1-6}$alkyl, or O-aryl, and wherein said 3-10 membered saturated or unsaturated ring independently contains 0, 1, or 2 more heteroatoms in addition to the nitrogen;

$R^7$ is hydrogen, C$_{1-10}$alkyl, C$_{2-10}$alkenyl, aryl, heteroaryl, heterocyclyl or C$_{3-10}$cycloalkyl, each of which except for hydrogen is unsubstituted or is substituted by one or more independent $R^6$; and $R^6$ is halo, —OR$^{31}$, —SH, —NH$_2$, —NR$^{34}$R$^{35}$, —NR$^{31}$R$^{32}$, —CO$_2$R$^{31}$, —CO$_2$aryl-C(=O)NR$^{31}$R$^{32}$, C(=O)NR$^{34}$R$^{35}$, —NO$_2$, —CN, —S(O)$_{0-2}$C$_{1-10}$alkyl, —S(O)$_{0-2}$aryl, —SO$_2$NR$^{34}$R$^{35}$, —SO$_2$NR$^{31}$R$^{32}$, C$_{1-10}$alkyl, C$_{2-10}$alkenyl, C$_{2-10}$alkynyl, aryl-C$_{1-10}$alkyl, aryl-C$_{2-10}$alkenyl, aryl-C$_{2-10}$alkynyl, hetaryl-C$_{1-10}$alkyl, hetaryl-C$_{2-10}$alkenyl, or hetaryl-C$_{2-10}$alkynyl, each of which is unsubstituted or is substituted with one or more independent halo, cyano, nitro, —OC$_{1-10}$alkyl, C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$.

In yet another aspect, the invention provides a compound of Formula II-A-1 or a pharmaceutically acceptable salt thereof wherein:

$E^2$ is —H; $X_1$ and $X_2$ are N;

$R_1$ is -L-C$_{1-10}$alkyl, -L-C$_{3-8}$cycloalkyl, -L-C$_{1-10}$alkylheterocylyl, or -L-heterocyclyl, each of which is unsubstituted or is substituted by one or more independent $R^3$;

L is absent, —(C=O)—, —C(=O)O—, —C(=O)N(R$^{31}$)—, —S—, —S(O)—, —S(O)$_2$—, —S(O)$_2$N(R$^{31}$)—, or —N(R$^{31}$)—;

R$^3$ is hydrogen, —OH, —OR$^{31}$, —NR$^{31}$R$^{32}$, —C(O)R$^{31}$, —C(=O)NR$^{31}$R$^{32}$, —C(=O)NR$^{34}$R$^{35}$, aryl, hetaryl, C$_{1-4}$alkyl, C$_{1-10}$alkyl, C$_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, r C(=O)NR$^{31}$R$^{32}$;

—(W$^2$)$_k$— is —NH—, —N(H)C(O)— or —N(H)S(O)$_2$;

R$^2$ is hydrogen, halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, —SC(=O)NR$^{31}$R$^{32}$, bicyclic aryl, substituted monocyclic aryl, hetaryl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{2-10}$alkyl-monocyclic aryl, monocyclic aryl-C$_{2-10}$alkyl, C$_{1-10}$alkylbicycloaryl, bicycloaryl-C$_{1-10}$alkyl, substituted C$_{1-10}$alkylaryl, substituted aryl-C$_{1-10}$alkyl, C$_{1-10}$alkylhetaryl, C$_{1-10}$alkylheterocyclyl, C$_{2-10}$alkenyl, C$_{2-10}$alkynyl, C$_{2-10}$alkenylaryl, C$_{2-10}$alkenylhetaryl, C$_{2-10}$alkenylheteroalkyl, C$_{2-10}$alkenylheterocyclcyl, C$_{2-10}$alkynylaryl, C$_{2-10}$alkynylhetaryl, C$_{2-10}$alkynylheteroalkyl, C$_{2-10}$alkynylheterocyclyl, C$_{2-10}$alkenyl-C$_{3-8}$cycloalkyl, C$_{2-10}$alkynyl-C$_{3-8}$cycloalkenyl, C$_{1-10}$alkoxy C$_{10-10}$alkyl, C$_{1-10}$alkoxyC$_{2-10}$alkenyl, C$_{1-10}$alkoxyC$_{2-10}$alkynyl, heterocyclyl, heterocyclyl C$_{1-10}$alkyl, heterocyclylC$_{2-10}$alkenyl, heterocyclyl-C$_{2-10}$alkynyl, aryl-C$_{1-10}$alkenyl, aryl-C$_{2-10}$alkynyl, aryl-heterocyclyl, hetaryl-C$_{1-10}$alkyl, hetaryl-C$_{2-10}$alkenyl, hetaryl-C$_{2-10}$alkynyl, hetaryl-C$_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_2$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more halo, —OH, —R$^{31}$, —CF$_3$, —OCF$_3$, —OR$^{31}$, —O-aryl, NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

R$^{31}$, R$^{32}$, and R$^{33}$, in each instance, are independently H or C$_{1-10}$alkyl, wherein the C$_{1-10}$alkyl is unsubstituted; and R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, hetaryl, C$_{1-6}$alkyl, or O-aryl, and wherein said 3-10 membered saturated or unsaturated ring independently contains 0, 1, or 2 more heteroatoms in addition to the nitrogen.

In a further aspect, the invention provides a compound of Formula II-A-1 or a pharmaceutically acceptable salt thereof wherein:

E$^2$ is —H;

X$_1$ and X$_2$ are N;

R$_1$ is -L-C$_{1-10}$alkyl, -L-C$_{3-8}$cycloalkyl, -L-C$_{1-10}$alkylheterocylyl, or -L-heterocyclyl, each of which is unsubstituted or is substituted by one or more independent R$^3$;

L is absent, —(C=O)—, —C(=O)O—, —C(=O)N(R$^{31}$)—, —S—, —S(O)—, —S(O)$_2$—, —S(O)$_2$N(R$^{31}$)—, or —N(R$^{31}$)—;

R$^3$ is hydrogen, —OH, —OR$^{31}$, —NR$^{31}$R$^{32}$, —C(O)R$^{31}$, —C(=O)NR$^{31}$R$^{32}$, —C(=O)NR$^{34}$R$^{35}$, aryl, hetaryl, C$_{1-4}$alkyl, C$_{1-10}$alkyl, C$_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, SC(=O)OR$^{31}$, —P(O)OR$^{31}$OR$^{32}$, or —SC(=O)NR$^{31}$R$^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

—(W$^2$)$_k$— is —NH—, —N(H)C(O)— or —N(H)S(O)$_2$;

R$^2$ is hydrogen, halogen, OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —S(O)$_{0-2}$R$^{31}$, —SO$_2$NR$^{31}$R$^{32}$, —SO$_2$NR$^{34}$R$^{35}$, bicyclic aryl, substituted monocyclic aryl, hetaryl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{2-10}$alkyl-monocyclic aryl, monocyclic aryl-C$_{2-10}$alkyl, C$_{1-10}$alkylbicycloaryl, bicycloaryl-C$_{1-10}$alkyl, substituted C$_{1-10}$alkylaryl, substituted aryl-C$_{1-10}$alkyl, C$_{1-10}$alkylhetaryl, C$_{1-10}$alkylheterocyclyl, C$_{2-10}$alkenyl, C$_{2-10}$alkynyl, C$_{2-10}$alkenylaryl, C$_{2-10}$alkenylhetaryl, C$_{2-10}$alkenylheteroalkyl, C$_{2-10}$alkenylheterocyclcyl, C$_{2-10}$alkynylaryl, C$_{2-10}$alkynylhetaryl, C$_{2-10}$alkynylheteroalkyl, C$_{2-10}$alkynylheterocyclyl, C$_{2-10}$alkenyl-C$_{3-8}$cycloalkyl, C$_{2-10}$alkynyl-C$_{3-8}$cycloalkenyl, C$_{1-10}$alkoxy C$_{1-10}$alkyl, C$_{1-10}$alkoxyC$_{2-10}$alkenyl, C$_{1-10}$alkoxyC$_{2-10}$alkynyl, heterocyclyl, heterocyclyl $C_{1-10}$alkyl, heterocyclyl $C_{2-10}$alkenyl, heterocyclyl-$C_{2-10}$alkynyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_2R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32'}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

$R^{31}$, $R^{32}$, and $R^{33}$, in each instance, are independently H or $C_{1-10}$alkyl, wherein the $C_{1-10}$alkyl is unsubstituted; and $R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen.

In another aspect, the compound of Formula II-A-1 is a compound of Formula II-A-1a:

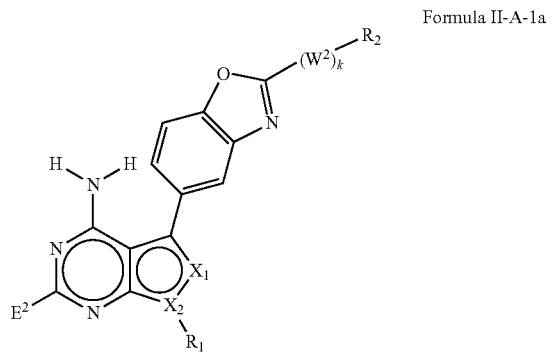

Formula II-A-1a or a pharmaceutically acceptable salt thereof, wherein:
$E^2$ is —H; $X_1$ and $X_2$ are N;
$R_1$ is -L-$C_{1-10}$alkyl, -L-$C_{3-8}$cycloalkyl, -L-$C_{1-10}$alkylheterocylyl, or -L-heterocyclyl, each of which is unsubstituted or is substituted by one or more independent $R^3$;

L is absent, —$C(=O)$—, —$C(=O)O$—, —$C(=O)N(R^{31})$—, —S—, —$S(O)$—, —$S(O)_2$—, —$S(O)_2N(R^{31})$—, or —$N(R^{31})$—;

$R^3$ is hydrogen, —OH, —$OR^{31}$, —$NR^{31}R^{32}$, —$C(O)R^{31}$, —$C(=O)NR^{31}R^{32}$, —$C(=O)NR^{34}R^{35}$, aryl, hetaryl, $C_{1-4}$alkyl, $C_{1-10}$alkyl, $C_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_2R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_2R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

—$(W^2)_k$— is —NH—, —N(H)C(O)— or —N(H)S(O)_2—;

$R^2$ is hydrogen, halogen, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$S(O)_{0-2}R^{31}$, —$SO_2NR^{31}R^{32}$, —$SO_2NR^{34}R^{35}$, bicyclic aryl, substituted monocyclic aryl, hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{2-10}$alkyl-monocyclic aryl, monocyclic aryl-$C_{2-10}$alkyl, $C_{1-10}$alkylbicycloaryl, bicycloaryl-$C_{1-10}$alkyl, substituted $C_{1-10}$alkylaryl, substituted aryl-$C_{1-10}$alkyl, $C_{1-10}$alkylhetaryl, $C_{1-10}$alkylheterocyclyl, $C_{2-10}$alkenyl, $C_{2-10}$alkynyl, heterocyclyl, heterocyclyl $C_{1-10}$alkyl, heterocyclyl-$C_{2-10}$alkenyl, heterocyclyl-$C_{2-10}$alkynyl, aryl-heterocyclyl, hetaryl-$C_{1-10}$alkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_2R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

$R^{31}$, $R^{32}$, and $R^{33}$, in each instance, are independently H or $C_{1-10}$alkyl, wherein the $C_{1-10}$alkyl is unsubstituted; and $R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen.

In another aspect, the invention provides a compound of Formula II-A-1:

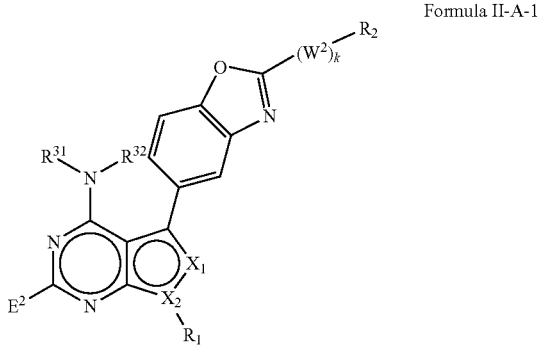

Formula II-A-1 or a pharmaceutically acceptable salt thereof, wherein:

$E^2$ is —H; $X_1$ is CH and $X_2$ is N;

$R_1$ is -L-$C_{1-10}$alkyl, -L-$C_{3-8}$cycloalkyl, -L-$C_{1-10}$alkylheterocylyl, or -L-heterocyclyl, each of which is unsubstituted or is substituted by one or more independent $R^3$;

L is absent, —C(=O)—, —C(=O)O—, —C(=O)N($R^{31}$)—, —S—, —S(O)—, —S(O)$_2$—, —S(O)$_2$N($R^{31}$)—, or —N($R^{31}$)—;

$R^3$ is hydrogen, OH, —OR$^{31}$, —NR$^{31}$R$^{32}$, C(O)R$^{31}$, C(=O)NR$^{31}$R$^{32}$, —C(=O)NR$^{34}$R$^{35}$, aryl, hetaryl, $C_{1-4}$alkyl, $C_{1-10}$alkyl, $C_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

—(W$^2$)$_k$— is —NR$^7$—, —N(R$^7$)C(O)— or N(R$^7$)S(O)$_2$;

k is 0 or 1;

$R^2$ is hydrogen, halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, —SC(=O)NR$^{31}$R$^{32}$, bicyclic aryl, substituted monocyclic aryl, hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{2-10}$alkyl-monocyclic aryl, monocyclic aryl-$C_{2-10}$alkyl, $C_{1-10}$alkylbicycloaryl, bicycloaryl-$C_{1-10}$alkyl, $C_{1-10}$alkylaryl, substituted aryl-$C_{1-10}$alkyl, $C_{1-10}$alkylhetaryl, $C_{1-10}$alkylheterocyclyl, $C_{2-10}$alkenyl, $C_{2-10}$alkynyl, $C_{2-10}$alkenylaryl, $C_{2-10}$alkenylhetaryl, $C_{2-10}$alkenylheteroalkyl, $C_{2-10}$alkenylheterocyclcyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkenyl-$C_{3-8}$cycloalkyl, $C_{2-10}$alkynyl-$C_{3-8}$cycloalkenyl, $C_{1-10}$alkoxy $C_{10-10}$alkyl, $C_{1-10}$alkoxyC$_{2-10}$alkenyl, $C_{1-10}$alkoxyC$_{2-10}$alkynyl, heterocyclyl, heterocyclyl $C_{1-10}$alkyl, heterocyclylC$_{2-10}$alkenyl, heterocyclyl-$C_{2-10}$alkynyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

$R^{31}$, $R^{32}$, and $R^{33}$, in each instance, are independently H or $C_{1-10}$alkyl, wherein the $C_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —$C_{1-10}$alkyl, —CF$_3$, —O-aryl, OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$C$_{1-10}$alkyl, —S(O)$_{0-2}$C$_{1-10}$alkylaryl, —S(O)$_{0-2}$ aryl, —SO$_2$N(aryl), —SO$_2$N(C$_{1-10}$alkyl)(C$_{1-10}$alkyl), —SO$_2$NH(C$_{1-10}$alkyl) or —SO$_2$NR$^{34}$R$^{35}$;

$R^{34}$ and $R^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen;

$R^7$ is hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$; and $R^6$ is halo, —OR$^{31}$, —SH, —NH$_2$, —NR$^{34}$R$^{35}$, —NR$^{31}$R$^{32}$, —CO$_2$R$^{31}$, —CO$_2$aryl-C(=O)NR$^{31}$R$^{32}$, C(=O)NR$^{34}$R$^{35}$, —NO$_2$, —CN, —S(O)$_{0-2}$C$_{1-10}$alkyl, —S(O)$_{0-2}$aryl, —SO$_2$NR$^{34}$R$^{35}$, —SO$_2$NR$^{31}$R$^{32}$, $C_{1-10}$alkyl, $C_{2-10}$alkenyl, $C_{2-10}$alkynyl, aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, or hetaryl-$C_{2-10}$alkynyl, each of which is unsubstituted or is substituted with one or more independent halo, cyano, nitro, —OC$_{1-10}$alkyl, $C_{1-10}$alkyl, $C_{2-10}$alkenyl, $C_{2-10}$alkynyl, haloC$_{1-10}$alkyl, haloC$_{2-10}$alkenyl, haloC$_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$.

In yet another aspect, the invention provides a compound of Formula II-A-1 or a pharmaceutically acceptable salt thereof wherein:

$E^2$ is —H; $X_1$ is CH and $X_2$ is N;

$R_1$ is -L-C$_{1-10}$alkyl, -L-C$_{3-8}$cycloalkyl, -L-C$_{1-10}$alkylheterocylyl, or -L-heterocyclyl, each of which is unsubstituted or is substituted by one or more independent $R^3$;

L is absent, —(C=O)—, —C(=O)O—, —C(=O)N(R$^{31}$)—, —S—, —S(O)—, —S(O)$_2$—, —S(O)$_2$N(R$^{31}$)—, or —N(R$^{31}$)—;

$R^3$ is hydrogen, —OH, —OR$^{31}$, —NR$^{31}$R$^{32}$, —C(O)R$^{31}$, —C(=O)NR$^{31}$R$^{32}$, —C(=O)NR$^{34}$R$^{35}$, aryl, hetaryl, C$_{1-4}$alkyl, C$_{1-10}$alkyl, C$_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_2$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, SC(=O)OR$^{31}$, —P(O)OR$^{31}$OR$^{32}$, or —SC(=O)NR$^{31}$R$^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

—(W$^2$)$_k$— is —NH—, —N(H)C(O)— or —N(H)S(O)$_2$—;

$R^2$ is hydrogen, halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, —SC(=O)NR$^{31}$R$^{32}$, bicyclic aryl, substituted monocyclic aryl, hetaryl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{2-10}$alkyl-monocyclic aryl, monocyclic aryl-C$_{2-10}$alkyl, C$_{1-10}$alkylbicycloaryl, bicycloaryl-C$_{1-10}$alkyl, substituted C$_{1-10}$alkylaryl, substituted aryl-C$_{1-10}$alkyl, C$_{1-10}$alkylhetaryl, C$_{1-10}$alkylheterocyclyl, C$_{2-10}$alkenyl, C$_{2-10}$alkynyl, C$_{2-10}$alkenylaryl, C$_{2-10}$alkenylhetaryl, C$_{2-10}$alkenylheteroalkyl, C$_{2-10}$alkenylheterocyclcyl, C$_{2-10}$alkynylaryl, C$_{2-10}$alkynylhetaryl, C$_{2-10}$alkynylheteroalkyl, C$_{2-10}$alkynylheterocyclyl, C$_{2-10}$alkenyl-C$_{3-8}$cycloalkyl, C$_{2-10}$alkynyl-C$_{3-8}$cycloalkenyl, C$_{1-10}$alkoxy C$_{1-10}$alkyl, C$_{1-10}$alkoxyC$_{2-10}$alkenyl, C$_{1-10}$alkoxyC$_{2-10}$alkynyl, heterocyclyl, heterocyclyl C$_{1-10}$alkyl, heterocyclylC$_{2-10}$alkenyl, heterocyclyl-C$_{2-10}$alkynyl, aryl-C$_{1-10}$alkenyl, aryl-C$_{2-10}$alkynyl, aryl-heterocyclyl, hetaryl-C$_{1-10}$alkyl, hetaryl-C$_{2-10}$alkenyl, hetaryl-C$_{2-10}$alkynyl, hetaryl-C$_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —R$^{31}$, —CF$_3$, OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_2$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more halo, —OH, —R$^{31}$, —CF$_3$, —OCF$_3$, —OR$^{31}$, —O-aryl, NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

$R^{31}$, $R^{32}$, and $R^{33}$, in each instance, are independently H or C$_{1-10}$alkyl, wherein the C$_{1-10}$alkyl is unsubstituted; and $R^{34}$ and $R^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, hetaryl, C$_{1-6}$alkyl, or O-aryl, and wherein said 3-10 membered saturated or unsaturated ring independently contains 0, 1, or 2 more heteroatoms in addition to the nitrogen.

In a further aspect, the invention provides a compound of Formula II-A-1 or a pharmaceutically acceptable salt thereof wherein:

$E^2$ is —H; $X_1$ is CH and $X_2$ is N;

$R_1$ is -L-C$_{1-10}$alkyl, -L-C$_{3-8}$cycloalkyl, -L-C$_{1-10}$alkylheterocylyl, or -L-heterocyclyl, each of which is unsubstituted or is substituted by one or more independent $R^3$;

L is absent, —(C=O)—, —C(=O)O—, —C(=O)N(R$^{31}$)—, —S—, —S(O)—, —S(O)$_2$—, —S(O)$_2$N(R$^{31}$)—, or —N(R$^{31}$)—;

$R^3$ is hydrogen, —OH, —OR$^{31}$, —NR$^{31}$R$^{32}$, —C(O)R$^{31}$, —C(=O)NR$^{31}$R$^{32}$, —C(=O)NR$^{34}$R$^{35}$, aryl, hetaryl, C$_{1-4}$alkyl, C$_{1-10}$alkyl, C$_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

—(W$^2$)$_k$— is —NH—, —N(H)C(O)— or —N(H)S(O)$_2$—;

$R^2$ is hydrogen, halogen, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —S(O)$_{0-2}$R$^{31}$, —SO$_2$NR$^{31}$R$^{32}$, —SO$_2$NR$^{34}$R$^{35}$, bicyclic aryl, substituted monocyclic aryl, hetaryl, C$_{1-10}$alkyl, C$_{3-8}$cycloalkyl, C$_{1-10}$alkyl-C$_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{2-10}$alkyl-monocyclic aryl, monocyclic aryl-$C_{2-10}$alkyl, $C_{1-10}$alkylbicycloaryl, bicycloaryl-$C_{1-10}$alkyl, substituted $C_{1-10}$alkylaryl, substituted aryl-$C_{1-10}$alkyl, $C_{1-10}$alkylhetaryl, $C_{1-10}$alkylheterocyclyl, $C_{2-10}$alkenyl, $C_{2-10}$alkynyl, $C_{2-10}$alkenylaryl, $C_{2-10}$alkenylhetaryl, $C_{2-10}$alkenylheteroalkyl, $C_{2-10}$alkenylheterocyclyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkenyl-$C_{3-8}$cycloalkyl, $C_{2-10}$alkynyl-$C_{3-8}$cycloalkenyl, $C_{1-10}$alkoxy $C_{1-10}$alkyl, $C_{1-10}$alkoxy$C_{2-10}$alkenyl, $C_{1-10}$alkoxy$C_{2-10}$alkynyl, heterocyclyl, heterocyclyl $C_{1-10}$alkyl, heterocyclyl$C_{2-10}$alkenyl, heterocyclyl-$C_{2-10}$alkynyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

$R^{31}$, $R^{32}$, and $R^{33}$, in each instance, are independently H or $C_{1-10}$alkyl, wherein the $C_{1-10}$alkyl is unsubstituted; and $R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen.

In another aspect, the compound of Formula II-A-1 is a compound of Formula II-A-1a:

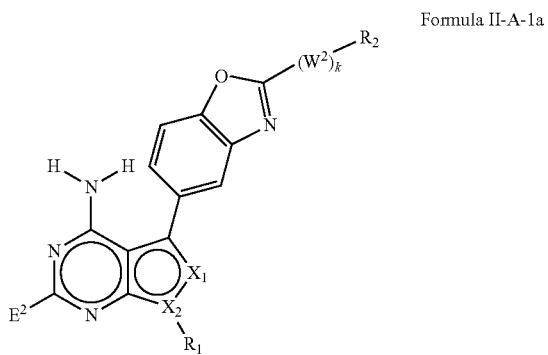

Formula II-A-1a or a pharmaceutically acceptable salt thereof, wherein: $E^2$ is —H; $X_1$ is CH and $X_2$ is N;

$R_1$ is -L-$C_{1-10}$alkyl, -L-$C_{3-8}$cycloalkyl, -L-$C_{1-10}$alkylheterocylyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)_2—, —S(O)_2N($R^{31}$)—, or —N($R^{31}$)—;

$R^3$ is hydrogen, —OH, —$OR^{31}$, —$NR^{31}R^{32}$, —$C(O)R^{31}$, —$C(=O)NR^{31}R^{32}$, —$C(=O)NR^{34}R^{35}$, aryl, hetaryl, $C_{1-4}$alkyl, $C_{1-10}$alkyl, $C_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

—$(W^2)_k$— is —NH—, —N(H)C(O)— or —N(H)S(O)_2—;

$R^2$ is hydrogen, halogen, $OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$S(O)_{0-2}R^{31}$, —$SO_2NR^{31}R^{32}$, —$SO_2NR^{34}R^{35}$, bicyclic aryl, substituted monocyclic aryl, hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{2-10}$alkyl-monocyclic aryl, monocyclic aryl-$C_{2-10}$alkyl, $C_{1-10}$alkylbicycloaryl, bicycloaryl-$C_{1-10}$alkyl, substituted $C_{1-10}$alkylaryl, substituted aryl-$C_{1-10}$alkyl, $C_{1-10}$alkylhetaryl, $C_{1-10}$alkylheterocyclyl, $C_{2-10}$alkenyl, $C_{2-10}$alkynyl, heterocyclyl, heterocyclyl $C_{1-10}$alkyl, heterocyclyl-$C_{2-10}$alkenyl, heterocyclyl-$C_{2-10}$alkynyl, aryl-heterocyclyl, hetaryl-$C_{1-10}$alkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

$R^{31}$, $R^{32}$, and $R^{33}$, in each instance, are independently H or $C_{1-10}$alkyl, wherein the $C_{1-10}$alkyl is unsubstituted; and $R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —NR³¹R³², hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen.

B. REACTION SCHEMES

The compounds disclosed herein may be prepared by the routes described below. Materials used herein are either commercially available or prepared by synthetic methods generally known in the art. These schemes are not limited to the compounds listed or by any particular substituents employed for illustrative purposes. Numbering does not necessarily correspond to that of claims or other tables.

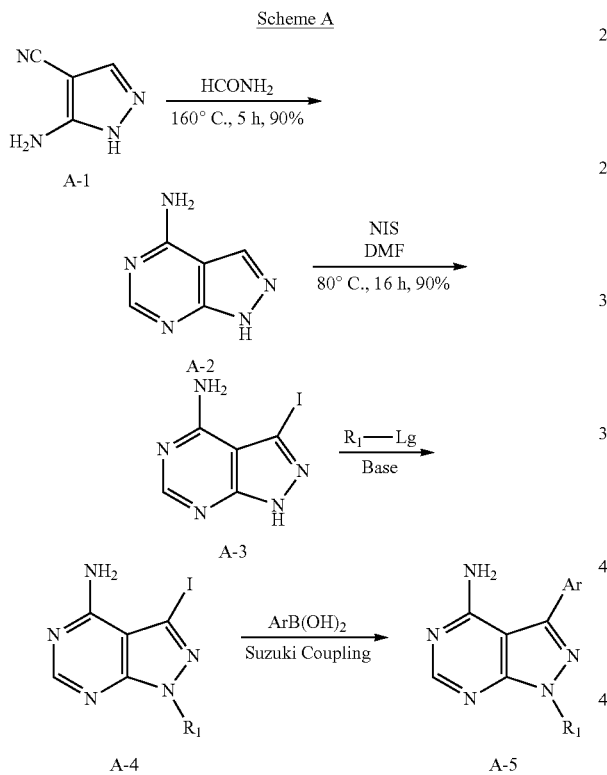

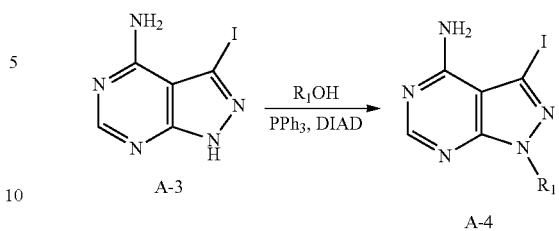

Alternatively, Mitsunobu chemistry can be used to obtain alkylated pyrazolopyrimidine A-4, as shown in Scheme A-1. Iodopyrazolopyrimidine A-3 is reacted with a suitable alcohol, in the presence of triphenylphosphine and diisopropylazodicarboxylate (DIAD) to produce pyrazolopyrimidine A-4.

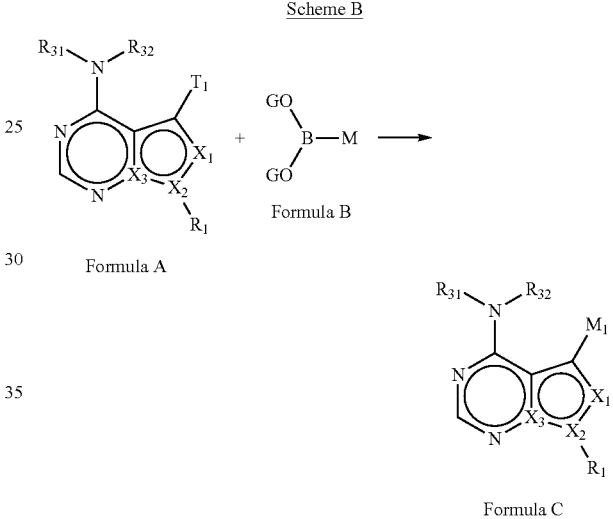

In one embodiment, compounds are synthesized by condensing a functionalized heterocycle A-1 with formamide, to provide a pyrazolopyrimidine A-2. The pyrazolopyrimidine is treated with N-iodosuccinimide, which introduces an iodo substituent in the pyrazole ring as in A-3. The $R_1$ substituent is introduced by reacting the pyrazolopyrimidine A3 with a compound of Formula $R_1$-Lg in the presence of a base such as potassium carbonate to produce a compound of Formula A-4. Other bases that are suitable for use in this step include but are not limited to sodium hydride and potassium t-butoxide. The compound of Formula $R_1$-Lg has a moiety $R_1$ as defined for $R_1$ of a compound of Formula I'-A', and wherein Lg is an appropriate leaving group such as halide (including bromo, iodo, and chloro), tosylate, or other suitable leaving group, The substituents corresponding to $M_1$ are thereafter introduced by reacting aryl or hetaryl boronic acids with the compound of Formula A-4 to obtain compound A-5.

The compounds of the invention may be synthesized via a reaction scheme represented generally in Scheme B. The synthesis proceeds via coupling a compound of Formula A with a compound of Formula B to yield a compound of Formula C. The coupling step is typically catalyzed by using, e.g., a palladium catalyst, including but not limited to palladium tetrakis(triphenylphosphine). The coupling is generally performed in the presence of a suitable base, a nonlimiting example being sodium carbonate. One example of a suitable solvent for the reaction is aqueous dioxane.

A compound of Formula A for use in Scheme B has a structure of Formula A, wherein $T_1$ is triflate or halo (including bromo, chloro, and iodo), and wherein $R_1$, $X_1$, $X_2$, $X_3$, $R_{31}$ and $R_{32}$ are defined as for a compound of Formula I'-A'. For boronic acids and acid derivatives as depicted in Formula B, M is either $M_1$ or $M_2$. $M_1$ is defined as for a compound of Formula I'-A'. For example, $M_1$ can be a 5-benzoxazolyl or a 6-benzoxazolyl moiety, including but not limited to those $M_1$ moieties disclosed herein. $M_2$ is a moiety which is synthetically transformed to form $M_1$, after the $M_2$ moiety has been coupled to the bicyclic core of the compound of Formula A.

For a compound of Formula B, G is hydrogen or $R_{G1}$, wherein $R_{G1}$ is alkyl, alkenyl, or aryl. Alternatively, $B(OG)_2$ is taken together to form a 5- or 6-membered cyclic moiety. In some embodiments, the compound of Formula B is a compound having a structure of Formula E:

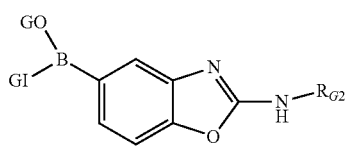

Formula E wherein G is H or $R_{G1}$; $R_{G1}$ is alkyl, alkenyl, or aryl. Alternatively,

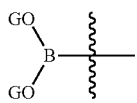

forms a 5- or 6-membered cyclic moiety; and $R_2$ is a $R_{G2}$ moiety, wherein the $R_{G2}$ moiety is H, acyl, or an amino protecting group including but not limited to tert-butyl carbamate (Boc), carbobenzyloxy (Cbz), benzyl (Bz), fluorenyl-methyloxycarbonyl (FMOC), p-methoxybenzyl (PMB), and the like.

Scheme C

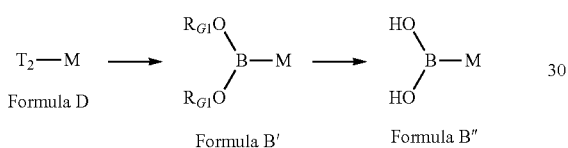

In some embodiments, a compound of Formula B is a compound of Formula B', wherein G is $R_{G1}$, or a compound of Formula B", wherein G is hydrogen. Scheme C depicts an exemplary scheme for synthesizing a compound of Formula B' or, optionally, Formula B" for use in Reaction Scheme C. This reaction proceeds via reacting a compound of Formula D with a trialkyl borate or a boronic acid derivative to produce a compound of Formula B'. The reaction is typically run a solvent such as dioxane or tetrahydrofuran. The trialkyl borate includes but is not limited to triisopropyl borate and the boronic acid derivative includes but is not limited to bis(pinacolato)diboron.

When the reaction is performed with trialkyl borate, a base such as n-butyllithium is first added to the compound of Formula D to generate an anion, prior to the addition of the borate. When the reaction is performed with a boronic acid derivative such as bis(pinacolato)diboron, a palladium catalyst and a base is used. Typical palladium catalysts include but is not limited to palladium chloride (diphenylphosphino)ferrocene). A suitable base includes but is not limited to potassium acetate.

A compound of Formula D for use in Scheme C is a compound wherein $T_2$ is halo or another leaving group, and M is as defined above in Scheme B. The compound of Formula B' may further be converted to a compound of Formula B" by treatment with an acid such as hydrochloric acid.

In one embodiment of a compound of Formula B, B', B", or E, the G groups are hydrogen. In another of a compound of Formula B, B', B", or E, the G groups are $R_{G1}$.

In some embodiments, no further synthetic transformation of $M_1$ moiety is performed after the coupling reaction when, e.g. $M_1$ is 2-N-acetyl-benzoxazol-5-yl.

Some exemplary compounds of Formula B that can be synthesized via Scheme C include but are not limited to compounds of the following formulae:

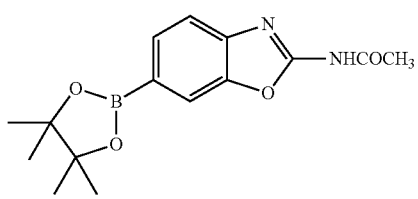

H-7

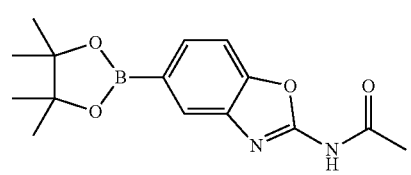

F-7

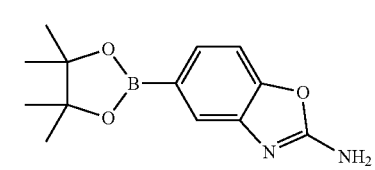

G-6

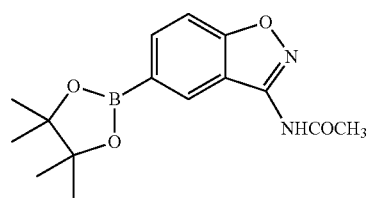

I-4

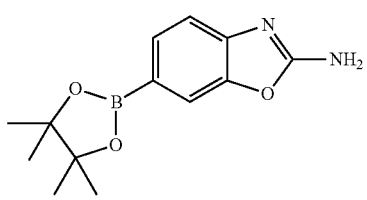

G-7

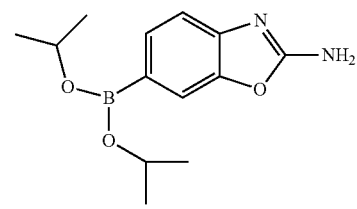

G-8

G-9

-continued

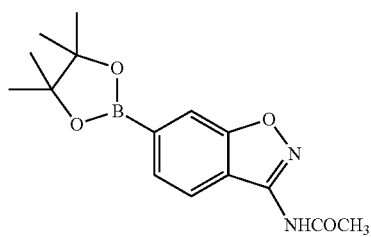

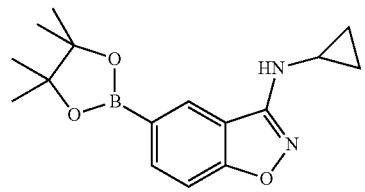

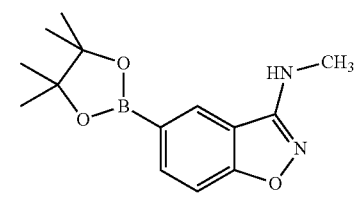

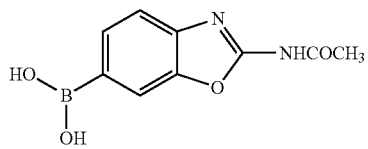

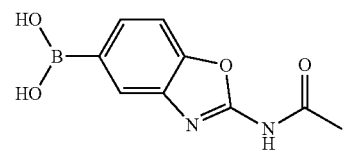

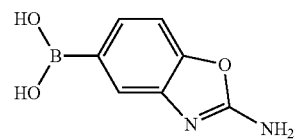

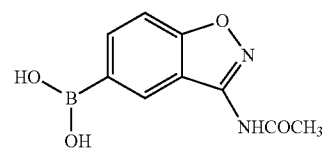

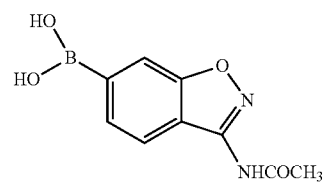

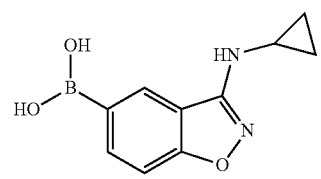

J-4

K-6

L-6

H-7-B

F-7-B

G-6-B

I-4-B

J-4-B

K-6-B

-continued

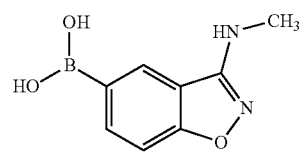

L-6-B

In other embodiments of the invention, a compound of Formula E is synthesized from a compound of Formula F, as shown in Scheme C-1:

Scheme C-1

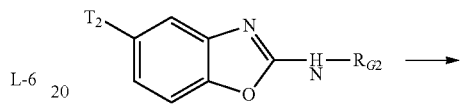

Formula F

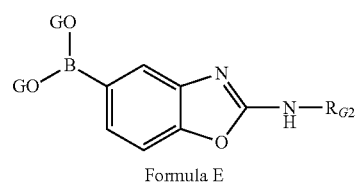

Formula E

Scheme C-1 depicts an exemplary scheme for synthesizing a compound of Formula E. This reaction proceeds via reacting a compound of Formula F with a trialkyl borate or a boronic acid derivative to produce a compound of Formula E. The conditions of the reaction are as described above in Scheme C.

A compound of Formula F for use in Scheme C-1 is a compound wherein $T_2$ is halo (including Br, Cl, and I) or another leaving group (including but not limited to triflate, tosylate, and mesylate), and the $G_p$ moiety is H, acyl, or an amino protecting group including but not limited to tert-butyl carbamate (Boc), carbobenzyloxy (Cbz), benzyl (Bz), fluorenylmethyloxycarbonyl (FMOC), p-methoxybenzyl (PMB), and the like.

The compound of Formula E, wherein G is alkyl, may further be converted to a compound of Formula E, wherein G is hydrogen, by treatment with an acid such as hydrochloric acid Where desired, deprotection of a substituent (e.g., removal of Boc protection from an amino substituent) on the benzoxazolyl moiety (i.e. $M_1$ of Formula C) is performed after coupling the compound of Formula B to the compound of Formula A.

Some exemplary compounds with such protecting groups, include but are not limited to compounds of the following formulae:

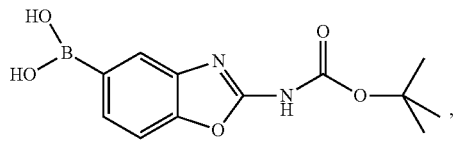

,

-continued

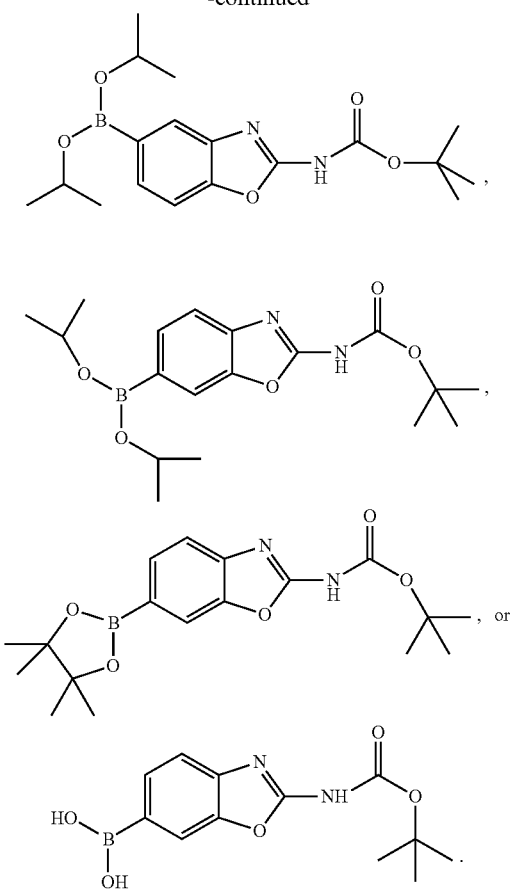

An exemplary transformation of $M_2$ to $M_1$ can be carried out via Scheme D as shown below.

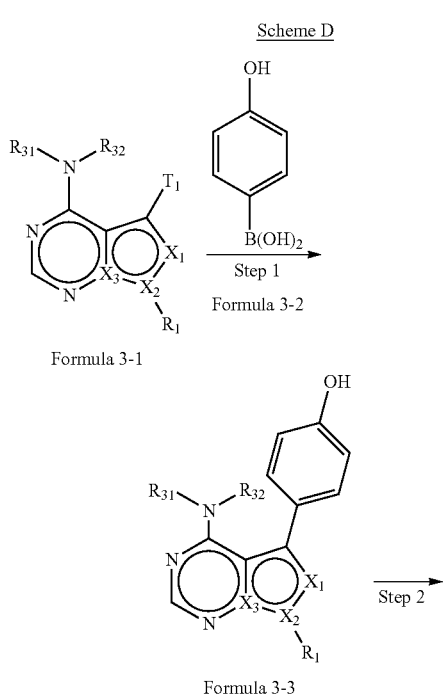

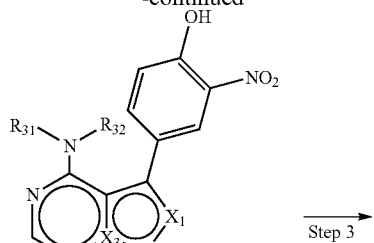

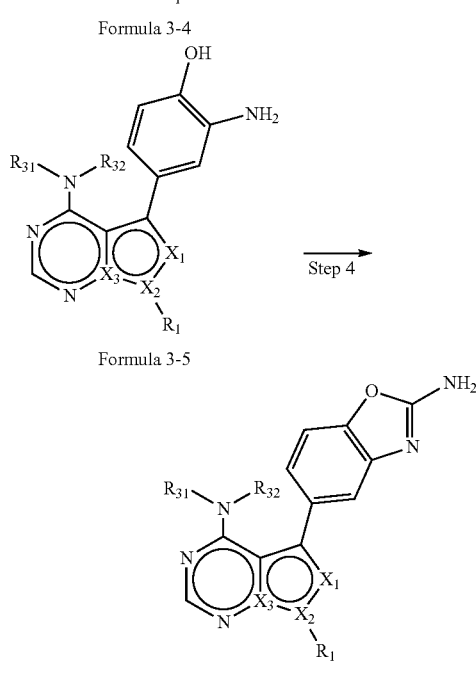

In Step 1, a compound of Formula 3-1 is reacted with boronic acid 3-2, in the presence of palladium tetrakis(triphenylphosphine) and a suitable base, such as sodium carbonate in an aqueous/organic solvent mixture to produce a compound of Formula 3-3. In Step 2, the compound of Formula 3-3 is reacted with about 2 equivalents of nitric acid in acetic acid as solvent to produce a compound of Formula 3-4. Two alternative transformations may be used to effect the next transformation of Step 3. In the first method, the compound of Formula 3-4 is treated with sodium dithionite and sodium hydroxide in water to produce a compound of Formula 3-5. Alternatively, the compound of Formula 3-4 is reduced using palladium on carbon in a suitable solvent under a hydrogen atmosphere to yield a compound of Formula 3-5.

In Step 4, compound 3-5 is reacted with about 1.2 equivalents of cyanogen bromide in a solvent such as methanol/tetrahydrofuran mixture to produce a compound of Formula 3-6. The compound of Formula 3-6 may be further transformed by other substitution or derivatization.

A compound of Formula 3-1 useful in the method of Scheme D is a compound having a structure of Formula 3-1, wherein $T_1$ is triflate or halo (including bromo, chloro, and iodo), and wherein $R_1$, $X_1$, $X_2$, $X_3$, $R_{31}$ and $R_{32}$ are defined as for a compound of Formula I'-A'.

Exemplary compounds having a pyrazolopyrimidine core can be synthesized via Scheme E.

Scheme E

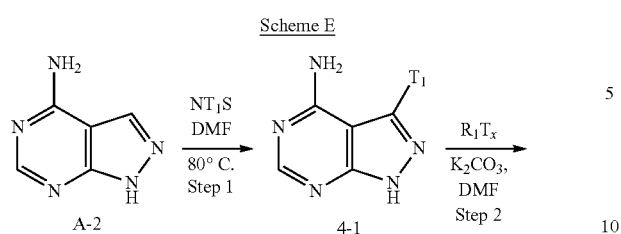

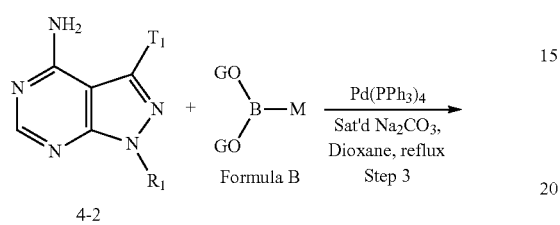

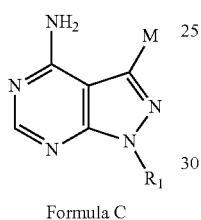

Formula C

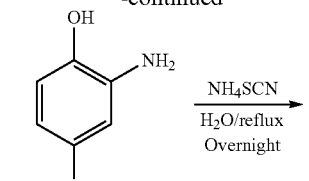

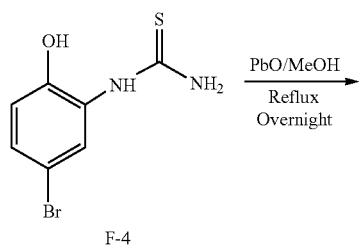

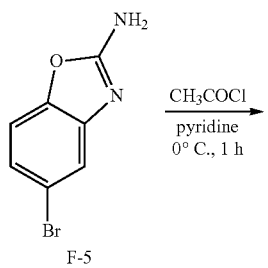

F-5

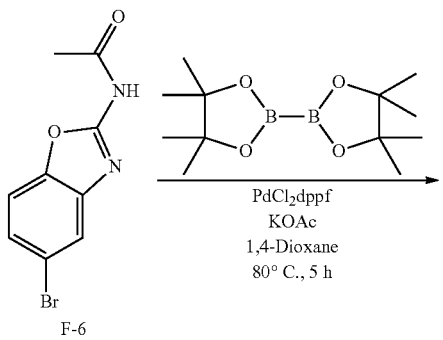

F-6

In Step 1 of Scheme E, compound A-2 in dimethylformamide (DMF), is reacted with an N-halosuccinimide ($NT_1S$) at about 80° C., to provide compound 4-1, where $T_1$ is iodo or bromo. In Step 2, compound 4-1 in DMF is reacted with a compound $R_1T_x$, in the presence of potassium carbonate, to provide compound 4-2. In Step 4, compound 4-2 is coupled with a compound of Formula B using palladium catalysis such as palladium tetrakis(triphenylphosphine), and in the presence of sodium carbonate, to yield a pyrazolopyrimidine compound as shown.

A compound of Formula $R_1T_x$ suitable for use in Reaction Scheme E is the compound wherein $R_1$ is cycloalkyl or alkyl and $T_x$ is halo (including bromo, iodo, or chloro) or a leaving group, including but not limited to mesylate or tosylate.

Reaction Schemes F-M illustrate methods of synthesis of borane reagents useful in preparing intermediates of use in synthesis of the compounds of the invention as described in Reaction Schemes A, B, and E above, to introduce $M_1$ substituents.

Reaction Scheme F

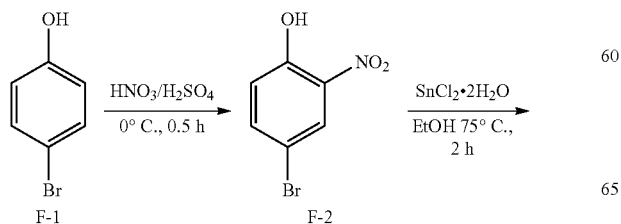

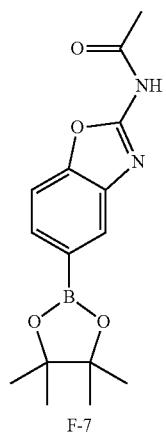

F-7

Reaction Scheme G
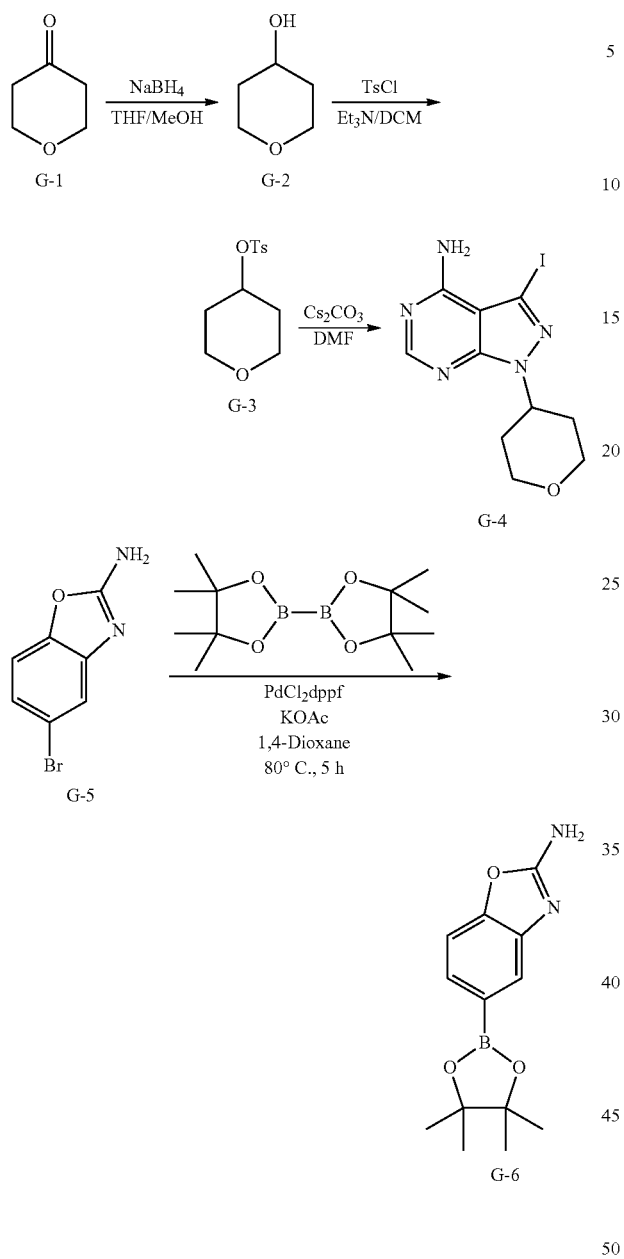
Reaction Scheme H
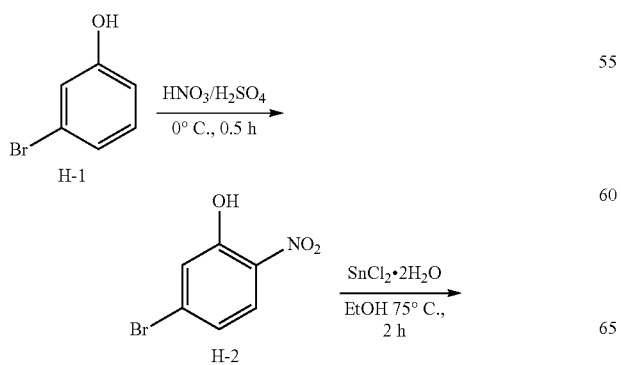
-continued
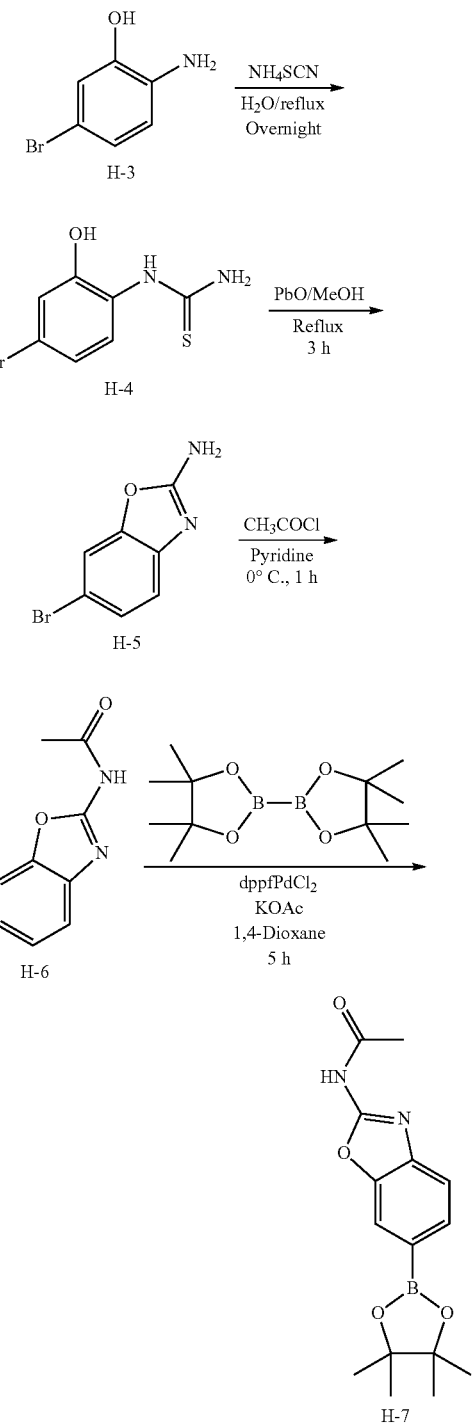
Reaction Scheme I
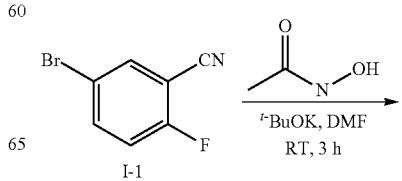

171
-continued
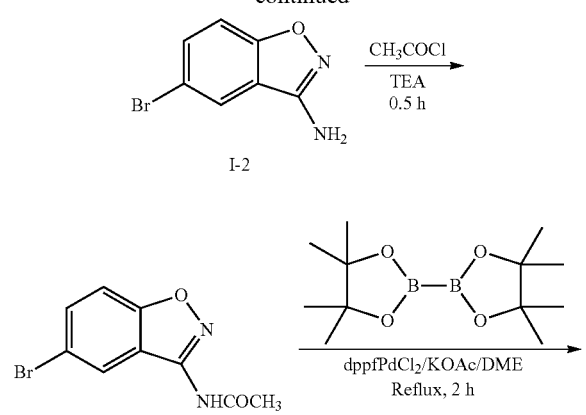
172
Reaction Scheme K
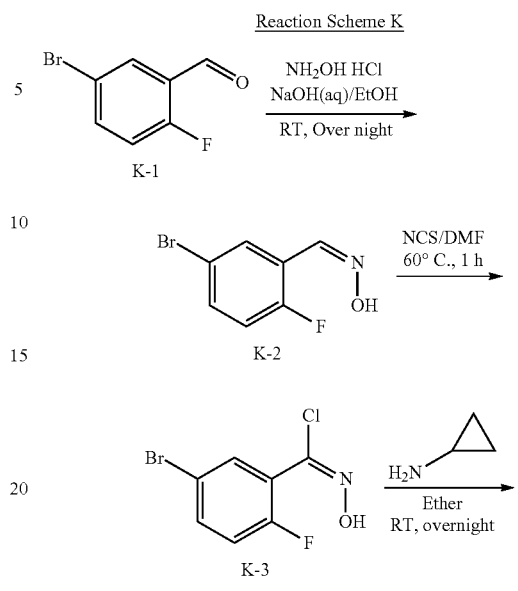
Reaction Scheme J
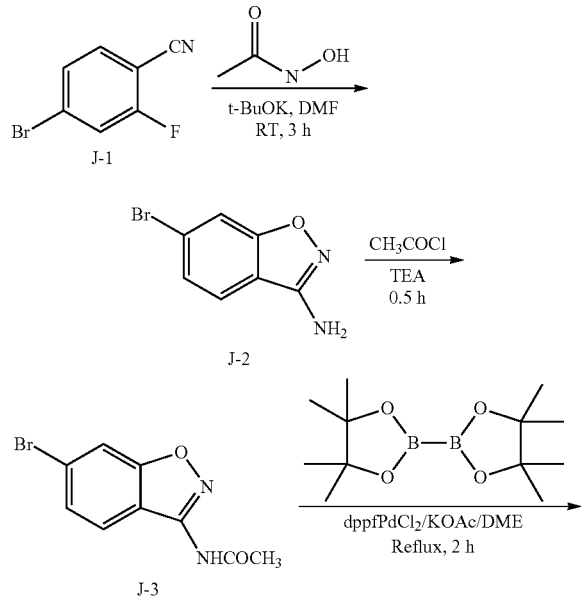
Reaction Scheme L
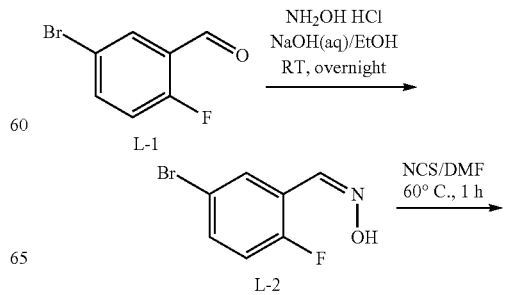

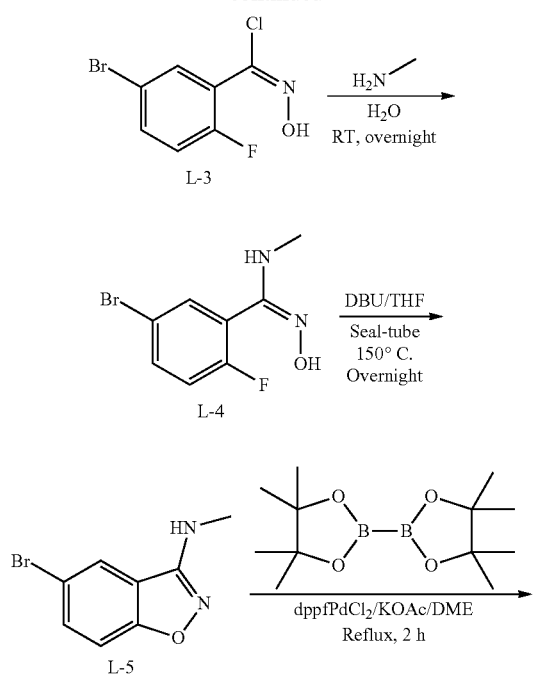

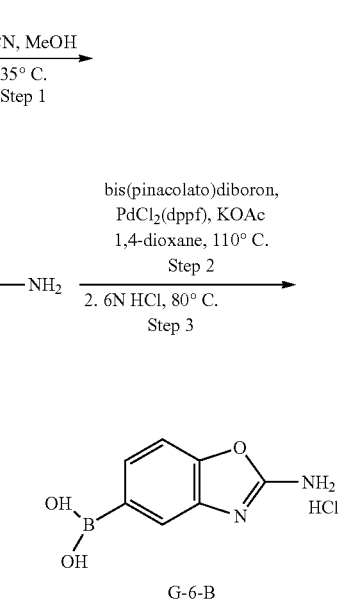

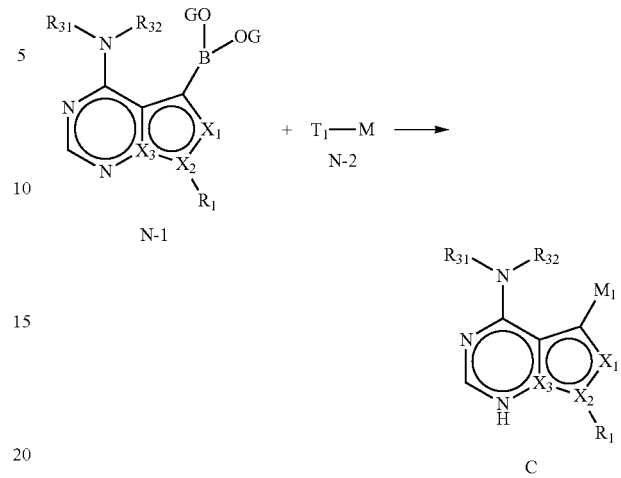

Reaction Scheme N

In an alternative method of synthesis, a compound of Formula N-1 and a compound of N-2 are coupled to produce a compound of Formula C. The coupling step is typically catalyzed by using, e.g., a palladium catalyst, including but not limited to palladium tetrakis(triphenylphosphine). The coupling is generally performed in the presence of a suitable base, a nonlimiting example being sodium carbonate. One example of a suitable solvent for the reaction is aqueous dioxane.

A compound of Formula N-1 for use in Scheme N has a structure of Formula N-1, wherein G is hydrogen or $R_{G1}$, wherein $R_{G1}$ is alkyl, alkenyl, or aryl. Alternatively, $B(OG)_2$ of the compound of Formula N-1 is taken together to form a 5- or 6-membered cyclic moiety. $R_1$, $X_1$, $X_2$, $X_3$, $R_{31}$ and $R_{32}$ of the compound of Formula N-1 are defined as for a compound of Formula I'-A'.

A compound of Formula N-2 for use in Scheme N has a structure of Formula N-2 wherein $T_1$ is triflate or halo (including bromo, chloro, and iodo). M of the compound of Formula N-2 is either $M_1$ or $M_2$. $M_1$ is defined as for a compound of Formula I. For example, $M_1$ can be a 5-benzoxazolyl or a 6-benzoxazolyl moiety, including but not limited to those $M_1$ moieties disclosed herein. $M_2$ is a moiety which is synthetically transformed to form $M_1$, after the $M_2$ moiety has been coupled to the bicyclic core of the compound of Formula N-1.

Scheme N-1

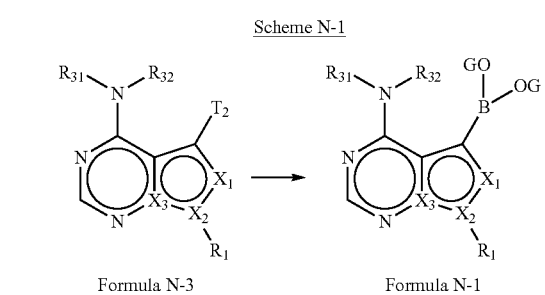

A compound of Formula N-1 may be synthesized as shown in Scheme N-1. A compound of Formula N-1 is reacted with a trialkyl borate or a boronic acid derivative to produce a compound of Formula N-1. The reaction is typically run a solvent such as dioxane or tetrahydrofuran. The trialkyl borate includes but is not limited to triisopropyl borate and the boronic acid derivative includes but is not limited to bis(pinacolato)diboron.

When the reaction is performed with trialkyl borate, a base such as n-butyllithium is first added to the compound of Formula N-3 to generate an anion, prior to the addition of the borate. When the reaction is performed with a boronic acid derivative such as bis(pinacolato)diboron, a palladium catalyst and a base is used. Typical palladium catalysts include but is not limited to palladium chloride (diphenylphosphino)ferrocene). A suitable base includes but is not limited to potassium acetate.

A compound of Formula N-3 suitable for use in Scheme N-1 is a compound wherein $T_2$ is halo or another leaving group such as mesylate, tosylate, or triflate. $X_1$, $X_2$, $X_3$, $R_1$, $R_{31}$, and $R_{32}$ of the compound of Formula N-3 is as defined for a compound of Formula I'-A'.

In some embodiments of the invention, a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3" is provided as its salt, including but not limited to hydrochloride, acetate, formate, nitrate, sulfate, and boronate.

In some embodiments of the invention, a palladium compound, including but not limited to palladium chloride (diphenylphosphino)ferrocene) and palladium tetrakis(triphenylphosphine), is used in the synthesis of a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3". When a palladium compound is present in the synthesis of a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3", it is present in an amount ranging from about 0.005 molar equivalents to about 0.5 molar equivalents, from about 0.05 molar equivalents to about 0.25 molar equivalents, from about 0.07 molar equivalents to about 0.15 molar equivalents, or about 0.8 molar equivalents to about 0.1 molar equivalents of the compound of Formula A, B, B', B", C, D, E, 3-1, 3-2, 3-3, 3-4, 3-5, 3-6, N-1, or N-3. In some embodiments, a palladium compound, including but not limited to palladium chloride (diphenylphosphino)ferrocene) and palladium tetrakis(triphenylphosphine) is present in the synthesis of a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3" in about 0.07, about 0.08, about 0.09, about 0.10, about 0.11, about 0.12, about 0.13, about 0.14, or about 0.15 molar equivalents of a starting material of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3" that is used to synthesize a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3".

In some embodiments of the above reaction schemes B, D, E, N or N-1, another embodiment of the compounds of Formula A, C, 3-1, 3-3, 3-4, 3-5, 3-6, A-2, 4-1, 4-2, N-1 and N-3 is as shown in Schemes B'. D'. E', N' or N-1' below. In these alternative syntheses, producing a compound of Formula C, 3-1, 3-3, 3-4, 3-5, 3-6, A-2, 4-1, 4-2, N-1 or N-3, use compounds that comprise an amino moiety having a $R_{G2}$ moiety present during one or more of the synthetic steps, wherein $R_{G2}$ is an amino protecting group including but not limited to tert-butyl carbamate (Boc), carbobenzyloxy (Cbz), benzyl (Bz), fluorenylmethyloxycarbonyl (FMOC), p-methoxybenzyl (PMB), and the like. These compounds include a compound of Formula A", C", 3-1", 3-3", 3-4", 3-5", 3-6", A-2", 4-1", 4-2", N-1" or N-3".

The $R_{G2}$ moiety is removed, using suitable methods, at any point desired, whereupon the compound of Formula C, 3-1, 3-3, 3-4, 3-5, 3-6, A-2, 4-1, 4-2, N-1 or N-3 has a $R_{31}$ hydrogen replacing the $R_{G2}$ moiety on the amino moiety. This transformation is specifically illustrated for the conversion of a compound of Formula C" to a compound of C (i.e., as in Step 4 of Scheme $E^1$) and for the conversion of a compound of Formula 3-6" to a compound of Formula 3-6 (i.e., as in Step 5 of Scheme D'). This illustration is in no way limiting as to the choice of steps wherein a compound comprising a $NR_{31}R_{G2}$ moiety may be converted to a compound comprising a $NR_{31}R_{32}$ moiety wherein the $R_{32}$ moiety is hydrogen.

Scheme B'

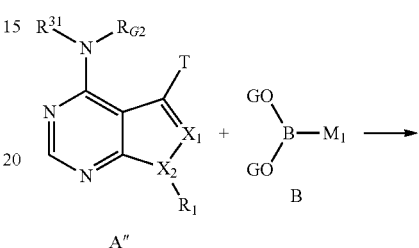

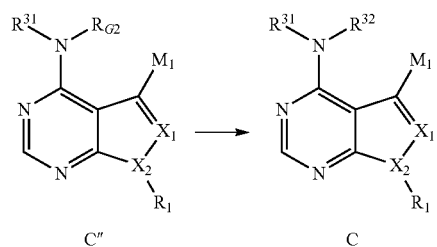

Scheme D'

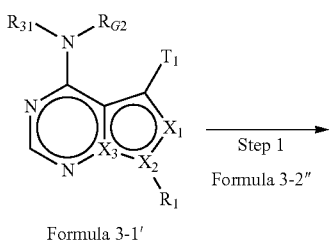

Formula 3-1'

Formula 3-2"

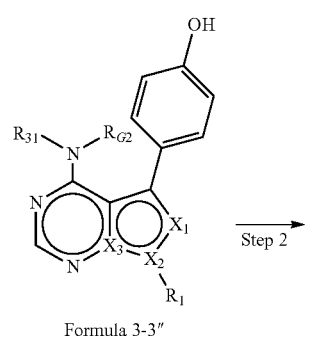

Formula 3-3"

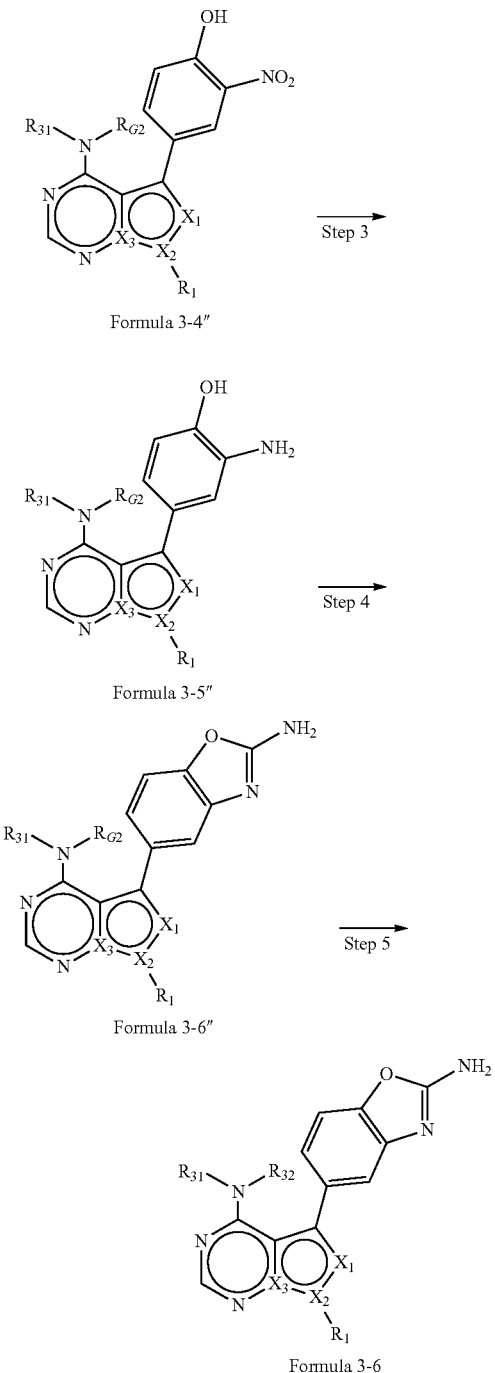
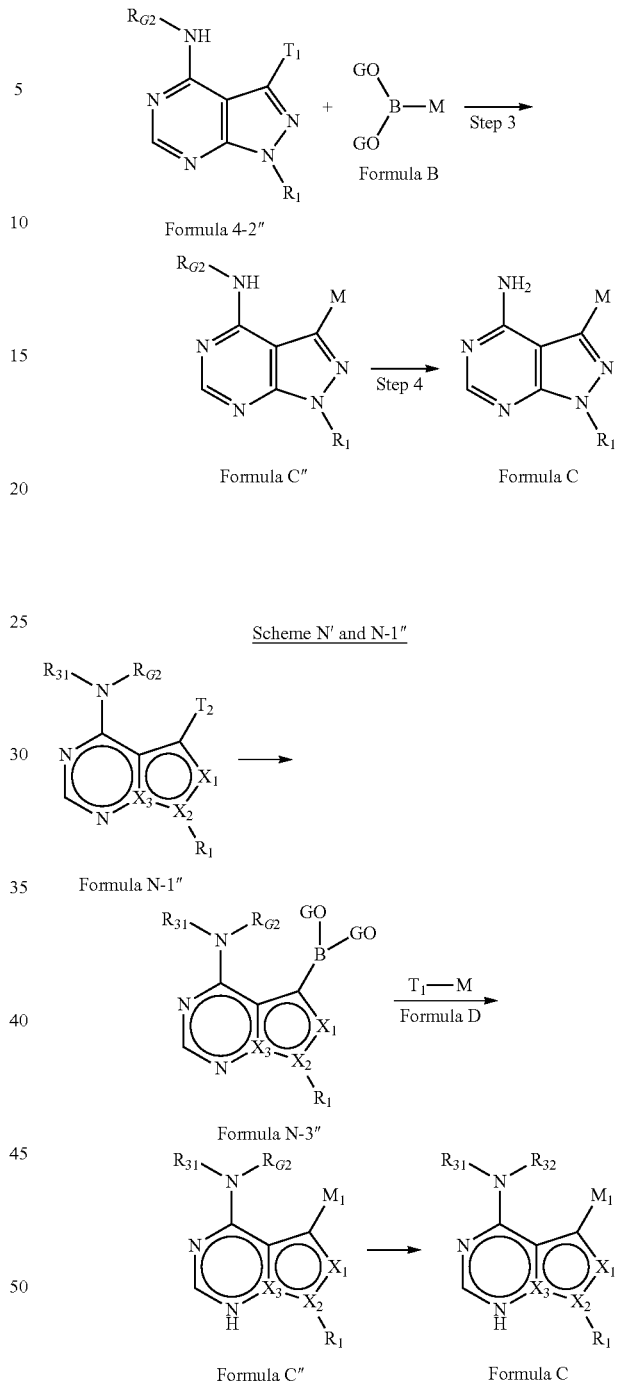
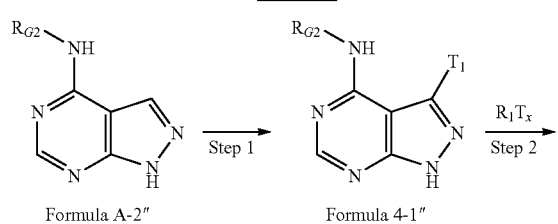

Additionally, the invention encompasses methods of synthesis of the compounds of A, B, B', B", C, E, 3-1, 3-2, 3-3, 3-4, 3-5, 3-6, N-1 or N-3, wherein one or more of M, $M_1$, or R has a protecting group present during one or more steps of the synthesis. Protecting groups suitable for use for a M, $M_1$, or $R_1$ moiety are well known in the art, as well as the methods of incorporation and removal, and the reagents suitable for such transformations.

Compounds of the invention where $X_4$ is C—$R^9$ may be prepared by methods analogous to the ones described in the Schemes illustrated above.

C. ILLUSTRATIVE SUBCLASSES OF COMPOUNDS OF THE INVENTION
Some illustrative compounds of the invention are described below. The compounds of the invention are not limited in any way to the compounds illustrated herein.
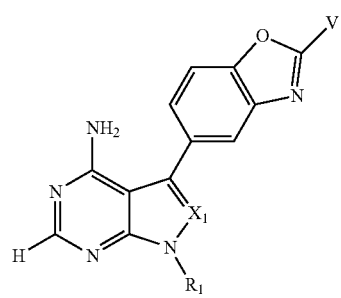
Subclass 1a
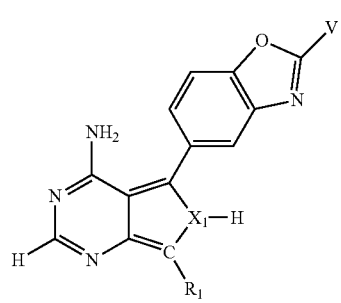
Subclass 1b
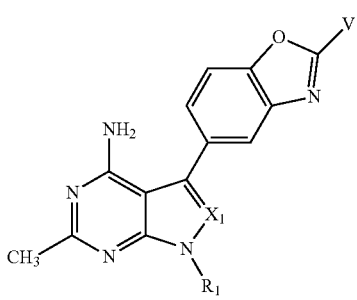
Subclass 2a
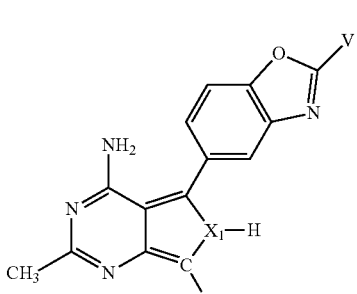
Subclass 2b
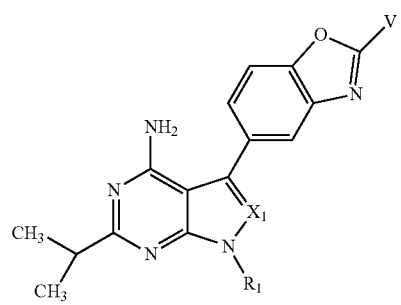
Subclass 3a
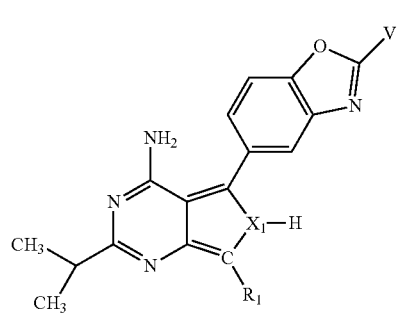
Subclass 3b
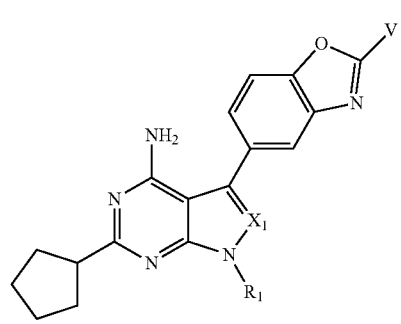
Subclass 4a
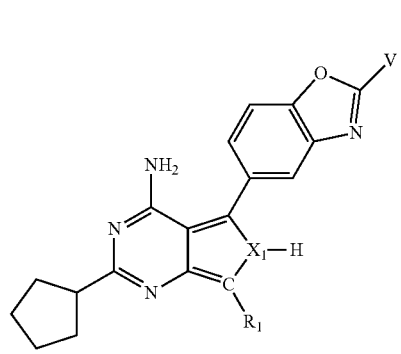
Subclass 4b
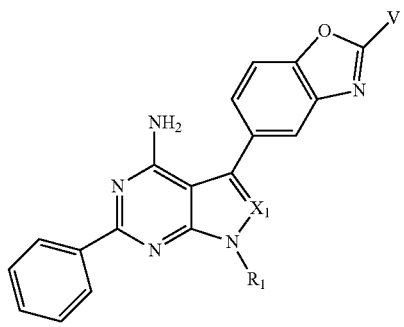
Subclass 5a Subclass 5b
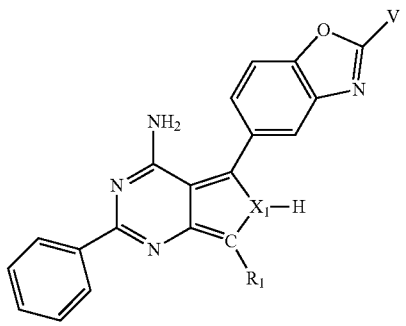
Subclass 6a
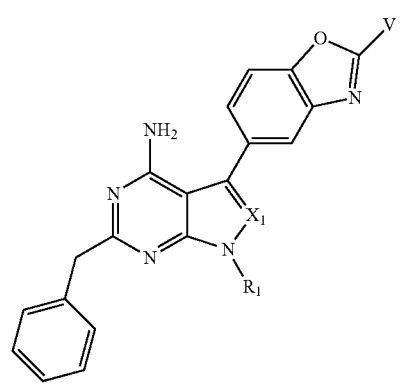
Subclass 6b
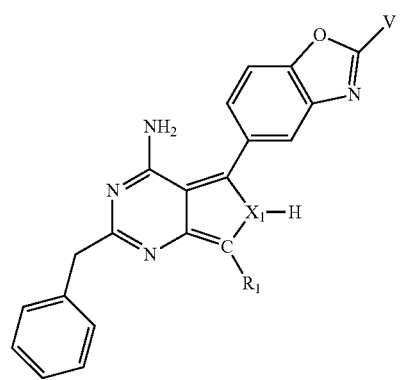
Subclass 7a
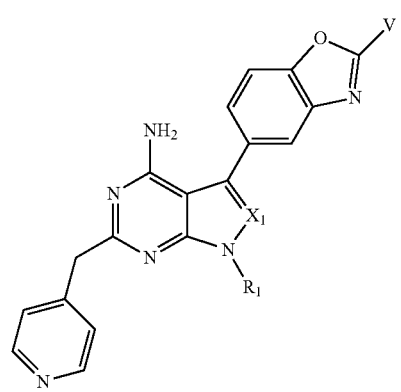
Subclass 7b
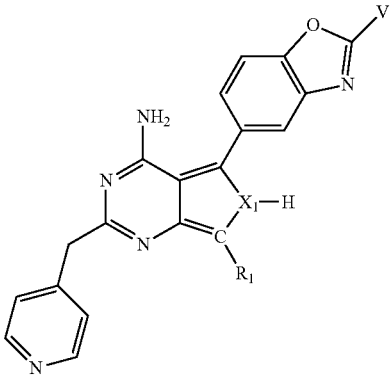
Subclass 8a
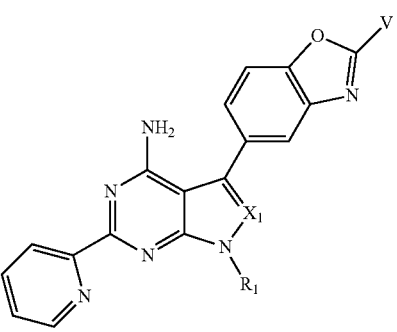
Subclass 8b
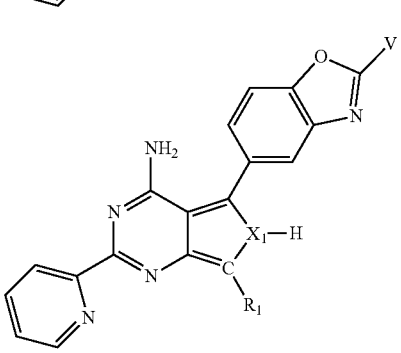
Subclass 9a
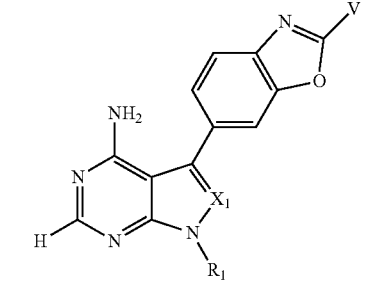
Subclass 9b
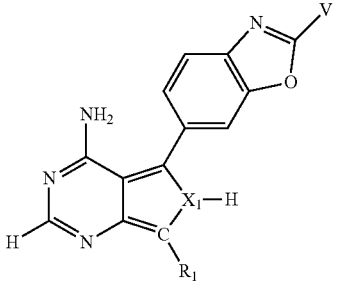

Subclass 10a
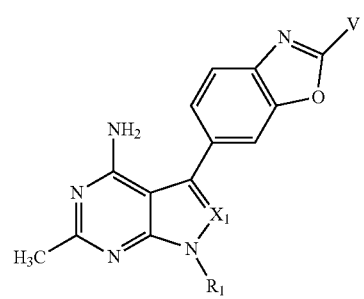
Subclass 10b
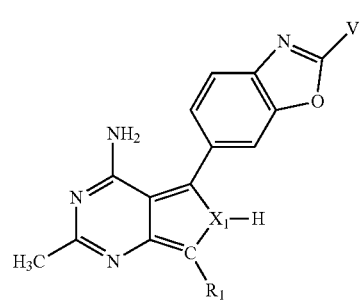
Subclass 11a
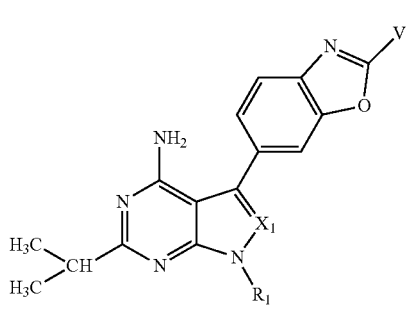
Subclass 11b
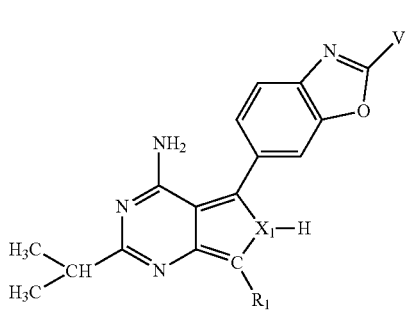
Subclass 12a
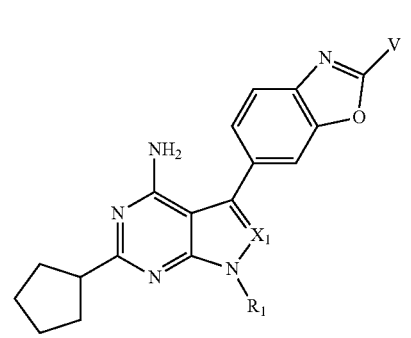
Subclass 12b
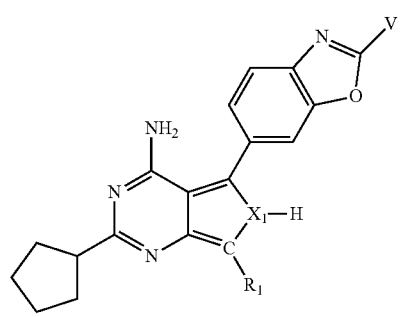
Subclass 13a
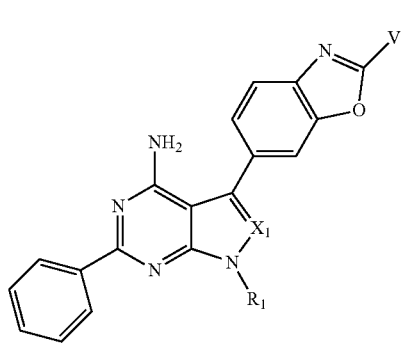
Subclass 13b
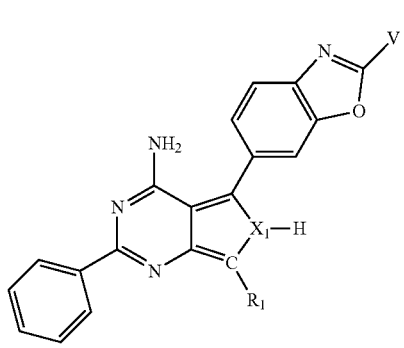
Subclass 14a
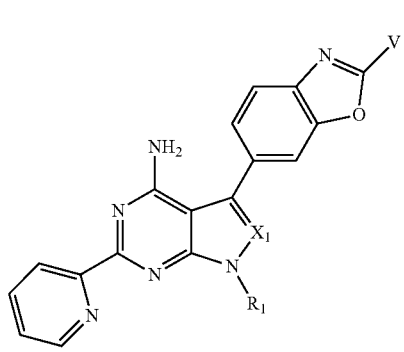
Subclass 14b
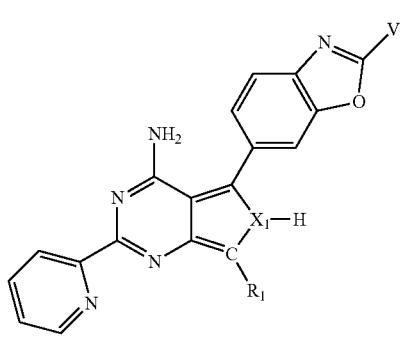

-continued

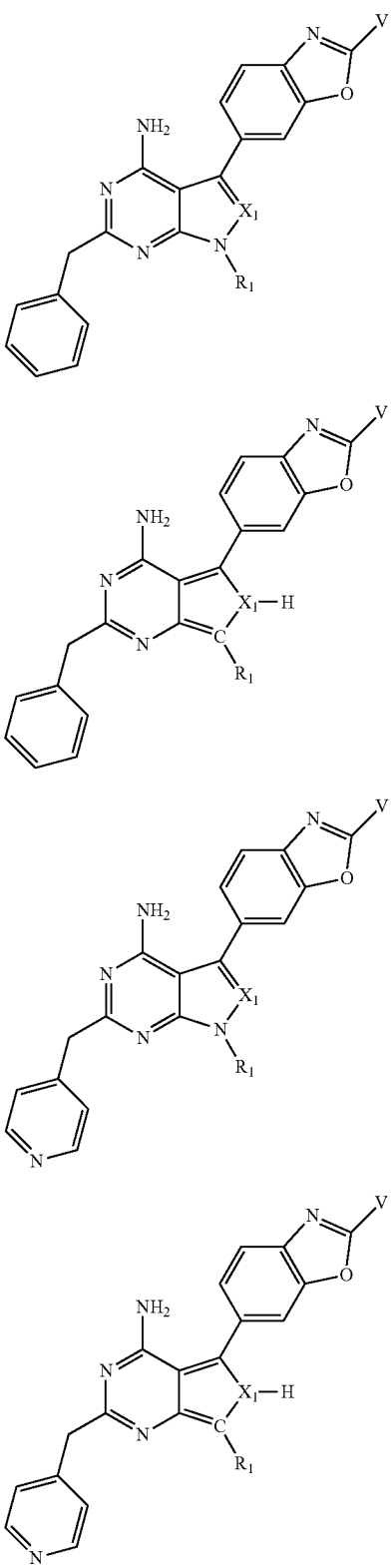

Subclass 15a

Subclass 15b

Subclass 16a

Subclass 16b

Illustrative compounds of the invention include those of subclass 1a, 1b, 2a, 2b, 3a, 3b, 4a, 4b, 5a, 5b, 6a, 6b, 7a, 7b, 8a, 8b, 9a, 9b, 10a, 10b, 11a, 11b, 12a, 12b, 13a, 13b, 14a, 14b, 15a, 15b, 16a, or 16b, where the substituents $R_1$, $X_1$, and V are as described below.

In some embodiments, when $R_1$ is H and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is H and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is $CH_3$ and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is $CH_3$ and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is Et and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is Et and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is iPr and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is iPr and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In one embodiment, $R_1$ is iPr, $X_1$ is N, and V is $NH_2$. In another embodiment, $R_1$ is iPr, $X_1$ is N, and V is NHCOMe. In other embodiments, when $R_1$ is cyclobutyl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is cyclobutyl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is cyclopentyl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is cyclopentyl and $X_1$ is N V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is phenyl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is phenyl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is pyridin-2-yl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is pyridin-2-yl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is N-methylaminocyclohex-4-yl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is N-methylaminocyclohex-4-yl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is N-methylpiperidin-4-yl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is N-methylpiperidin-4-yl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is N-methylaminocyclobut-3-yl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is N-methylaminocyclobut-3-yl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is tert-butyl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is tert-butyl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is 1-cyano-but-4-yl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is 1-cyano-but-4-yl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is 1-cyano-prop-3-yl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is 1-cyano-prop-3-yl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is 3-azetidinyl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is 3-azetidinyl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$.

In other embodiments, when $R_1$ is

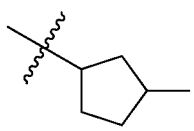 [SMILES: *C1CCC(C)C1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

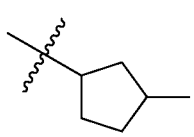

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

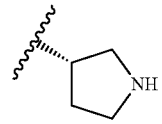

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

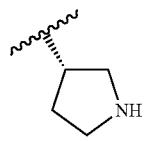 [SMILES: *[C@H]1CCNC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

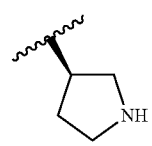 [SMILES: *[C@@H]1CCNC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

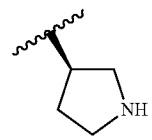 [SMILES: *[C@@H]1CCNC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

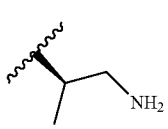 [SMILES: *[C@H](C)CN]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

189

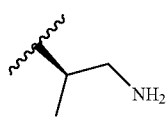

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

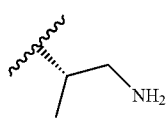

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

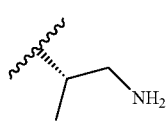 [SMILES: *[C@@H](C)CN]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

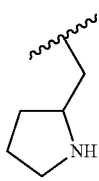 [SMILES: *CC1CCCN1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

190

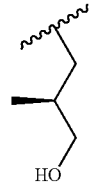

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

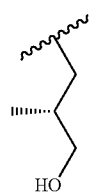

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

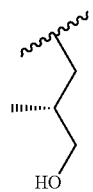

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

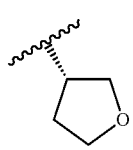 [SMILES: *[C@H]1CCOC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

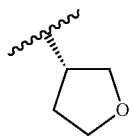 [SMILES: *[C@H]1CCOC1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

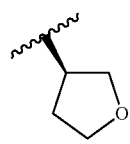 [SMILES: *[C@@H]1CCOC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

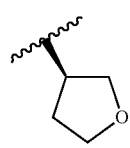 [SMILES: *[C@@H]1CCOC1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

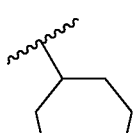

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

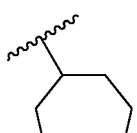

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

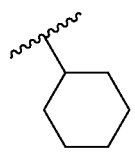 [SMILES: *C1CCCCC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

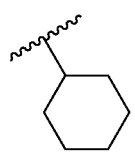

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

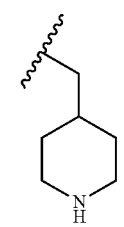 [SMILES: *CC1CCNCC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

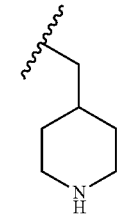 [SMILES: *CC1CCNCC1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

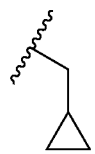 [SMILES: *CC1CC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

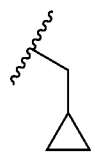

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

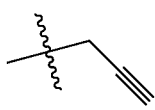 [SMILES: *CC#C]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

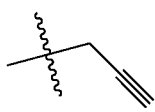 [SMILES: *CC#C]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

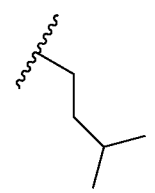 [SMILES: *CCC(C)C]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

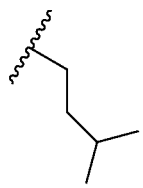 [SMILES: *CCC(C)C]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

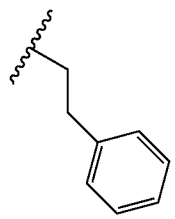 [SMILES: *CCc1ccccc1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

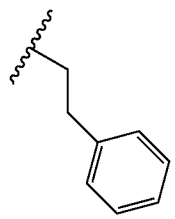 [SMILES: *CCc1ccccc1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

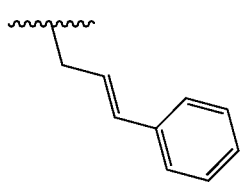 [SMILES: *C/C=C/c1ccccc1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

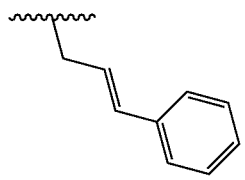 [SMILES: *C/C=C/c1ccccc1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

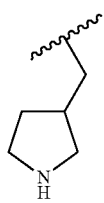 [SMILES: *CC1CCNC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

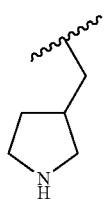

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

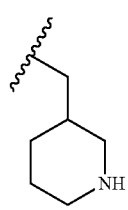 [SMILES: *CC1CCCNC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

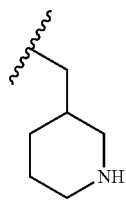 [SMILES: *CC1CCCNC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

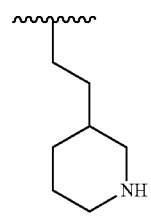

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

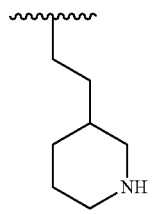 [SMILES: *CCC1CCCNC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

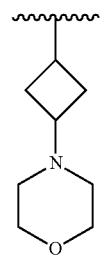 [SMILES: *C1CC(N2CCOCC2)C1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

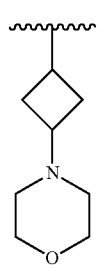

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

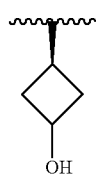

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

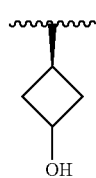

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

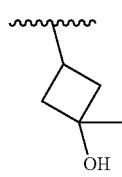 [SMILES: *C1CC(C)(O)C1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

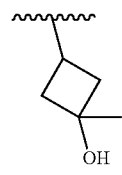

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

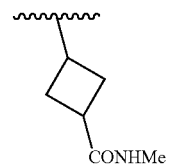

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

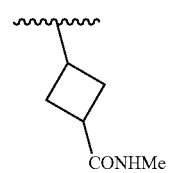

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

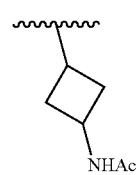 [SMILES: *C1CC(NC(C)=O)C1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

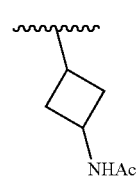 [SMILES: *C1CC(NC(C)=O)C1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

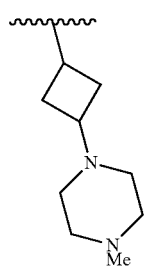 [SMILES: *C1CC(N2CCN(C)CC2)C1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

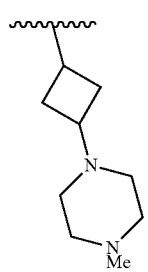 [SMILES: *C1CC(N2CCN(C)CC2)C1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

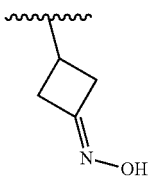

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

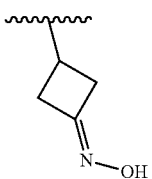 [SMILES: *C1CC(=NO)C1]

and X₁ is N, V is phenylamino, benzyl, phenyl, NHMe, NHEt, NHCOH, NHCOMe, NHCOEt, NHCOiPr, NHCOOMe, CONHMe, or NHSO₂Me. In other embodiments, when R₁ is

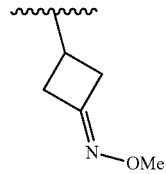

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

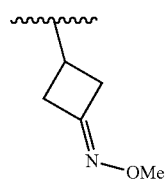 [SMILES: *C1CC(=NOC)C1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

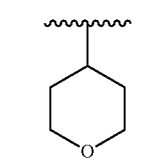

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

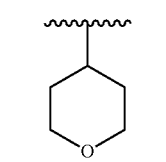

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

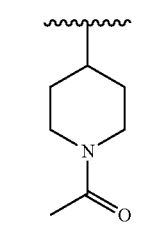 [SMILES: *C1CCN(C(C)=O)CC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

201

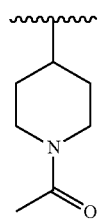

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

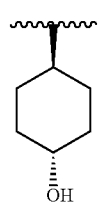

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

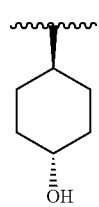

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

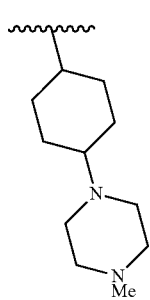 [SMILES: *C1CCC(N2CCN(C)CC2)CC1]

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

202

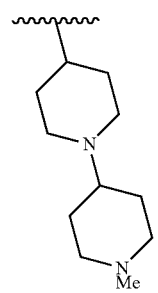 [SMILES: *C1CCN(C2CCN(C)CC2)CC1]

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

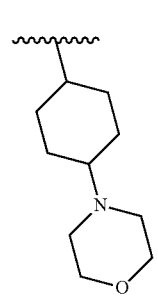 [SMILES: *C1CCC(N2CCOCC2)CC1]

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

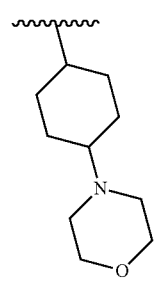 [SMILES: *C1CCC(N2CCOCC2)CC1]

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

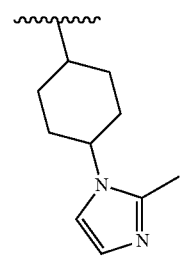 [SMILES: *C1CCC(n2ccnc2C)CC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

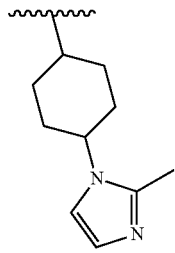 [SMILES: *C1CCC(n2ccnc2C)CC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

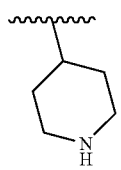

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

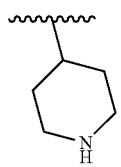

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

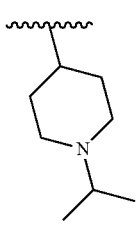 [SMILES: *C1CCN(C(C)C)CC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

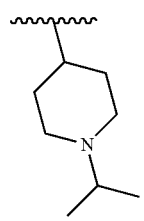

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

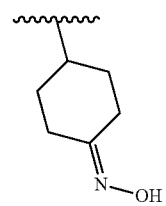 [SMILES: *C1CCC(=NO)CC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

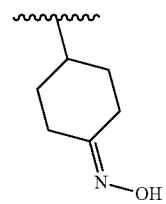 [SMILES: *C1CCC(=NO)CC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

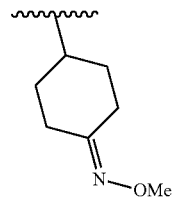 [SMILES: *C1CCC(=NOC)CC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

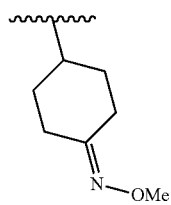 [SMILES: *C1CCC(=NOC)CC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

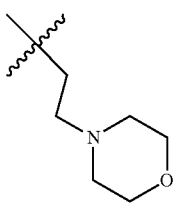 [SMILES: *CCN1CCOCC1]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

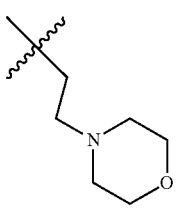 [SMILES: *CCN1CCOCC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

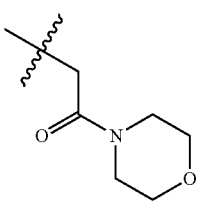 [SMILES: *CC(=O)N1CCOCC1]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

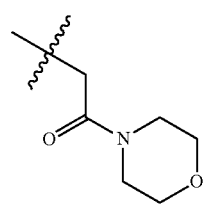 [SMILES: *CC(=O)N1CCOCC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me.

In other embodiments, when $R_1$ is

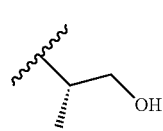

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

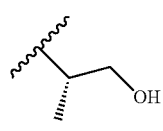

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

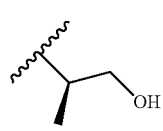 [SMILES: *[C@H](C)CO]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

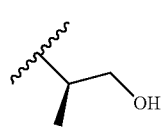 [SMILES: *[C@H](C)CO]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

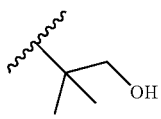 [SMILES: *C(C)(C)CO]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

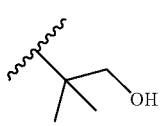 [SMILES: *C(C)(C)CO]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

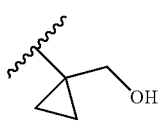

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

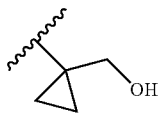 [SMILES: *C1(CO)CC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

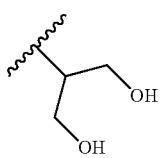 [SMILES: *C(CO)CO]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

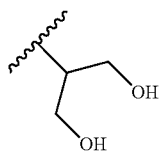

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

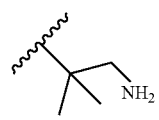 [SMILES: *C(C)(C)CN]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

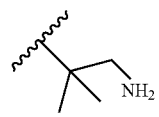 [SMILES: *C(C)(C)CN]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$.

In other embodiments, when $R_1$ is

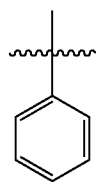

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

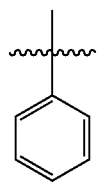

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

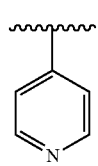

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

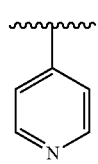

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

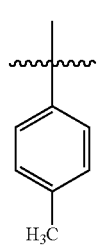

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

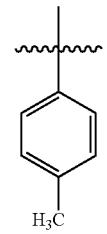 [SMILES: *c1ccc(C)cc1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

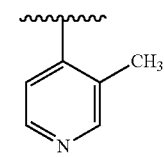

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

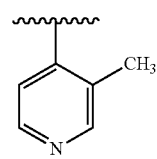

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

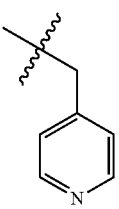 [SMILES: *Cc1ccncc1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

211

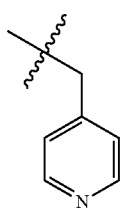 [SMILES: *Cc1ccncc1]

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

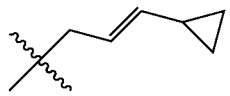 [SMILES: *C/C=C/C1CC1]

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

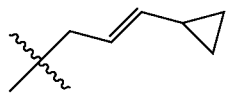 [SMILES: *C/C=C/C1CC1]

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

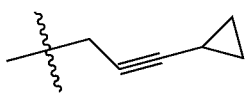 [SMILES: *CC#CC1CC1]

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

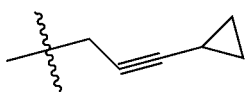 [SMILES: *CC#CC1CC1]

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

212

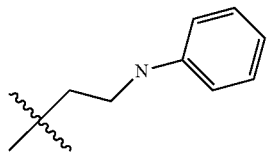 [SMILES: *CCNc1ccccc1]

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

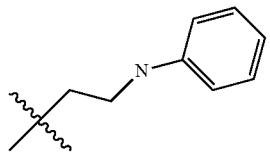 [SMILES: *CCNc1ccccc1]

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

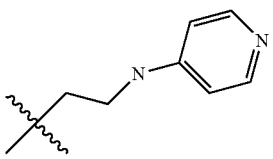 [SMILES: *CCNc1ccncc1]

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

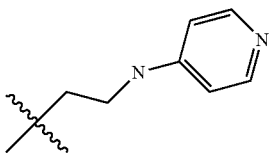 [SMILES: *CCNc1ccncc1]

and X$_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

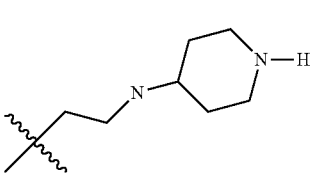 [SMILES: *CCNC1CCNCC1]

and X$_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when R$_1$ is

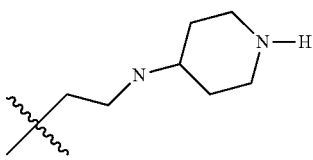 [SMILES: *CCNC1CCNCC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me.

In the noted embodiments, pyridin-2-yl is

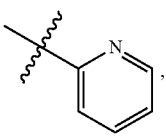 [SMILES: *c1ccccn1]

N-methylaminocyclohex-4-yl is

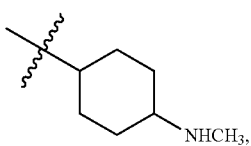 [SMILES: *C1CCC(NC)CC1]

N-methylpiperidin-4-yl is

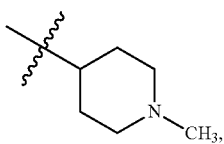

and N-methylaminocyclobut-3-yl is

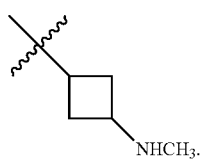 [SMILES: *C1CC(NC)C1]

Illustrative compounds of the invention include those of subclass 1a, 1b, 2a, 2b, 3a, 3b, 4a, 4b, 5a, 5b, 6a, 6b, 7a, 7b, 8a, 8b, 9a, 9b, 10a, 10b, 11a, 11b, 12a, 12b, 13a, 13b, 14a, 14b, 15a, 15b, 16a, or 16b, where the substituents $R_1$, $X_1$, and V are as described below. In some embodiments, when $R_1$ is H and $X_1$ is CH, V is cyclopropanecarboxamido, cyclopropylamino, morpholinoethylamino, hydroxyethylamino, or N-morpholino. In other embodiments, when $R_1$ is H and $X_1$ is N, V is cyclopropanecarboxamido, cyclopropylamino, morpholinoethylamino, hydroxyethylamino, or N-morpholino. In some embodiments, when $R_1$ is CH$_3$ and $X_1$ is CH, V is cyclopropanecarboxamido, cyclopropylamino, morpholinoethylamino, hydroxyethylamino, or N-morpholino. In other embodiments, when $R_1$ is CH$_3$ and $X_1$ is N, V is cyclopropanecarboxamido, cyclopropylamino, morpholinoethylamino, hydroxyethylamino, or N-morpholino. In some embodiments, when $R_1$ is Et and $X_1$ is CH, V is cyclopropanecarboxamido, cyclopropylamino, morpholinoethylamino, hydroxyethylamino, or N-morpholino. In other embodiments, when $R_1$ is Et and $X_1$ is N, V is cyclopropanecarboxamido, cyclopropylamino, morpholinoethylamino, hydroxyethylamino, or N-morpholino. In some embodiments, when $R_1$ is iPr and $X_1$ is CH, V is cyclopropanecarboxamido, cyclopropylamino, morpholinoethylamino, hydroxyethylamino, or N-morpholino. In other embodiments, when $R_1$ is iPr and $X_1$ is N, V is cyclopropanecarboxamido, cyclopropylamino, morpholinoethylamino, hydroxyethylamino, or N-morpholino. In some embodiments, when $R_1$ is cyclobutyl and $X_1$ is CH, V is cyclopropanecarboxamido, cyclopropylamino, morpholinoethylamino, hydroxyethylamino, or N-morpholino. In other embodiments, when $R_1$ is cyclobutyl and $X_1$ is N, V is cyclopropanecarboxamido, cyclopropylamino, morpholinoethylamino, hydroxyethylamino, or N-morpholino. In some embodiments, when $R_1$ is cyclopentyl and $X_1$ is CH, V is cyclopropanecarboxamido, cyclopropylamino, morpholinoethylamino, hydroxyethylamino, or N-morpholino. In other embodiments, when $R_1$ is cyclopentyl and $X_1$ is N, V is cyclopropanecarboxamido, cyclopropylamino, morpholinoethylamino, hydroxyethylamino, or N-morpholino. In some embodiments, when $R_1$ is phenyl and $X_1$ is CH, V is cyclopropanecarboxamido, cyclopropylamino, morpholinoethylamino, hydroxyethylamino, or N-morpholino. In other embodiments, when $R_1$ is phenyl and $X_1$ is N, V is cyclopropanecarboxamido, cyclopropylamino, morpholinoethylamino, hydroxyethylamino, or N-morpholino. In some embodiments, when $R_1$ is pyridin-2-yl and $X_1$ is CH, V is cyclopropanecarboxamido, cyclopropylamino, morpholinoethylamino, hydroxyethylamino, or N-morpholino. In other embodiments, when $R_1$ is pyridin-2-yl and $X_1$ is N, V is cyclopropanecarboxamido, cyclopropylamino, morpholinoethylamino, hydroxyethylamino, or N-morpholino. In some embodiments, when $R_1$ is N-methylaminocyclohex-4-yl and $X_1$ is CH, V is cyclopropanecarboxamido, cyclopropylamino, morpholinoethylamino, hydroxyethylamino, or N-morpholino. In other embodiments, when $R_1$ is N-methylaminocyclohex-4-yl and $X_1$ is N, V is cyclopropanecarboxamido, cyclopropylamino, morpholinoethylamino, hydroxyethylamino, or N-morpholino. In some embodiments, when $R_1$ is N-methylpiperidin-4-yl and $X_1$ is CH, V is cyclopropanecarboxamido, cyclopropylamino, morpholinoethylamino, hydroxyethylamino, or N-morpholino. In other embodiments, when $R_1$ is N-methylpiperidin-4-yl and $X_1$ is N, V is cyclopropanecarboxamido, cyclopropylamino, morpholinoethylamino, hydroxyethylamino, or N-morpholino. In some embodiments, when $R_1$ is N-methylaminocyclobut-3-yl and $X_1$ is CH, V is cyclopropanecarboxamido, cyclopropylamino, morpholinoethylamino, hydroxyethylamino, or N-morpholino. In other embodiments, when $R_1$ is N-methylaminocyclobut-3-yl and $X_1$ is N, V is cyclopropanecarboxamido, cyclopropylamino, morpholinoethylamino, hydroxyethylamino, or N-morpholino. In other embodiments, when $R_1$ is tert-butyl and $X_1$ is CH, V is cyclopropanecarboxamido, cyclopropylamino, morpholinoethylamino, hydroxyethylamino, or N-morpholino. In other embodiments, when $R_1$ is tert-butyl and $X_1$ is N, V is cyclopropanecarboxamido, cyclopropylamino, morpholinoethylamino, hydroxyethylamino, or N-morpholino. In other embodiments, when $R_1$ is 1-cyanobut-4-yl and $X_1$ is CH, V is cyclopropanecarboxamido, cyclopropylamino, morpholinoethylamino, hydroxyethylamino, or N-morpholino. In other embodiments, when $R_1$ is 1-cyanobut-4-yl and $X_1$ is N, V is cyclopropanecarboxamido, cyclopropylamino, morpholinoethylamino, hydroxyethylamino, or N-morpholino. In other embodiments, when $R_1$ is 1-cyanoprop-3-yl and $X_1$ is CH, V is cyclopropanecarboxamido, cyclopropylamino, morpholinoethylamino, hydroxyethylamino, or N-morpholino. In other embodiments, when $R_1$ is 1-cyano-prop-3-yl and $X_1$ is N, V is cyclopropanecarboxamido, cyclopropylamino, morpholinoethylamino, hydroxyethylamino, or N-morpholino. In other embodiments, when $R_1$ is 3-azetidinyl and $X_1$ is CH, V is cyclopropanecarboxamido, cyclopropylamino, morpholinoethylamino, hydroxyethylamino, or N-morpholino. In other embodiments, when $R_1$ is 3-azetidinyl and $X_1$ is N, V is cyclopropanecarboxamido, cyclopropylamino, morpholinoethylamino, hydroxyethylamino, or N-morpholino. In other embodiments, when $R_1$ is

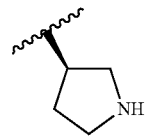

and $X_1$ is CH, V is cyclopropanecarboxamido, cyclopropylamino, morpholinoethylamino, hydroxyethylamino, or N-morpholino. In other embodiments, when $R_1$ is

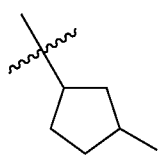 [SMILES: *C1CCC(C)C1]

and $X_1$ is CH, V is cyclopropanecarboxamido, cyclopropylamino, morpholinoethylamino, hydroxyethylamino, or N-morpholino. In other embodiments, when $R_1$ is

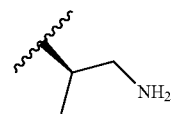

and $X_1$ is N, V is cyclopropanecarboxamido, cyclopropylamino, morpholinoethylamino, hydroxyethylamino, or N-morpholino. In other embodiments, when $R_1$ is

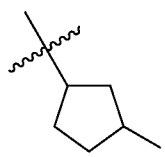 [SMILES: *C1CCC(C)C1]

and $X_1$ is N, V is cyclopropanecarboxamido, cyclopropylamino, morpholinoethylamino, hydroxyethylamino, or N-morpholino. In other embodiments, when $R_1$ is

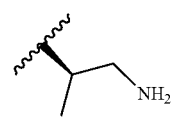

and $X_1$ is CH, V is cyclopropanecarboxamido, cyclopropylamino, morpholinoethylamino, hydroxyethylamino, or N-morpholino. In other embodiments, when $R_1$ is

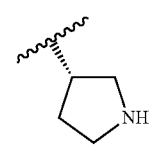 [SMILES: *[C@H]1CCNC1]

and $X_1$ is CH, V is cyclopropanecarboxamido, cyclopropylamino, morpholinoethylamino, hydroxyethylamino, or N-morpholino. In other embodiments, when $R_1$ is

and $X_1$ is N, V is cyclopropanecarboxamido, cyclopropylamino, morpholinoethylamino, hydroxyethylamino, or N-morpholino. In other embodiments, when $R_1$ is

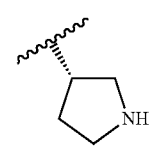 [SMILES: *[C@H]1CCNC1]

and $X_1$ is N, V is cyclopropanecarboxamido, cyclopropylamino, morpholinoethylamino, hydroxyethylamino, or N-morpholino. In other embodiments, when $R_1$ is

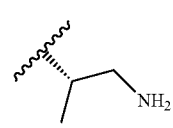 [SMILES: *[C@@H](C)CN]

and $X_1$ is CH, V is cyclopropanecarboxamido, cyclopropylamino, morpholinoethylamino, hydroxyethylamino, or N-morpholino. In other embodiments, when $R_1$ is and $X_1$ is N, V is cyclopropanecarboxamido, cyclopropylamino, morpholinoethylamino, hydroxyethylamino, or N-morpholino. In other embodiments, when $R_1$ is

and $X_1$ is CH, V is cyclopropanecarboxamido, cyclopropylamino, morpholinoethylamino, hydroxyethylamino, or N-morpholino. In other embodiments, when $R_1$ is

and $X_1$ is N, V is cyclopropanecarboxamido, cyclopropylamino, morpholinoethylamino, hydroxyethylamino, or N-morpholino. In other embodiments, when $R_1$ is

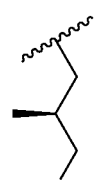

and $X_1$ is CH, V is cyclopropanecarboxamido, cyclopropylamino, morpholinoethylamino, hydroxyethylamino, or N-morpholino. In other embodiments, when $R_1$ is

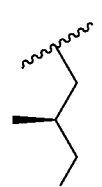

and $X_1$ is N, V is cyclopropanecarboxamido, cyclopropylamino, morpholinoethylamino, hydroxyethylamino, or N-morpholino. In other embodiments, when $R_1$ is

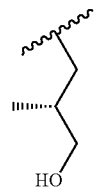

and $X_1$ is CH, V is cyclopropanecarboxamido, cyclopropylamino, morpholinoethylamino, hydroxyethylamino, or N-morpholino. In other embodiments, when $R_1$ is

and $X_1$ is N, V is cyclopropanecarboxamido, cyclopropylamino, morpholinoethylamino, hydroxyethylamino, or N-morpholino. In other embodiments, when $R_1$ is

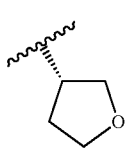 [SMILES: *[C@H]1CCOC1]

and $X_1$ is CH, V is cyclopropanecarboxamido, cyclopropylamino, morpholinoethylamino, hydroxyethylamino, or N-morpholino. In other embodiments, when $R_1$ is

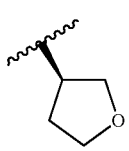 [SMILES: *[C@@H]1CCOC1]

and $X_1$ is N, V is cyclopropanecarboxamido, cyclopropylamino, morpholinoethylamino, hydroxyethylamino, or N-morpholino. In other embodiments, when $R_1$ is

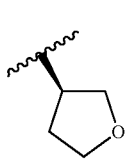 [SMILES: *[C@@H]1CCOC1]

and $X_1$ is CH, V is cyclopropanecarboxamido, cyclopropylamino, morpholinoethylamino, hydroxyethylamino, or N-morpholino. In other embodiments, when $R_1$ is and $X_1$ is N, V is cyclopropanecarboxamido, cyclopropylamino, morpholinoethylamino, hydroxyethylamino, or N-morpholino. In other embodiments, when $R_1$ is

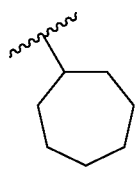 [SMILES: *C1CCCCCC1]

and X₁ is CH, V is cyclopropanecarboxamido, cyclopropylamino, morpholinoethylamino, hydroxyethylamino, or N-morpholino. In other embodiments, when R₁ is

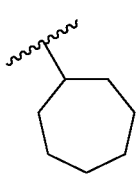 [SMILES: *C1CCCCCC1]

and X₁ is N, V is cyclopropanecarboxamido, cyclopropylamino, morpholinoethylamino, hydroxyethylamino, or N-morpholino. In other embodiments, when R₁ is

and X₁ is CH, V is cyclopropanecarboxamido, cyclopropylamino, morpholinoethylamino, hydroxyethylamino, or N-morpholino. In other embodiments, when R₁ is

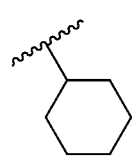

and X₁ is N, V is cyclopropanecarboxamido, cyclopropylamino, morpholinoethylamino, hydroxyethylamino, or N-morpholino. In other embodiments, when R₁ is

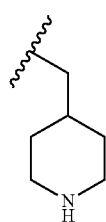

and X₁ is CH, V is cyclopropanecarboxamido, cyclopropylamino, morpholinoethylamino, hydroxyethylamino, or N-morpholino. In other embodiments, when R₁ is

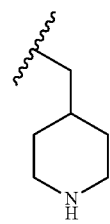 [SMILES: *CC1CCNCC1]

and X₁ is N, V is cyclopropanecarboxamido, cyclopropylamino, morpholinoethylamino, hydroxyethylamino, or N-morpholino. In other embodiments, when R₁ is

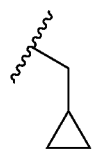 [SMILES: *CC1CC1]

and X₁ is CH, V is cyclopropanecarboxamido, cyclopropylamino, morpholinoethylamino, hydroxyethylamino, or N-morpholino. In other embodiments, when R₁ is

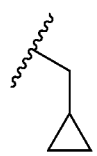

and X₁ is N, V is cyclopropanecarboxamido, cyclopropylamino, morpholinoethylamino, hydroxyethylamino, or N-morpholino. In other embodiments, when R₁ is

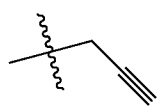 [SMILES: *CC#C]

and X₁ is CH, V is cyclopropanecarboxamido, cyclopropylamino, morpholinoethylamino, hydroxyethylamino, or N-morpholino. In other embodiments, when R₁ is

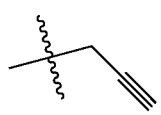

and X₁ is N, V is cyclopropanecarboxamido, cyclopropylamino, morpholinoethylamino, hydroxyethylamino, or N-morpholino. In other embodiments, when R₁ is

221

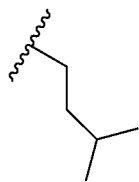 [SMILES: *CCC(C)C]

and X₁ is CH, V is cyclopropanecarboxamido, cyclopropylamino, morpholinoethylamino, hydroxyethylamino, or N-morpholino. In other embodiments, when R₁ is

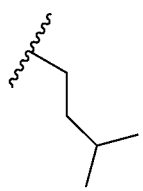 [SMILES: *CCC(C)C]

and X₁ is N, V is cyclopropanecarboxamido, cyclopropylamino, morpholinoethylamino, hydroxyethylamino, or N-morpholino. In other embodiments, when R₁ is

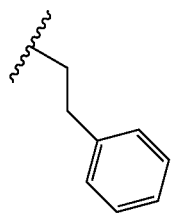 [SMILES: *CCc1ccccc1]

and X₁ is CH, V is cyclopropanecarboxamido, cyclopropylamino, morpholinoethylamino, hydroxyethylamino, or N-morpholino. In other embodiments, when R₁ is

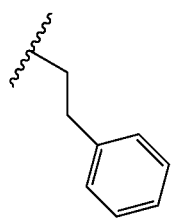 [SMILES: *CCc1ccccc1]

and X₁ is N, V is cyclopropanecarboxamido, cyclopropylamino, morpholinoethylamino, hydroxyethylamino, or N-morpholino. In other embodiments, when R₁ is

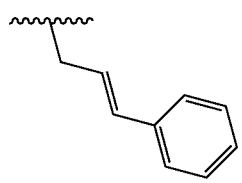 [SMILES: *C/C=C/c1ccccc1]

and X₁ is CH, V is cyclopropanecarboxamido, cyclopropylamino, morpholinoethylamino, hydroxyethylamino, or N-morpholino. In other embodiments, when R₁ is

222

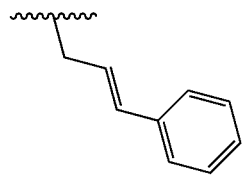 [SMILES: *C/C=C/c1ccccc1]

and X₁ is N, V is cyclopropanecarboxamido, cyclopropylamino, morpholinoethylamino, hydroxyethylamino, or N-morpholino. In other embodiments, when R₁ is

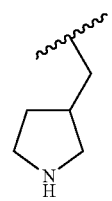 [SMILES: *CC1CCNC1]

and X₁ is CH, V is cyclopropanecarboxamido, cyclopropylamino, morpholinoethylamino, hydroxyethylamino, or N-morpholino. In other embodiments, when R₁ is

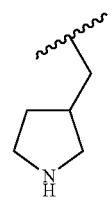 [SMILES: *CC1CCNC1]

and X₁ is N, V is cyclopropanecarboxamido, cyclopropylamino, morpholinoethylamino, hydroxyethylamino, or N-morpholino. In other embodiments, when R₁ is

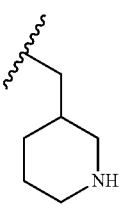 [SMILES: *CC1CCCNC1]

and X₁ is CH, V is cyclopropanecarboxamido, cyclopropylamino, morpholinoethylamino, hydroxyethylamino, or N-morpholino. In other embodiments, when R₁ is

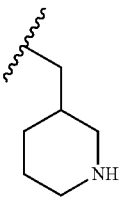 [SMILES: *CC1CCCNC1]

and X₁ is N, V is cyclopropanecarboxamido, cyclopropylamino, morpholinoethylamino, hydroxyethylamino, or N-morpholino. In other embodiments, when R₁ is

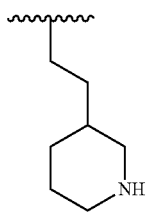 [SMILES: *CCC1CCCNC1]

and $X_1$ is CH, V is cyclopropanecarboxamido, cyclopropylamino, morpholinoethylamino, hydroxyethylamino, or N-morpholino. In other embodiments, when $R_1$ is

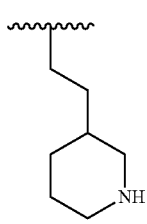

and $X_1$ is N, V is cyclopropanecarboxamido, cyclopropylamino, morpholinoethylamino, hydroxyethylamino, or N-morpholino. In other embodiments, when $R_1$ is

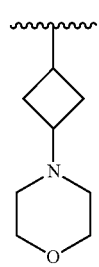

and $X_1$ is CH, V is cyclopropanecarboxamido, cyclopropylamino, morpholinoethylamino, hydroxyethylamino, or N-morpholino. In other embodiments, when $R_1$ is

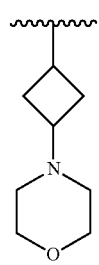

and $X_1$ is N, V is cyclopropanecarboxamido, cyclopropylamino, morpholinoethylamino, hydroxyethylamino, or N-morpholino. In other embodiments, when $R_1$ is

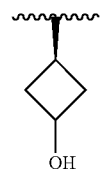

and $X_1$ is CH, V is cyclopropanecarboxamido, cyclopropylamino, morpholinoethylamino, hydroxyethylamino, or N-morpholino. In other embodiments, when $R_1$ is

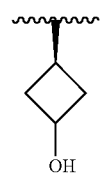

and $X_1$ is N, V is cyclopropanecarboxamido, cyclopropylamino, morpholinoethylamino, hydroxyethylamino, or N-morpholino. In other embodiments, when $R_1$ is

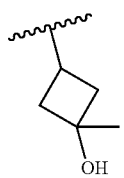 [SMILES: *C1CC(C)(O)C1]

and $X_1$ is CH, V is cyclopropanecarboxamido, cyclopropylamino, morpholinoethylamino, hydroxyethylamino, or N-morpholino. In other embodiments, when $R_1$ is

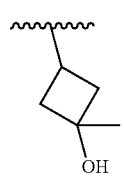 [SMILES: *C1CC(C)(O)C1]

and $X_1$ is N, V is cyclopropanecarboxamido, cyclopropylamino, morpholinoethylamino, hydroxyethylamino, or N-morpholino. In other embodiments, when $R_1$ is

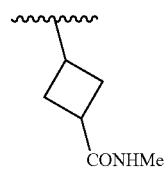

and $X_1$ is CH, V is cyclopropanecarboxamido, cyclopropylamino, morpholinoethylamino, hydroxyethylamino, or N-morpholino. In other embodiments, when $R_1$ is

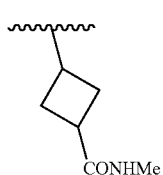

and $X_1$ is N, V is cyclopropanecarboxamido, cyclopropylamino, morpholinoethylamino, hydroxyethylamino, or N-morpholino. In other embodiments, when $R_1$ is

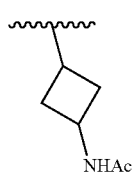 [SMILES: *C1CC(NC(C)=O)C1]

and $X_1$ is CH, V is cyclopropanecarboxamido, cyclopropylamino, morpholinoethylamino, hydroxyethylamino, or N-morpholino. In other embodiments, when $R_1$ is

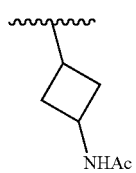 [SMILES: *C1CC(NC(C)=O)C1]

and $X_1$ is N, V is cyclopropanecarboxamido, cyclopropylamino, morpholinoethylamino, hydroxyethylamino, or N-morpholino. In other embodiments, when $R_1$ is

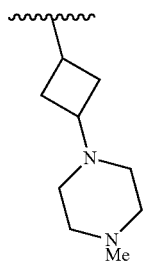 [SMILES: *C1CC(N2CCN(C)CC2)C1]

and $X_1$ is CH, V is cyclopropanecarboxamido, cyclopropylamino, morpholinoethylamino, hydroxyethylamino, or N-morpholino. In other embodiments, when $R_1$ is

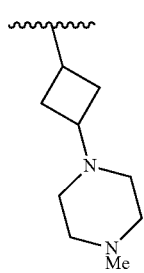 [SMILES: *C1CC(N2CCN(C)CC2)C1]

and $X_1$ is N, V is cyclopropanecarboxamido, cyclopropylamino, morpholinoethylamino, hydroxyethylamino, or N-morpholino. In other embodiments, when $R_1$ is

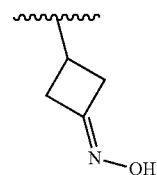 [SMILES: *C1CC(=NO)C1]

and $X_1$ is CH, V is cyclopropanecarboxamido, cyclopropylamino, morpholinoethylamino, hydroxyethylamino, or N-morpholino. In other embodiments, when $R_1$ is

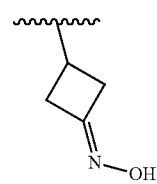 [SMILES: *C1CC(=NO)C1]

and $X_1$ is N, V is cyclopropanecarboxamido, cyclopropylamino, morpholinoethylamino, hydroxyethylamino, or N-morpholino. In other embodiments, when $R_1$ is

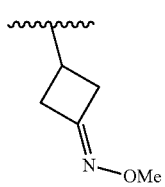

and $X_1$ is CH, V is cyclopropanecarboxamido, cyclopropylamino, morpholinoethylamino, hydroxyethylamino, or N-morpholino. In other embodiments, when $R_1$ is

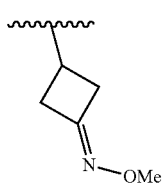 [SMILES: *C1CC(=NOC)C1]

and $X_1$ is N, V is cyclopropanecarboxamido, cyclopropylamino, morpholinoethylamino, hydroxyethylamino, or N-morpholino. In other embodiments, when $R_1$ is

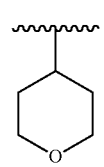 [SMILES: *C1CCOCC1]

and $X_1$ is CH, V is cyclopropanecarboxamido, cyclopropylamino, morpholinoethylamino, hydroxyethylamino, or N-morpholino. In other embodiments, when $R_1$ is

227

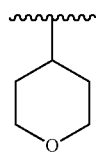

and $X_1$ is N, V is cyclopropanecarboxamido, cyclopropylamino, morpholinoethylamino, hydroxyethylamino, or N-morpholino. In other embodiments, when $R_1$ is

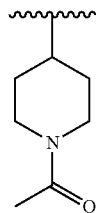 [SMILES: *C1CCN(C(C)=O)CC1]

and $X_1$ is CH, V is cyclopropanecarboxamido, cyclopropylamino, morpholinoethylamino, hydroxyethylamino, or N-morpholino. In other embodiments, when $R_1$ is

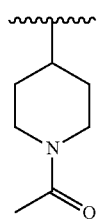

and $X_1$ is N, V is cyclopropanecarboxamido, cyclopropylamino, morpholinoethylamino, hydroxyethylamino, or N-morpholino. In other embodiments, when $R_1$ is

and $X_1$ is CH, V is cyclopropanecarboxamido, cyclopropylamino, morpholinoethylamino, hydroxyethylamino, or N-morpholino. In other embodiments, when $R_1$ is

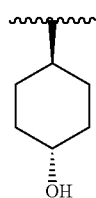 [SMILES: *[C@H]1CC[C@H](O)CC1]

and $X_1$ is N, V is cyclopropanecarboxamido, cyclopropylamino, morpholinoethylamino, hydroxyethylamino, or N-morpholino. In other embodiments, when $R_1$ is

228

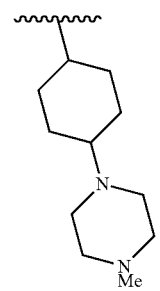 [SMILES: *C1CCC(N2CCN(C)CC2)CC1]

and $X_1$ is CH, V is cyclopropanecarboxamido, cyclopropylamino, morpholinoethylamino, hydroxyethylamino, or N-morpholino. In other embodiments, when $R_1$ is

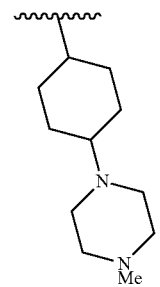 [SMILES: *C1CCC(N2CCN(C)CC2)CC1]

and $X_1$ is N, V is cyclopropanecarboxamido, cyclopropylamino, morpholinoethylamino, hydroxyethylamino, or N-morpholino. In other embodiments, when $R_1$ is

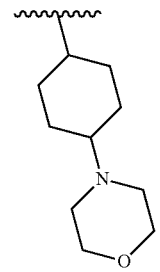 [SMILES: *C1CCC(N2CCOCC2)CC1]

and $X_1$ is CH, V is cyclopropanecarboxamido, cyclopropylamino, morpholinoethylamino, hydroxyethylamino, or N-morpholino. In other embodiments, when $R_1$ is

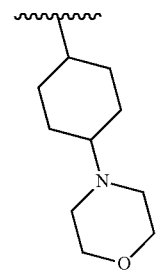 [SMILES: *C1CCC(N2CCOCC2)CC1]

and $X_1$ is N, V is cyclopropanecarboxamido, cyclopropylamino, morpholinoethylamino, hydroxyethylamino, or N-morpholino. In other embodiments, when $R_1$ is

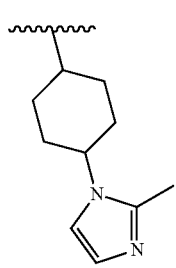 [SMILES: *C1CCC(n2ccnc2C)CC1]

and X₁ is CH, V is cyclopropanecarboxamido, cyclopropylamino, morpholinoethylamino, hydroxyethylamino, or N-morpholino. In other embodiments, when R₁ is

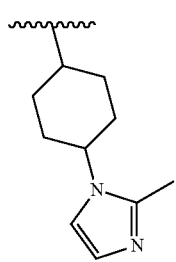 [SMILES: *C1CCC(n2ccnc2C)CC1]

and X₁ is N, V is cyclopropanecarboxamido, cyclopropylamino, morpholinoethylamino, hydroxyethylamino, or N-morpholino. In other embodiments, when R₁ is

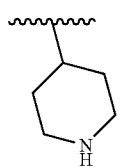 [SMILES: *C1CCNCC1]

and X₁ is CH, V is cyclopropanecarboxamido, cyclopropylamino, morpholinoethylamino, hydroxyethylamino, or N-morpholino. In other embodiments, when R₁ is

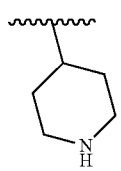

and X₁ is N, V is cyclopropanecarboxamido, cyclopropylamino, morpholinoethylamino, hydroxyethylamino, or N-morpholino. In other embodiments, when R₁ is

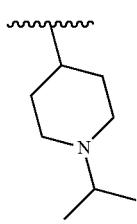 [SMILES: *C1CCN(C(C)C)CC1]

and X₁ is CH, V is cyclopropanecarboxamido, cyclopropylamino, morpholinoethylamino, hydroxyethylamino, or N-morpholino. In other embodiments, when R₁ is

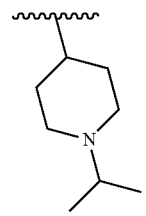

and X₁ is N, V is cyclopropanecarboxamido, cyclopropylamino, morpholinoethylamino, hydroxyethylamino, or N-morpholino. In other embodiments, when R₁ is

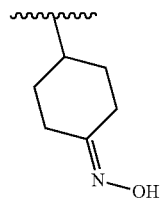 [SMILES: *C1CCC(=NO)CC1]

and X₁ is CH, V is cyclopropanecarboxamido, cyclopropylamino, morpholinoethylamino, hydroxyethylamino, or N-morpholino. In other embodiments, when R₁ is

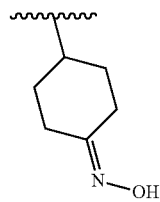 [SMILES: *C1CCC(=NO)CC1]

and X₁ is N, V is cyclopropanecarboxamido, cyclopropylamino, morpholinoethylamino, hydroxyethylamino, or N-morpholino. In other embodiments, when R₁ is

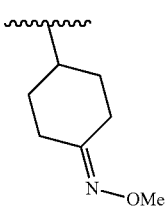 [SMILES: *C1CCC(=NOC)CC1]

and X₁ is CH, V is cyclopropanecarboxamido, cyclopropylamino, morpholinoethylamino, hydroxyethylamino, or N-morpholino. In other embodiments, when R₁ is

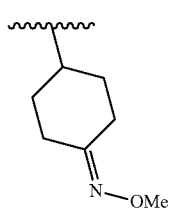 [SMILES: *C1CCC(=NOC)CC1]

and $X_1$ is N, V is cyclopropanecarboxamido, cyclopropylamino, morpholinoethylamino, hydroxyethylamino, or N-morpholino. In other embodiments, when $R_1$ is

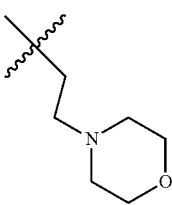 [SMILES: *CCN1CCOCC1]

and $X_1$ is CH, V is cyclopropanecarboxamido, cyclopropylamino, morpholinoethylamino, hydroxyethylamino, or N-morpholino. In other embodiments, when $R_1$ is

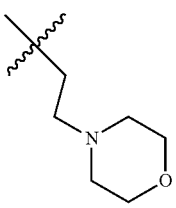 [SMILES: *CCN1CCOCC1]

and $X_1$ is N, V is cyclopropanecarboxamido, cyclopropylamino, morpholinoethylamino, hydroxyethylamino, or N-morpholino. In other embodiments, when $R_1$ is

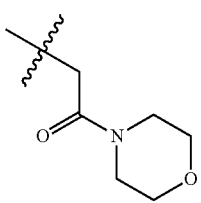 [SMILES: *CC(=O)N1CCOCC1]

and $X_1$ is CH, V is cyclopropanecarboxamido, cyclopropylamino, morpholinoethylamino, hydroxyethylamino, or N-morpholino. In other embodiments, when $R_1$ is

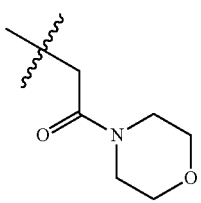 [SMILES: *CC(=O)N1CCOCC1]

and $X_1$ is N, V is cyclopropanecarboxamido, cyclopropylamino, morpholinoethylamino, hydroxyethylamino, or N-morpholino.
In other embodiments, when $R_1$ is

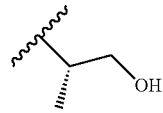 [SMILES: *[C@@H](C)CO]

and $X_1$ is CH, V is cyclopropanecarboxamido, cyclopropylamino, morpholinoethylamino, hydroxyethylamino, or N-morpholino. In other embodiments, when $R_1$ is

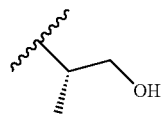 [SMILES: *[C@@H](C)CO]

and $X_1$ is N, V is cyclopropanecarboxamido, cyclopropylamino, morpholinoethylamino, hydroxyethylamino, or N-morpholino. In other embodiments, when $R_1$ is

and $X_1$ is CH, V is cyclopropanecarboxamido, cyclopropylamino, morpholinoethylamino, hydroxyethylamino, or N-morpholino. In other embodiments, when $R_1$ is

and $X_1$ is N, V is cyclopropanecarboxamido, cyclopropylamino, morpholinoethylamino, hydroxyethylamino, or N-morpholino. In other embodiments, when $R_1$ is

and $X_1$ is CH, V is cyclopropanecarboxamido, cyclopropylamino, morpholinoethylamino, hydroxyethylamino, or N-morpholino. In other embodiments, when $R_1$ is

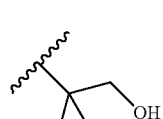

and $X_1$ is N, V is cyclopropanecarboxamido, cyclopropylamino, morpholinoethylamino, hydroxyethylamino, or N-morpholino. In other embodiments, when $R_1$ is

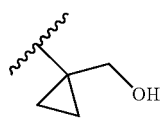 [SMILES: *C1(CO)CC1]

and $X_1$ is CH, V is cyclopropanecarboxamido, cyclopropylamino, morpholinoethylamino, hydroxyethylamino, or N-morpholino. In other embodiments, when $R_1$ is

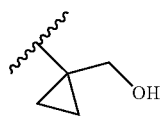 [SMILES: *C1(CO)CC1]

and $X_1$ is N, V is cyclopropanecarboxamido, cyclopropylamino, morpholinoethylamino, hydroxyethylamino, or N-morpholino. In other embodiments, when $R_1$ is

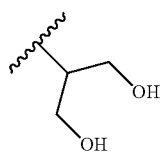 [SMILES: *C(CO)CO]

and $X_1$ is CH, V is cyclopropanecarboxamido, cyclopropylamino, morpholinoethylamino, hydroxyethylamino, or N-morpholino. In other embodiments, when $R_1$ is

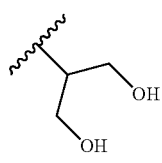 [SMILES: *C(CO)CO]

and $X_1$ is N, V is cyclopropanecarboxamido, cyclopropylamino, morpholinoethylamino, hydroxyethylamino, or N-morpholino. In other embodiments, when $R_1$ is

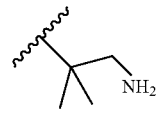 [SMILES: *C(C)(C)CN]

and $X_1$ is CH, V is cyclopropanecarboxamido, cyclopropylamino, morpholinoethylamino, hydroxyethylamino, or N-morpholino. In other embodiments, when $R_1$ is

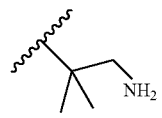

and $X_1$ is N, V is cyclopropanecarboxamido, cyclopropylamino, morpholinoethylamino, hydroxyethylamino, or N-morpholino In other embodiments, when $R_1$ is

and $X_1$ is CH, V is cyclopropanecarboxamido, cyclopropylamino, morpholinoethylamino, hydroxyethylamino, or N-morpholino. In other embodiments, when $R_1$ is

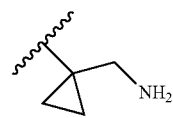

and $X_1$ is N, V is cyclopropanecarboxamido, cyclopropylamino, morpholinoethylamino, hydroxyethylamino, or N-morpholino. and $X_1$ is CH, V is cyclopropanecarboxamido, cyclopropylamino, morpholinoethylamino, hydroxyethylamino, or N-morpholino.

In other embodiments, when $R_1$ is

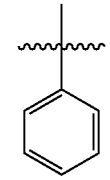

and $X_1$ is CH, V is cyclopropanecarboxamido, cyclopropylamino, morpholinoethylamino, hydroxyethylamino, or N-morpholino. In other embodiments, when $R_1$ is

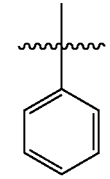

and $X_1$ is N, V is cyclopropanecarboxamido, cyclopropylamino, morpholinoethylamino, hydroxyethylamino, or N-morpholino. In other embodiments, when $R_1$ is

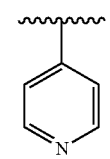

and $X_1$ is CH, V is cyclopropanecarboxamido, cyclopropylamino, morpholinoethylamino, hydroxyethylamino, or N-morpholino. In other embodiments, when $R_1$ is

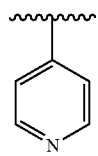

and X₁ is N, V is cyclopropanecarboxamido, cyclopropylamino, morpholinoethylamino, hydroxyethylamino, or N-morpholino. In other embodiments, when R₁ is

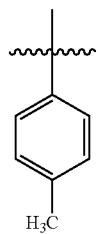

and X₁ is CH, V is cyclopropanecarboxamido, cyclopropylamino, morpholinoethylamino, hydroxyethylamino, or N-morpholino. In other embodiments, when R₁ is

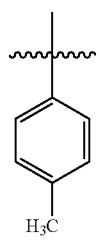

and X₁ is N, V is cyclopropanecarboxamido, cyclopropylamino, morpholinoethylamino, hydroxyethylamino, or N-morpholino. In other embodiments, when R₁ is

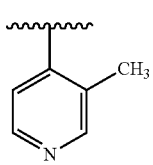 [SMILES: *c1ccncc1C]

and X₁ is CH, V is cyclopropanecarboxamido, cyclopropylamino, morpholinoethylamino, hydroxyethylamino, or N-morpholino. In other embodiments, when R₁ is

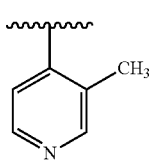 [SMILES: *c1ccncc1C]

and X₁ is N, V is cyclopropanecarboxamido, cyclopropylamino, morpholinoethylamino, hydroxyethylamino, or N-morpholino. In other embodiments, when R₁ is

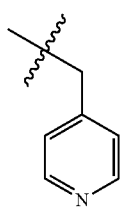 [SMILES: *Cc1ccncc1]

and X₁ is CH, V is cyclopropanecarboxamido, cyclopropylamino, morpholinoethylamino, hydroxyethylamino, or N-morpholino. In other embodiments, when R₁ is

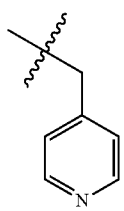 [SMILES: *Cc1ccncc1]

and X₁ is N, V is cyclopropanecarboxamido, cyclopropylamino, morpholinoethylamino, hydroxyethylamino, or N-morpholino. In other embodiments, when R₁ is

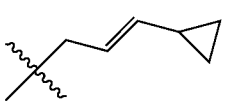 [SMILES: *C/C=C/C1CC1]

and X₁ is CH, V is cyclopropanecarboxamido, cyclopropylamino, morpholinoethylamino, hydroxyethylamino, or N-morpholino. In other embodiments, when R₁ is

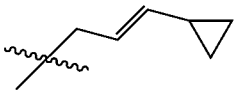 [SMILES: *C/C=C/C1CC1]

and X₁ is N, V is cyclopropanecarboxamido, cyclopropylamino, morpholinoethylamino, hydroxyethylamino, or N-morpholino. In other embodiments, when R₁ is

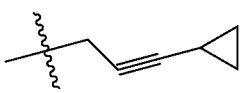 [SMILES: *CC#CC1CC1]

and X₁ is CH, V is cyclopropanecarboxamido, cyclopropylamino, morpholinoethylamino, hydroxyethylamino, or N-morpholino. In other embodiments, when R₁ is

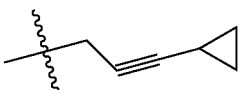 [SMILES: *CC#CC1CC1]

and X₁ is N, V is cyclopropanecarboxamido, cyclopropylamino, morpholinoethylamino, hydroxyethylamino, or N-morpholino. In other embodiments, when R₁ is

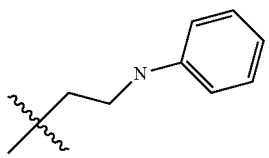 [SMILES: *CCNc1ccccc1]

and $X_1$ is CH, V is cyclopropanecarboxamido, cyclopropylamino, morpholinoethylamino, hydroxyethylamino, or N-morpholino. In other embodiments, when $R_1$ is

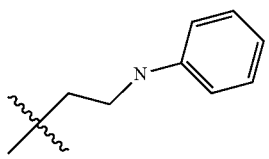 [SMILES: *CCNc1ccccc1]

and $X_1$ is N, V is cyclopropanecarboxamido, cyclopropylamino, morpholinoethylamino, hydroxyethylamino, or N-morpholino. In other embodiments, when $R_1$ is

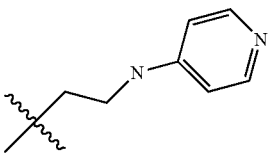 [SMILES: *CCNc1ccncc1]

and $X_1$ is CH, V is cyclopropanecarboxamido, cyclopropylamino, morpholinoethylamino, hydroxyethylamino, or N-morpholino. In other embodiments, when $R_1$ is

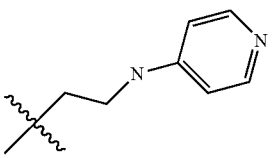 [SMILES: *CCNc1ccncc1]

and $X_1$ is N, V is cyclopropanecarboxamido, cyclopropylamino, morpholinoethylamino, hydroxyethylamino, or N-morpholino. In other embodiments, when $R_1$ is

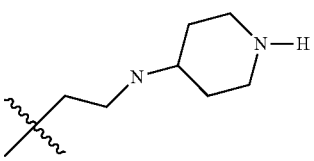 [SMILES: *CCNC1CCNCC1]

and $X_1$ is CH, V is cyclopropanecarboxamido, cyclopropylamino, morpholinoethylamino, hydroxyethylamino, or N-morpholino. In other embodiments, when $R_1$ is

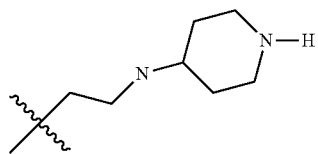 [SMILES: *CCNC1CCNCC1]

and $X_1$ is N, V is cyclopropanecarboxamido, cyclopropylamino, morpholinoethylamino, hydroxyethylamino, or N-morpholino.

In the noted embodiments, cyclopropanecarboxamido is

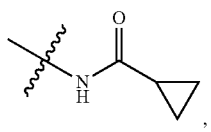

cyclopropylamino is

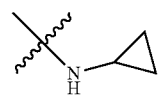 [SMILES: *NC1CC1]

2-morpholinoethylamino is

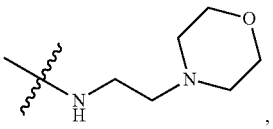 [SMILES: *NCCN1CCOCC1]

hydroxyethylamino is

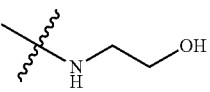

and N-morpholino is

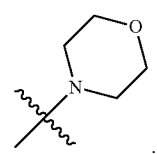 [SMILES: *N1CCOCC1]

TABLE 1

Biological activity of several illustrative compounds of the invention.

| Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|
| 1 | ++++ | +++ | ++ | ++++ | +++ | ++++ |
| 2 | ++++ | ++ | + | +++ | +++ | +++ |
| 3 | ++ | + | ++ | ++ | ++ | |
| 4 | +++ | ++ | ++ | +++ | +++ | ++ |

TABLE 1-continued

Biological activity of several illustrative compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|---|
| 5 | 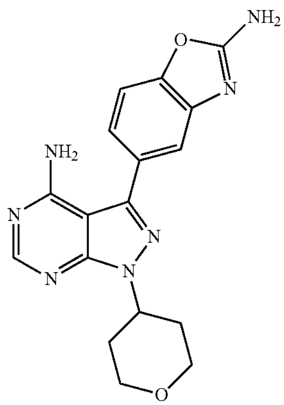 [SMILES: Nc1nc2cc(-c3nn(C4CCOCC4)c4ncnc(N)c34)ccc2o1] | ++++ | +++ | ++ | ++++ | +++ | ++++ |
| 6 | 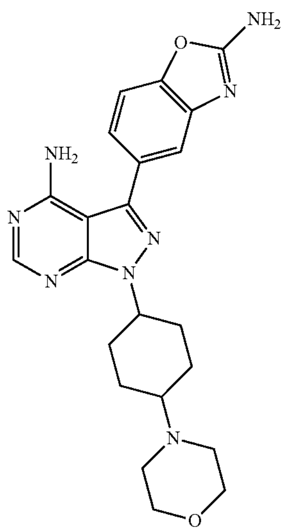 [SMILES: Nc1nc2cc(-c3nn(C4CCC(N5CCOCC5)CC4)c4ncnc(N)c34)ccc2o1] | ++++ | ++ | + | ++ | +++ | +++ |
| 7 | 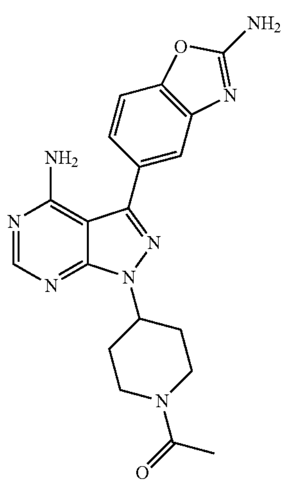 [SMILES: CC(=O)N1CCC(n2nc(-c3ccc4oc(N)nc4c3)c3c(N)ncnc32)CC1] | ++++ | +++ | ++ | ++ | +++ | ++ |

TABLE 1-continued

Biological activity of several illustrative compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|---|
| 8 | 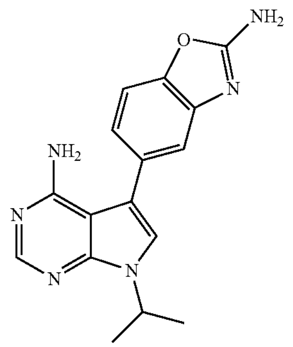 [SMILES: CC(C)n1cc(-c2ccc3oc(N)nc3c2)c2c(N)ncnc21] | ++++ | +++ | + | +++ | +++ | ++++ |
| 9 | 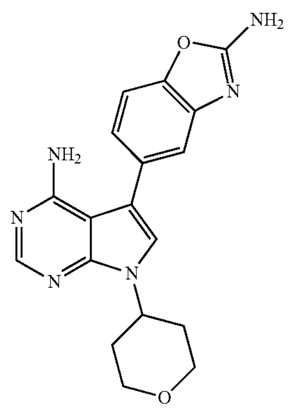 [SMILES: Nc1nc2cc(-c3cn(C4CCOCC4)c4ncnc(N)c34)ccc2o1] | ++++ | ++ | + | +++ | +++ | ++++ |
| 10 | 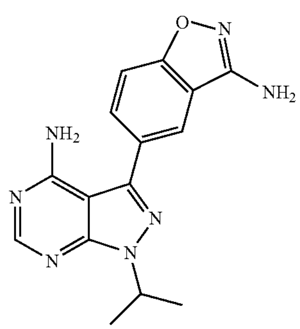 [SMILES: CC(C)n1nc(-c2ccc3onc(N)c3c2)c2c(N)ncnc21] | ++ | | | | | + |
| 11 | 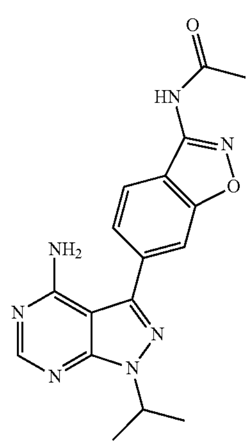 [SMILES: CC(=O)Nc1noc2cc(-c3nn(C(C)C)c4ncnc(N)c34)ccc12] | +++ | | | | | + |

TABLE 1-continued

Biological activity of several illustrative compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|---|
| 12 | 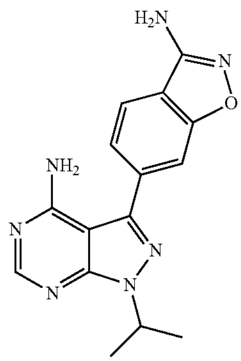 [SMILES: CC(C)n1nc(-c2ccc3c(N)noc3c2)c2c(N)ncnc21] | +++ | | | | | + |
| 13 | 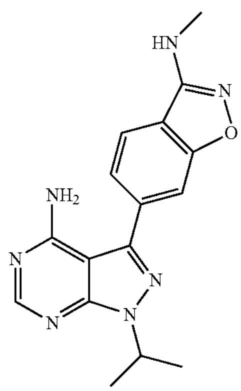 [SMILES: CNc1noc2cc(-c3nn(C(C)C)c4ncnc(N)c34)ccc12] | ++ | ++ | | +++ | +++ | |
| 14 | 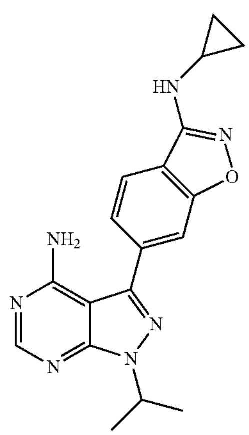 [SMILES: CC(C)n1nc(-c2ccc3c(NC4CC4)noc3c2)c2c(N)ncnc21] | ++ | ++ | | +++ | ++ | |
| 15 | 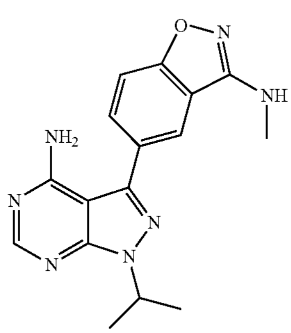 [SMILES: CNc1noc2ccc(-c3nn(C(C)C)c4ncnc(N)c34)cc12] | + | + | | + | + | |

TABLE 1-continued

Biological activity of several illustrative compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|---|
| 16 | 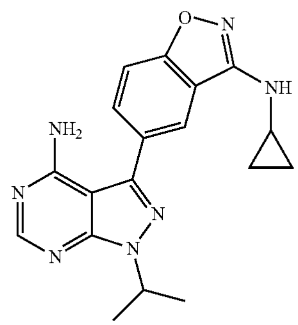 [SMILES: CC(C)n1nc(-c2ccc3onc(NC4CC4)c3c2)c2c(N)ncnc21] | + | + | | ++ | + | |
| 17 | 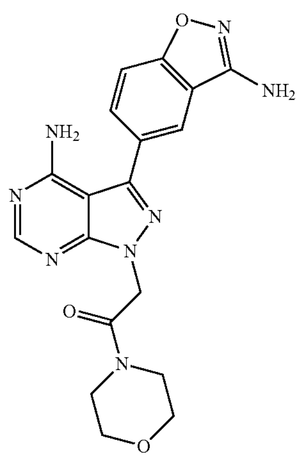 [SMILES: Nc1noc2ccc(-c3nn(CC(=O)N4CCOCC4)c4ncnc(N)c34)cc12] | + | + | | + | + | |
| 18 | 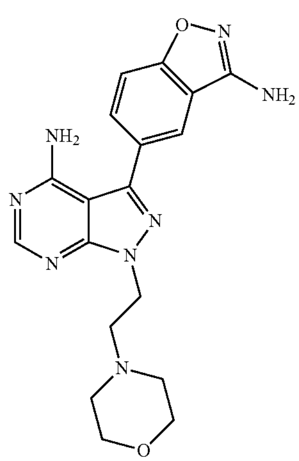 [SMILES: Nc1noc2ccc(-c3nn(CCN4CCOCC4)c4ncnc(N)c34)cc12] | + | + | | + | + | |
| 19 | 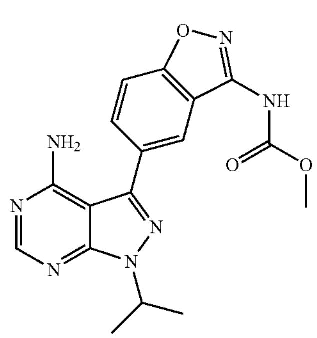 [SMILES: COC(=O)Nc1noc2ccc(-c3nn(C(C)C)c4ncnc(N)c34)cc12] | ++ | + | + | | + | |

TABLE 1-continued

Biological activity of several illustrative compounds of the invention.

| Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|
| 20 | ++ | ++ | + |  | ++ |  |
| 21 | +++ | + | + | + | + |  |
| 22 | ++++ | ++++ | ++ | +++ | +++ | ++ |
| 23 | ++++ | ++ | + | ++ | ++ |  |

TABLE 1-continued

Biological activity of several illustrative compounds of the invention.

| Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|
| 24 | | + | + | + | + | |
| 25 | | +++ | ++ | ++++ | +++ | |
| 26 | | ++++ | +++ | ++++ | +++ | |

TABLE 1-continued

Biological activity of several illustrative compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 IC50 (nM) |
|---|---|---|---|---|---|---|---|
| 27 | 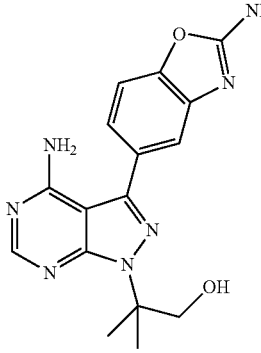 | | ++ | + | + | +++ | |

Table 1 shows the biological activity in mTOR and PI3K kinase assays of several compounds of the invention. The scale utilized in Table 1 is as follows: ++++ less than 100 nM; +++ less than 1.0 µM; ++ less than 10 µM; and + greater than 10 µM.

In other embodiments, the present invention provides the following compounds:

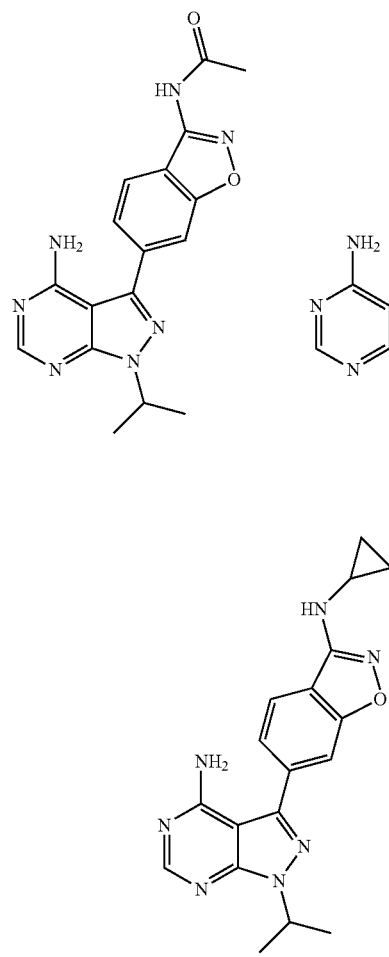

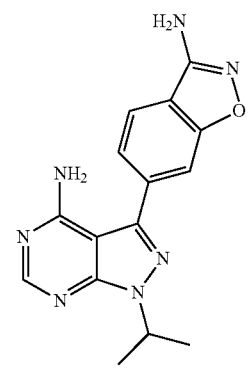

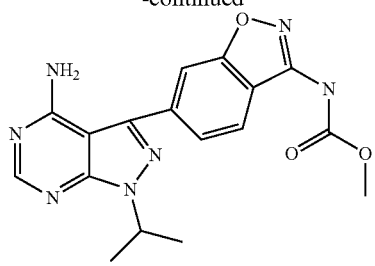

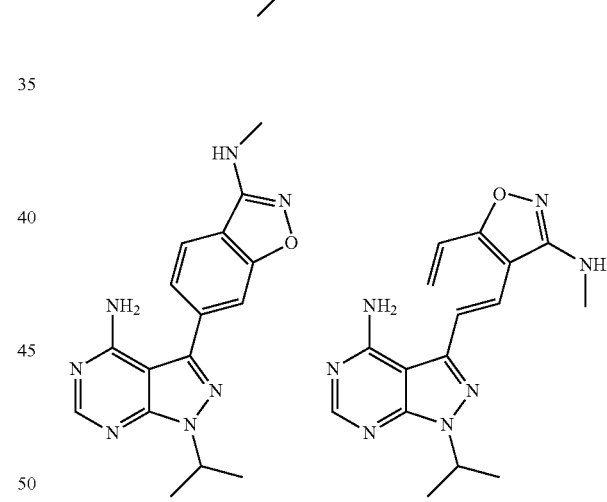

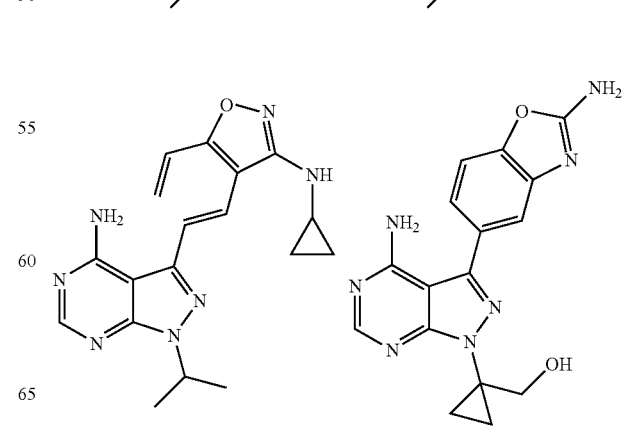

Any of the compounds shown above may show a biological activity in an mTOR or PI3K inhibition assay of between about 0.5 nM and 25 µM ($IC_{50}$).

In some embodiments, one or more compounds of the invention may bind specifically to a PI3 kinase or a protein kinase selected from the group consisting of mTor, DNA-dependent protein kinase DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and any other protein kinases listed in the appended tables and figures, as well as any functional mutants thereof. In some embodiments, the IC50 of a compound of the invention for p110α, p110β, p110γ, or p110δ is less than about 1 uM, less than about 100 nM, less than about 50 nM, less than about 10 nM, less than 1 nM or even less than about 0.5 nM. In some embodiments, the IC50 of a compound of the invention for mTor is less than about 1 uM, less than about 100 nM, less than about 50 nM, less than about 10 nM, less than 1 nM or even less than about 0.5 nM. In some other embodiments, one or more compounds of the invention exhibit dual binding specificity and are capable of inhibiting a PI3 kinase (e.g., a class I PI3 kinase) as well as a protein kinase (e.g., mTor) with an IC50 value less than about 1 uM, less than about 100 nM, less than about 50 nM, less than about 10 nM, less than 1 nM or even less than about 0.5 nM. In some embodiments, one or more compounds of the invention may be capable of inhibiting tyrosine kinases including, for example, DNA-dependent protein kinase DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP-004110), platelet-derived growth factor receptor alpha (PPAN NP_990080), RET (PPAN CAA73131), and functional mutants thereof. In some embodiments, the tyrosine kinase is Abl, Bcr-Abl, EGFR, or Flt-3, and any other kinases listed in the Tables herein.

In some embodiments, one or more compounds of the invention yield selective inhibition of mTor-mediated signal transduction as compared to upstream PI3K. In some other embodiments, the compounds provided herein can inhibit mTor-mediated activity more effectively than rapamycin, hence providing an alternative treatment for rapamycin-resistant conditions.

In some embodiments, the compounds of the invention including but not limited to those shown in Table 1 selectively inhibit both mTorC1 and mTorC2 activity relative to one, two, three or all type I phosphatidylinositol 3-kinases (PI3-kinase). As noted above type I PI3-kinases are PI3-kinase α, PI3-kinase β, PI3-kinase γ, and PI3-kinase δ. For instance, one or more compounds of the invention may inhibit mTORC1 and mTORC2 with an $IC_{50}$ that is $1/10^{th}$, $1/20^{th}$ $1/25^{th}$, $1/50^{th}$, $1/100^{th}$, $1/200^{th}$, $1/300^{th}$, $1/400^{th}$, $1/500^{th}$, $1/1000^{th}$, $1/2000^{th}$ or less than the IC50 for one or more type I PI3-kinases consisting of PI3-kinase α, PI3-kinase β, PI3-kinase γ, and PI3-kinase δ. In some embodiments, one or more compounds of the invention are substantially ineffective in inhibiting a type I PI3-kinase at a concentration of 100 nM, 200 nM, 500 nM, or 1 uM, 5 uM or 10 uM, or higher in an in vitro kinase assay.

In other embodiments, the compounds of the invention including but not limited to compound 1 and others shown in Table 1 selectively inhibit both mTORC1 and mTORC2 activity relative to one, two, three or all type II or III PI3-kinases, for example, PI3KC2α, PI3KC2β, and VPS34. In particular, one or more of the compounds of the invention may inhibit mTORC1 and mTORC2 with an $IC_{50}$ that is $1/10^{th}$, $1/20^{th}$, $1/25^{th}$, $1/50^{th}$, $1/100^{th}$, $1/200^{th}$, $1/300^{th}$, $1/400^{th}$, $1/500^{th}$, $1/1000^{th}$ $1/2000^{th}$ or less than the IC50 for one or more type II or III PI3-kinases.

In yet another embodiment, compounds of the invention including but not limited to compound 1 and others shown in Table 1 selectively inhibit both mTORC1 and mTORC2 activity relative to one or more PI4-kinases such as PI4Kα and PI4Kβ. For instance, one or more compounds of the invention may inhibit mTORC1 and mTORC2 with an $IC_{50}$ that is $1/10^{th}$, $1/20^{th}$, $1/25^{th}$, $1/50^{th}$, $1/100^{th}$, $1/200^{th}$, $1/300^{th}$, $1/400^{th}$, $1/500^{th}$, $1/1000^{th}$, $1/2000^{th}$ or less than the $IC_{50}$ for one or more PI4-kinases.

In still another embodiment, the compounds of the invention including but not limited to those shown in Table 1 selectively inhibit both mTORC1 and mTORC2 activity relative to one or more protein kinases including serine/threonine kinase such as DNA-PK. Such selective inhibition can be evidenced by, e.g., the IC50 value of the compound of the invention that can be $1/2$, $1/3^{rd}$, $1/4^{th}$, $1/5^{th}$, $1/7^{th}$, $1/10^{th}$, $1/15^{th}$, $1/20^{th}$, $1/25^{th}$, $1/30^{th}$, $1/40^{th}$, $1/50^{th}$, $1/100^{th}$, $1/150^{th}$, $1/200^{th}$, $1/300^{th}$-$1/400^{th}$, $1/500^{th}$, $1/1000^{th}$, $1/2000^{th}$ or less as compared to that of a reference protein kinase. In some instances, the compounds of the invention including but not limited to those shown in Table 1 lack substantial cross-reactivity with at least about 100, 200, 300, or more protein kinases other than mTORC1 or mTORC2. The lack of substantial cross-reactivity with other non-mTor protein kinases can be evidenced by, e.g., at least 50%, 60%, 70%, 80%, 90% or higher kinase activity retained when the compound of the invention is applied to the protein kinase at a concentration of 1 μM, 5 μM, 10 μM or higher.

In some embodiments, one or more compounds of the invention selectively inhibits both mTor activity with an IC50 value of about 100 nM, 50 nM, 10 nM, 5 nM, 100 pM, 10 pM or even 1 pM, or less as ascertained in an in vitro kinase assay.

In some embodiments, one or more compounds of the invention inhibits phosphorylation of Akt (S473) and Akt (T308) more effectively than rapamycin when tested at a comparable molar concentration in an in vitro kinase assay.

In some embodiments, one or more compounds of the invention competes with ATP for binding to ATP-binding site on mTorC1 and/or mTorC2.

In some embodiments, one or more compounds of the invention are capable of inhibiting and/or otherwise modulating cellular signal transduction via one or more protein kinases or lipid kinases disclosed herein. For example, one or more compounds of the invention are capable of inhibiting or modulating the output of a signal transduction pathway. Output of signaling transduction of a given pathway can be measured by the level of phosphorylation, dephosphorylation, fragmentation, reduction, oxidation of a signaling molecule in the pathway of interest. In another specific embodiment, the output of the pathway may be a cellular or phenotypic output (e.g. modulating/inhibition of cellular proliferation, cell death, apoptosis, autophagy, phagocytosis, cell cycle progression, metastases, cell invasion, angiogenesis, vascularization, ubiquitination, translation, transcription, protein trafficking, mitochondrial function, golgi function, endoplasmic reticular function, etc). In some embodiments, one or more compounds of the invention are capable of, by way of example, causing apoptosis, causing cell cycle arrest, inhibiting cellular proliferation, inhibiting tumor growth, inhibiting angiogenesis, inhibiting vascularization, inhibiting metastases, and/or inhibiting cell invasion.

In some embodiments, one or more compounds of the invention causes apoptosis of said cell or cell cycle arrest. Cell cycle can be arrested at the G0/G1 phase, S phase, and/or G2/M phase by the subject compounds.

In some embodiments, one or more compounds of the invention including but not limited to the compounds listed in Table 1 are capable of inhibiting cellular proliferation. For example, in some cases, one or more compounds of the invention listed in Table 1 may inhibit proliferation of tumor cells or tumor cell lines with a wide range of genetic makeup. In some cases, the compounds of the invention may inhibit PC3 cell proliferation in vitro or in an in vivo model such as a xenograft mouse model. In some cases, in vitro cultured PC3 cell proliferation may be inhibited with an IC50 of less than 100 nM, 75 nM, 50 nM, 25 nM, 15 nM, 10 nM, 5 nM, 3 nM, 2 nM, 1 nM, 0.5 nM, 0.1 nM or less by one or more compounds of the invention listed in Table 1.

In some cases, phosphorylation of AKT may be inhibited with an $IC_{50}$ of less than 100 nM, 75 nM, 50 nM, 25 nM, 15 nM, 10 nM, 5 nM, 3 nM, 2 nM, 1 nM, 0.5 nM, 0.1 nM or less by one or more compounds of the invention listed in Table 1. Inhibition of phosphorylation of AKT may be a partially or completely blocked by the addition of human whole blood. In some cases, the one or more compounds of the invention listed in Table 1 exhibit specific binding and/or inhibition of mTOR as evidenced by a small (e.g. less than about 0.5-fold, 1-fold, 2-fold, or 3-fold) increase in $IC_{50}$ for inhibition of AKT phosphorylation of cells cultured in whole blood as compared to standard culture media (e.g. DMEM 10% FBS).

In some cases, proliferation of primary tumors derived from subjects (e.g. cancer patients) can be inhibited by a compound of the invention as shown by in vitro assays, or in vivo models (e.g. using the subjects' tumor cells for generating a xenograft mode). In some cases primary tumor cell line proliferation may be inhibited with an $IC_{50}$ of less than 100 nM, 75 nM, 50 nM, 25 nM, 15 nM, 10 nM, 5 nM, 3 nM, 2 nM, 1 nM, 0.5 nM, 0.1 nM or even less by one or more compounds of the invention listed in Table 1. In some cases, the average $IC_{50}$ of a compound of the invention for inhibiting a panel 10, 20, 30, 40, 50, 100 or more primary tumor cells may be about 200 nM, 100 nM, 75 nM, 50 nM, 25 nM, 15 nM, 10 nM, 5 nM, 3 nM, 2 nM, 1 nM, 0.5 nM, 0.1 nM or even less. The tumor cells that can be inhibited by the compounds of the present invention include but are not limited to pancreatic, renal (kidney), bone, nasopharyngeal, gastric, stomach, ovarian, oral, breast, blood, prostate, rectal, colon, colorectal, blial, neural, lung, and dermal cells.

In some embodiments, the compounds of the invention are effective in blocking cell proliferation signals in cells deficient in PTEN activity but expressing PI3Kα. In some cases, cell proliferation signalling may be inhibited by one or more compounds of the invention including but not limited to those shown in Table 1 as evidenced by Western blot analysis of phosphorylation of proteins such as AKT (phosphorylation at T308 or S473), 4EBP1 (phosphorylation at S65), S6 (phosphorylation at S240/244), FOXO1 (phosphorylation at T24/3a T32), GSK3β (phosphorylation at S9), PRAS40 (phosphorylation at T246), or MAPK phosphorylation. In some cases, the compounds of the invention can inhibit phosphorylation of any one of these targets to a greater degree than rapamycin under the conditions tested. In other cases, the compounds of the invention can inhibit phosphorylation of signaling proteins and suppress proliferation of cells containing these signaling proteins but are resistant to existing chemotherapeutic agents including but not limited to rapamycin, Gleevec, dasatinib, alkylating agents, antimetabolites, anthracyclines, plant alkaloids, topoisomerase inhibitors and other antitumor agents disclosed herein.

In some embodiments, the compounds of the invention including but not limited to those shown in Table 1, may inhibit tumor cells comprising a wide range of activating or tumor-causing mutations. Such mutations include but are not limited to mutations in KRAS, PI3KCα, BRAF, TSC1/2, PBKclass A, LAT1, and PTEN. For example, one or more compounds of the invention such as the compounds in Table 1, including but not limited to compound 1 may inhibit proliferation of tumor cells comprising mutations in KRAS at G12, G13, or mutations in Q61 including but not limited to the G12V, G12S, G13D, Q61K, and Q61H mutations. In another example, one or more compounds of the invention may inhibit proliferation of tumor cells comprising mutations in BRAF at V600 including but not limited to the mutation V600E. In another example, one or more compounds of the invention such as the compounds in Table 1 may inhibit proliferation of tumor cells comprising a mutation in PI3KCα at E545, P449, or H1047 including but not limited to the E545K, H1047R, and P449T mutations. In yet another example, one or more compounds of the invention such as the compounds in Table 1, may inhibit proliferation of tumor cells comprising activating mutations in one or more combinations of genes such as for example activating mutations in PTEN and KRAS, PTEN and BRAF, or PTEN and PI3KCα. In yet another example, one or more compounds of the invention such as the compounds in Table 1 may inhibit tumor cells or tumor cell lines comprising activating mutations in one or more combinations of genes such as for example activating mutations in BRAF and PI3KCα.

In some embodiments, one or more compounds of the invention including those in Table 1 may cause cell cycle arrest. In some cases, cells treated with one or more compounds of the invention including compound 1 and others in Table 1, may arrest or take longer to proceed through one or more cell cycle stages such as $G_0/G_1$, S, or $G_2/M$. For example, cells treated with one or more compounds of the invention may arrest or take longer to proceed through the $G_0/G_1$ cell cycle stage. In some cases, about 35%, 40%, 50%, 55%, 60%, 65%, 70% or more of cells treated with one or more compounds of the invention may be in the $G_0/G_1$ cell cycle stage. In some cases, cells exhibiting cell cycle arrest in the $G_0/G_1$ cell cycle stage in response to treatment with the compounds of the invention are tumor cells or rapidly dividing cells. In some cases, cells exhibiting cell cycle arrest in the $G_0/G_1$ cell cycle stage in response to treatment with one or more compounds of the present invention are HCT116 cells or SW620 cells. In some cases, one or more compounds of the invention such as the compounds in Table 1, including but not limited to compound 1 exhibit a comparable or a greater degree of $G_0/G_1$ arrest as compared to an inhibitor that inhibits one or more PI3-kinases. In some cases, the compounds of the invention effect a comparable or a greater degree of $G_0/G_1$ arrest as compared to an inhibitor that inhibits both mTOR and one or more PI3Ks in tumor cells. In some cases, the compounds of the invention effect a comparable or a greater degree of $G_0/G_1$ arrest as compared to rapamycin or doxorubicin.

In some embodiments, cell signalling in tumor cells xenografted into female athymic nude mice may be inhibited by one or more compounds of the invention such as the compounds in Table 1, including but not limited to compound 1. In some cases, cell signalling may be inhibited by one or more compounds of the invention as evidenced by western blot detection of phosphorylation of proteins extracted from homogenized tumors, such as AKT phosphorylation at T308 or S473, 4EBP1 phosphorylation at S65, S6 phosphorylation at S240/244. In some cases, inhibition of phosphorylation may be comparable to or greater than that provided by known inhibitors of phosphorylation such as a Pan PI3K inhibitor that also inhibits one or more isoforms of mTOR (Pan PI3K/mTor inhibitor) under the conditions tested. In other cases, one or more compounds of the invention may inhibit phosphorylation of proteins that other inhibitors such as Pan PI3K/mTor inhibitors do not affect, or have little effect on, e.g., phosphorylation of AKT at T308 and S473.

In some embodiments, the compounds of the invention including but not limited to compound 1 and others shown in Table 1, cause a reduction in tumor volume of xenograft tumors in female nude athymic mice. For example, treatment with one or more compounds of the invention results in a reduction in the growth or tumor volume caused by engraftment of U87-MG, A549, ZR-75-1, or 786-0 tumor cells in nude mice. The compounds of the invention may be administered orally, subcutaneously, or intravenously, or any other compound administration methods provided herein. In some cases, the compounds are administered once a week, every other day, once a day, twice a day, three times a day, four times a day or more. In some cases, 0.01 mg/kg of compound is administered, 0.05 mg/kg, 0.1 mg/kg, 0.2 mg/kg, 0.4 mg/kg, 0.5 mg/kg, 1 mg/kg, 1.5 mg/kg, 2 mg/kg, 3 mg/kg, 4 mg/kg, 5 mg/kg, 7.5 mg/kg, 10 mg/kg, 100 mg/kg or more compound is administered at a time. In some cases, a significant reduction in tumor volume may be detected within 5, 10, 15, 20, 25, or 30 days of tumor engraftment.

The invention provides a pharmaceutical composition comprising one or more compounds disclosed herein. In some embodiments the invention provides pharmaceutical compositions for the treatment of disorders such as hyperproliferative disorders including but not limited to cancers such as acute myeloid leukemia, lymphoma, thymus, brain, lung, squamous cell, skin, eye, retinoblastoma, intraocular melanoma, mesothelioma, mediastinum, oral cavity and oropharyngeal, bladder, gastric, stomach, pancreatic, bladder, breast, cervical, head, neck, renal, kidney, liver, hepatobiliary system, small intestine, colon, rectum, anus, prostate, colorectal, urethra, esophageal, testicular, gynecological, penis, testis, ovarian, endocrine system, skin, thyroid, CNS, PNS, AIDS related AIDS-Related (e.g. Lymphoma and Kaposi's Sarcoma), other viral-induced cancers, sarcomas of the soft tissue and bone, and melanomas of cutaneous and intraocular origin. Cancers includes solid tumors as well as hematological malignancies. In addition, a cancer at any stage of progression can be treated, such as primary, metastatic, and recurrent cancers.

In some embodiments, said pharmaceutical composition is for the treatment of a non-cancerous hyperproliferative disorder such as a benign tumor, for example but not limited to, for the treatment of a benign hyperplasia of the skin (e. g., psoriasis), breast, lung, kidney, pancreas, restenosis, or prostate (e. g., benign prostatic hypertrophy (BPH)).

In some embodiments, the invention provides pharmaceutical compositions for treating diseases or conditions related to an undesirable, over-active, harmful or deleterious immune response in a mammal. Such undesirable immune response can be associated with or result in e.g. asthma, emphysema, bronchitis, psoriasis, allergy, anaphylaxis, autoimmune diseases, rheumatoid arthritis, graft versus host disease, and lupus erythematosus. The pharmaceutical compositions of the present invention can be used to treat other respiratory diseases including but not limited to disease affecting the lobes of the lung, the pleural cavity, bronchial tubes, trachea, upper respiratory tract, or the nerves and muscle responsible for breathing.

The invention also provides compositions for the treatment of multiorgan failure.

The invention also provides compositions for the treatment of liver diseases (including diabetes), pancreatitis, gall bladder disease (including gallstones), or kidney disease (including proliferative glomerulonephritis and diabetes-induced renal disease) or pain in a mammal.

The invention further provides a composition for the prevention of blastocyte implantation in a mammal.

The invention also relates to a composition for treating a disease related to vasculogenesis or angiogenesis in a mammal, which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention further provides compositions for the treatment of disorders involving platelet aggregation or platelet adhesion, including but not limited to Bernard-Soulier syndrome, Glanzmann's thrombasthenia, Scott's syndrome, von Willebrand disease, Hermansky-Pudlak Syndrome, and Gray platelet syndrome.

In some embodiments, compositions are provided for treating a disease which is skeletal muscle atrophy, skeletal or muscle hypertrophy. The invention further provides compositions for the treatment of disorders that include but are not limited to cancers as discussed herein, transplantation-related disorders (e.g., lowering rejection rates, graft-versus-host disease, etc.), muscular sclerosis (MS), allergic disorders (e.g. arthritis, allergic encephalomyelitis) and other immunosuppressive-related disorders, metabolic disorders (e.g., diabetes), reducing intimal thickening following vascular injury, and misfolded protein disorders (e.g., Alzheimer's Disease, Gaucher's Disease, Parkinson's Disease, Huntington's Disease, cystic fibrosis, macular degeneration, retinitis pigmentosa, and prion disorders) (as mTOR inhibition can alleviate the effects of misfolded protein aggregates). The disorders also include hamartoma syndromes, such as tuberous sclerosis and Cowden Disease (also termed Cowden syndrome and multiple hamartoma syndrome)

In some embodiments, the invention provides a pharmaceutical composition for treating ophthalmic disorders. The composition is formulated for ocular administration and it contains an effective amount of a compound of the present invention and a pharmaceutical excipient suitable for ocular administration. Pharmaceutical compositions of the invention suitable for ocular administration can be presented as discrete dosage forms, such as drops or sprays each containing a predetermined amount of an active ingredient a solution, or a suspension in an aqueous or non-aqueous liquid, an oil-in-water emulsion, or a water-in-oil liquid emulsion. Eye drops may be prepared by dissolving the active ingredient in a sterile aqueous solution such as physiological saline, buffering solution, etc., or by combining powder compositions to be dissolved before use. Other vehicles may be chosen, as is known in the art, including but not limited to: balance salt solution, saline solution, water soluble polyethers such as polyethylene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The subject pharmaceutical compositions are typically formulated to provide a therapeutically effective amount of a compound of the present invention as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more compounds of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5 g, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (e.g., a compound) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration.

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts;

sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ϵ-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ϵ-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, antifoaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g., Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins, 2000; Martindale, *The Extra Pharmacopoeia*, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. No. 5,451,233; U.S. Pat. No. 5,040,548; U.S. Pat. No. 5,061,273; U.S. Pat. No. 5,496,346; U.S. Pat. No. 5,292,331; U.S. Pat. No. 5,674,278; U.S. Pat. No. 3,657,744; U.S. Pat. No. 4,739,762; U.S. Pat. No. 5,195,984; U.S. Pat. No. 5,292,331; U.S. Pat. No. 5,674,278; U.S. Pat. No. 5,879,382; U.S. Pat. No. 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include a compound or compounds of the present invention as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

The invention also provides methods of using the compounds or pharmaceutical compositions of the present invention to treat disease conditions, including but not limited to conditions implicated by mTORC1, mTORC2 and/or PI3-kinases malfunction.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related (e.g. Lymphoma and Kaposi's Sarcoma) or Viral-Induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention, or a pharmaceutically acceptable salt, ester, prodrug, solvate, hydrate or derivative thereof. diseases associated with malfunctioning of one or more types of mTOR (including Examples of autoimmune diseases includes but is are not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

In some embodiments, the method of treating inflammatory or autoimmune diseases comprises administering to a subject (e.g. a mammal) a therapeutically effective amount of one or more compounds of the present invention that selectively inhibit PI3Kδ and/or PI3K-γ as compared to all other type I PI3 kinases. Such selective inhibition of PI3Kδ and/or PI3K-γ may be advantageous for treating any of the diseases or conditions described herein. For example, selective inhibition of PI3Kδ may inhibit inflammatory responses associated with inflammatory diseases, autoimmune disease, or diseases related to an undesirable immune response including but not limited to asthma, emphysema, allergy, dermatitis, rheumatoid arthritis, psoriasis, lupus erythematosus, or graft versus host disease. Selective inhibition of PI3Kδ may further provide for a reduction in the inflammatory or undesirable immune response without a concomitant reduction in the ability to reduce a bacterial, viral, and/or fungal infection. Selective inhibition of both PI3Kδ and PI3K-γ may be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one of more of the subject methods are effective in ameliorating symptoms associated with rheumatoid arthritis including but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 5%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 30%, 40%, 50%, 60%, 75%, 80%, 90% or more.

In other embodiments, the present invention provides methods of using the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the compounds described herein are used for the treatment of asthma. Also, the compounds or pharmaceutical compositions described herein may be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

The invention also relates to a method of treating diseases related to vasculogenesis or angiogenesis in a mammal that comprises administering to said mammal a therapeutically effective amount of a compound of the invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Subjects that can be treated with compounds of the invention, or pharmaceutically acceptable salt, ester, prodrug, solvate, hydrate or derivative of said compounds, according to the methods of this invention include, for example, subjects that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotrophic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer The invention also relates to a method of treating diabetes in a mammal that comprises administering to said mammal a therapeutically effective amount of a compound of the invention, or a pharmaceutically acceptable salt, ester, prodrug, solvate, hydrate or derivative thereof.

In addition, the compounds described herein may be used to treat acne.

In addition, the compounds described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compounds described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barré syndrome (GBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a compound of the invention, or a pharmaceutically acceptable salt, ester, prodrug, solvate, hydrate or derivative thereof. Examples of cardiovascular conditions include, but are not limited to, atherosclerosis, restenosis, vascular occlusion and carotid obstructive disease.

In another aspect, the invention provides methods of disrupting the function of a leukocyte or disrupting a function of an osteoclast. The method includes contacting the leukocyte or the osteoclast with a function disrupting amount of a compound of the invention.

In another aspect of the present invention, methods are provided for treating ophthalmic disease by administering one or more compounds of the invention or pharmaceutical compositions to the eye of a subject.

Methods are further provided for administering the compounds of the present invention via eye drop, intraocular injection, intravitreal injection, topically, or through the use of a drug eluting device, microcapsule, implant, or microfluidic device. In some cases, the compounds of the present invention are administered with a carrier or excipient that increases the intraocular penetrance of the compound such as an oil and water emulsion with colloid particles having an oily core surrounded by an interfacial film. It is contemplated that all local routes to the eye may be used including topical, subconjunctival, periocular, retrobulbar, subtenon, intracameral, intravitreal, intraocular, subretinal, juxtascleral and suprachoroidal administration. Systemic or parenteral administration may be feasible including but not limited to intravenous, subcutaneous, and oral delivery. An exemplary method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel or cream formulation.

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quaternary ammonium compound, a cationic lipid, an amino alcohol, a biguanidine salt, a cationic compound or a mixture thereof. In some cases the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, rnyristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising polyoxyl-40 hydrogenated castor oil, polyoxyl-60 hydrogenated castor oil or polyoxyl-100 hydrogenated castor oil.

The invention further provides methods of modulating a PI3K and/or mTor kinase activity by contacting the kinase with an effective amount of a compound of the invention. Modulation can be inhibiting or activating kinase activity. In some embodiments, the invention provides methods of inhibiting kinase activity by contacting the kinase with an effective amount of a compound of the invention in solution. In some embodiments, the invention provides methods of inhibiting the kinase activity by contacting a cell, tissue, organ that express the kinase of interest. In some embodiments, the invention provides methods of inhibiting kinase activity in subject including but not limited to rodents and mammal (e.g., human) by administering into the subject an effective amount of a compound of the invention. In some embodiments, the percentage of inhibiting exceeds 25%, 30%, 40%, 50%, 60%, 70%, 80%, or 90%.

In some embodiments, the kinase is selected from the group consisting of mTor, including different isoforms such as mTORC1 and mTORC2; PI3 kinase including different isoforms such as PI3 kinase α, PI3 kinase β, PI3 kinase γ, PI3 kinase δ; DNA-PK; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Inulsin Receptor (IR) and IGFR.

The invention further provides methods of modulating mTOR activity by contacting mTOR with an amount of a compound of the invention sufficient to modulate the activity of mTOR. Modulate can be inhibiting or activating mTOR activity. In some embodiments, the invention provides methods of inhibiting mTOR by contacting mTOR with an amount of a compound of the invention sufficient to inhibit the activity of mTOR. In some embodiments, the invention provides methods of inhibiting mTOR activity in a solution by contacting said solution with an amount of a compound of the invention sufficient to inhibit the activity of mTOR in said solution. In some embodiments, the invention provides methods of inhibiting mTOR activity in a cell by contacting said cell with an amount of a compound of the invention sufficient to inhibit the activity of mTOR in said cell. In some embodiments, the invention provides methods of inhibiting mTOR activity in a tissue by contacting said tissue with an amount of a compound of the invention sufficient to inhibit the activity of mTOR in said tissue. In some embodiments, the invention provides methods of inhibiting mTOR activity in an organism by contacting said organism with an amount of a compound of the invention sufficient to inhibit the activity of mTOR in said organism. In some embodiments, the invention provides methods of inhibiting mTOR activity in an animal by contacting said animal with an amount of a compound of the invention sufficient to inhibit the activity of mTOR in said animal. In some embodiments, the invention provides methods of inhibiting mTOR activity in a mammal by contacting said mammal with an amount of a compound of the invention sufficient to inhibit the activity of mTOR in said mammal. In some embodiments, the invention provides methods of inhibiting mTOR activity in a human by contacting said human with an amount of a compound of the invention sufficient to inhibit the activity of mTOR in said human. The present invention provides methods of treating a disease mediated by mTOR activity in a subject in need of such treatment.

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, hydrate or derivative thereof. In one aspect, such therapy includes but is not limited to the combination of one or more compounds of the invention with chemotherapeutic agents, therapeutic antibodies, and radiation treatment, to provide a synergistic or additive therapeutic effect.

In one aspect, the compounds or pharmaceutical compositions of the invention may present synergistic or additive efficacy when administered in combination with agents that inhibit IgE production or activity. Such combination can reduce the undesired effect of high level of IgE associated with the use of one or more PI3Kδ inhibitors, if such effect occurs. This may be particularly useful in treatment of autoimmune and inflammatory disorders (AIID) such as rheumatoid arthritis.

Additionally, the administration of PI3Kδ or PI3Kδ/γ inhibitors of the invention in combination with inhibitors of mTOR may also exhibit synergy through enhanced inhibition of the PI3K pathway.

In a separate but related aspect, the invention provides a combination treatment of a disease associated with PI3Kδ comprising administering to a PI3Kδ inhibitor and an agent that inhibits IgE production or activity. Other exemplary PI3Kδ inhibitors are applicable and they are described, e.g., U.S. Pat. No. 6,800,620. Such combination treatment is particularly useful for treating autoimmune and inflammatory diseases (AIID) including but not limited to rheumatoid arthritis.

Agents that inhibit IgE production are known in the art and they include but are not limited to one or more of TEI-9874, 2-(4-(6-cyclohexyloxy-2-napthyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

For treatment of autoimmune diseases, the compounds of the invention or pharmaceutical compositions can be used in combination with commonly prescribed drugs including but not limited to Enbrel®, Remicade®, Humira®, Avonex®, and Rebif®. For treatment of respiratory diseases, the compounds of the invention or pharmaceutical compositions can be administered in combination with commonly prescribed drugs including but not limited to Xolair®, Advair®, Singulair®, and Spiriva®.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin.

In another aspect, this invention also relates to methods and pharmaceutical compositions for inhibiting abnormal cell growth in a mammal which comprises an amount of a compound of the invention, or a pharmaceutically acceptable salt, ester, prodrug, solvate, hydrate or derivative thereof, in combination with an amount of an anti-cancer agent (e.g. a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126, and Zosuquidar.

This invention further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the invention can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloprotienase 9) inhibitors, and COX-11 (cyclooxygenase 11) inhibitors, can be used in conjunction with a compound of the invention and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

The invention also relates to a method of and to a pharmaceutical composition for treating a cardiovascular disease in a mammal which comprises an amount of a compound of the invention, or a pharmaceutically acceptable salt, ester, prodrug, solvate, hydrate or derivative thereof, or an isotopically-labeled derivative thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

The compounds described herein may be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which may be administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]

methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a compound of the invention include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a compound of the invention may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the one or more compounds of the invention will be co-administer with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the invention and any of the agents described above can be simultaneously administered, wherein both the agents are present in separate formulations. In another alternative, a compound of the present invention can be administered just followed by and any of the agents described above, or vice versa. In the separate administration protocol, a compound of the invention and any of the agents described above may be administered a few minutes apart, or a few hours apart, or a few days apart.

Administration of the compounds of the present invention can be effected by any method that enables delivery of the compounds to the site of action. An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

When a compound of the invention, is administered in a composition that comprises one or more agents, and the agent has a shorter half-life than the compound of the invention, unit dose forms of the agent and the compound of the invention may be adjusted accordingly.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

Expression and Inhibition Assays of p110α/p85α, p110β/p85α, p110δ/p85α, and p110γ

Class I PI3-Ks can be either purchased (p110α/p85α, p110β/p85α, p110δ/p85α from Upstate, and p110γ from Sigma) or expressed as previously described (Knight et al., 2004). IC50 values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM MgCl2), and freshly sonicated phosphatidylinositol (100 μg/ml). Reactions are initiated by the addition of ATP containing 10 μCi of γ-32P-ATP to a final concentration 10 or 100 μM and allowed to proceed for 5 minutes at room temperature. For TLC analysis, reactions are then terminated by the addition of 105 μl 1N HCl followed by 160 μl CHCl3:MeOH (1:1). The biphasic mixture is vortexed, briefly centrifuged, and the organic phase is transferred to a new tube using a gel loading pipette tip precoated with CHCl3. This extract is spotted on TLC plates and developed for 3-4 hours in a 65:35 solution of n-propanol:1M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 μM). For compounds showing significant activity, IC50 determinations are repeated two to four times, and the reported value is the average of these independent measurements.

Other commercial kits or systems for assaying PI3-K activities are available. The commercially available kits or systems can be used to screen for inhibitors and/or agonists of PI3-Ks including but not limited to PI 3-Kinase α, β, δ, and γ. An exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtitre plate (e.g., a 384 well microtitre plate). The total reaction volume is approximately 20 ul per well. In the first step, each well receives 2 ul of test compound in 20% dimethylsulphoxide resulting in a 2% DMSO final concentration. Next, approximately 14.5 ul of a kinase/PIP2 mixture (diluted in 1× reaction buffer) is added per well for a final concentration of 0.25-0.3 ug/ml kinase and 10 uM PIP2. The plate is sealed and incubated for 15 minutes at room temperature. To start the reaction, 3.5 ul of ATP (diluted in 1× reaction buffer) is added per well for a final concentration of 10 uM ATP. The plate is sealed and incubated for 1 hour at room temperature. The reaction is stopped by adding 5 ul of Stop Solution per well and then 5 ul of Detection Mix is added per well. The plate is sealed, incubated for 1 hour at room temperature, and then read on an appropriate plate reader. Data is analyzed and IC50s are generated using GraphPad Prism 5.

Example 2

Expression and Inhibition Assays of Abl

The cross-activity or lack thereof of one or more compounds of the invention against Abl kinase can be measured according to any procedures known in the art or methods disclosed below. For example, the compounds described herein can be assayed in triplicate against recombinant full-length Abl or Abl (T315I) (Upstate) in an assay containing 25 mM HEPES, pH 7.4, 10 mM MgCl2, 200 μM ATP (2.5 μCi of γ-32P-ATP), and 0.5 mg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 3

Expression and Inhibition Assays of Hck

The cross-activity or lack thereof of one or more compounds of the invention against Hck kinase can be measured according to any procedures known in the art or methods disclosed below. The compounds described herein can be assayed in triplicate against recombinant full-length Hck in an assay containing 25 mM HEPES, pH 7.4, 10 mM MgCl2, 200 µM ATP (2.5 µCi of γ-32P-ATP), and 0.5 mg/mL BSA. The optimized Src family kinase peptide substrate EIYGEFKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 4

Expression and Inhibition Assays of Inulsin Receptor (IR)

The cross-activity or lack thereof of one or more compounds of the invention against IR receptor kinase can be measured according to any procedures known in the art or methods disclosed below. The compounds described herein can be assayed in triplicate against recombinant insulin receptor kinase domain (Upstate) in an assay containing 25 mM HEPES, pH 7.4, 10 mM MgCl2, 10 mM MnCl2, 200 µM ATP (2.5 µCi of γ-32P-ATP), and 0.5 mg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 5

Expression and Inhibition Assays of Src

The cross-activity or lack thereof of one or more compounds of the invention against Src kinase can be measured according to any procedures known in the art or methods disclosed below. The compounds described herein can be assayed in triplicate against recombinant full-length Src or Src (T338I) in an assay containing 25 mM HEPES, pH 7.4, 10 mM MgCl2, 200 µM ATP (2.5 µCi of γ-32P-ATP), and 0.5 mg/mL BSA. The optimized Src family kinase peptide substrate EIYGEFKKK is used as phosphoacceptor (200 µM). Reactions are terminated by spotting onto phosphocellulose sheets, which are washed with 0.5% phosphoric acid (approximately 6 times, 5-10 minutes each). Sheets were dried and the transferred radioactivity quantitated by phosphorimaging.

Example 6

Expression and Inhibition Assays of DNA-PK (DNAK)

The cross-activity or lack thereof of one or more compounds of the invention against DNAK kinase can be measured according to any procedures known in the art. DNA-PK can be purchased from Promega and assayed using the DNA-PK Assay System (Promega) according to the manufacturer's instructions.

Example 7

Expression and Inhibition Assays mTOR

The ability of one or more compounds of the invention to inhibit mTor activity can be measured according to any procedures known in the art or methods disclosed below. The compounds described herein can be tested against recombinant mTOR (Invitrogen) in an assay containing 50 mM HEPES, pH 7.5, 1 mM EGTA, 10 mM MgCl2, 2.5 mM, 0.01% Tween, 10 µM ATP (2.5 µCi of µ-32P-ATP), and 3 µg/mL BSA. Rat recombinant PHAS-1/4EBP1 (Calbiochem; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Other kits or systems for assaying mTOR activity are commercially available. For instance, one can use Invitrogen's LanthaScreen™ Kinase assay to test the inhibitors of mTOR disclosed herein. This assay is a time resolved FRET platform that measures the phosphorylation of GFP labeled 4EBP1 by mTOR kinase. The kinase reaction is performed in a white 384 well microtitre plate. The total reaction volume is 20 ul per well and the reaction buffer composition is 50 mM HEPES pH 7.5, 0.01% Polysorbate 20, 1 mM EGTA, 10 mM MnCl2, and 2 mM DTT. In the first step, each well receives 2 ul of test compound in 20% dimethylsulphoxide resulting in a 2% DMSO final concentration. Next, 8 ul of mTOR diluted in reaction buffer is added per well for a 60 ng/ml final concentration. To start the reaction, 10 ul of an ATP/GFP-4EBP1 mixture (diluted in reaction buffer) is added per well for a final concentration of 10 uM ATP and 0.5 uM GFP-4EBP1. The plate is sealed and incubated for 1 hour at room temperature. The reaction is stopped by adding 10 ul per well of a Tb-anti-pT46 4EBP1 antibody/EDTA mixture (diluted in TR-FRET buffer) for a final concentration of 1.3 nM antibody and 6.7 mM EDTA. The plate is sealed, incubated for 1 hour at room temperature, and then read on a plate reader set up for LanthaScreen™ TR-FRET. Data is analyzed and IC50s are generated using GraphPad Prism 5.

Example 8

Expression and Inhibition Assays of Vascular Endothelial Growth Receptor

The cross-activity or lack thereof of one or more compounds of the invention against VEGF receptor can be measured according to any procedures known in the art or methods disclosed below. The compounds described herein can be tested against recombinant KDR receptor kinase domain (Invitrogen) in an assay containing 25 mM HEPES, pH 7.4, 10 mM MgCl2, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 9

Expression and Inhibition Assays of Ephrin Receptor B4 (EphB4)

The cross-activity or lack thereof of one or more compounds of the invention against EphB4 can be measured according to any procedures known in the art or methods disclosed below. The compounds described herein can be tested against recombinant Ephrin receptor B4 kinase domain (Invitrogen) in an assay containing 25 mM HEPES, pH 7.4, 10 mM MgCl2, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 10

Expression and Inhibition Assays of Epidermal Growth Factor Receptor (EGFR)

The cross-activity or lack thereof of one or more compounds of the invention against EGFR kinase can be measured according to any procedures known in the art or methods disclosed below. The compounds described herein can be tested against recombinant EGF receptor kinase domain (Invitrogen) in an assay containing 25 mM HEPES, pH 7.4, 10 mM MgCl2, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 11

Expression and Inhibition Assays of KIT Assay

The cross-activity or lack thereof of one or more compounds of the invention against KIT kinase can be measured according to any procedures known in the art or methods disclosed below. The compounds described herein can be tested against recombinant KIT kinase domain (Invitrogen) in an assay containing 25 mM HEPES, pH 7.4, 10 mM MgCl2, 1 mM DTT, 10 mM MnCl2, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 12

Expression and Inhibition Assays of RET

The cross-activity or lack thereof of one or more compounds of the invention against RET kinase can be measured according to any procedures known in the art or methods disclosed below. The compounds described herein can be tested against recombinant RET kinase domain (Invitrogen) in an assay containing 25 mM HEPES, pH 7.4, 10 mM MgCl2, 2.5 mM DTT, 10 µM ATP (2.5 µCi of µ-32P-ATP), and 3 µg/mL BSA. The optimized Abl peptide substrate EAIYAAPFAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 13

Expression and Inhibition Assays of Platelet Derived Growth Factor Receptor (PDGFR)

The cross-activity or lack thereof of one or more compounds of the invention against PDGFR kinase can be measured according to any procedures known in the art or methods disclosed below. The compounds described herein can be tested against recombinant PDG receptor kinase domain (Invitrogen) in an assay containing 25 mM HEPES, pH 7.4, 10 mM MgCl2, 2.5 mM DTT, 10 µM ATP (2.5 µCi of µ-32P-ATP), and 3 µg/mL BSA. The optimized Abl peptide substrate EAIYAAPFAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 14

Expression and Inhibition Assays of FMS-Related Tyrosine Kinase 3 (FLT-3)

The cross-activity or lack thereof of one or more compounds of the invention against FLT-3 kinase can be measured according to any procedures known in the art or methods disclosed below. The compounds described herein can be tested against recombinant FLT-3 kinase domain (Invitrogen) in an assay containing 25 mM HEPES, MgCl2, 2 mM DTT, 10 mM MnCl2, 10 µM ATP (2.5 µCi of µ-32P-ATP), and 3 µg/mL BSA. Poly E-Y (Sigma; 2 mg/mL) is substrate EAIYAAPFAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 15

Expression and Inhibition Assays of TEK Receptor Tyrosine Kinase (TIE2)

The cross-activity or lack thereof of one or more compounds of the invention against TIE2 kinase can be measured according to any procedures known in the art or methods disclosed below. The compounds described herein can be tested against recombinant TIE2 kinase domain (Invitrogen) in an assay containing 25 mM HEPES, pH 7.4, 10 mM MgCl2, 2 mM DTT, 10 mM MnCl2, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 16

B Cell Activation and Proliferation Assay

The ability of one or more compounds of the invention to inhibit B cell activation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Plaque™ PLUS gradient followed by magnetic cell separation using a MACS B cell Isolation Kit (Miletenyi). Cells are plated in 90 ul at 50,000 cells/well in B Cell Media (RPMI+ 10% FBS+Penn/Strep+50 uM bME+5 mM HEPES). A compound disclosed herein is diluted in B Cell Media and added in a 10 ul volume. Plates are incubated for 30 min at 37 C and 5% $CO_2$ (0.2% DMSO final concentration). A 50 ul B cell stimulation cocktail is then added containing either 10 ug/ml LPS or 5 ug/ml F(ab')2 Donkey anti-mouse IgM plus 2 ng/ml recombinant mouse IL4 in B Cell Media. Plates are incubated for 72 hours at 37° C. and 5% $CO_2$. A volume of 15 uL of Alamar Blue reagent is added to each well and plates are incubated for 5 hours at 37° C. and 5% $CO_2$. Alamar Blue fluoresce is read at 560Ex/590Em, and IC50 or EC50 values are calculated using GraphPad Prism 5.

Example 17

Tumor Cell Line Proliferation Assay

The ability of one or more compounds of the invention to inhibit tumor cell line proliferation is determined according to standard procedures known in the art. For instance, an in vitro cellular proliferation assay can be performed to measure the metabolic activity of live cells. The assay is performed in a 96 well microtiter plate using Alamar Blue reduction. Human tumor cell lines are obtained from ATCC (e.g., MCF7, U-87 MG, MDA-MB-468, PC-3, and any other cell lines listed in FIG. 1A-B), grown to confluency in T75 flasks, trypsinized with 0.25% trypsin, washed one time with Tumor Cell Media (DMEM+10% FBS), and plated in 90 ul at 5,000 cells/well in Tumor Cell Media. A compound disclosed herein is diluted in Tumor Cell Media and added in a 10 ul volume. Plates are incubated for 72 hours at 37 C and 5% $CO_2$. A volume of 10 uL of Alamar Blue reagent is added to each well and plates are incubated for 3 hours at 37 C and 5% $CO_2$. Alamar Blue fluoresce is read at 560Ex/590Em, and IC50 values are calculated using GraphPad Prism 5. The results depicted in FIG. 1A, FIG. 1B and FIG. 7A show that a compound of the present invention effectively inhibits proliferation of a wide range of tumor cells. In some instance, the compound of the invention yields 50% inhibition of cell proliferation at a concentration that is one or two orders of magnitude less than that of a conventional anti-cancer drug when tested under the same condition.

Example 18

Antitumor Activity In Vivo

The compounds described herein can be evaluated in a panel of human and murine tumor models.
Paclitaxel-Refractory Tumor Models
1. Clinically-Derived Ovarian Carcinoma Model.

This tumor model is established from a tumor biopsy of an ovarian cancer patient. Tumor biopsy is taken from the patient.

The compounds described herein are administered to nude mice bearing staged tumors using an every 2 days×5 schedule.

2. A2780Tax Human Ovarian Carcinoma Xenograft (Mutated Tubulin).

A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein.

The compounds described herein can be administered to mice bearing staged tumors on an every 2 days×5 schedule.

3. HCT116/VM46 Human Colon Carcinoma Xenograft (Multi-Drug Resistant).

HCT116/VM46 is an MDR-resistant colon carcinoma developed from the sensitive HCT116 parent line. In vivo, grown in nude mice, HCT116/VM46 has consistently demonstrated high resistance to paclitaxel.

The compounds described herein can be administered to mice bearing staged tumors on an every 2 days×5 schedule.

5. M5076 Murine Sarcoma Model

M5076 is a mouse fibrosarcoma that is inherently refractory to paclitaxel in vivo.

The compounds described herein can be administered to mice bearing staged tumors on an every 2 days×5 schedule.

One or more compounds of the invention can be used in combination other therapeutic agents in vivo in the multidrug resistant human colon carcinoma xenografts HCT/VM46 or any other model known in the art including those described herein.

It is expected that one or more compounds of the present invention are potent inhibitors of tumor growth in vivo under the conditions tested.

Example 19

Microsome Stability Assay

The stability of one or more compounds of the invention is determined according to standard procedures known in the art. For example, stability of one or more compounds of the invention is established by an in vitro assay. In particular, an in vitro microsome stability assay is established that measures stability of one or more compounds of the invention when reacting with mouse, rat or human microsomes from liver. The microsome reaction with compounds is performed in 1.5 mL Eppendorf tube. Each tube contains 0.1 µL of 10.0 mg/ml NADPH; 75 µL of 20.0 mg/ml mouse, rat or human liver microsome; 0.4 µL of 0.2 M phosphate buffer, and 425 µL of $ddH_2O$. Negative control (without NADPH) tube contains 75 µL of 20.0 mg/ml mouse, rat or human liver microsome; 0.4 µL of 0.2 M phosphate buffer, and 525 µL of $ddH_2O$. The reaction is started by adding 1.0 µL of 10.0 mM tested compound. The reaction tubes are incubated at 37° C. 100 µL sample is collected into new Eppendorf tube containing 300 µL cold Methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS). The microsome stability of one or more compounds of the present invention when assayed under this condition have T½ (min) well within a range required for clinical development.

Example 20

Plasma Stability Assay

The stability of one or more compounds of the invention in plasma is determined according to standard procedures known in the art. See, e.g., *Rapid Commun. Mass Spectrom.*, 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A compound of the invention is added from a 400 M stock solution to an aliquot of pre-warmed plasma to give a final assay volume of 400 µL (or 800 µL for half-life determination), containing 5 M test compound and 0.5% DMSO. Reactions are incubated, with shaking, for 0 minutes and 60 minutes at 37° C., or for 0, 15, 30, 45 and 60 minutes at 37° C. for half life determination. Reactions are stopped by transferring 50 µL of the incubation mixture to 200 µL of ice-cold acetonitrile and mixed by shaking for 5 minutes. The samples are centrifuged at 6000×g for 15 minutes at 4° C. and 120 µL of supernatant removed into clean tubes. The samples are then evaporated to dryness and submitted for analysis by HPLC-MS/MS.

Where desired, one or more control or reference compounds (5 M) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 21

Chemical Stability

The chemical stability of one or more compounds of the invention is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A compound of the invention is added from a 100 M stock solution to an aliquot of PBS (in duplicate) to give a final assay volume of 400 µL, containing 5 M test compound and 1% DMSO (for half-life determination a total sample volume of 700 µL is prepared). Reactions are incubated, with shaking, for 0 minutes and 24 hours at 37° C.; for half-life determination samples are incubated for 0, 2, 4, 6, and 24 hours. Reactions are stopped by adding immediately 100 µL of the incubation mixture to 100 µL of acetonitrile and vortexing for 5 minutes. The samples are then stored at −20° C. until analysis by HPLC-MS/MS. Where desired, a control compound or a reference compound such as chlorambucil (5 M) is tested simultaneously with a compound of the invention of interest, as this compound is largely hydrolyzed over the course of 24 hours. Samples are analyzed via (RP) HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 22

Akt Kinase Assay

Cells comprising components of the Akt/mTOR pathway, including but not limited to L6 myoblasts, B-ALL cells, B-cells, T-cells, leukemia cells, bone marrow cells, p190 transduced cells, Philadelphia chromosome positive cells (Ph+), and mouse embryonic fibroblasts, are typically grown in cell growth media such as DMEM supplemented with fetal bovine serum and/or antibiotics, and grown to confluency.

In order to compare the effect of one or more compounds disclosed herein on Akt activation, the selected cells are serum starved overnight and incubated with one or more compounds disclosed herein or about 0.1% DMSO for approximately 1 minute to about 1 hour prior to stimulation with insulin (e.g. 100 nM) for about 1 minutes to about 1 hour. Cells are lysed by scraping into ice cold lysis buffer containing detergents such as sodium dodecyl sulfate and protease inhibitors (e.g., PMSF). After contacting cells with lysis buffer, the solution is briefly sonicated, cleared by centrifugation, resolved by SDS-PAGE, transferred to nitrocellulose or PVDF and immunoblotted using antibodies to phospho-Akt S473, phospho-Akt T308, Akt, and 3-actin (Cell Signaling Technologies).

The results demonstrate that one or more compounds of the invention inhibit insulin stimulated phosphorylation of Akt at S473. Alternatively, some compounds of the invention additionally inhibit insulin stimulated phosphorylation of Akt at T308. The class of compounds that can inhibit Akt signalling more effectively than rapamycin as shown herein include those (e.g., compounds shown in Table 1) that inhibit mTORC2 and mTORC1.

Example 23

Kinase Signaling in Blood

PI3K/Akt/mTor signaling is measured in blood cells using the phosflow method (Methods Enzymol. 2007; 434:131-54). The advantage of this method is that it is by nature a single cell assay so that cellular heterogeneity can be detected rather than population averages. This allows concurrent distinction of signaling states in different populations defined by other markers. Phosflow is also highly quantitative. To test the effects of one or more compounds of the invention, unfractionated splenocytes, or peripheral blood mononuclear cells are stimulated with anti-CD3 to initiate T-cell receptor signaling. The cells are then fixed and stained for surface markers and intracellular phosphoproteins. It is expected that inhibitors disclosed herein inhibit anti-CD3 mediated phosphorylation of Akt-S473 and S6, whereas rapamycin inhibits S6 phosphorylation and enhances Akt phosphorylation under the conditions tested.

Similarly, aliquots of whole blood are incubated for 15 minutes with vehicle (e.g. 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g. with cold 4% paraformaldehyde) and used for phosflow. Surface staining is used to distinguish T and B cells using antibodies directed to cell surface markers that are known to the art. The level of phosphylation of kinase substrates such as Akt and S6 are then measured by incubating the fixed cells with labeled antibodies specific to the phosphorylated isoforms of these proteins. The population of cells is then analyzed by flow cytometry. The results are expected to show that one or more of the compounds of the invention can selectively inhibit signaling of one or more members of PI3K, mTOR, and Akt in blood cells under the conditions tested.

Example 24

Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope. It is expected that compounds of the invention potentiate the effects of a half maximal concentration of known chemotherapeutic agents such as and without limitation imatinib, rapamycin, and dasatinib at the concentrations examined.

Alternatively, human peripheral blood mononuclear cells are obtained from Philadelphia chromosome positive (Ph+) and negative (Ph−) subjects upon initial diagnosis or relapse. Live cells are isolated and enriched for CD19+CD34+B cell progenitors. After overnight liquid culture, cells are plated in methocult GF+H4435, Stem Cell Technologies) supplemented with cytokines (IL-3, IL-6, IL-7, G-CSF, GM-CSF, CF, Flt3 ligand, and erythropoietin) and various concentrations of known chemotherapeutic agents in combination with either compounds of the invention. Colonies are counted by microscopy 12-14 days later. This method can be used to test for the additive or synergistic activity of various combination therapies utilizing the subject composition. It is expected that one or more the compounds of the present invention are potent and selective inhibitors of p190 transduced cell colony formation under the conditions tested.

Example 25

In Vivo Effect of Kinase Inhibitors on Leukemic Cells

Female recipient mice are lethally irradiated from a γ source in two doses about 4 hr apart, with approximately 5 Gy each. About 1 hr after the second radiation dose, mice are injected i.v. with about $1 \times 10^6$ leukemic cells (e.g. Ph+ human or murine cells, or p190 transduced bone marrow cells). These cells are administered together with a radioprotective dose of about $5 \times 10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about 10 days after leukemic cell injection and continues daily until the mice become sick or a maximum of approximately 35 days post-transplant. Inhibitors are given by oral lavage.

Peripheral blood cells are collected approximately on day 10 (pre-treatment) and upon euthanization (post treatment), contacted with labeled anti-hCD4 antibodies and counted by flow cytometry. This method can be used to demonstrate that the synergistic effect of one or more compounds of the invention alone or in combination with known chemotherapeutic agents significantly reduce leukemic blood cell counts as compared to treatment with known chemotherapeutic agents (e.g. Gleevec) alone under the conditions tested.

Example 26

Inhibition of Proliferation of Tumor Cells Deficient in PTEN Activity but Expressing PI3-Kinases The ability of one or more compounds of the invention to inhibit proliferation of tumor cells deficient in PTEN Activity but expressing PI3-kinases is tested according to the procedure detailed in example 17. As is shown in FIG. 7A, a compound of the present invention (e.g., a compound of Table 1) yields 50% inhibition of PC-3 cell proliferation at a concentration that is at least about two orders of magnitude less as compared to rapamycin.

Western blot analysis revealed that the compound of the invention is capable of inhibiting phosphorylation of AKT (S473) and AKT (T308) as well as other downstream targets of the mTor signaling pathway to a greater degree than rapamycin. See FIG. 7B. In particular, PC-3 cells were plated at about $1 \times 10^5$ cells/well in 24 well plates in a culture media containing 10% FBS. The cells were allowed to grow to about 80% confluent. Cells were treated for 2 hours at 37° C. in $CO_2$ incubator with fresh cell culture media (10% FBS) with a compound of the present invention or rapamycin at indicated concentrations. After incubation, cells were lysed by adding 1× Cell Lysis Buffer (200 µl per well of 24-well plate of confluent cells). Proteins were separated via SDS-PAGE on 4-20% gradient gels and standard semi-dry blotting techniques are used to transfer the protein to nitrocellulose membranes. p-AKT(473), p-S6K, and µ-4EBP1 were detected by using rabbit anti-human primary antibodies (Cell Signaling, Danvers, Mass.) followed by an HRP-conjugated anti-rabbit secondary antibody (Cell Signaling, Danvers, Mass.). The LumiGLO substrate (KPL, Inc., Gaithersburg, Md.) is used to detect the phospho-proteins on the Western blot.

Example 27

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus subjects show decreased expression or function of FcγRIIb (S. Bolland and J. V. Ravtech 2000. *Immunity* 12:277-285).

The R2KO mice develop lupus-like disease with anti-nuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.Sle1z.Sle3z model (T. Wu et al. *J. Clin Invest.* 117:2186-2196).

Lupus disease model mice such as R2KO, BXSB or MLR/lpr are treated at about 2 months old, approximately for about two months. Mice are given doses of: vehicle, RAD001 at about 10 mg/kg, or compounds disclosed herein at approximately 10 mg/kg to about 50 mg/kg. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA. Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This model established in the art can be employed to test that the kinase inhibitors disclosed herein can suppress or delay the onset of lupus symptoms in lupus disease model mice.

Example 28

Murine Bone Marrow Transplant Assay

Female recipient mice are lethally irradiated from a γ ray source. About 1 hr after the radiation dose, mice are injected with about 1×106 leukemic cells from early passage p190 transduced cultures (e.g. as described in *Cancer Genet Cytogenet.* 2005 August; 161(1):51-6). These cells are administered together with a radioprotective dose of approximately 5×106 normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment a dose of chemotherapeutic that is not curative but delays leukemia onset by about one week or less is identified; controls are vehicle-treated or treated with chemotherapeutic agent, previously shown to delay but not cure leukemogenesis in this model (e.g. imatinib at about 70 mg/kg twice daily). For the first phase p190 cells that express eGFP are used, and post-mortem analysis is limited to enumeration of the percentage of leukemic cells in bone marrow, spleen and lymph node (LN) by flow cytometry. In the second phase, p190 cells that express a tailless form of human CD4 are used and the post-mortem analysis includes magnetic sorting of hCD4+ cells from spleen followed by immunoblot analysis of key signaling endpoints: p Akt-T308 and S473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 µl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein. It is expected that the results of the analysis demonstrate effective therapeutic doses of the compounds disclosed herein for inhibiting the proliferation of leukemic cells. It is further expected that combination therapy of the inhibitors disclosed herein with other chemotherapeutic agents including but not limited to those disclosed herein (e.g. Gleevec and dasatinib) exhibit a greater degree of efficacy or decreased toxicity in comparison to the use of a single chemotherapeutic agent.

Example 29

Rodent Pharmacokinetic Assay

In order to study the pharmacokinetics of the compounds of the invention a set of 4-10 week old mice are grouped according to the following table:

| Group# | Mice/group | Compound Administration from day-1 to day-7 | | |
|---|---|---|---|---|
| | | (mg/kg) | Route | Regimen |
| 1 | 3 | 1 | Po | BID for 7 days |
| 2 | 3 | 3 | | |
| 3 | 3 | 10 | | |
| 4 | 3 | 30 | | |
| 5 | 3 | 60 | | |

Alternatively, compounds are dosed acutely (e.g. once) and after a time (e.g. about 0, 30 s, 1 m, 5 m, 10 m, 20 m, 30 m, 1 hr, 2 hr, 3 hr, 5 hr, 8 hr, 10 hr, 12 hr, 1 d, 2 d, etc.) blood is collected and analyzed as described below.

Compounds of the invention are dissolved in an appropriate vehicle (e.g. 5% 1-methyl-2-pyrrolidinone, 85% polyethylene glycol 400, 10% Solutor) and administered orally at 12 hour intervals daily. All animals are euthanized in $CO_2$ 2 hours after the final compound is administered. Blood is collected immediately and kept on ice for plasma isolation. Plasma is isolated by centrifuging at 5000 rpm for 10 minutes. Harvested plasma is frozen for pharmacokinetic detection.

The results are expected to demonstrate the pharmacokinetic parameters such as absorption, distribution, metabolism, excretion, and toxicity for the compounds of the invention.

Example 30

Combination Use of PI3Kδ Inhibitors and Agents that Inhibit IgE Production or Activity The compounds of the invention may present synergistic or additive efficacy when administered in combination with an inhibitors selective for one or more PI3-kinase, e.g., PI3Kδ.

PI3Kδ inhibitors may be efficacious in treatment of autoimmune and inflammatory disorders (AIID) for example rheumatoid arthritis. When a PI3Kδ inhibitor cause an undesired level of IgE production, one may choose to administer it in combination with an agent that inhibits IgE production or IgE activity such as an mTORC1 and/or mTORC2 inhibitor disclosed herein. Additionally, the administration of PI3Kδ or PI3Kδ/γ inhibitors in combination with inhibitors of mTOR may also exhibit synergy through enhanced inhibition of the PI3K pathway. Various in vivo and in vitro models may be used to establish the effect of such combination treatment on AIID including but not limited to (a) in vitro B-cell antibody production assay, (b) in vivo TNP assay, and (c) rodent collagen induced arthritis model.

(a) B-Cell Assay

Mice are euthanized, and the spleens are removed and dispersed through a nylon mesh to generate a single-cell suspension. The splenocytes are washed (following removal of erythrocytes by osmotic shock) and incubated with anti-CD43 and anti-Mac-1 antibody-conjugated microbeads (Miltenyi Biotec). The bead-bound cells are separated from unbound cells using a magnetic cell sorter. The magnetized column retains the unwanted cells and the resting B cells are collected in the flow-through. Purified B-cells are stimulated with lipopolysaccharide or an anti-CD40 antibody and interleukin 4. Stimulated B-cells are treated with vehicle alone or with a PI3Kδ inhibitor with and without mTOR inhibitors such as rapamycin, rapalogs, or mTORC1/C2 inhibitors disclosed herein. The results are expected to show that in the presence of mTOR inhibitors alone (e.g., rapamycin as well as the subject inhibitors capable of inhibiting both mTORC1 and mTORC2), there is little to no substantial effect on IgG and IgE response. However, in the presence of PI3Kδ and mTOR inhibitors, the B-cells are expected to exhibit a decreased IgG response as compared to the B-cells treated with vehicle alone, and the B-cells are expected to exhibit a decreased IgE response as compared to the response from B-cells treated with PI3Kδ inhibitors alone.

(b) TNP Assay

Mice are immunized with TNP-Ficoll or TNP-KHL and treated with: vehicle, a PI3Kδ inhibitor, an mTOR inhibitor, for example rapamycin, or a PI3Kδ inhibitor in combination with an mTOR inhibitor such as rapamycin. Antigen-specific serum IgE is measured by ELISA using TNP-BSA coated plates and isotype specific labeled antibodies. This assay can be used to test that mice treated with an mTOR inhibitor alone exhibit little or no substantial effect on antigen specific IgG3 response and no statistically significant elevation in IgE response as compared to the vehicle control. This assay can also be used to test that mice treated with both PI3Kδ inhibitor and mTOR inhibitor exhibit a reduction in antigen specific IgG3 response as compared to the mice treated with vehicle alone. Additionally, this assay can be employed to test that the mice treated with both PI3Kδ inhibitor and mTOR inhibitor exhibit a decrease in IgE response as compared to the mice treated with PI3Kδ inhibitor alone.

(c) Rat Collagen Induced Arthritis Model

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats are randomized into treatment groups. Randomization is performed after ankle joint swelling is obviously established and there is good evidence of bilateral disease.

After an animal is selected for enrollment in the study, treatment is initiated. Animals are given vehicle, PI3Kδ inhibitor, or PI3Kδ inhibitor in combination with an mTOR inhibitor. Dosing is administered on days 1-6. Rats are weighed on days 1-7 following establishment of arthritis and caliper measurements of ankles taken every day. Final body weights are taken on day 7 and animals are euthanized.

This assay can be used to test that the combination treatment using PI3Kδ inhibitor and an inhibitor of mTOR provides greater efficacy than treatment with PI3Kδ inhibitor alone.

Example 31

Inhibition of Tumor Growth In Vivo

Cell Lines:

Tumor cell lines such as A549, U87, ZR-75-1 and 786-0 are obtained from American Type Culture Collection (ATCC, Manassas, Va.). Cells are proliferated and preserved cryogenically at early passage (e.g. passage 3). One aliquot is used for further proliferation to get enough cells for one TGI study (at about passage 9).

Animals

Female athymic nude mice are supplied by Harlan. Mice are received at 4 to 6 weeks of age. All mice are acclimated for about one day to two weeks prior to handling. The mice are housed in microisolator cages and maintained under specific pathogen-free conditions. The mice are fed with irradiated mouse chow and freely available autoclaved water is provided.

Tumor Xenograft Model:

Mice are inoculated subcutaneously in the right flank with 0.01 to 0.5 ml of tumor cells such as those listed above (approximately $1.0 \times 10^5$ to $1.0 \times 10^8$ cells/mouse). Five to 10 days following inoculation, tumors are measured using calipers and tumor weight is calculated, for example using the animal study management software, such as Study Director V.1.6.70 (Study Log). Mice with tumor sizes of about 120 mg are pair-matched into desired groups using Study Director (Day 1). Body weights are recorded when the mice are pair-matched. Tumor volume and bodyweight measurements are taken one to four times weekly and gross observations are made at least once daily. On Day 1, compounds of the present invention and reference compounds as well as vehicle control are administered by oral gavage or iv as indicated. At the last day of the experiment, mice are sacrificed and their tumors are collected 1-4 hours after the final dose. The tumors are excised and cut into two sections. One third of the tumor is fixed in formalin and embedded in paraffin blocks and the remaining two thirds of tumor is snap frozen and stored at −80° C.

Data and Statistical Analysis:

Mean tumor growth inhibition (TGI) is calculated utilizing the following formula:

Tumors that regress from the Day 1 starting size are removed from the calculations. Individual tumor shrinkage (TS) is calculated using the formula below for tumors that show regression relative to Day 1 tumor weight. The mean tumor shrinkage of each group is calculated and reported.

The model can be employed to show whether the compounds of the invention can inhibit tumor cell growth including but not limited to renal carcinoma cell growth, breast cancer cell growth, lung cancer cell growth, or glioblastoma cell growth under the conditions tested.

$$TS = \left[1 - \frac{(\text{Tumor Weight}_{(Final)})}{(\text{Tumor Weight}_{(Day\ 1)})}\right] \times 100\%$$

Figure 3A:
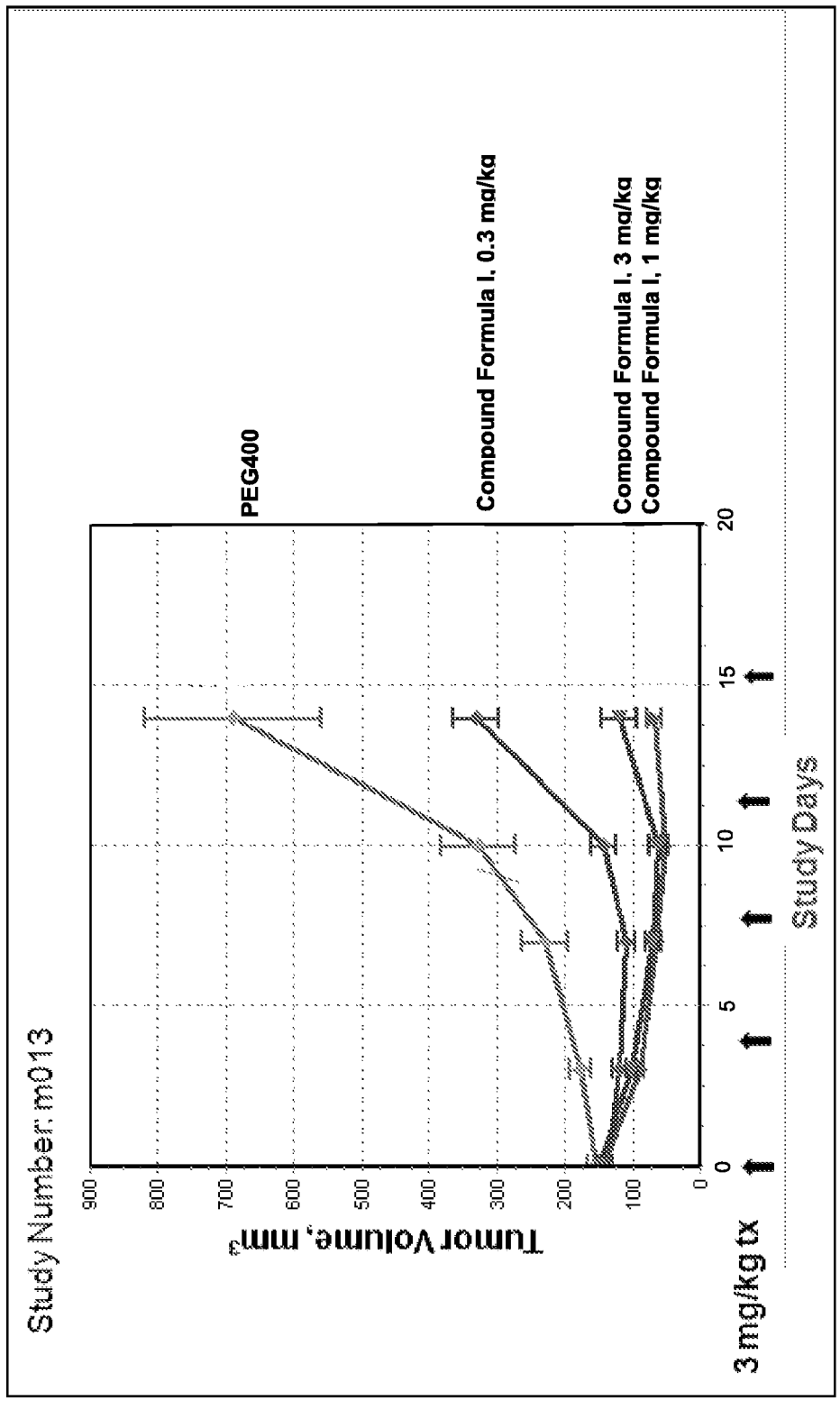
FIG. 3A depicts the in vivo effect of a compound of Table 1 of the subject invention in inhibiting tumor growth in a tumor model such as the U87 human glioblastoma xenograft mouse model over a course of about 14 study days upon administration of the compound at the dose of 3 mg/kg, 1 mg/kg, or 0.3 mg/kg.
Figure 3B:
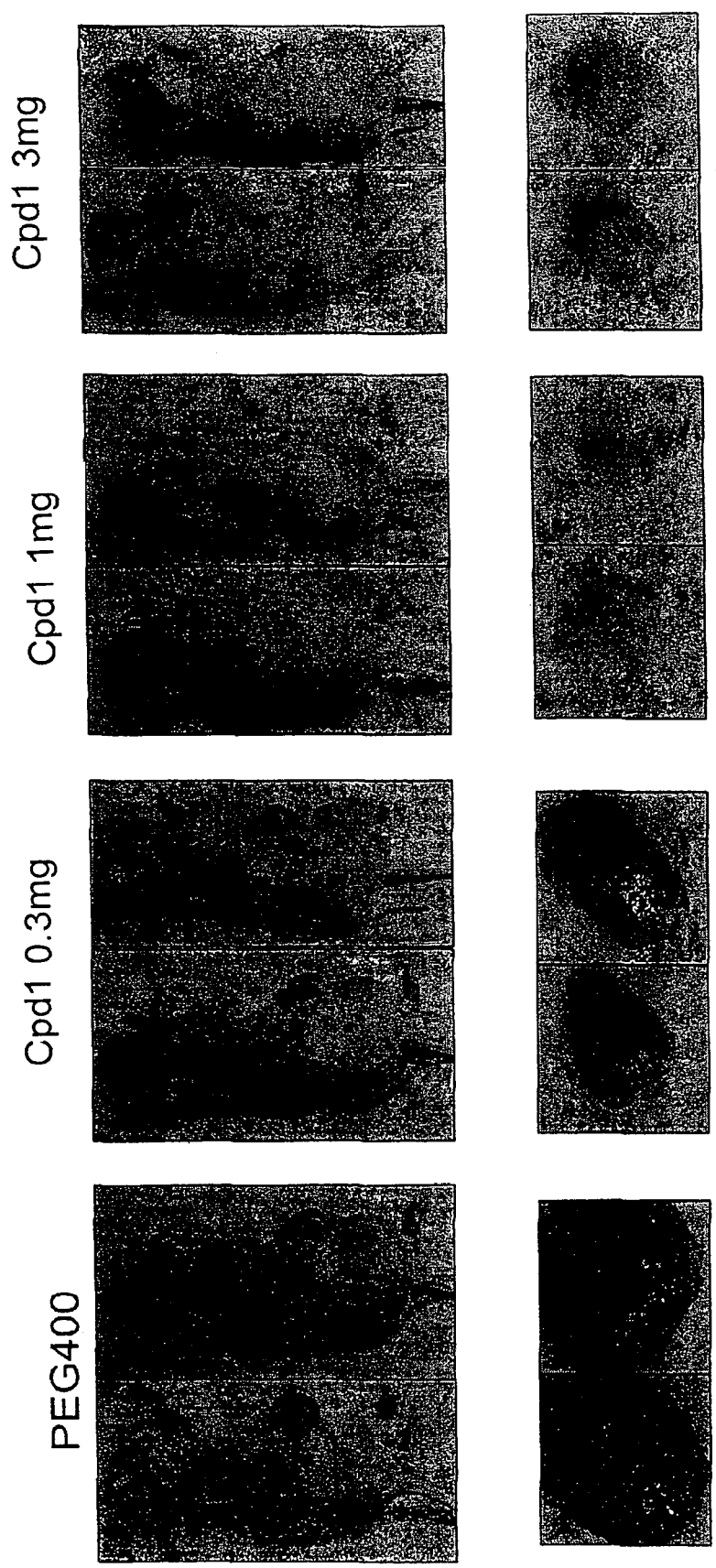
FIG. 3B shows the test animals and the size of the tumor taken from the negative control animal (PEG400 treated) or from the test animals treated with 0.3 mg/kg, 1 mg/kg, or 3 mg/kg of a compound of Table 1.
Figure 3C:
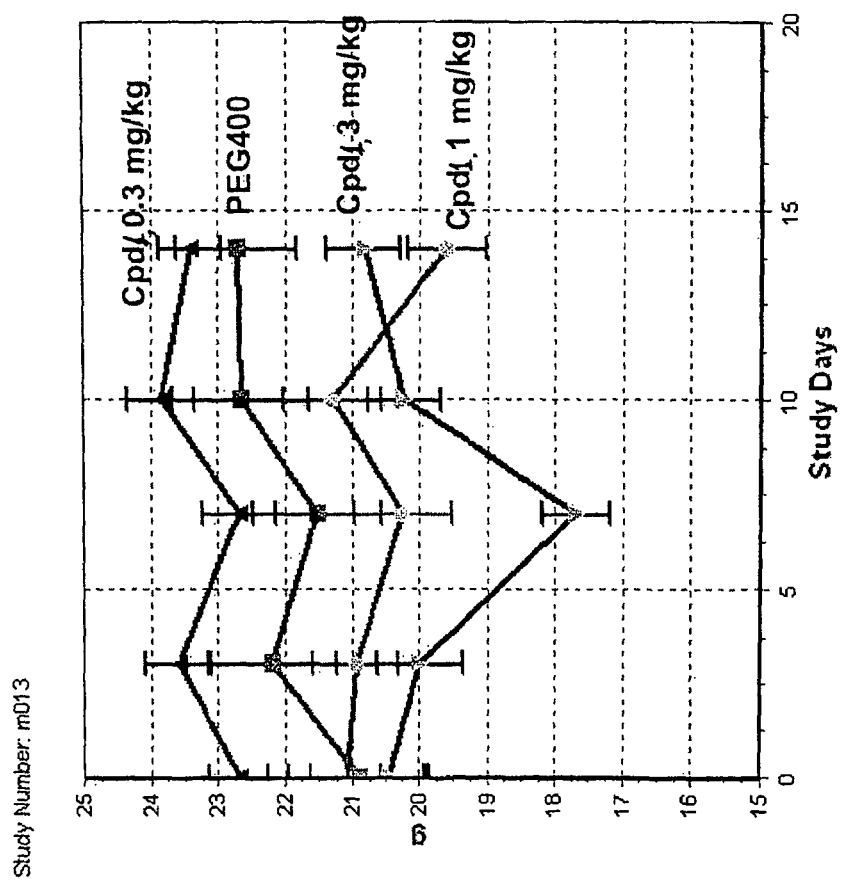
FIG. 3C is a plot of body weight of the negative control and test animals measured over the course of treatment. The results demonstrate that the compound is well tolerated and no significant weight loss is detected during the treatment period, and that tumor growth is significantly inhibited by administration of one or more compounds of the present invention under the conditions tested.
Figure 4A:
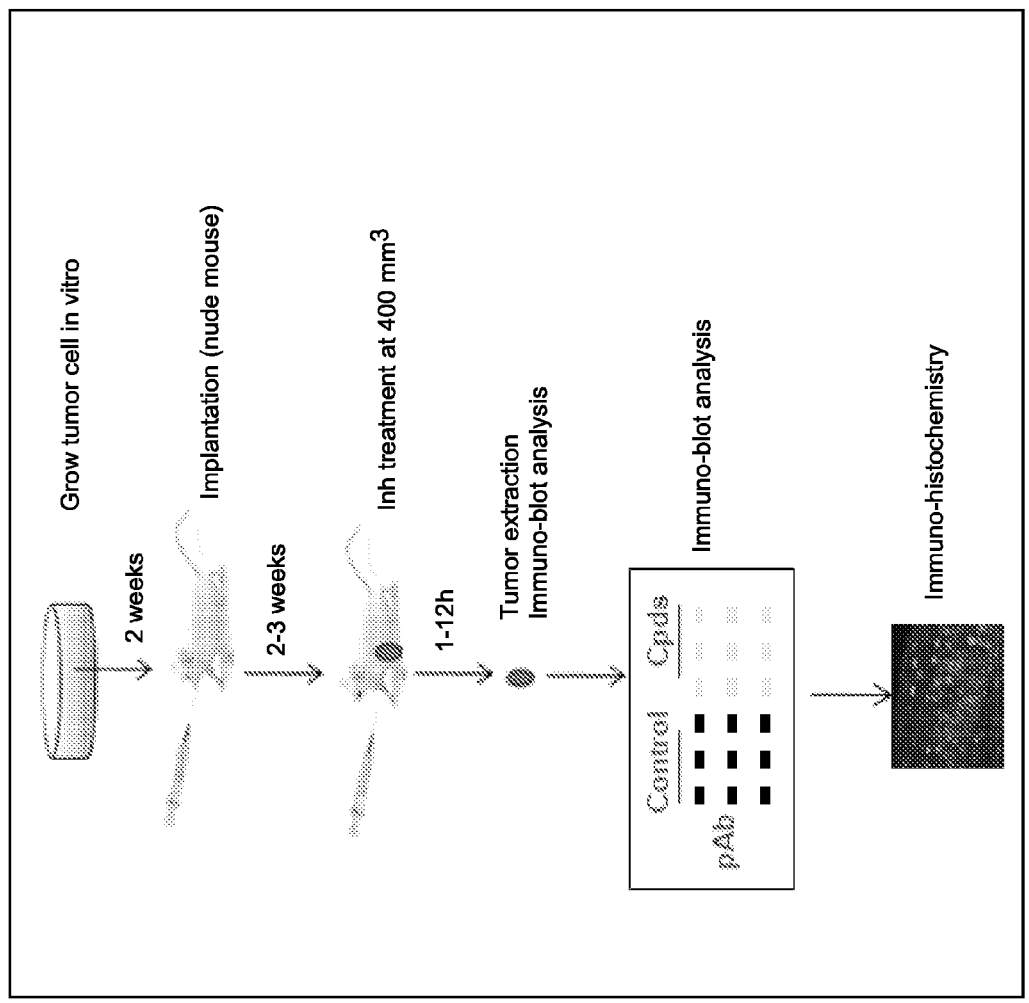
FIG. 4A illustrates an experimental procedure for assessing the ability of the compounds of the invention to inhibit mTOR signalling, especially phosphorylation of AKT(473), PRAS40, S6(240), and 4EBP-1. The phosphorylation pattern of these signalling molecules are shown in FIG. 4B.
Figure 4B:
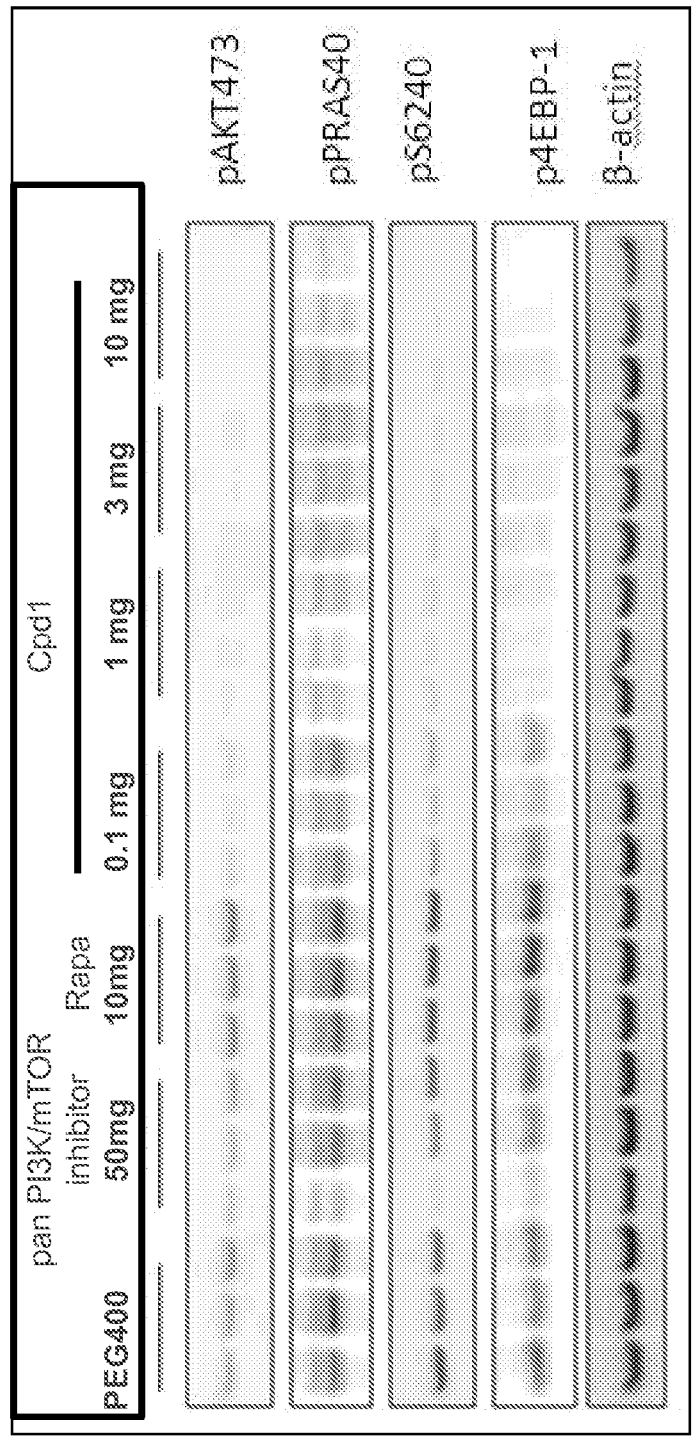
Figure 5:
FIG. 5 depicts the results of lipid and protein kinase selectivity assays with a compound of Table 1.
Figure 8B:
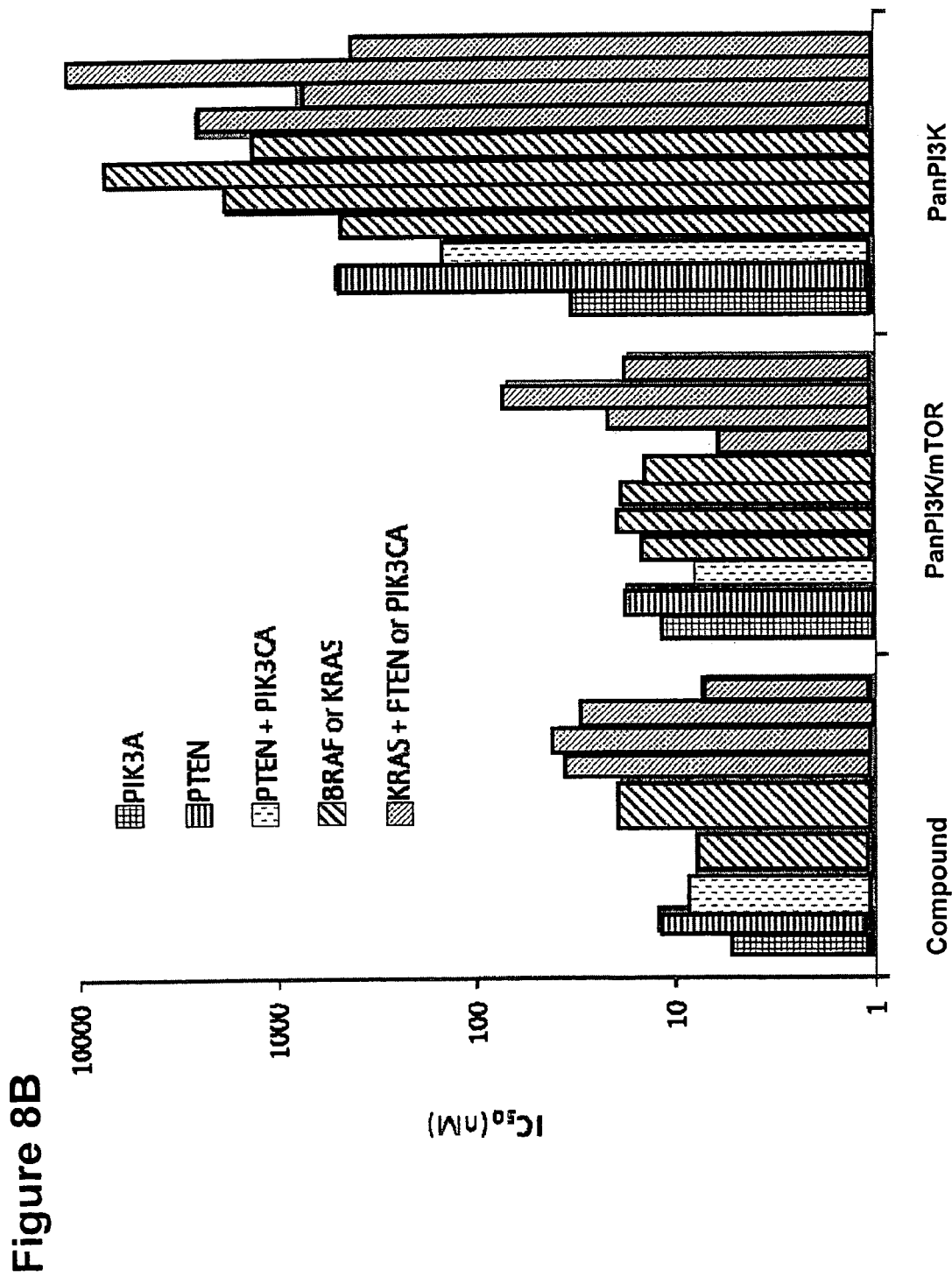
Figure 10:
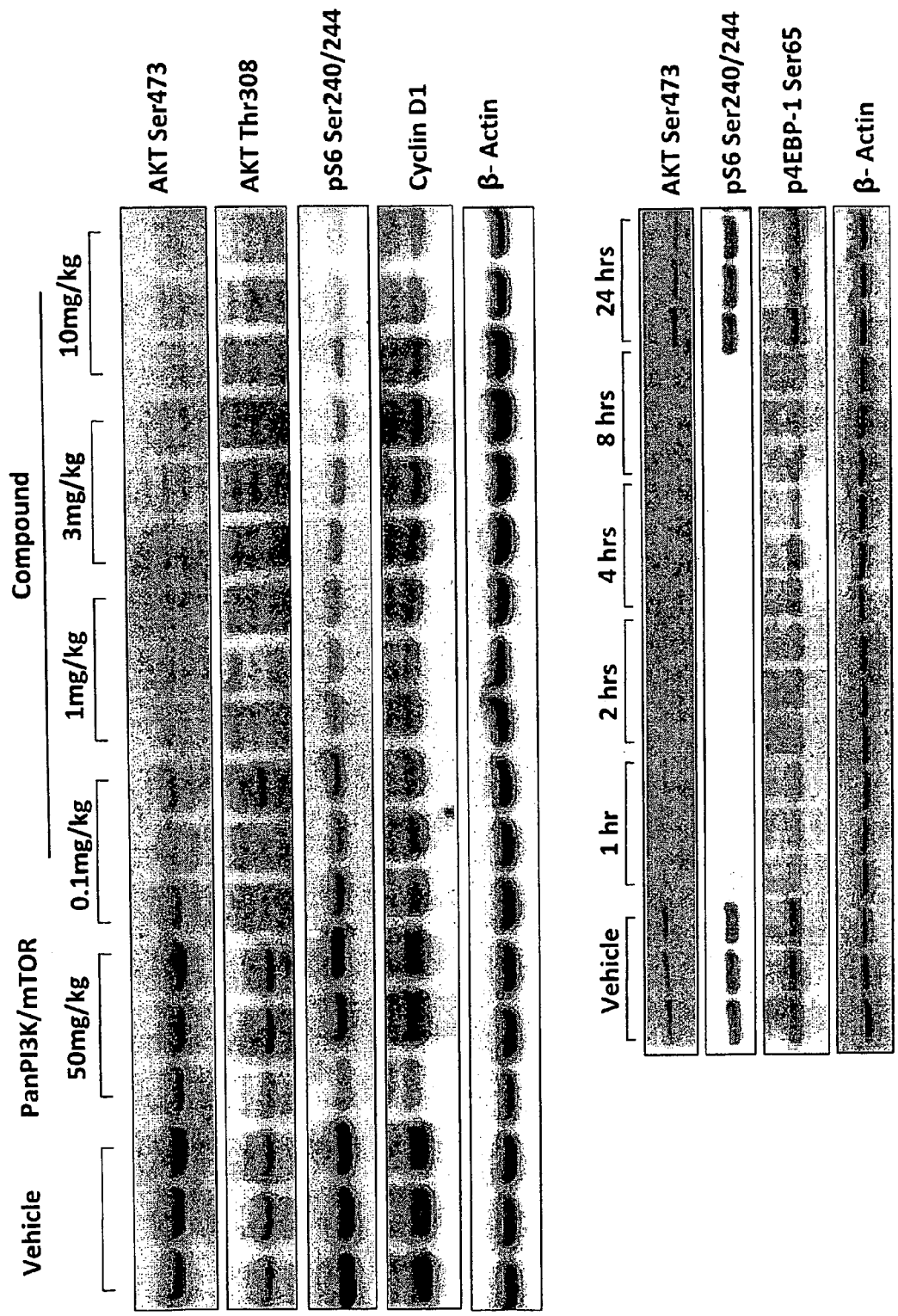
FIG. 10 depicts a western blot analysis of the effect of a compound of Table 1 of the present invention on phosphorylation in tumor cells from a U87-MG xenograft tumor mouse model.
Figure 12:
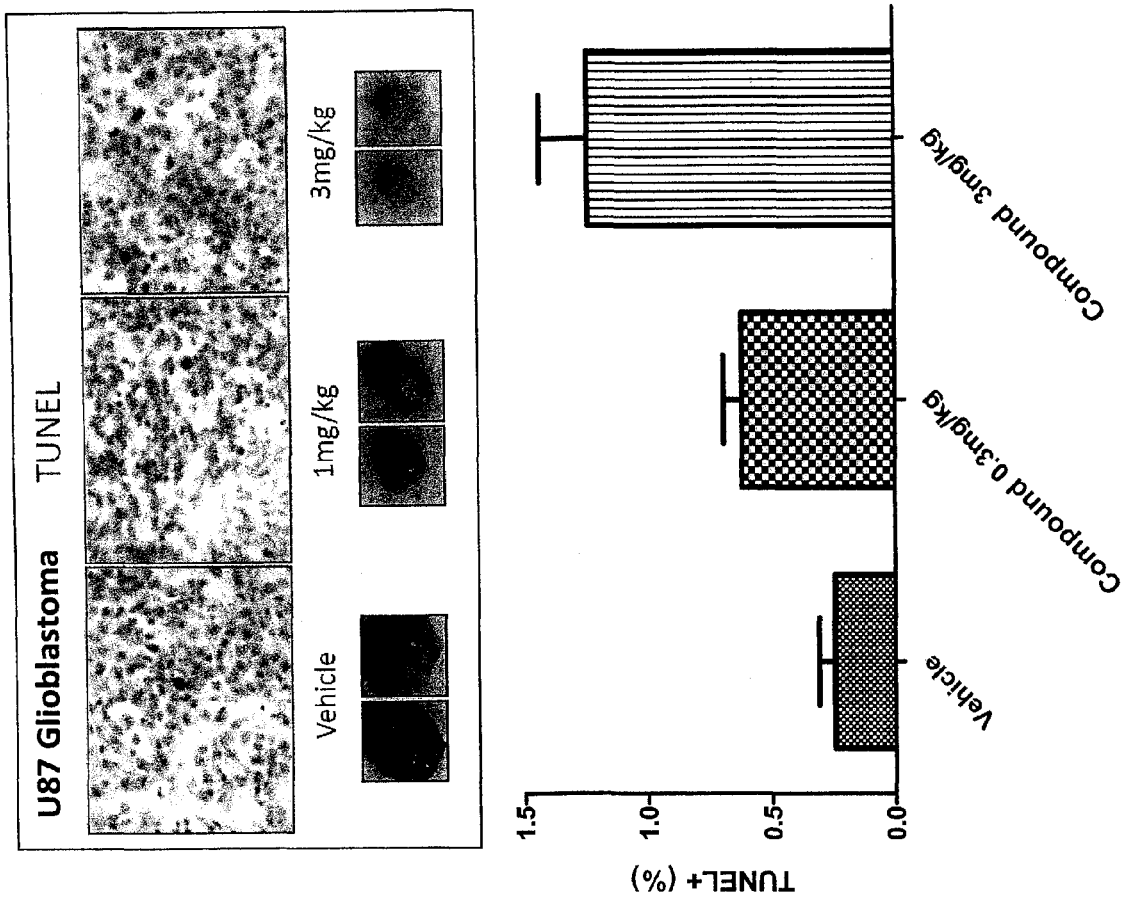
FIG. 12 depicts the results of TUNEL staining of the tumor mass of U87-MG xenograft tumors excised from mice, which were administered vehicle, 1 mg/kg, or 3 mg/kg of the compound of the invention orally. These results show increased in vivo apoptosis in the presence of a compound of Table 1 of the present invention.

As shown in FIGS. 3A-3B, a compound of the invention of Formula I'-A' reduces tumor size in the U87 human glioblastoma xenograft model in a dose dependent manner over a period of 14-day treatment. FIG. 3C shows that the compound has no substantial toxic effect on the animal as there was no significant weight loss during the treatment. Excised tumors (FIG. 3C) were further examined by Western blot analysis which revealed inhibition of mTOR/Akt signalling by the compound of the invention (FIGS. 4B and 10). In particular, inhibition of mTOR/Akt signalling was evidenced by a decrease in phosphorylated Akt at residues S473 and T308, pS6, p4EBP-1, and Cyclin D1. The compound of the invention is more potent in inhibiting mTOR/Akt signalling as compared to an inhibitor that is not selective for mTORs, such as one commonly referred to as PanPI3K/mTor inhibitor. The excised tumors were also subject to TUNEL staining (FIG. 12) which shows tumor cell death after the treatment.

Figure 11A:
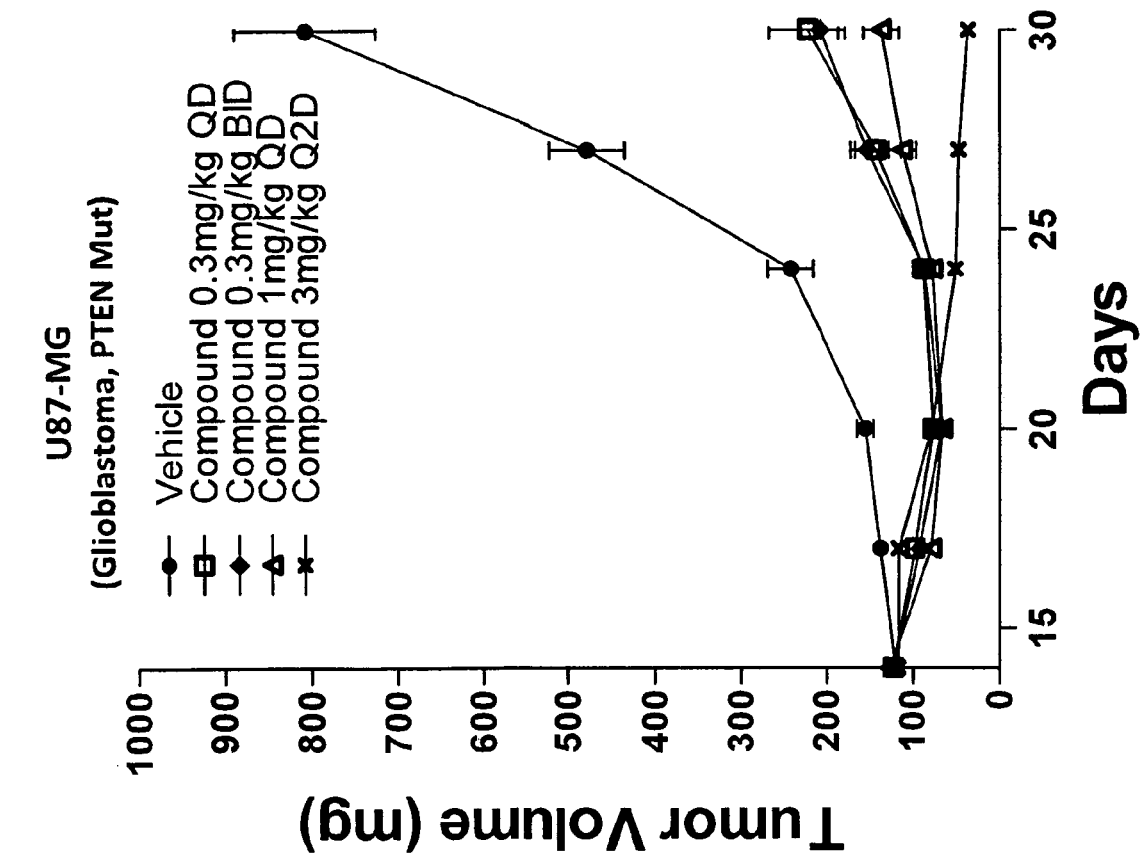
FIGS. 11A-11D depicts the efficacy of oral administration of a compound of Table 1 of the present invention for inhibiting growth of U87-MG, A549, ZR-75-1, and 786-0 xenograft tumors in female athymic nude mice.
Figure 11B:
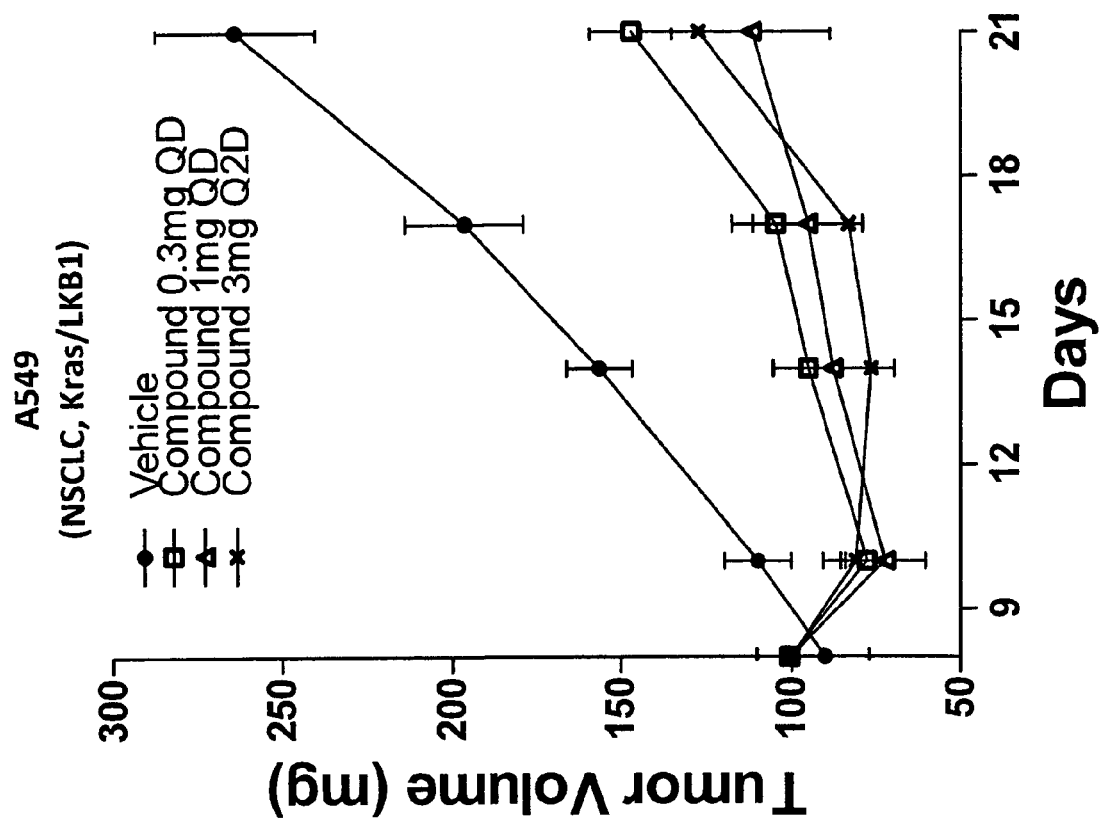
Figure 11C:
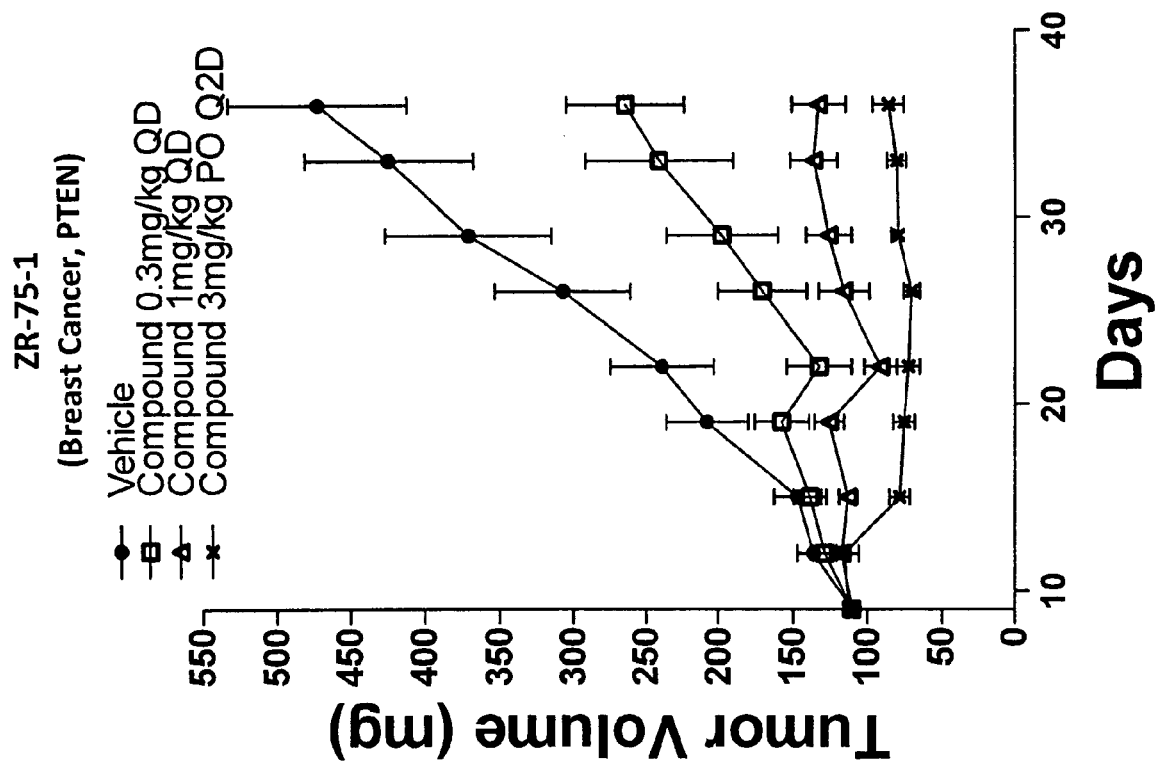
Figure 11D:
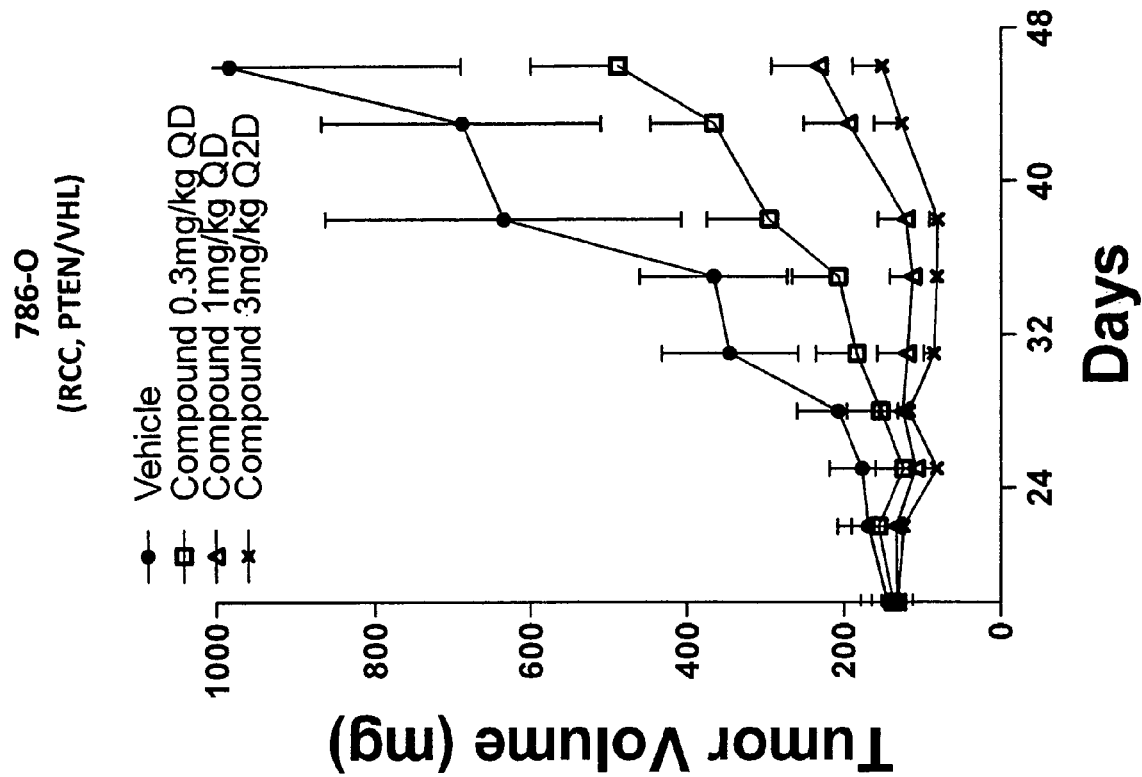

The same experiment was performed with several other tumor models including tumor cell A549 induced NSCLC (non-small cell lung cancer), tumor cell ZR-75-1 induced breast cancer, and tumor cell 786-0 induced RCC (renal cell carcinoma). FIGS. 11B-11D indicate that the efficacy of the compound of the invention in treating all of these tumors became detectable as early as one week after treatment. The effect of reduction in tumor size in all instances last at least 1 month.

The invention claimed is:
1. A pharmaceutical composition comprising a therapeutically effective amount of the following compound

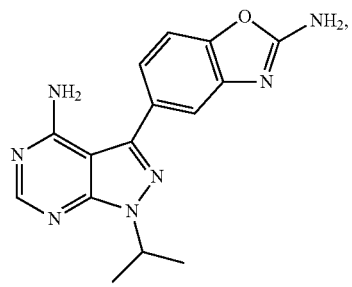 [SMILES: CC(C)n1nc(-c2ccc3oc(N)nc3c2)c2c(N)ncnc21]

or a pharmaceutically acceptable salt thereof, and a pharmaceutically acceptable carrier.

* * * * *